(12) United States Patent
Donald

(10) Patent No.: US 8,431,546 B2
(45) Date of Patent: *Apr. 30, 2013

(54) TARGETING PAX2 FOR THE INDUCTION OF DEFB1-MEDIATED TUMOR IMMUNITY AND CANCER THERAPY

(75) Inventor: Carlton D. Donald, Mount Pleasant, SC (US)

(73) Assignee: Phigenix, Inc., Atlanta, GA (US)

( * ) Notice: Subject to any disclaimer, the term of this patent is extended or adjusted under 35 U.S.C. 154(b) by 158 days.

This patent is subject to a terminal disclaimer.

(21) Appl. No.: 13/010,867

(22) Filed: Jan. 21, 2011

(65) Prior Publication Data

US 2011/0236403 A1    Sep. 29, 2011

Related U.S. Application Data

(63) Continuation of application No. 12/090,191, filed as application No. PCT/US2006/040215 on Oct. 16, 2006, now Pat. No. 7,964,577.

(60) Provisional application No. 60/726,921, filed on Oct. 14, 2005.

(51) Int. Cl.
*A61K 31/70* (2006.01)
*C07H 21/04* (2006.01)

(52) U.S. Cl.
USPC .......................................... 514/44; 536/24.5

(58) Field of Classification Search .................. None
See application file for complete search history.

(56) References Cited

U.S. PATENT DOCUMENTS

| | | | |
|---|---|---|---|
| 3,610,795 A | 10/1971 | Antoine et al. |
| 3,687,808 A | 8/1972 | Merigan, Jr. et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,868,116 A | 9/1989 | Morgan et al. |
| 4,876,335 A | 10/1989 | Yamane et al. |
| 4,897,355 A | 1/1990 | Eppstein et al. |
| 4,904,582 A | 2/1990 | Tullis |
| 4,948,882 A | 8/1990 | Ruth |
| 4,958,013 A | 9/1990 | Letsinger |
| 4,980,286 A | 12/1990 | Morgan et al. |
| 4,981,957 A | 1/1991 | Lebleu et al. |
| 5,023,243 A | 6/1991 | Tullis |
| 5,034,506 A | 7/1991 | Summerton et al. |
| 5,082,830 A | 1/1992 | Brakel et al. |
| 5,084,824 A | 1/1992 | Lam et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,135,917 A | 8/1992 | Burch |
| 5,138,045 A | 8/1992 | Cook et al. |
| 5,166,315 A | 11/1992 | Summerton et al. |
| 5,168,053 A | 12/1992 | Altman et al. |
| 5,175,273 A | 12/1992 | Bischofberger et al. |
| 5,176,996 A | 1/1993 | Hogan et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |

(Continued)

FOREIGN PATENT DOCUMENTS

WO    WO8907136    8/1989
WO    WO9002806    3/1990

(Continued)

OTHER PUBLICATIONS

Jemal, A., et al., "Cancer statistics", CA Cancer J. Clin. 2004, vol. 54, No. 1, pp. 8-29 (2004).
Prasad, M. A., et al, "Homozygous and frequent deletion of proximal 8p sequences in human prostate cancers: identification of a potential tumor suppressor gene site", Genes Chromosomes Cancer, vol. 23, No. 3, pp. 255-262 (1998).
McNeel, D. G., et al., "Immune-based therapies for prostate cancer", Immunology Letters, vol. 96, No. 1, pp. 3 (2005).
Tien, A. H., et al., "Altered immunity accompanies disease progression in a mouse model of prostate dysplasia". Cancer Res., vol. 65, No, 7, pp. 2947-2955 (2005).
Banchereau, J., et al., "Immune and clinical responses in patients with metastatic melanoma to CD34+progenitor-derived dendritic cell vaccine", Cancer Res., vol. 61, No. 17, pp. 6451-6458 (2001).

(Continued)

*Primary Examiner* — Tracy Vivlemore
(74) *Attorney, Agent, or Firm* — Ping Wang; Andrews Kurth LLP

(57) ABSTRACT

Provided is a method of treating cancer in a subject by inhibiting expression of PAX2. An example of a cancer treated by the present method is prostate cancer. In the cancer treatment methods disclosed, the method of inhibiting expression of PAX2 can be by administration of a nucleic acid encoding an siRNA for PAX2. A method of treating cancer in a subject by administering DEFB1 is also provided. Similarly, provided is a method of treating cancer in a subject by increasing expression of DEFB1 in the subject.

6 Claims, 21 Drawing Sheets
(6 of 21 Drawing Sheet(s) Filed in Color)

U.S. PATENT DOCUMENTS

| | | |
|---|---|---|
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,288,514 A | 2/1994 | Ellman |
| 5,292,873 A | 3/1994 | Rokita et al. |
| 5,294,533 A | 3/1994 | Lupski et al. |
| 5,317,098 A | 5/1994 | Shizuya et al. |
| 5,319,080 A | 6/1994 | Leumann |
| 5,321,131 A | 6/1994 | Agrawal et al. |
| 5,334,711 A | 8/1994 | Sproat et al. |
| 5,359,044 A | 10/1994 | Cook et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,436,330 A | 7/1995 | Taira et al. |
| 5,446,137 A | 8/1995 | Maag et al. |
| 5,449,754 A | 9/1995 | Nishioka |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,766 A | 12/1995 | Gold et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,503,978 A | 4/1996 | Schneider et al. |
| 5,506,337 A | 4/1996 | Summerton et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,539,083 A | 7/1996 | Cook et al. |
| 5,541,306 A | 7/1996 | Agrawal et al. |
| 5,541,307 A | 7/1996 | Cook et al. |
| 5,541,313 A | 7/1996 | Ruth |
| 5,543,293 A | 8/1996 | Gold et al. |
| 5,545,568 A | 8/1996 | Ellman |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,556,762 A | 9/1996 | Pinilla et al. |
| 5,561,225 A | 10/1996 | Maddry et al. |
| 5,563,253 A | 10/1996 | Agrawal et al. |
| 5,565,324 A | 10/1996 | Still et al. |
| 5,565,332 A | 10/1996 | Hoogenboom et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,573,905 A | 11/1996 | Lerner et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,580,737 A | 12/1996 | Polisky et al. |
| 5,580,967 A | 12/1996 | Joyce |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,595,873 A | 1/1997 | Joyce et al. |
| 5,596,079 A | 1/1997 | Smith et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | DeMesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,616,466 A | 4/1997 | Cantor et al. |
| 5,618,704 A | 4/1997 | Sanghvi et al. |
| 5,618,825 A | 4/1997 | Baldwin et al. |
| 5,619,680 A | 4/1997 | Berkovich et al. |
| 5,623,070 A | 4/1997 | Cook et al. |
| 5,624,824 A | 4/1997 | Yuan et al. |
| 5,625,050 A | 4/1997 | Beaton et al. |
| 5,627,053 A | 5/1997 | Usman et al. |
| 5,627,158 A | 5/1997 | Cho-Chung |
| 5,627,210 A | 5/1997 | Valerion et al. |
| 5,631,115 A | 5/1997 | Ohtsuka et al. |
| 5,631,146 A | 5/1997 | Szostak et al. |
| 5,633,133 A | 5/1997 | Long |
| 5,633,360 A | 5/1997 | Bischofberger et al. |
| 5,639,873 A | 6/1997 | Barascut et al. |
| 5,641,754 A | 6/1997 | Iversen |
| 5,645,985 A | 7/1997 | Froehler et al. |
| 5,646,020 A | 7/1997 | Swiggen et al. |
| 5,646,031 A | 7/1997 | DeYoung et al. |
| 5,646,042 A | 7/1997 | Stinchcomb et al. |
| 5,646,265 A | 7/1997 | McGee |
| 5,646,285 A | 7/1997 | Baindur et al. |
| 5,650,316 A | 7/1997 | Aggarwal et al. |
| 5,652,094 A | 7/1997 | Usman et al. |
| 5,652,107 A | 7/1997 | Lizardi et al. |
| 5,658,873 A | 8/1997 | Bertsch-Frank et al. |
| 5,663,046 A | 9/1997 | Baldwin et al. |
| 5,663,312 A | 9/1997 | Chaturvedula |
| 5,670,326 A | 9/1997 | Beutel |
| 5,670,633 A | 9/1997 | Cook et al. |
| 5,677,195 A | 10/1997 | Winkler et al. |
| 5,677,437 A | 10/1997 | Teng et al. |
| 5,677,439 A | 10/1997 | Weis et al. |
| 5,681,941 A | 10/1997 | Cook et al. |
| 5,683,873 A | 11/1997 | George et al. |
| 5,683,874 A | 11/1997 | Kool |
| 5,683,899 A | 11/1997 | Stuart |
| 5,683,902 A | 11/1997 | Hampel et al. |
| 5,688,670 A | 11/1997 | Szostak et al. |
| 5,688,696 A | 11/1997 | Lebl |
| 5,688,941 A | 11/1997 | Cook et al. |
| 5,688,997 A | 11/1997 | Baldwin et al. |
| 5,691,317 A | 11/1997 | Cho-Chung |
| 5,693,535 A | 12/1997 | Draper et al. |
| 5,693,773 A | 12/1997 | Kandimalla et al. |
| 5,698,685 A | 12/1997 | Summerton et al. |
| 5,700,920 A | 12/1997 | Altmann et al. |
| 5,712,146 A | 1/1998 | Khosla et al. |
| 5,712,384 A | 1/1998 | Symonds et al. |
| 5,714,331 A | 2/1998 | Buchardt et al. |
| 5,719,262 A | 2/1998 | Buchardt et al. |
| 5,721,099 A | 2/1998 | Still et al. |
| 5,723,598 A | 3/1998 | Lerner et al. |
| 5,728,521 A | 3/1998 | Yuan et al. |
| 5,731,295 A | 3/1998 | Draper et al. |

| | | | | | | |
|---|---|---|---|---|---|---|
| 5,731,424 | A | 3/1998 | Toothman et al. | 5,989,908 A | 11/1999 | Scanlon |
| 5,741,713 | A | 4/1998 | Brown et al. | 5,990,088 A | 11/1999 | Ensoli et al. |
| 5,770,715 | A | 6/1998 | Sugiyama et al. | 5,994,320 A | 11/1999 | Low et al. |
| 5,780,228 | A | 7/1998 | Parma et al. | 5,998,193 A | 12/1999 | Keese et al. |
| 5,780,607 | A | 7/1998 | Goodnow, Jr. et al. | 5,998,203 A | 12/1999 | Matulic-Adamic et al. |
| 5,786,138 | A | 7/1998 | Swenson | 5,998,602 A | 12/1999 | Torrence |
| 5,786,462 | A | 7/1998 | Schneider et al. | 5,999,086 A | 12/1999 | Ecker |
| 5,792,431 | A | 8/1998 | Moore et al. | 6,001,579 A | 12/1999 | Still et al. |
| 5,792,613 | A | 8/1998 | Schmidt et al. | 6,001,988 A | 12/1999 | Parma et al. |
| 5,795,721 | A | 8/1998 | Rabin et al. | 6,004,617 A | 12/1999 | Schultz et al. |
| 5,807,683 | A | 9/1998 | Brenner et al. | 6,005,095 A | 12/1999 | Capaccioli et al. |
| 5,807,718 | A | 9/1998 | Joyce et al. | 6,007,995 A | 12/1999 | Baker et al. |
| 5,807,754 | A | 9/1998 | Zambias et al. | 6,008,321 A | 12/1999 | Li et al. |
| 5,811,300 | A | 9/1998 | Sullivan et al. | 6,011,020 A | 1/2000 | Gold et al. |
| 5,821,130 | A | 10/1998 | Baldwin et al. | 6,013,443 A | 1/2000 | Heilig et al. |
| 5,824,520 | A | 10/1998 | Mulligan-Kehoe | 6,013,522 A | 1/2000 | Monia et al. |
| 5,831,014 | A | 11/1998 | Cook et al. | 6,017,756 A | 1/2000 | Draper |
| 5,834,185 | A | 11/1998 | Ts'o et al. | 6,017,768 A | 1/2000 | Baldwin et al. |
| 5,834,195 | A | 11/1998 | Benkovic et al. | 6,017,898 A | 1/2000 | Pietrzkowski et al. |
| 5,834,318 | A | 11/1998 | Buettner | 6,018,042 A | 1/2000 | Mett et al. |
| 5,834,588 | A | 11/1998 | Wasserman et al. | 6,020,130 A | 2/2000 | Gold et al. |
| 5,837,855 | A | 11/1998 | Chowrira et al. | 6,022,962 A | 2/2000 | Chowrira et al. |
| 5,840,500 | A | 11/1998 | Pei et al. | 6,025,198 A | 2/2000 | Bennett et al. |
| 5,846,713 | A | 12/1998 | Pagratis et al. | 6,025,371 A | 2/2000 | Gordeev et al. |
| 5,847,150 | A | 12/1998 | Dorwald | 6,028,186 A | 2/2000 | Tasset et al. |
| 5,849,903 | A | 12/1998 | Pietrzkowski et al. | 6,030,776 A | 2/2000 | Eaton et al. |
| 5,856,103 | A | 1/1999 | Gray et al. | 6,030,917 A | 2/2000 | Weinberg et al. |
| 5,856,107 | A | 1/1999 | Ostresh et al. | 6,031,071 A | 2/2000 | Mandeville et al. |
| 5,856,188 | A | 1/1999 | Hampel et al. | 6,033,910 A | 3/2000 | Monia et al. |
| 5,856,463 | A | 1/1999 | Prydz et al. | 6,040,193 A | 3/2000 | Winkler et al. |
| 5,856,496 | A | 1/1999 | Fagnola et al. | 6,040,296 A | 3/2000 | Nyce |
| 5,858,660 | A | 1/1999 | Eaton et al. | 6,045,671 A | 4/2000 | Wu et al. |
| 5,859,190 | A | 1/1999 | Meyer et al. | 6,045,755 A | 4/2000 | Lebl et al. |
| 5,861,254 | A | 1/1999 | Schneider et al. | 6,046,004 A | 4/2000 | Wu et al. |
| 5,861,288 | A | 1/1999 | Usman et al. | 6,046,319 A | 4/2000 | Power et al. |
| 5,864,010 | A | 1/1999 | Cook et al. | 6,051,698 A | 4/2000 | Janjic et al. |
| 5,864,026 | A | 1/1999 | Jensen et al. | 6,057,437 A | 5/2000 | Kamiya et al. |
| 5,866,701 | A | 2/1999 | Hampel et al. | 6,060,596 A | 5/2000 | Lerner et al. |
| 5,869,246 | A | 2/1999 | Matsuo et al. | 6,061,636 A | 5/2000 | Horlbeck |
| 5,869,248 | A | 2/1999 | Yuan et al. | 6,261,834 B1 | 7/2001 | Srivastava |
| 5,869,253 | A | 2/1999 | Draper | 6,841,350 B2 | 1/2005 | Ogden et al. |
| 5,869,339 | A | 2/1999 | Hampel et al. | 2002/0142320 A1 | 10/2002 | Ogden et al. |
| 5,869,641 | A | 2/1999 | Jayasena et al. | 2003/0143732 A1 | 7/2003 | Fosnaugh et al. |
| 5,874,443 | A | 2/1999 | Kiely et al. | 2003/0170891 A1 | 9/2003 | McSwiggen et al. |
| 5,874,566 | A | 2/1999 | Veerapanane et al. | 2005/0095257 A1 | 5/2005 | Kwak et al. |
| 5,877,021 | A | 3/1999 | Stinchcomb et al. | 2006/0135422 A1 | 6/2006 | Moskowitz |
| 5,877,022 | A | 3/1999 | Stinchcomb et al. | 2006/0247318 A1 | 11/2006 | Song et al. |
| 5,877,162 | A | 3/1999 | Werner et al. | 2006/0270643 A1 | 11/2006 | Chang et al. |
| 5,877,214 | A | 3/1999 | Kim | 2007/0031844 A1 | 2/2007 | Khvorova et al. |
| 5,880,972 | A | 3/1999 | Horlbeck | | | |
| 5,886,126 | A | 3/1999 | Newkome et al. | | | |
| 5,886,127 | A | 3/1999 | Newkome et al. | | | |

FOREIGN PATENT DOCUMENTS

| | | |
|---|---|---|
| WO | WO9203566 | 3/1992 |
| WO | WO9322434 | 11/1993 |
| WO | WO9524489 | 9/1995 |
| WO | WO9718312 | 5/1997 |
| WO | WO9807833 A1 | 2/1998 |
| WO | WO9858057 | 12/1998 |
| WO | WO9858058 | 12/1998 |
| WO | WO0049175 A1 | 8/2000 |
| WO | WO0146405 A2 | 6/2001 |
| WO | WO0222686 A2 | 3/2002 |
| WO | WO0244321 | 6/2002 |

| | | | |
|---|---|---|---|
| 5,891,683 | A | 4/1999 | Usman et al. |
| 5,891,684 | A | 4/1999 | Usman et al. |
| 5,891,737 | A | 4/1999 | Baindur et al. |
| 5,910,408 | A | 6/1999 | Szostak et al. |
| 5,916,899 | A | 6/1999 | Kiely et al. |
| 5,919,772 | A | 7/1999 | Szyf et al. |
| 5,919,955 | A | 7/1999 | Fancelli et al. |
| 5,925,527 | A | 7/1999 | Hayes et al. |
| 5,939,268 | A | 8/1999 | Boger |
| 5,942,387 | A | 8/1999 | Hollinshead |
| 5,945,070 | A | 8/1999 | Kath et al. |
| 5,948,696 | A | 9/1999 | Dolle, III et al. |
| 5,955,590 | A | 9/1999 | Levina et al. |
| 5,958,691 | A | 9/1999 | Pieken et al. |
| 5,958,702 | A | 9/1999 | Benner |
| 5,958,792 | A | 9/1999 | Desai et al. |
| 5,962,337 | A | 10/1999 | Ohlmeyer |
| 5,962,426 | A | 10/1999 | Glazer |
| 5,965,719 | A | 10/1999 | Hindsgaul |
| 5,972,699 | A | 10/1999 | Draper |
| 5,972,704 | A | 10/1999 | Draper et al. |
| 5,972,719 | A | 10/1999 | Dolle, III et al. |
| 5,976,894 | A | 11/1999 | Dolle, III et al. |
| 5,980,704 | A | 11/1999 | Cherukuri et al. |
| 5,985,356 | A | 11/1999 | Schultz et al. |
| 5,985,621 | A | 11/1999 | Usman et al. |
| 5,989,906 | A | 11/1999 | Thompson |

OTHER PUBLICATIONS

Fong, L., et al., "Dendritic cell-based Xenoantigen vaccination for prostate cancer immunotherapy", J. Immunol., vol. 167, No. 12, pp. 7150-7156 (2001).

Linzmeier, R., et al., "A 450-kb contig of defensin genes on human chromosome 8p23", Gene, vol. 233, No. 1-2, pp. 205-211 (1999).

Yang, D. et al., "Multiple roles of antimicrobial defensins, cathelicidins, and eosinophil-derived neurotoxin in host defense", Annual Review of Immunology, vol. 22, No. 1, pp. 181-215 (2004).

Donald, C. D., et al., "Cancer-specific loss of beta-defensin 1 in renal and prostatic carcinomas", Lab Invest., vol. 83, No. 4, pp. 501-505 (2003).

Ganz, T., et al., "Defensins: antimicrobial peptides of vertebrates", C. R. Biol. vol. 327, No. 6, pp. 539-549 (2004).

Mazzucchelli, R., et al., "Molecular mechanisms in prostate cancer", Anal. Quant. Cytoi. Histol., vol. 26, No. 3, pp. 127-133 (2004).

Ganz, T., "Defensins and host defense", Science, vol. 286, No. 5439, 420-421 (1999).

Ganz, T., "Immunology, versatile defensins", Science, Vol.298, No. 5595, pp. 977-999 (2002).

Braida, L., et al., "A single-nucleotide polymorphism in the human beta-defensin 1 gene is associated with HIV-1 infection in Italian children", Aids, vol. 18, No. 11, pp. 1598-1600 (2004).

Gropp, R., et al., "Epithelial defensins impair adenoviral infection: implication for adenovirus-mediated gene therapy", Hum. Gene Then, vol. 10, pp. 6, pp. 957-964 (1999).

Catalano, M. G., et al., "Altered expression of androgen-receptor isoforms in human colon-cancer tissues", Int. J. Cancer, vol. 86, No. 3, pp. 325-330 (2000).

Takeuchi, S. et al., "Differential effects of phthalate esters on transcriptional activities via human estrogen receptors alpha and beta, and androgen receptor", Toxicology, vol. 210, No. 2-3, pp. 223-233 (2005).

Wang, Z., et al., "Analysis of loss of heterozygosity on chromosome 8 in human prostate carcinoma and high grade prostatic interepithelial neoplasis", Zhong Hua Nan Ke Xue, vol. 10, No. 1, pp. 26-28.

Nishimura,M., et al., "Effect of defensin peptides on eukaryotic cells: primary epithelial cells, fibroblasts and squamous cell carcinoma cell lines" Journal of Dermatological Science, vol. 36, No. 2, pp. 87 (2004).

Fromont, G., et al., "Allelic losses in localized prostate cancer: association with prognostic factors". J. Urol vol. 170 pp. 1394-1397 (2003).

Hugel, A., et al., "Loss of heterozygosity (LOH), malignancy grade and clonality in microdissected prostate cancer", Br. J. Cancer, vol. 79, No. 3-4, pp. 551-557 (1999).

Bockmuhl, U., et al., "Association of 8p23 deletions with poor survival in head and neck cancer", Otolaryngol. Head Neck Surg., vol. 124, No. 4, pp. 451-455 (2001).

Macoska, J. A., et al., "Evolution of 8p loss in transformed human prostate epithelial cells", Cancer Genet. Cytogenet., vol. 154, No. 1, pp. 36-43 (2004).

Chaib, H., et al., "Haploinsufficiency and reduced expression of genes localized to the 8p chromosomal region in human prostate tumors", Genes Chromosomes Cancer, vol. 37, No. 3, pp. 306-313 (2003).

Teixeira, M. R., et al., "Genomic analysis of prostate carcinoma specimens obtained via ultrasound-guided needle biopsy may be of use in preoperative decision-making", Cancer, Vol. 101, No. 8, pp. 1786-1793 (2004).

Vecchione, A., et al., "FEZ1/LZTS1 is down-regulated in high-grade bladder cancer, and its restoration suppresses tumorigenicity in transitional cell carcinoma cells". Am. J. Pathol., vol. 160, No. 4, pp. 1345-1352 (2002).

Valore, E. V., et al., "Human beta-defensin-1: an antimicrobial peptide of urogenital tissues", J. Clin. Invest., vol. 101, No. 8, pp. 1633-1642 (1998).

Gunther, M., et al., "Specific targets in tumor tissue for the delivery of therapeutic genes", Curr. Med. Chem. Anti-Canc. Agents, vol. 5, No. 2, pp. 157-171 (2005).

Dressler, G. R., "Pax-2, kidney development, and oncogenesis", Med. Pediatr. Oncol., vol. 27, No. 5, pp. 440-444 (1996).

Eccles, M, R., et al., "PAX genes in development and disease: the role of PAX2 in urogenital tract development", Int J. Dev. Biol., vol. 46, No. 4, pp. 535-544 (2002).

Dressler, G. R., "Pax2 in development and renal disease", Int. J. Dev. Biol., vol. 43, No. 5, pp. 463-468 (1999).

Khoubehi, B., et al., "Expression of the developmental and oncogenic PAX2 gene in human prostate cancer", J. Urol., vol. 165, pp. 2115-2120 (2001).

Havik, B., et al., "A novel paired domain DNA recognition motif can mediate Pax2 repression of gene transcription", Biochem. Biophys. Res. Commun., vol. 266, No. 2, pp. 532-541 (1999).

Discenza, M. T., et al., "WT1 is a modifier of the Pax2 mutant phenotype: cooperation and interaction between WT1 and Pax2", Oncogene, vol. 22, No. 50, pp. 8145-8155 (2003).

McConnell, M. J., et al., "Differential regulation of the human Wilms tumour suppressor gene (WT1) promoter by two isoforms of PAX2", Oncogene, vol. 14, No. 22, pp. 2689-2700 (1997).

Yuan, S. S., et al., "Pax-2 interacts with RB and reverses its repression on the promoter of Rig-1, a Robo member", Biochem. Biophys. Res. Commun., vol. 296, No. 4, pp. 1019-1025 (2002).

Stuart, E. T., et al., "Loss of p53 function through PAX-mediated transcriptional repression", EMBO J., vol. 14, No. 22, pp. 5638-5645 (1995).

Michalak,E., et al., "Death squads enlisted by the tumour suppressor p53", Biochem. Biophys. Res. Commun., vol. 331, No. 3, pp. 786-798 (2005).

Tokino, T., et al., "The role of p53-target genes in human cancer", Crit. Rev. Oncol. Hematol., vol. 33, No. 1, pp. 1-6, (2000).

Muratovska, A., et al., "Paired-Box genes are frequently expressed in cancer and often required for cancer cell survival", Oncogene, vol. 22, No. 39, pp. 7989-7997 (2003).

Tagge, E. P., et al., "Paired box gene expression in Wilms' tumor", J. Pediatr. Surg., vol. 29, No. 2, pp. 134-141 (1994).

Murer, L., et al., "Expression of nuclear transcription factor PAX2 in renal biopsies of juvenile nephronophthisis", Nephron, vol. 91, No. 4, pp. 588-593 (2002).

Eccles, M. R., et al., "Expression of the PAX2 gene in human fetal kidney and Wilms' tumor", Cell Growth Differ.. vol. 3, No. 5, pp. 279-289 (1992).

Ogata, T., et al., "Genetic evidence for a novel gene(s) involved in urogenital development on 10q26", Kidney Int., vol. 58, No. 6, pp. 2281-2290 (2000).

Ostrom, L, et al., "Reduced Pax2 gene dosage increases apoptosis and slows the progression of renal cystic disease", Dev. Biol., vol. 219, No. 2, pp. 250-258 (2000).

Perfettini, J. L, et al., "Fatal liaisons of p53 with Bax and Bak", Nat. Cell. Biol., vol. 6, No. 5, pp. 386-388 (2004).

Coultas, L, et al., "The role of the Bcl-2 protein family in cancer", Semin. Cancer Biol., vol. 13, No. 2, pp. 115-123 (2003).

Mrgue,C. M., et al., "Transcriptional modulation of the anti-apoptotic protein BCL-XL by the paired box transcription factors PAX3 and PAX3/FKHR", Oncogene, vol. 19, No. 25, pp. 2921-2929 (2000).

Nakamura,Y., "Isolation of p53-target genes and their functional analysis", Cancer Sci., vol. 95, No. 1, pp. 7-11 (2004).

Perfettini, J. L., et al., "Mitochondrial fusion and fission in the control of apoptosis", Trends. Cell Biol., vol. 15, No. 4 pp. 179-183 (2005).

Orlando, V., et al., "Mapping chromosomal proteins in vivo by formaldehyde-crosslinked-chromatin immunoprecipitation", Trends. Biochem. Sci., vol. 25, pp. 99-104 (2000).

Boyd, K. E., et al., "Coexamination of site-specific transcription factor binding and promoter activity in living cells", Mol. Cell Bioi., vol. 19, pp. 8393-8399 (1999).

Wells, J., et al., "Characterizing transcription factor binding sites using formaldehyde crosslinking and immunoprecipitation", Methods, vol. 26, pp. 48-56 (2002).

Sikorski, R. S., et al, "A system of shuttle vectors and yeast host strains designed for efficient manipulation of DNA in *Saccharomyces cerevisiae*", Genetics, vol. 122, pp. 19-27 (1989).

Nigro, J. M., et al, "Human p53 and CDC2Hs genes combine to inhibit the proliferation of *Saccharomyces cerevisiae*", Mol Cell. Biol, vol. 12, pp. 1357-1365 (1992).

Wilson, T. E., et al, "Identification of the DNA binding site for NGFI-B by genetic selection in yeast", Science, vol. 252, pp. 1296-1300(1991).

Liu, J., et al, "Identifying DNA-binding sites and analyzing DNA-binding domains using a yeast selection system", Methods: A companion to Methods in Enzymology, vol. 5, pp. 125-137 (1993).

Jackers, P., et al., "Ets-dependent regulation of target gene expression during megakaryopoiesis", J. Biol. Chem., vol. 279, pp. 52183-52190 (2004).

Fonsato, V., et al, "Expression of PAX2 in human renal tumor-derived endothelial cells sustains apoptosis resistance and angiogenesis", American Journal of Pathology, vol. 168, pp. 706-713 (2006).

Almquist, R. G., et al., "Synthesis and biological activity of a ketomethylene analogue of a tripeptide inhibitor of angiotensin converting enzyme", J. Med. Chem., vol. 23, pp. 1392-1398 (1980).

Askew, B., et al., "Molecular recognition with convergent functional groups. 6. synthetic and structural studies with a model receptor for nucleic acid components", J. Am. Chem. Soc., vol. 111, pp. 1082-1090 (1989).

Bagshawe, K. D., et al., "A cytotoxic agent can be generated selectively at cancer sites", Br. J. Cancer, vol. 58, pp. 700-703 (1988).

Battelli, M. G., et al., "T lymphocyte kiling by a xanthine-oxidase-containing immunotoxin", Cancer Immunology Immunotherapy, vol. 35, pp. 421-425 (1992).

Benner, S. A.," Expanding the genetic lexicon: incorporatng non-standard amino acids into proteins by ribosome-based synthesis", TIB Tech., vol. 12, pp. 158-163 (1994).

Berkner, K. L, et al., "Abundant expression of polyomavirus middle T antigen and dihydrofolate reductase in an adenovirus recombinant", J. Virology, vol. 61, pp. 1213-1220 (1987).

Bout, A., et al., "Lung gene therapy: In Vivo adenovirus-mediated gene transfer to Rhesus monkey airway epithelium", Human Gene Therapy, vol. 5, pp. 3-10 (1994).

Brigham, K. L., et al., "Expression of a prokaryotic gene in culture lung endothelial cells after lipofection with a plasmid vector", Am. J. Respir. Cell Mol. Biol., vol. 1, pp. 95-100 (1989).

Brown, D. T., et al., "Penetration of host cell membranes by adenovirus 2", J. Virology, vol. 12, pp. 386-396 (1973).

Brown, V. I., et al., "Molecular and cellular mechanisms of receptor-medicated endocytosis", DNA and Cell Biology, vol. 10, pp. 399-409 (1991).

Cahill, S. J., et al., "Site-specific mutagenesis with unnatural amino acids", TIBS, vol. 14, No. 10, pp. 400-403 (1989).

Caillaud, C, et al., "Adenviral vector as a gene delivery system into cultured rat neuronal and glial cells", Eur. J. Neuroscience, vol. 5, pp. 1287-1291 (1993).

Carrara, G., et al., "Two helices plus a linker: a small model substrate for eukaryotic RNase P", Proc. Natl. Acad. Sci., USA, vol. 92, pp. 2627-2631 (1995).

Chardonnet, Y., et al, "Early events in the interaction of adenoviruses with HeLa cells I. penetration of Type 5 and intracellular release of the DNA genome", Virology, vol. 40, pp. 462-477 (1970).

Check, E., et al, "RNA to the rescue", nature, vol. 425, pp. 10-12 (2003).

Creighton, T. E., "Posttranslational covalent modifications of polypeptide chains", Proteins: Structure and Molecular Properties, W. H. Freeman & Co., San Francisco, pp. 79-86 (1983).

Cohen, B. A., et al., "An artificial cell-cycle inhibitor isolated from a combinatorial library", Proc. Natl. Acad. Sci USA, vol. 95, pp. 14272-14277 (1998).

Cotter, U. A., et al., "Molecular genetic analysis of herpesviruses and their potential use as vectors for gene therapy applications", Current Opinion in Molecular Therapeutics, vol. 1, No. 5, pp. 633-644 (1999).

Crooke, S. T., et al., "Pharmacokinetic properties of several novel oligonucleotide analogs in mice", J. Pharmacol. Exp. Ther., vol. 277, pp. 923-937 (1996).

Davidson, D., et al., "overproduction of polyomavirus middle T antigen in mammalian cells through the use of an adenovirus vector", J. Virology, vol. 61, pp. 1226-1239 (1987).

Davies, J. A., et al., "Development of an siRNA-based method for repressing specific genes in renal organ culture and its use to show that the Wt1 tumour suppressor is required for nephron differentiation", Human Molecular Genetics, vol. 13, pp. 235-246 (2004).

English, U., et al., "Chemically modified oligonucleotides as probes and inhibitors", Angewandte Chemie, International Edition in English, vol. 30, pp. 613-722 (1991).

Felgner, P. L, et al., "Lipofection: a highly efficient, lipid-mediated DNA-transfection procedure", Proc. Natl. Acad. Sci., USA, vol. 84, pp. 7413-7417 (1987).

Fields, S., et al., "A novel genetic system to detect protein-protein interactions", Nature, vol. 340, pp. 245-256 (1989).

Gomez-Foix, A. M., et al., "Adenovirus-mediated transfer of the muscle glycogen phosphorylase gene into hepatocytes confers altered regulation of glycogen metabolism", J. Biol. Chem., vol. 267, pp. 25129-25134 (1992).

Guzman, R. J., et al., "Efficient gene transfer into myocardium by direct injection of adenovirus vectors", Circulation Research, vol. 73, pp. 1201-1207 (1993).

Hann, M., et al, "On the double bond isostere of the peptide bond: preparation of an enkephaline analogue", J. Chem. Soc. Perkin. Trans., pp. 307-314 (1982).

Haj-Ahmad, Y., et al., "Development of a helper-independent human adenovirus vector and its use in the transfer of herpes simplex virus thymidine kinase gene", J. Virology, vol. 57, pp. 267-274 (1986).

Hammond, S. M., et al., "post-transcriptional gene silencing by double-stranded RNA", Nature Rev. Gen., vol. 2, pp. 110-119 (2001).

Holladay, M. W., et ai., "Synthesis of hydroxyethylene and ketornethylene dipeptide isosteres", Tetrahedron Letters, vol. 24, pp. 4401-4404 (1983).

Hruby, V. J., et al., "Conformational restrictions of biologically active peptides via amino acid side chain groups", Life Sciences, vol. 31, pp. 189-199 (1982).

Hudson, D., et al., "Methionine enkephalin and isosteric analogues", Int. J. Peptide Protein Res., vol. 14, pp. 177-185 (1979).

Hueber, P-A., et al., "PAX2 inactivation enhances cisplatin-induced apoptosis in renal carcinoma cells", Kidney International, vol. 69, pp. 1139-1145 (2006).

Hughes, B. J., et al., "Monoclonal antibody targeting of liposomes to mouse lung in vivo", vol. 49, pp. 6214-6220 (1989).

Ibba, M., et al., "Towards engineering proteins by site-directed incorporation in vivo of non-natural amino acids", Nature Biotechnology, vol. 12, pp. 678-682 (1994).

Ibba, M., et al., "Strategies for n vitro and in vivo translation with non-natural amino acids", Biotechnology & Genetic Engineering Reviews, vol. 13, pp. 197-216 (1995).

Itakura, K., et al., "Synthesis and use of synthetic oligonucleotides", Ann. Rev. Biochem., vol. 53, pp. 323-356 (1984).

Jaeger, J. A., et al., "Predicting optimal and suboptimal secondary structure for RNA", Methods in Enzymology, vol. 183, pp. 281-306 (1989).

Jaeger, J. A., et al., "Improved predictins of secondary structures for RNA", Proc. Natl. Acad. Sci., USA, vol. 86, pp. 7706-7710 (1989).

Jennings-White, C, et al., "Synthesis of ketomethylene analogs of dipeptides", Terahedron Letter, vol. 23, pp. 2533-2534 (1982).

Kabanove, A. V., et al, "A new class of antivirals; antisense oligonucleotides combine with a hydrophobic substituent effectively inhibit influenza virus reproduction and synthesis of virus-specific proteins in MDCK cells", FEBS letter., vol. 259, pp. 327-330 (1990).

Kirshenbaum, L. A., et al., "Highly efficient gene transfer into adult ventricular myocytes by recombinant adenovirus", J. Clin. Invest., vol. 92, pp. 381-387 (1993).

Kunkel, T. A., et al., "Rapid and efficient site-specific mutagenesis without phenotypic selection", Methods in Enzymology, vol. 154, pp. 367-382 (1987).

Lamins, L. A., et al., "Osmotic control of kdp operon expression in *Escherichia coif*" Proc. Natl. Acad. Sci., USA, vol. 78, pp. 464-468 (1981).

Letsinger, R. L, et al., "Cholesteryl-conjugate oligonucleotides: synthesis, properties, and activity as inhibitors of replciation of human immunodeficiency virus in cell culture", Proc. Natt. Acad. Sci., USA, vol. 86, pp. 6553-6556 (1989).

Lewis, R. A., et al., "Automated site-directed drug design: the conception of spacer skeleton for primary structure generation", Proc. R. Soc. Lond., vol. 236, pp. 125-140 (1989).

Litzinger, D. C, et al., "Biodistribution and immunotargetability of ganglioside-stabilized dioleoylphosphatidylethanofamine liposomes", Biochimica et Biophysica Acta, vol. 1104, pp. 179-187 (1992).

Lusky, M., etal., "Bovine papilloma virus contains an activator of gene expression at the distal end of the early transcription unit", Mol. Cell. Biol., vol. 3, pp. 1108-1122 (1983).

Manoharan, M., et al., "Chemical modifications to improve uptake and bioavailability of antisense oligonucleotides", Ann. N.Y. Acad. Sci., vol. 660, pp. 306-309 (1992).

Manoharan, M., et al., "Introduction of a lipophilic thioether tether in the minor groove of nucleic acids for antisense applications", Bioorganic & Medicinal Chemistry Letters, vol. 3, pp. 2765-2770 (1993).

Manoharan, M., et al., "Cholic acid-oligonucleotide conjugates for antisense applications", Bioorganic & Medicinal Chemistry Letters, vol. 4, pp. 1053-1060 (1994).

Manoharan, M., et al., "Oligonucleotide conjugates: alteration of the pharmacokinetic properties of antisense agents", Nucleotides & Nucleotides, vol. 14, pp. 969-973 (1995).

Manoharan, M., et al., "Lipidic nucleic acids", Tetrahedron Letters, vol. 36, pp. 3651-3654 (1995).

Massie, B., et al., "Construction of a helper-free recombinant adenovirus that expresses polyomavirus large T antigen", Molecular and Cellular Biology, vol. 6, pp. 2872-2883 (1986).

McKinlay, M. A., et al., "Rational design of antiviral agents", Annu. Rev. Pharmacol. Toxicol., vol. 29, pp. 111-122 (1989).

Mishra, R. K., et al., "Improve leishmanicidal effect of phosphorotioate antisense oligonucleotides by LDL-mediated delivery", Biochimica et Biophysica Acta, vol. 1264, pp. 229-237 (1995).

Morley, J. S., "Modulation of the action of regulatory peptides by structural modification", Trends. Pharm. Sci., pp. 463-468 (1980).

Morsy, M. A., et al., "Efficient adenoviral-mediated ornithine transcarbamylase expression in deficient mouse and human hepatocytes", J. Clin. Invest., vol. 92, pp. 1580-1586 (1993).

Muratovska, A., et al., "Paired-Box genes are frequently expressed in cancer and often required for cancer cell survival", Oncogene, vol. 22, pp. 7989-7997 (2003).

Narang, S. A., et al., "Chemical synthesis of deoxyoligonucleotides by the modified triester method", Methods in Enzymology, vol. 65, pp. 610-620 (1980).

Needleman, S., B., et al., "A general method applicable to the search for similarities in the amino acid sequence of two proteins", J. Mol. Biol., vol. 48, pp. 443-453 (1970).

Nielsen, P. E., et al., "Peptide nucleic acid (PNA). A DNA mimic with a peptide backbone", Bioconjugate Chem., vol. 5, pp. 3-7 (1994).

Oberhauser, B., et al., "Effective incorporation of 2-O-methyl-oligoribonucleotides into liposomes and enhanced cell association through modification with thiocholesterol", Nucleic Acids Research, vol. 20, pp. 533-538 (1992).

Osborne, T. F., et al., "Transcription control region within the protein-coding portion of adenovirus E1A genes", Molecular and Cellular Biology, vol. 4, 1293-1305 (1984).

Pearson, W. R., et al., "Improved tools for biological sequence comparison", Proc. Natl. Acad. Sci., USA, vol. 85, pp. 2444-2448 (1988).

Perry, N.C., et al., "The use of 3D modeling databases for identifying structure activity relationships", QSAR: Quantitative Structure-Activity Relationships in Drug Design, pp. 189-193 (1989).

Pietersz, G. A., et al., "Antibody conjugates for the treatment of cancer", Immunological Reviews, vol. 129, pp. 57-80 (1992).

Ragot, T., et al., "Replication-defective recombinant adenovirus expressing the Epstein-Barr virus (EBV) envelop glycoprotein gp340/220 induces protective immunity against EBV-induced lymphomas in the cottontop tamarin", Journal of General Virology, vol. 74, pp. 501-507 (1993).

Ram, Z., et al., "In situ retroviral-mediated gene transfer fro the treatment of brain tumors in rats", Cancer Research, vol. 53, pp. 83-88 (1993).

Remington: The Science and Practice of Pharmacy (19th ed.) A. R. Gennaro, Mack Publishing Company, Easton, PA 1995. (tabel of content).

Rich, D. P., et al., "Development and analysis of recombinant adenovirus for gene therapy for cystic fibrosis", Human Gene Therapy, vol. 4, pp. 461-476 (1993).

Ripka, W., et al., "Computers picture of the perfect drug", New Scientist, pp. 54-57 (Jun. 16, 1988).

Rizo, J., et al., "Constrained peptides; models of bioactive peptides and protein substructures", Annu. Rev. Biochem., vol. 61, pp. 387-418 (1992).

Roberts, R. W., et al., "RNA-peptide fusions for the in vitro selection of peptides and proteins", Proc. Natl. Acad. Sci., USA, vol. 94, pp. 12297-12302 (1997).

Roessler, B. J., et al., "Adenoviral-mediated gene transfer to rabbit synovium in vivo", J. Clin. Invest, vol. 92, pp. 1085-1092 (1993).

Roffler, S. P., et al., "Anti-nelplastic glucuronide prodrug treatment of human tumor cells targeted with a monoclonal antibody-enzyme conjugate", Biochemical Pharmacology, vol. 42, pp. 2062-2065 (1994).

Rouvinen, J., et al, "Computer-aided drug design", Acta Pharmaceutica Fennica, vol. 97, pp. 159-166 (1988).

Saison-Behmoaras, T., et al., Short modified antisense oligonucleotides directed against Ha-ras point mutation induce selective cleavage of the mRNA and inhibit T24 cells proliferation;, The EMBO Journal, vol. 10, pp. 1111-1118 (1991).

Senter, P. D., et al., "Generation of 5-fluorouracil from 5-fluorocytosine by monoclonal antibody-cytosine deaminase conjugates", Biocojugate Chem., vol. 2, 447-451 (1991).

Senter, P. D., et al., "Generation of cytotoxic agents by targeted enzymens", vol. 4, pp. 3-9 (1993).

Seth, P., et al., "Role of a Low-pH environment in adenovirus enhancement of the toxicity of a Pseudomonas exotoxin-epidermal growth factor conjugate", J. Virology, vol. 51, pp. 650-655 (1984).

Seth, P., et al., "Evidnece that the penton base of adenovirus is involved in potentiation of toxicity of Pseudomonas exotoxin conjugated to epidermal growth factor", Molecular and Cellular Biology, vol. 4, pp. 1528-1533 (1984).

Sharp, P. A., et al, "RNA interference-2001", Genes & Dev., vol. 15, pp. 485-490 (2001).

Shea, R. G., et al, "Synthesis, hybridization properties and antiviral activity of lipid-oiigodeoxynucleotide conjugates". Nucleic Acids Research, vol. 18, pp. 3777-3783 (1990).

Svensson, U., et al., "Role of vesicles during adenovirus 2 internalization into HeLa cells", J. Virology, vol. 55, pp. 442-149 (1985).

Svinarchuk, F. P., et al., "Inhibition of HIV proliferation in MT-4 cells by antisense oligonucleotide conjugated to lipophilic groups.", Biochimie, vol. 75, pp. 49-54 (1993).

Smith, T. F., et al., "Comparison of biosequences", Advances in Applied Mathematics, vol. 2, pp. 482-489 (1981).

Smith, T. W., et al., "Cardiac glycoside-specific antibodies in the treatment of digitalis intoxication", Antibodies in Human Diagnosis and Therapy, edited by Edgar Haber and Richard M. Krause, Raven Press, New York, pp. 365-389 (1977).

Spatola, A. F., et al., "Structure-activity relationships of enkephalins containing serially replaced thiomethylene amide bond surrogates", Life Sciences, vol. 38, pp. 1243-1249 (1986).

Spatola, A. F., "Peptide backbone modifications: a structure-activity analysis of peptides containing amide bond surrogates conformational constraints, and rela", Chemistry and Biochemistry of Amino acids, Peptides, and Proteins, Marcel Dekker, New York, pp. 267-357 (1983).

Sun, T., et al, "Human artificial episomal chromosomes for cloning large DNA fragments in human cells", Nature genetics, vol. 8, pp. 33-41 (1994).

Szelke, M., et al., "Enzyme inhibitors, European Patent Application, EP 45,665", Chemical Abstracts, vol. 97, pp. 624 (1982).

Szostak, J. W., "In vitro genetics", TIBS, vol. 17, pp. 89 (1992).

Thorson, J. S., et al., "A biosynthetic approach for the incorporation of unnatural amino acids into proteins", Methods in Molecular Biology, vol. 77, pp. 43-73 (1991).

Tolcher, A. W., et al., "A phase I pharmacokinetic and biological correlative study of oblimersen sodium (Genasense, G3139), an Antisense oligonucleotide to the Bcl-2 mRNA, and of docetaxel in patients with hormone-refractory prostate cancer", Clinical Cancer Research, vol. 10, pp. 5048-5057 (2004).

Varga, M. J., et al., "Infectious entry pathway of adenovirus Type 2", J. Virology, vol. 65, pp. 6061-6070 (1991).

Verma, I. M., "Retroviral vectors for gene transfer", Microbiology, pp. 229-232 (1985).

Waterhouse, P. M., et al,, "Virus resistance and gene silencing in plants can be induced by simultaneous expression of sense and antisense RNA", Proc. Natl. Acad. Sci., USA, vol. 95, pp. 13959-13964 (1998).

Wickham, T. J., et al., "Ingerins alpha V beta 3 and alpha V beta 5 promote adenovirus internalization but not virus attachment", Cell, vol. 73, pp. 309-319 (1993).

Xu, Q., et al., "Crystal structure of a paired domain-DNA complex at 2.5 A resolution reveals structural basis for Pax developmental mutations", Cell, vol. 80, pp. 639-650 (1995).
Yuan, Y., et al., "Substrate recognition by human RNase P: identification of small, model substrates for the enzyme", The EMBO Journal, vol. 14, pp. 159-168 (1995).
Yuan, Y., et al., "Targeted cleavage of mRNA by human RNase P", Proc. Natl. Acad. Sci., USA, vol. 89, pp. 8006-8010 (1992).
Zabner, J., et al., "Adenovirus-mediated gene transfer transiently corrects the chloride transport defect in nasal epithelia of patients with cystic fibrosis", Cell, vol. 75, pp. 207-216 (1993).
Zabner, J., et al., "Safety and efficacy of repetitive adenovirus-mediated transfer of CFTR cDNA to airway epithelia of primates and cotton rats", Nature, vol. 6, pp. 75-83 (1994).
Zucht, H. D., et al., "Human p-defensin-1: a urinary peptide present in variant molecular forms and its putative functional implication", European Journal of Medical Research, vol. 3, pp. 315-323 (1998).
Zoller, U. J., et al., "New recombinant DNA methodology for protein engineering", Current Opinion in Biotechnology, vol. 3, pp. 348-354 (1992).
Banerji, J., et al., "A lymphocyte-specific cellular enhancer is located downstream of the joining region in immunoglobulin heavy chain genes", Cell, vol. 33, pp. 729-740 (1983).
Greenway, P. J., et al., "Human cytomegalovirus DNA: BamHI, EcoRl and Pstl restriction endonuclease cleavage maps", Gene, vol. 18, pp. 355-360 (1982).
Fiers, W., et al., "Complete nucleotide sequence of SV40 DNA", Nature, vol. 273, pp. 113-120 (1978).
Forster, A. C., et al., "External guide sequences for an RNA enzyme", Science, vol. 249, pp. 783-786 (1990).
La Salle, G. L. G., et al., "An adenovirus vector for gene transfer into neurons and glia in the brain", Science, vol. 259, pp. 988-990 (1993).
Mulligan, R., et al., "The basic science of gene therapy", Science, vol. 260, pp. 926-932 (1993).
Nielsen, P. E., et al., "Sequence-selective recognition of DNA by strand displacement with a Thymine-substituted polyamide", Science, vol. 254, pp. 1497-1500 (1991).
Wolff, J. A., et al., "Direct gene transfer into mouse muscle in vivo", Science, vol. 247, pp. 1465-1468 (1990).
Zuker, M., et al., "On finding all suboptimal foldings of an RNA molecule", Science, vol. 244, pp. 48-52 (1989).
Bensch, K., et al., "hBD-1 a novel beta-defensin from human plasma", FEBS Lett., vol. 368, pp. 331-335 (1995).
Bose, S., et al., "PAX2 oncogene negatively regulates the expression of the host defense peptide human beta defensin-1 in prostate cancer", Mol Immunol., vol. 46, pp. 1140-1148 (2009).
Gibson, W., et al., "Inhibition of PAX2 expression results in alternate cell death pathways in prostate cancer cells differing in p53 status", Cancer Letters, vol. 248, pp. 251-261 (2007).
Harder, J., et al., "Isolation and characterization of human beta-defensin-3, a novel human inducible peptide antibiotic", J. Bio. Chem., vol. 276, pp. 5707-5713 (2001).
Harder, J., et al., "A peptide antibiotic from human skin", Nature, vol. 387, pp. 861 (1997).
Jia, H-P., et al., "Discovery of new human beta-defensins using a genomics-based approach", Gene, vol. 263, pp. 211-218 (2001).
Morrison, S., et al., "Chimeric human antibody molecules: mouse antigen-binding domains with human constant region domains", vol. 81, pp. 6851-6855 (1984).
Book reviews: Sociology and Pharmacy Practice, Am. J. Pharm. Edu., vol. 70, pp. 1-3 (2006).
Wilson, D., "High resolution crystal structure of a paired (PAX) class cooperative homeodomain dimer on DNA", Cell, vol. 82, pp. 709-719 (1995).
Lin, S., et al., "Differentially expressed genes in activin-induced apoptotic LNCaP cells", Biochem. Biophys. Res. Commun. vol. 257, No. 1, pp. 187-192 (1999).
Written Opinion of the International Searching Authority (International Patent Application No. PCT/US2006/040215 filed Oct. 16, 2006).
International Preliminary Report on Patentability (International Patent Application No. PCT/US2006/040215 filed Oct. 16, 2006).
International Search Report (International Patent Application No. PCT/US2006/040215 filed Oct. 16, 2006).
European Search Report (European Application No. 06816925.9 filed Apr. 14, 2008).
Mazal, P. R., et al., "Expression of aquaporins and PAX-2 compared to CD10 and cytokeratin 7 in renal neoplasms: a tissue microarray study", Mod. Pathol., vol. 18, No. 4, pp. 535-540 (2005).
Hueber P., et al., "PAX2 inactivation enhances cisplatin-induced apoptosis in renal carcinoma cells", Kidney International, vol. 69, No. 7, pp. 1139-1145 (2006).
Gibson W., et al., "Comparison of RNA interference silencing of PAX 2 expression in PC3 and Du145 prostate cancer cell lines", Proceedings of the American Association for Cancer Research Annual Meeting & 96th meeting of the American-Association-for-Cancer-Research, vol. 46, pp. 16 (2005).
Gnarra, J. R., et al., "Expression of Pax-2 in human renal cell carcinoma and growth inhibition by antisense oligonucleotides", Cancer Res., vol. 55, No. 18, pp. 4092-4098 (1995).
Strasser, A., "The role of BH3-only proteins in the immune system", Nat. Rev. Immunol., vol. 5, No. 3, pp. 189-200 (2005).
Buttiglieri, S., et al., "Role of Pax2 in apoptosis resistance and proinvasive phenotype of Kaposi's sarcoma cells", J. Biol. Chem., vol. 279, No. 6, pp. 4136-4143 (2004).
Papo, N., et al. "Host defense peptides as new weapons in cancer treatment", Cell. Mol. Life Sci., vol. 62, pp. 784-790 (2005).
Donald, C., et al., "Cancer-specific loss of beta-defensin 1 in renal and prostatic carcinomas", Laboratory Investigation, vol. 83, pp. 501-505 (2003).
Casey, G., "The BRCA1 and BRCA2 breast cancer genes", Current Opinion in Oncology, vol. 9, pp. 88-93 (1997).
Stuart, E., et al., "Mammalian Pax Genes", Annu. Rev. Genet., vol. 27, pp. 219-236 (1993).
Jatoi, I., et al., "Breast Cancer Screening", Am. J. Surg., vol. 177, pp. 518-524 (1999).
Marcus, J., et al., "Hereditary Breast Cancer", Cancer, vol. 77, pp. 697-709 (1996).
Miki, Y., et al., "A strong candidate for the breast and ovarian cancer susceptibility gene BRCA1", Science, vol. 266, pp. 66-93 (1994).
Katz, A., et al., "Gene activity during the early phase of androgen-stimulated rat prostate regrowth", Cancer Research, vol. 49, pp. 5889-5894 (1989).
Bass Nature, vol. 411, pp. 428-429 (2001).
International Preliminary Report on Patentability (International Patent Application No. PCT/US2008/051168 filed Jan. 16, 2008).
International Search Report (International Patent Application No. PCT/US2008/051168 filed Jan. 16, 2008).
Belgrave, A.K., et al., "Functional analysis of human beta defensin-1 in prostate cancer", vol. 45, pp. 619, Proceedings of the American Association for Cancer Research Annual Meeting (2004).
European Search Report (European Application No. 09178274.8 filed Dec. 8, 2009).

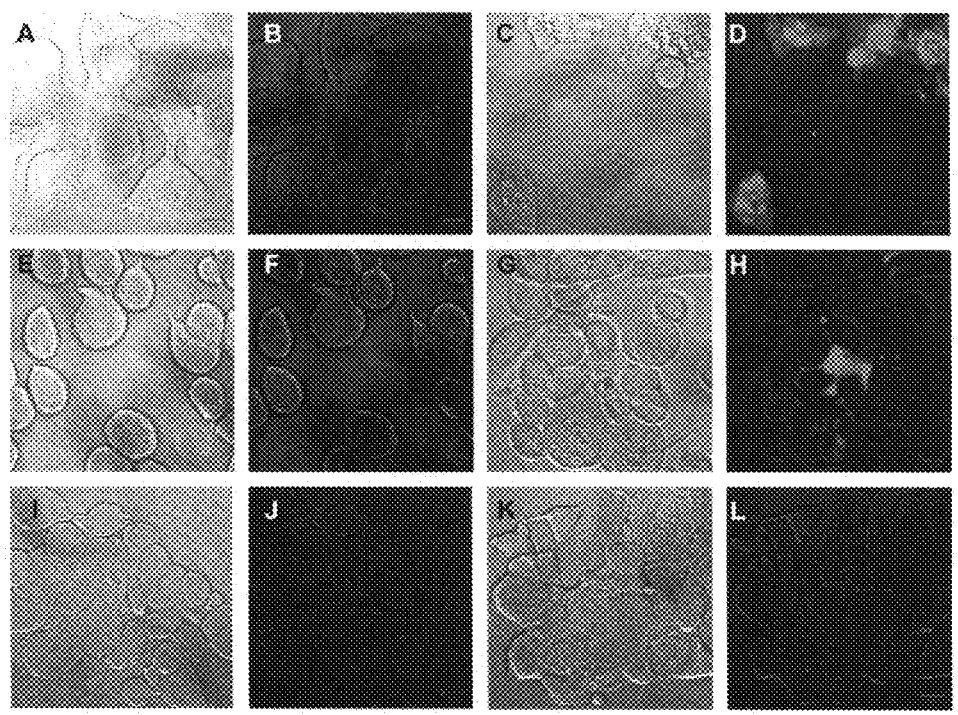
FIG. 5A-L

TARGETING PAX2 FOR THE INDUCTION OF DEFB1-MEDIATED TUMOR IMMUNITY AND CANCER THERAPY

This application is a continuation application of U.S. patent application Ser. No. 12/090,191, filed on Sep. 15, 2008 as the national entry of PCT Application No. PCT/US2006/040215, filed on Oct. 16, 2006, which claims priority to U.S. Patent Application No. 60/726,921, filed on Oct. 14, 2005, all of the aforementioned applications are incorporated herein by reference in their entirety.

This invention was made with United States Government support under NIH NCI Grant Number: CA096788-02. The Government may have certain rights in the invention.

SUMMARY

Current anticancer chemotherapies that are based on alkylating agents, anti-metabolites and natural products are heterogeneous in their mechanism of action. Consequently, most of them also act against normal cells resulting in severe side effects and toxicity to the patient. Disclosed herein is a method for the treatment of advanced prostate cancer using human beta defensin-1 (DEFB1), which is a naturally component of the innate immune system, to induce prostate cancer tumor immunity. This is accomplished through endogenously added DEFB1, ectopically expressed DEFB1 or de novo expression of EFB1 by inhibiting the transcriptional repressor PAX2 by a variety of mechanisms or agents. Inhibiting PAX2 expression by siRNA therapy turns on DEFB1 expression and generates DEFB1-mediated cell death in prostate cancer. With this, the technology described here is used for the design of small molecules to specifically block PAX2 expression. Alternatively provided are molecules containing the CCTTG (SEQ ID NO:1) recognition sequence (in either forward of reverse orientation) that to bind to the DNA-binding domain of PAX2 preventing its binding to the DEFB1 promoter through competitive inhibition. This permits DEFB1 expression, triggering both an innate and adaptive immune response, and resulting in the killing of prostate cancer cells and the suppression of prostate tumor formation. In conclusion, these modulators of innate tumor immunity, PAX2 and DEFB1, and the molecular therapies based on them provide for the treatment of prostate cancer with little toxicity to the patient.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The accompanying drawings illustrate one or more embodiments of the invention and, together with the written description, serve to explain the principles of the invention. Wherever possible, the same reference numbers are used throughout the drawings to refer to the same or like elements of an embodiment.

FIG. 5. Pan-caspase analysis following DEFB1 induction. DU145 and PC3 cells were stained with FAM-VAD-FMK-labeled fluoromethyl ketone to detect caspase activity. Cells were visible under DIC for each condition. Confocal microscopic analysis revealed no caspase staining in control DU145 (B), PC3 cells (F) and LNCaP (J). Cells treated with PonA for 24 hours to induce DEFB1 revealed caspase activity in DU145 (D) and PC3 (H). No caspase activity was detected in LNCaP (L).

However, cell treated with PAX2 siRNA induced caspase activity in DU145 (D), PC3 (H) and LNCaP (L).

FIG. 10. Analysis of Apoptotic Factors Following PAX2 siRNA Treatment. Changes in expression of pro-apoptotic factors were compared in untreated control cells and in cells treated for six days with PAX2 siRNA. A, BAX expression levels increased in DU145, PC3 and LNCaP. B, BID expression increased in DU145 and LNCaP, but change in PC3. C, BAD expression levels increased in all three cell lines.

Figure 11:
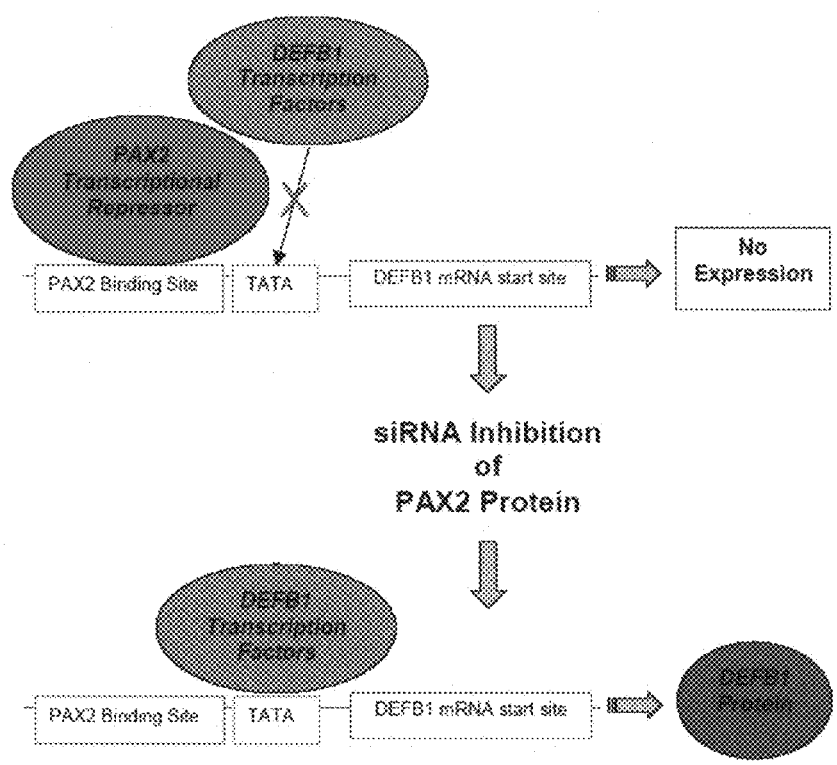

FIG. 11. Model of PAX2 Binding to DNA Recognition Sequence. The PAX2 transcriptional repressor binds to a CCTTG (SEQ ID NO:1) recognition site immediately adjacent to the DEFB1 TATA box preventing transcription and DEFB1 protein expression. Inhibition of PAX2 protein expression allows normal DEFB1 expression.

Figure 12:
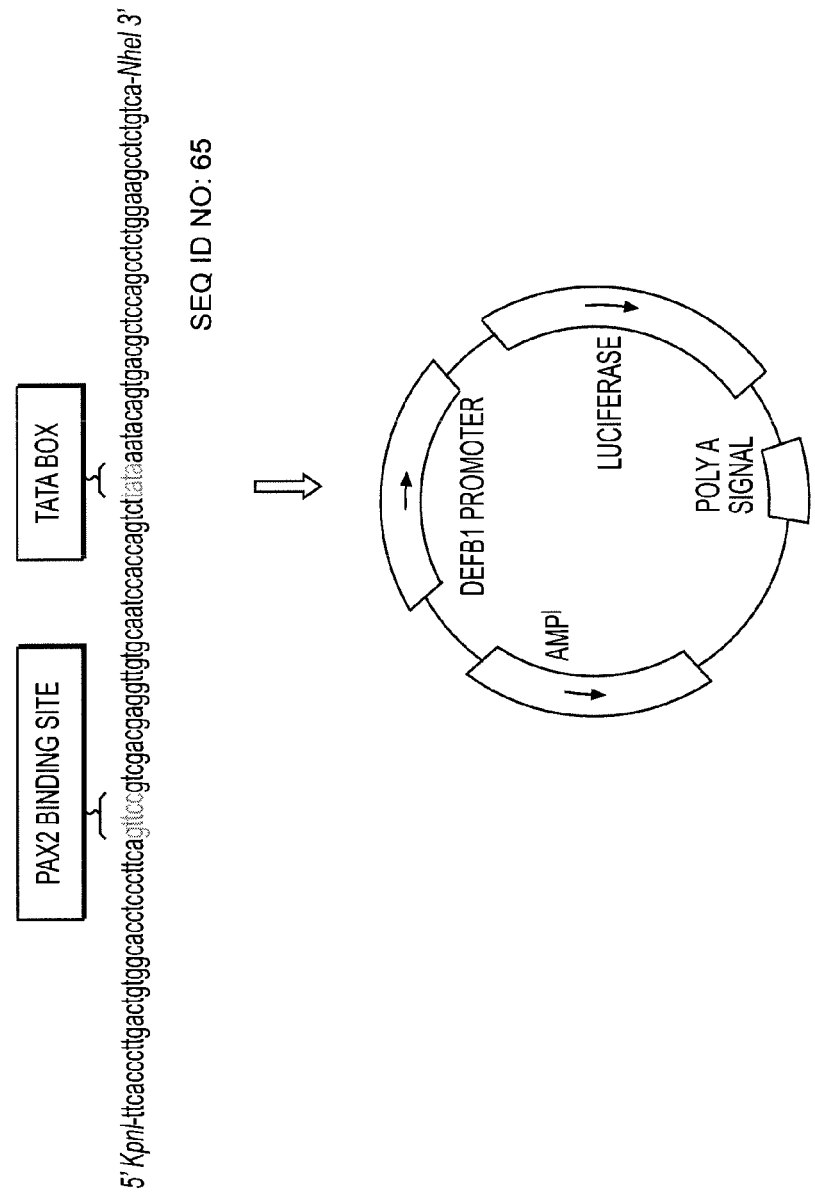

FIG. 12. Illustration of the DEFB1 Reporter Construct. The DEFB1 promoter consisting of the first 160 bases upstream of the mRNA start site was PCR amplified from DU145 cell and ligated into the pGL3 luciferase reporter plasmid. SEQ ID NO:65 represents the KpnI/NheI fragment of the DEFB1 promoter.

Figure 13:
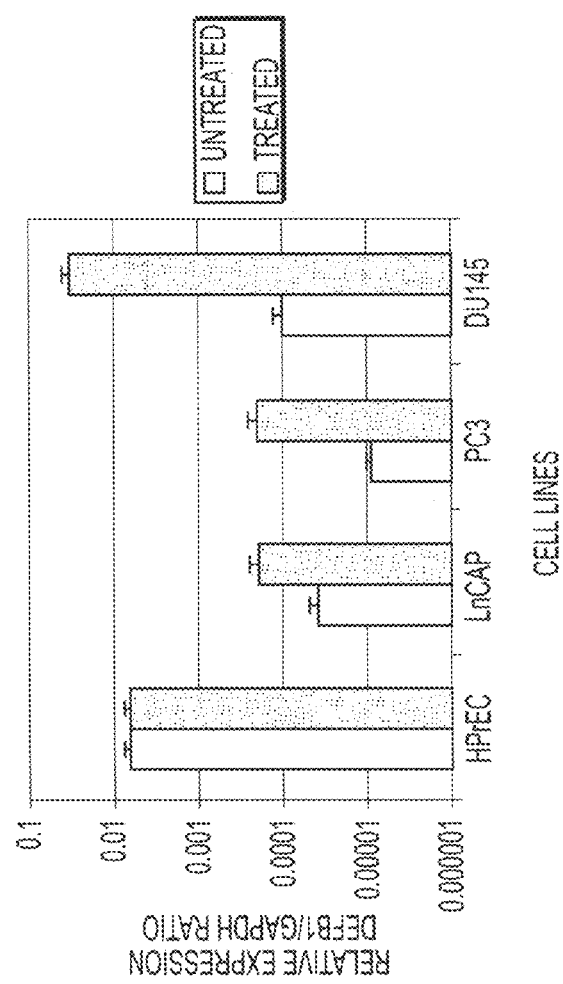

FIG. 13. Inhibition of PAX2 Results in DEFB1 Expression. DU145, PC3, LNCaP and HPrEC were treated for 48 hours with PAX2 siRNA. QRT-PCR analysis before treatment showed no DEFB1 expression in DU145, PC3 and LNCaP. However, DEFB1 expression was restored following treatment in all lines. There was no change in DEFB1 expression following siRNA treatment of PAX2-null HprEC.

Figure 14:
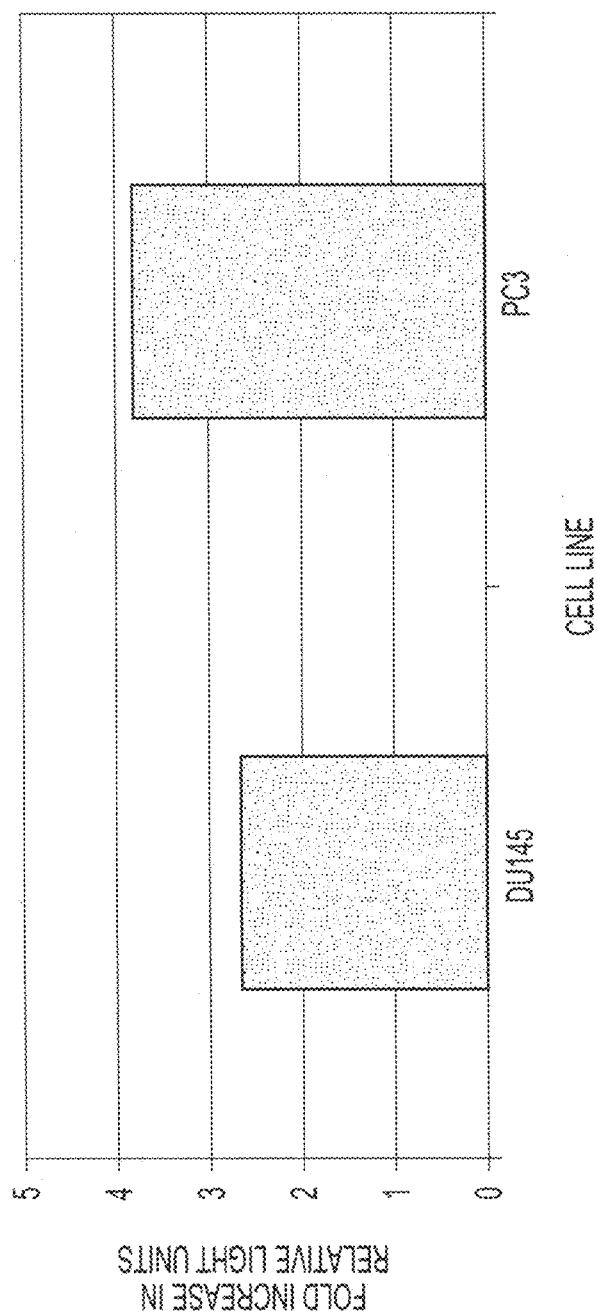

FIG. 14. Inhibition of PAX2 Results in Increased DEFB1 Promoter Activity. PC3 promoter/pGL3 and DU145 promoter/pGL3 construct were generated and were transfected into PC3 and DU145 cells, respectively. Promoter activity was compared before and after PAX2 inhibition by siRNA treatment. DEFB1 promoter activity increased 2.65-fold in DU145 and 3.78 fold in PC3 following treatment.

Figure 15:
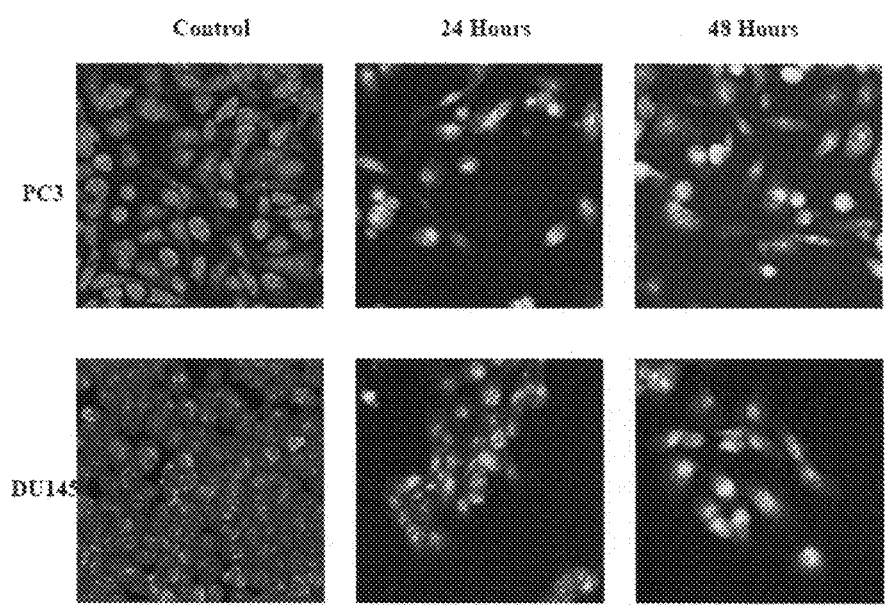

FIG. 15. DEFB1 Causes Loss of Membrane Integrity. Membrane integrity of PC3 and DU145 cells was analyzed by confocal laser microscopy following the induction of DEFB1 expression for 48 hours. Green staining was indicative of the localization of AO, and red staining represents EtBr. Yellow staining represents the co-localization of both AO and EtBr in the nucleus.

Figure 16:
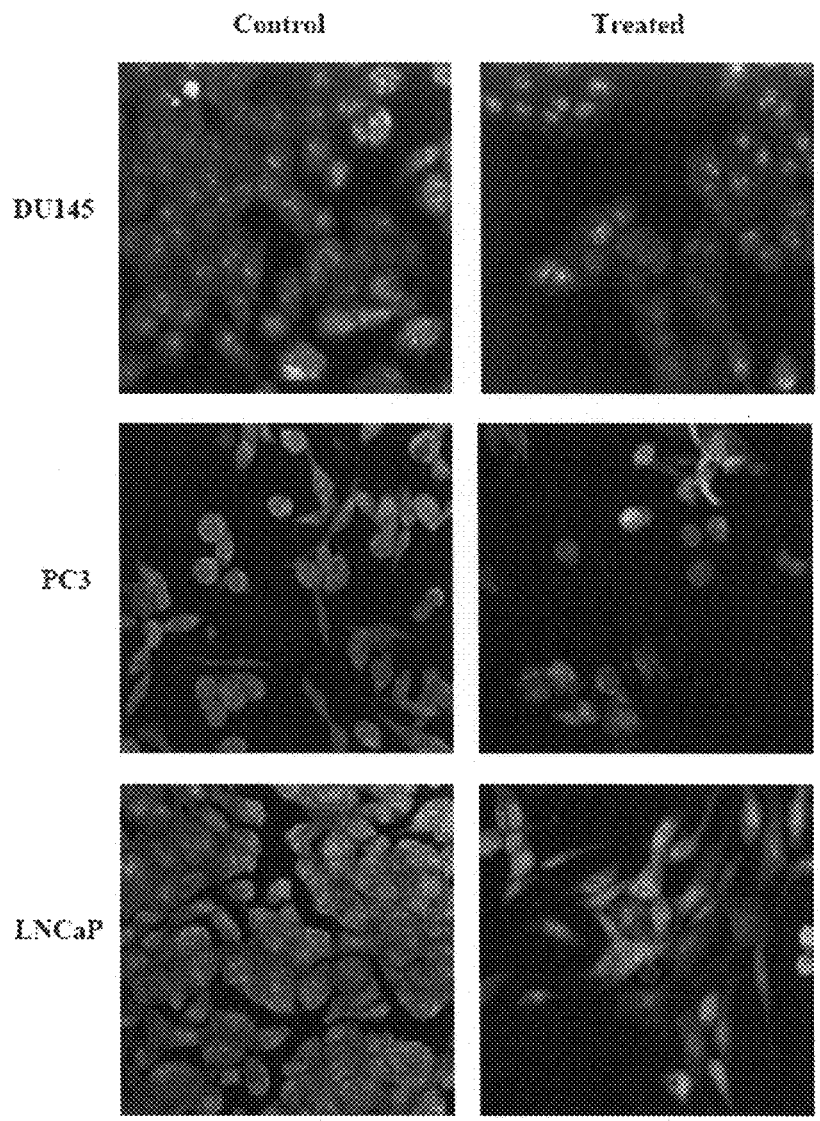

FIG. 16. PAX2 Inhibition Results in Loss of Membrane Integrity. Cells were treated for 48 hours with PAX2 siRNA and membrane integrity was analyzed by confocal laser microscopy.

Figure 17:
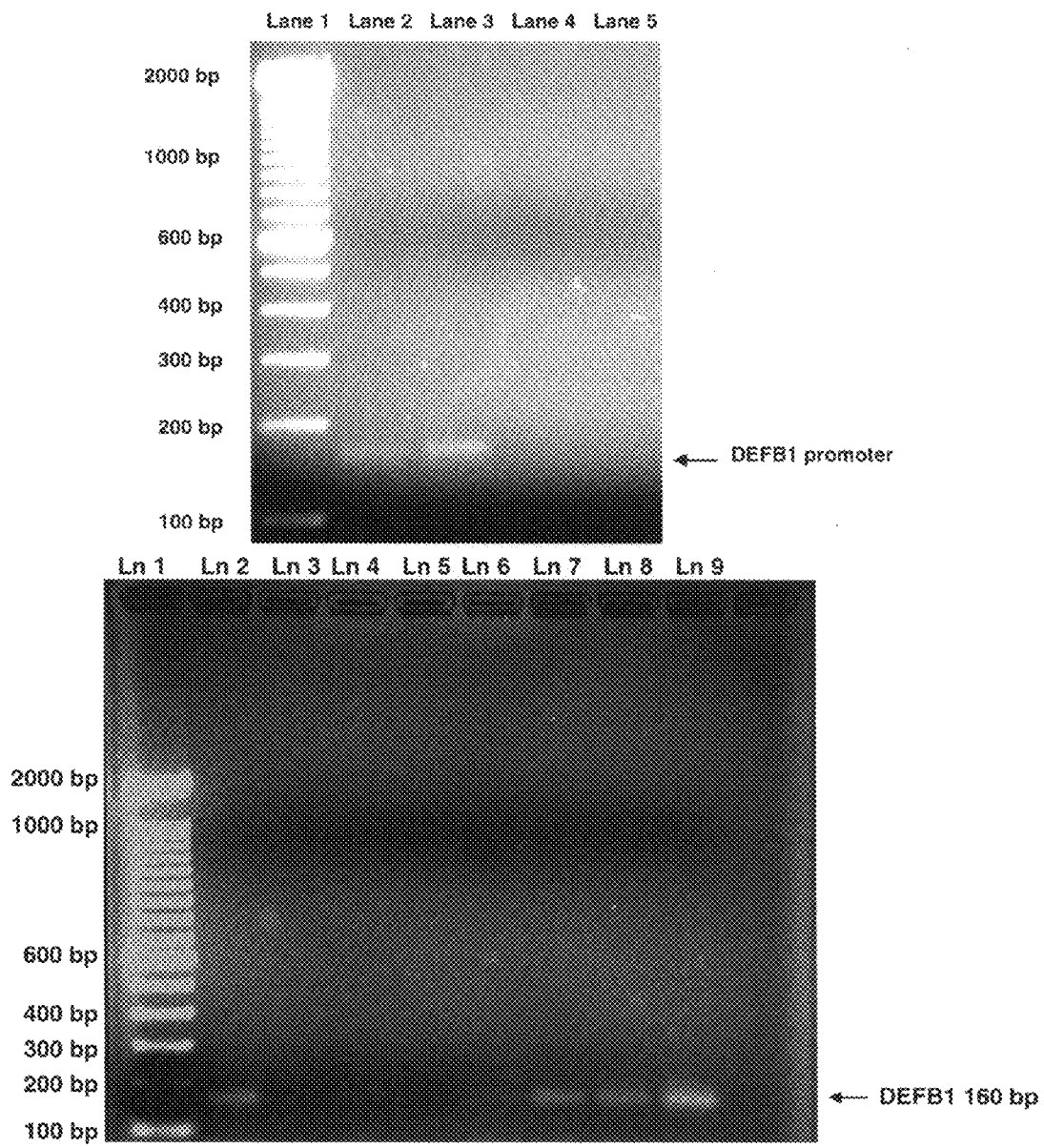

FIG. 17. ChIP Analysis of PAX2 binding to DEFB1 Promoter. ChIP analysis was performed on DU145 and PC3 cells. Following immunoprecipitation with an anti-PAX2 antibody, PCR was performed to detect the DEFB1 promoter region containing the GTTCC (SEQ ID NO: 2) PAX2 recognition site. This demonstrates that the PAX2 transcriptional repressor is bound to the DEFB1 promoter in prostate cancer cell lines.

Figure 18:
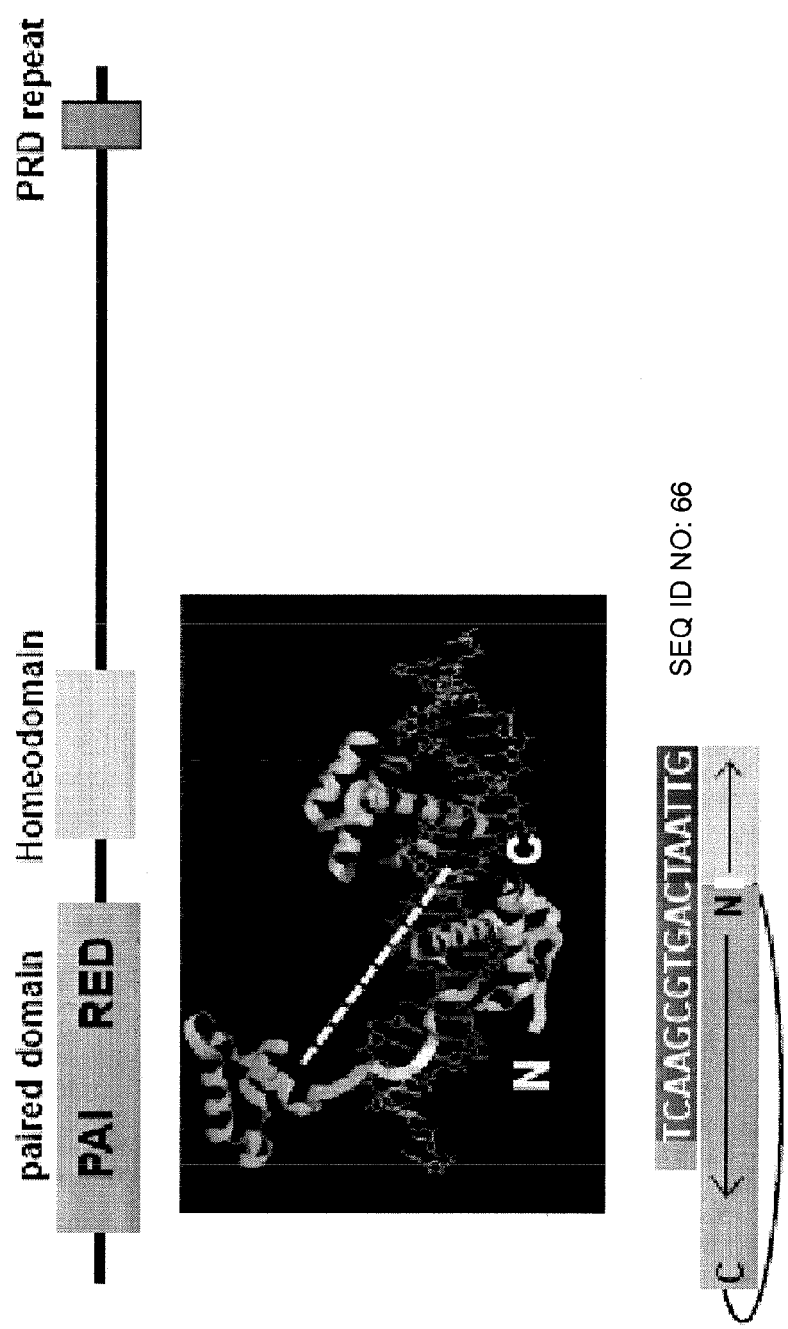

FIG. 18. Predicted Structure of the PrdPD and PrdHD with DNA. The coordinates of the structures of the PrdPD bound to DNA (Xu et al., 1995 and the PrdHD bound to DNA (Wilson et al., 1995) were used to construct a model of the two domains as they bound to a PH0 site (SEQ ID NO:66). The individual binding sites are abutted next to each other with a specific orientation as indicated. The PAI binding site is in red, the HD binding site is in blue, and the corresponding PAI domain is in turquoise, and HD is in yellow. The RED domain is oriented based on the PrdPD crystal structure.

Figure 19:
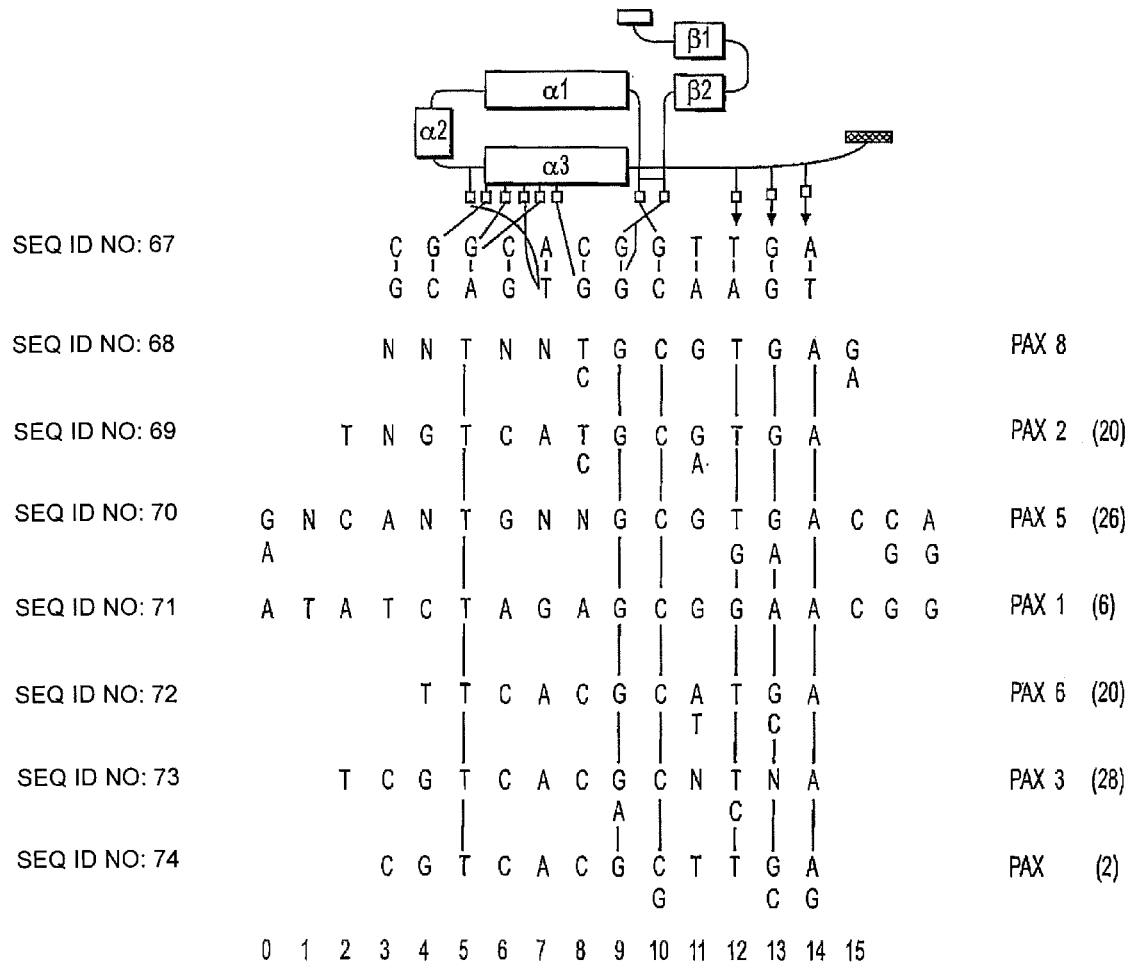

FIG. 19. Comparison of Consensus Sequences of Different Paired Domains. At the top of the Figure is drawn a schematic representation of protein±DNA contacts described in the crystallographic analysis of the Prd-paired-domain±DNA complex [9]. Empty boxes indicate a-helices, shaded boxes indicates b-sheets and a thick line indicate a b-turn. Contacting amino acids are shown by single-letter code. Only direct amino acid±base contacts are shown. Empty circles indicate major groove contacts while red arrows indicate minor groove contacts. This scheme is aligned to all known consensus sequences for paired-domain proteins (top strands only are shown). Vertical lines between consensus sequences indicate conserved base-pairs. Numbering of the positions is shown at the bottom of the Figure and it is the same as that used in [9].

DETAILED DESCRIPTION

As shown herein, PAX2 inhibits expression of DEFB1, and DEFB1 is shown to have tumor cell killing activity. Thus, provided is a method of treating cancer in a subject by inhibiting expression of PAX2. An example of a cancer treated by the present method is prostate cancer. The present methods are particularly effective for treatment of late stage prostate cancer.

In the cancer treatment methods disclosed, the method of inhibiting expression of PAX 2 can be by administration of a nucleic acid encoding a siRNA for PAX 2. Dharmachon is a commercial source for such siRNAs.

The siRNA for use in the methods can be selected from the group consisting of:

```
AUAGACUCGACUUGACUUCUU     (SEQ ID NO: 3)

AUCUUCAUCACGUUUCCUCUU     (SEQ ID NO: 4)

GUAUUCAGCAAUCUUGUCCUU     (SEQ ID NO: 5)

GAUUUGAUGUGCUCUGAUGUU     (SEQ ID NO: 6)
```

The following table illustrates the above antisense sequences and their corresponding sense sequences.

| | Sense (5'-3') | Antisense (5'-3') |
|---|---|---|
| Sequence A | 5'-GAAGUCAAGUC GAGUCUAUUU-3' (SEQ ID NO: 7) | 5'-AUAGACUCGAC UUGACUUCUU-3' (SEQ ID NO: 3) |
| Sequence B | 5'-GAGGAAACGUG AUGAAGAUUU-3' (SEQ ID NO: 8) | 5'-AUCUUCAUCAC GUUUCCUCUU-3' (SEQ ID NO: 4) |
| Sequence C | 5'-GGACAAGAUUG CUGAAUACUU-3' (SEQ ID NO: 9) | 5'-GUAUUCAGCAA UCUUGUCCUU-3' (SEQ ID NO: 5) |
| Sequence D | 5'-CAUCAGAGCA- CAUCAAAUCUU-3' (SEQ ID NO: 10) | 5'-GAUUUGAUGUG CUCUGAUGUU-3' (SEQ ID NO: 6) |

Further examples of molecules that inhibit PAX2 include:

```
#1 ACCCGACTATGTTCGCCTGG,     (SEQ ID NO: 11)

#2 AAGCTCTGGATCGAGTCTTTG,    (SEQ ID NO: 12)
and

#4 ATGTGTCAGGCACACAGACG.     (SEQ ID NO: 13)
#4 was shown to inhibit PAX2 (Davies et al.,
Hum. Mol. Gen Jan. 15, 13 (2); 235).
```

Another paper (Muratovska et al., Paired-Box genes are frequently expressed in cancer and often required for cancer cell survival Oncogene (2003) 22, 7989-7997) discloses the following siRNAs: GUCGAGUCUAUCUGCAUCCUU (SEQ ID NO: 14) and GGAUGCAGAUAGACUCGACUU (SEQ ID NO: 15).

To down-regulate Pax2 expression, Fonsato et al. transfected tumor-derived endothelial cells with an anti-sense PAX2 vector. See Fonsato V. et al (Expression of Pax2 in human renal tumor-derived endothelial cells sustains apoptosis resistance and angiogenesis, Am J Pathol. 2006 February; 168(2):706-1), incorporated herein by reference for its description of this molecule. Similarly, Hueber et al. teach that PAX2 antisense cDNA and PAX2-small interfering RNA (100 nM) reduce endogenous PAX2 protein. See Hueber et al. PAX2 inactivation enhances cisplatin-induced apoptosis in renal carcinoma cells, Kidney Int. 2006 April; 69(7):1139-45 incorporated herein for its teaching of PAX2 antisense and PAX2 siRNA.

Additional inhibitors of PAX2 expression or the binding of PAX2 to the DEFB1 promoter are provided to increase DEFB1 expression in the presently disclosed methods. For example, small molecules and antibodies are designed based on the present studies to interfere with or inhibit the binding of PAX2 to the DEFB1 promoter.

As shown herein, PAX2 inhibits expression of DEFB1, and DEFB1 is shown to have tumor cell killing activity. Thus, a method of treating cancer in a subject by administering DEFB1 is also provided. An example of a cancer treated by the present method is prostate cancer.

Similarly, provided is a method of treating cancer in a subject by increasing expression of DEFB1 in the subject. The present methods of administering or increasing the expression of DEFB1 are particularly effective for treatment of late stage prostate cancer.

In one embodiment of the methods of the invention for treating cancer by administering DEFB1 or increasing DEFB1 expression (e.g., by inhibiting expression or binding of PAX2), the subject is a subject diagnosed with prostate cancer. In a further embodiment of the methods of the invention for treating cancer by administering DEFB1 or increasing DEFB1 expression (e.g., by inhibiting expression or binding of PAX2), the subject is a subject diagnosed with advanced (late stage) prostate cancer.

In the method wherein the expression of DEFB1 is increased, it can be increased by blocking the binding of PAX2 to the DEFB1 promoter. The blocking of binding of PAX2 to the DEFB1 promoter can be by administration of an oligonucleotide containing the PAX2 DNA binding site of DEFB1. This oligonucleotide can be complementary to the sequence of PAX2 that binds to the DEFB1 promoter. Alternatively, the oligonucleotide can interact with the PAX2 in a way that inhibits binding to DEFB1. This interaction can be based on three-dimensional structure rather than primary nucleotide sequence.

PAX proteins are a family of transcription factors conserved during evolution and able to bind specific DNA sequences through a domains called a "paired domain" and a "homeodomain". The paired domain (PD) is a consensus sequence shared by certain PAX proteins (e.g., PAX2 and PAX6). The PD directs DNA binding of amino acids located in the α3-helix forming a DNA-Protein complex. For PAX2, the amino acids in the HD recognize and interact specifically with a CCTTG (SEQ ID NO: 1) DNA core sequence. Therefore, the critical region for PAX2 binding to DEFB1 would be AAGTTCACCCTTGACTGTG (SEQ ID NO: 16). Oligonucleotides up to and exceeding 64 bases in length, which include this sequence or its complement are expected to be inhibitors.

The DNA-binding specificity of the PAX-8 paired domain was investigated. Site selection experiments indicate that PAX-8 binds to a consensus sequence similar to those bound by PAX-2 and PAX-5. When consensus sequences of various paired domains are observed in light of recent structural studies describing paired-domain-DNA interaction [Xu, Rould, Jun, Desplan and Pabo (1995) Cell 80, 639-650], it appears that base-pairs contacted in the minor groove are conserved, while most of the base-pairs contacted in the major groove are not. Therefore a network of specific minor groove contacts is a common characteristic of paired-domain-DNA interactions. The functional importance of such a network can be successfully tested by analyzing the effect of consensus-based mutations on the PAX2 binding site of the DEFB1 promoter.

The PAX2 DNA binding site of DEFB1 can comprise SEQ ID NO:1 (CCTTG).

The oligonucleotide comprising to the PAX2 DNA binding site of DEFB1 is selected from the group consisting of X1 CCTTG $X_2$ (SEQ ID NO: 17), wherein $X_1$=NNNNNNN NNNNNNNNNNNNNNNNNNNNNNNNNNN and is/are from 1 to 35 contiguous flanking nucleotides of DEFB1 and $X_2$=NNNNNNNNNNNNNNNNNNNNNNNNNN NNNNNNNNN and is/are from 1 to 35 contiguous flanking nucleotides of DEFB1. The nucleotides can be contiguous nucleotides that normally flank the PAX2 DNA binding site of DEFB1. Alternatively, they can be unrelated to DEFB1, and selected routinely to avoid interference with the recognition sequence.

For example, the inhibitory oligonucleotides can be selected from the group consisting of:

```
CTCCCTTCAGTTCCGTCGAC                           (SEQ ID NO: 18)

CTCCCTTCACCTTGGTCGAC                           (SEQ ID NO: 19)

ACTGTGGCACCTCCCTTCAGTTCCGTCGACGAGGTTGTGC       (SEQ ID NO: 20)

ACTGTGGCACCTCCCTTCACCTTGGTCGACGAGGTTGTGC.      (SEQ ID NO: 21)
```

The disclosed compositions can be used to treat any disease where uncontrolled cellular proliferation occurs such as cancers. A non-limiting list of different types of cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer. Compounds disclosed herein may also be used for the treatment of pre-cancer conditions such as cervical and anal dysplasias, other dysplasias, severe dysplasias, hyperplasias, atypical hyperplasias, and neoplasias. Further, a number of diseases stemming from chronic inflammation, e.g., prostatitis and Benign Prostatic Hypertrophy (BPH), as well as various cancers of the prostate, can be impacted by the present methods and compounds.

DEFB1's gene locus (8p23.3) is a hotspot for deletions and has been linked to patients with poorer prognosis. Thus, DEFB1 (and perhaps PAX2) can be used as a biomarker, e.g., in a screening for the early detection of prostate cancer. Furthermore, data presented here indicate that its loss may occur as early as PIN (or even before), and may be a major contributing factor to the onset of prostate cancer.

Nucleic Acid Homology/Identity/Similarity

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Hybridization/Selective Hybridization

The term hybridization typically means a sequence driven interaction between at least two nucleic acid molecules, such as an oligonucleotide inhibitor, a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting nucleic acid is in for example, 10 or 100 or 1000 fold excess. This type of assay can be performed at under conditions where both the limiting and non-limiting nucleic acid are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of nucleic acid that gets enzymatically manipulated under conditions where hybridization is required to promote the desired enzymatic manipulation, e.g., for primers. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide which contains some type of modification to any of the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, -azaguanine and 8-azaadenine, -deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science, 1991, 254, 1497-1500).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Numerous United States patents teach the preparation of such conjugates and include, but are not limited to U.S. Pat. Nos. 4,828,979; 4,948,882; 5,218,105; 5,525, 465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

Sequences

There are a variety of sequences related to the DEFB1 gene and to the PAX2 transcriptional factor, respectively, having the following GenBank Accession Numbers: U50930 and NM_003989.1. These sequences and others are herein incorporated by reference in their entireties as well as for individual subsequences contained therein.

The one particular sequence set forth in SEQ ID NO: 64 and having GenBank accession number U50930 is used herein as an example to exemplify a source for the disclosed DEFB1 nucleic acids. The one particular sequence set forth in SEQ ID NO: 46 and having GenBank accession number NM_003989.1 is used herein as an example, to exemplify a source for the disclosed PAX2 nucleic acids. Other examples of PAX2 sequences, based on alternative splicing are also found in GenBank. These are variants a-e, shown in Appendices B-F. It is understood that the description related to this sequence is applicable to any sequence related to unless specifically indicated otherwise. Those of skill in the art understand how to resolve sequence discrepancies and differences and to adjust the compositions and methods relating to a particular sequence to other related sequences. siRNA molecules, competitive inhibitors of DEFB1 promoter-PAX2, and primers and/or probes can be designed for any DEFB1 or PAX2 sequence given the information disclosed herein and known in the art.

Nucleic Acid Synthesis

The nucleic acids, such as, the oligonucleotides to be used as inhibitors can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual,* 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.,* 65:610-620 (1980), (phosphotriester method). Protein nucleic acid molecules can be made using known methods such as those described by Nielsen et al., *Bioconjug. Chem.* 5:3-7 (1994).

Primers and Probes

Disclosed are compositions including primers and probes, which are capable of interacting with the DEFB1 gene as disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner.

The size of the primers or probes for interaction with the DEFB1 or PAX2 gene in certain embodiments can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the DEFB1 or PAX2 gene typically will be used to produce an amplified DNA product that contains the region of the DEFB1 gene to which PAX2 binds. In general, typically the size of the product will be such that the size can be accurately determined to within 3, or 2 or 1 nucleotides.

In certain embodiments this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

Functional Nucleic Acids
  RNAi

It is also understood that the disclosed nucleic acids can be used for RNAi or RNA interference. It is thought that RNAi involves a two-step mechanism for RNA interference (RNAi): an initiation step and an effector step. For example, in the first step, input double-stranded (ds) RNA (siRNA) is processed into small fragments, such as 21-23-nucleotide 'guide sequences'. RNA amplification occurs in whole animals. Typically then, the guide RNAs can be incorporated into a protein RNA complex which is capable of degrading RNA, the nuclease complex, which has been called the RNA-induced silencing complex (RISC). This RISC complex acts in the second effector step to destroy mRNAs that are recognized by the guide RNAs through base-pairing interactions. RNAi involves the introduction by any means of double stranded RNA into the cell which triggers events that cause the degradation of a target RNA. RNAi is a form of post-transcriptional gene silencing. In addition to the siRNAs disclosed herein, disclosed are RNA hairpins that can act in RNAi. For description of making and using RNAi molecules see, e.g., Hammond et al., Nature Rev Gen 2: 110-119 (2001); Sharp, Genes Dev 15: 485-490 (2001), Waterhouse et al., Proc. Natl. Acad. Sci. USA 95(23): 13959-13964 (1998) all of which are incorporated herein by reference in their entireties and at least form material related to delivery and making of RNAi molecules.

RNAi has been shown to work in many types of cells, including mammalian cells. For work in mammalian cells it is preferred that the RNA molecules which will be used as targeting sequences within the RISC complex are shorter. For example, less than or equal to 50 or 40 or 30 or 29, 28, 27, 26, 25, 24, 23, 22, 21, 20, 19, 18, 17, 16, 15, 14, 13, 12, 11, or 10 nucleotides in length. These RNA molecules can also have overhangs on the 3' or 5' ends relative to the target RNA which is to be cleaved. These overhangs can be at least or less than or equal to 1, 2, 3, 4, 5, 6, 7, 8, 9, 10, 15, or 20 nucleotides long. RNAi works in mammalian stem cells, such as mouse ES cells. Examples of siRNAs can be found in Table 4.

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with mRNA or the genomic DNA of PAX2. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616, 466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S.

Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there three strands of DNA are forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukaryotic cells. (Yuan et al., *Proc. Natl. Acad. Sci.* USA 89:8006-8010 (1992); WO 93/22434 by Yale; WO 95/24489 by Yale; Yuan and Altman, *EMBO J* 14:159-168 (1995), and Carrara et al., *Proc. Natl. Acad. Sci.* (USA) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162.

Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991) Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as DEFB1 coding sequences, PAX2 siRNAs or other antisense molecules into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virions are generated in a cell line such as the human 293 cell line. In another preferred embodiment both the E1 and E3 genes are removed from the adenovirus genome.

Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

1. The disclosed vectors thus provide DNA molecules which are capable of integration into a mammalian chromosome without substantial toxicity.

2. The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Large Payload Viral Vectors

Molecular genetic experiments with large human herpes viruses have provided a means whereby large heterologous DNA fragments can be cloned, propagated and established in cells permissive for infection with herpes viruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable. The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed vectors for example, lipids such as liposomes, such as cationic liposomes (e.g., DOTMA, DOPE, and DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95-100 (1989); Feigner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo.

The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellular, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

In Vivo/Ex Vivo

As described herein, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

Protein Variants

Variants of the DEFB1 protein are provided. Derivatives of the DEFB1 protein function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
|---|---|
| alanine | AlaA |
| allosoleucine | AIle |
| arginine | ArgR |

TABLE 1-continued

Amino Acid Abbreviations

| Amino Acid | Abbreviations |
|---|---|
| asparagine | AsnN |
| aspartic acid | AspD |
| cysteine | CysC |
| glutamic acid | GluE |
| glutamine | GlnK |
| glycine | GlyG |
| histidine | HisH |
| isolelucine | IleI |
| leucine | LeuL |
| lysine | LysK |
| phenylalanine | PheF |
| proline | ProP |
| pyroglutamic acidp | Glu |
| serine | SerS |
| threonine | ThrT |
| tyrosine | TyrY |
| tryptophan | TrpW |
| valine | ValV |

TABLE 2

Amino Acid Substitutions
Original Residue Exemplary Conservative
Substitutions, others are known in the art.

| |
|---|
| Alaser |
| Arglys, gln |
| Asngln; his |
| Aspglu |
| Cysser |
| Glnasn, lys |
| Gluasp |
| Glypro |
| Hisasn; gln |
| Ileleu; val |
| Leuile; val |
| Lysarg; gln; |
| MetLeu; ile |
| Phemet; leu; tyr |
| Serthr |
| Thrser |
| Trptyr |
| Tyrtrp; phe |
| Valile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 63 sets forth a particular sequence of DEFB1 and SEQ ID NO: 45 sets forth a particular sequence of PAX2. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the DEFB1 protein sequence set forth in SEQ ID NO: 63 is set forth in SEQ ID NO: 64. It is also understood that while no amino acid sequence indicates what particular DNA sequence encodes that protein within an organism, where particular variants of a disclosed protein are disclosed herein, the known nucleic acid sequence that encodes that protein in the particular DEFB1 from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include —CH$_2$NH—, —CH$_2$S—, —CH$_2$—CH$_2$—, —CH═CH— (cis and trans), —COCH$_2$—, —CH(OH)CH$_2$—, and —CHH$_2$SO— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH$_2$NH—, CH$_2$CH$_2$—); Spatola et al. Life Sci 38:1243-1249 (1986) (—CHH$_2$—S); Hann J. Chem. Soc Perkin Trans. 1307-314 (1982) (—CH—CH—, cis and trans); Almquist et al. J. Med. Chem. 23:1392-1398 (1980) (—COCH$_2$—); Jennings-White et al. Tetrahedron Lett 23:2533 (1982) (—COCH$_2$—); Szelke et al. European Appln, EP 45665 CA (1982): 97:39405 (1982) (—CH(OH)CH$_2$—); Holladay et al. Tetrahedron. Lett 24:4401-4404 (1983) (—C(OH)CH$_2$—); and Hruby Life Sci 31:189-199 (1982) (—CH$_2$—S—); each of which is incorporated herein by reference. A particularly preferred non-peptide linkage is —CH$_2$NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993);

Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Pharmaceutically Acceptable Carriers

The compositions, including DEFB1, DEFB1-encoding nucleic acids, oligonucleotide inhibitors of PAX2 binding, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Therapeutic Uses

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the oligonucleotide used alone might range from about 1 µg/kg to up to 100 mg/kg of body weight or more per day, depending on the factors mentioned above. In a more specific example, 5 to 7 mg/kg/day can be used. This is appropriate for i.v. administration and higher dosages, up to about 150 mg/m$^2$/day s.c. are appropriate. This can be administered daily for a week in from 1 to 24 courses. See for example A Phase I Pharmacokinetic and Biological Correlative Study of Oblimersen Sodium (Genasense, G3139), an Antisense Oligonucleotide to the Bcl-2 mRNA, and of Docetaxel in Patients with Hormone-Refractory Prostate Cancer, Clinical Cancer Research, Vol. 10, 5048-5057, Aug. 1, 2004, incorporated herein for it's teaching of dosages for oligonucleotides.

Following administration of a disclosed composition for treating cancer, the efficacy of the therapeutic composition can be assessed in various ways well known to the skilled practitioner. For instance, one of ordinary skill in the art will understand that a composition, DEFB1, DEFB1-encoding nucleic acid, inhibitor of PAX2, disclosed herein is efficacious in treating cancer in a subject by observing that the composition reduces tumor load or prevents a further increase in tumor load. Methods of assessing tumor load are known in the art The compositions that inhibit the interactions between PAX2 and the DEFB1 promoter can be administered prophylactically to patients or subjects who are at risk for cancer.

Other molecules that interact with PAX2 to inhibit its interaction with the DEFB1 promoter can be delivered in ways similar to those described for the pharmaceutical products.

The disclosed compositions and methods can also be used for example as tools to isolate and test new drug candidates for a variety of related diseases. Thus, a method of identifying inhibitors of the binding of PAX2 to the DEFB1 promoter is provided. The method can comprise contacting a system that expresses DEFB1 with a putative inhibitor in the presence and/or absence of PAX2 to determine whether there is an inhibitory effect on this interaction.

Compositions Identified by Screening with Disclosed Compositions/Combinatorial Chemistry Combinatorial Chemistry The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions disclosed as the PAX2 sequence or portions thereof (e.g., PAX2 DNA-binding domain), are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, DEFB1 or PAX2, are also disclosed. Thus, the products produced using the combinatorial or screening approaches that involve the disclosed compositions are also considered herein disclosed.

It is understood that the disclosed methods for identifying molecules that inhibit the interactions between, for example, DEFB1 promoter and PAX2 can be performed using high through put means. For example, putative inhibitors can be identified using Fluorescence Resonance Energy Transfer (FRET) to quickly identify interactions. The underlying theory of the techniques is that when two molecules are close in space, ie, interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94 (23) 12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptidyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94 (23) 12997-302 (1997)).

Another preferred method for combinatorial methods designed to isolate peptides is described in Cohen et al. (Cohen B. A., et al., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449, 754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972, 719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916, 899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856, 107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

Screening molecules similar to the disclosed siRNA molecules for inhibition of PAX2 suppression of DEFB1 expression is a method of isolating desired compounds.

Molecules isolated which can either be competitive inhibitors or non-competitive inhibitors.

In another embodiment the inhibitors are non-competitive inhibitors. One type of non-competitive inhibitor will cause allosteric rearrangements.

As used herein combinatorial methods and libraries included traditional screening methods and libraries as well as methods and libraries used in iterative processes.

Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation of the target molecule's function. The molecules identified and isolated when using the disclosed compositions, such as, SEQ ID NO:1, are also disclosed. Thus, the products produced using the molecular modeling approaches that involve the disclosed compositions, such as, SEQ ID NO:1, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable mediums comprising the sequences and information regarding the sequences set forth herein. Also disclosed are computer readable mediums comprising the sequences and information regarding the sequences set forth.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in C or is at ambient temperature, and pressure is at or near atmospheric.

Example I

Human Beta Defensin-1 is Cytotoxic to Late-Stage Prostate Cancer and Plays a Role in Prostate Cancer Tumor Immunity Abstract DEFB1 was cloned into an inducible expression system to examine what effect it had on normal prostate epithelial cells, as well as androgen receptor positive ($AR^+$) and androgen receptor negative ($AR^-$) prostate cancer cell lines. Induction of DEFB1 expression resulted in a decrease in cellular growth in $AR^-$ cells DU145 and PC3, but had no effect on the growth of the $AR^+$ prostate cancer cells LNCaP. DEFB1 also caused rapid induction of caspase-mediated apoptosis. Data presented here are the first to provide evidence of its role in innate tumor immunity and indicate that its loss contributes to tumor progression in prostate cancer.

Materials and Methods

Cell Lines

The cell lines DU145 were cultured in DMEM medium, PC3 were grown in F12 medium, and LNCaP were grown in RPMI medium (Life Technologies, Inc., Grand Island, N.Y.). Growth media for all three lines was supplemented with 10% (v/v) fetal bovine serum (Life Technologies). The hPrEC cells were cultured in prostate epithelium basal media (Cambrex Bio Science, Inc., Walkersville, Md.). All cell lines were maintained at 37° C. and 5% $CO_2$.

Tissue Samples and Laser Capture Microdissection

Prostate tissues obtained from consented patients that underwent radical prostatectomy were acquired through the Hollings Cancer Center tumor bank in accordance with an Institutional Review Board-approved protocol. This included guidelines for the processing, sectioning, histological characterization, RNA purification and PCR amplification of samples. Following pathologic examination of frozen tissue sections, laser capture microdissection (LCM) was performed to ensure that the tissue samples assayed consisted of pure populations of benign prostate cells. For each tissue section analyzed, LCM was performed at three different regions containing benign tissue and the cells collected were then pooled.

Cloning of DEFB1 Gene

DEFB1 cDNA was generated from RNA by reverse transcription-PCR. The PCR primers were designed to contain ClaI and KpnI restriction sites. DEFB1 PCR products were restriction digested with ClaI and KpnI and ligated into a TA cloning vector. The TA/DEFB1 vector was then transfected into *E. coli* by heat shock and individual clones were selected and expanded. Plasmids were isolated by Cell Culture DNA Midiprep (Qiagen, Valencia, Calif.) and sequence integrity verified by automated sequencing. The DEFB1 gene fragment was then ligated into the pTRE2 digested with ClaI and KpnI, which served as an intermediate vector for orientation purposes. Then the pTRE2/DEFB1 construct was digested with ApaI and KpnI to excise the DEFB1 insert, which was ligated into pIND vector of the Ecdysone Inducible Expression System (Invitrogen, Carlsbad, Calif.) also double digested with ApaI and KpnI. The construct was again transfected into *E. coli* and individual clones were selected and expanded. Plasmids were isolated and sequence integrity of pIND/DEFB1 was again verified by automated sequencing.

Transfection

Cells ($1 \times 10^6$) were seeded onto 100-mm Petri dishes and grown overnight. Then the cells were co-transfected using Lipofectamine 2000 (Invitrogen, Carlsbad, Calif.) with 1 μg of pVgRXR plasmid, which expresses the heterodimeric ecdysone receptor, and 1 μg of the pIND/DEFB1 vector construct or empty pIND control vector in Opti-MEM media (Life Technologies, Inc., Grand Island, N.Y.).

RNA Isolation and Quantitative RT-PCR

In order to verify DEFB1 protein expression in the cells transfected with DEFB1 construct, RNA was collected after a 24 hour induction period with Ponasterone A (Pon A). Briefly, total RNA was isolated using the SV Total RNA Isolation System (Promega, Madison, Wis.) from approximately $1 \times 10^6$ cells harvested by trypsinizing. Here, cells were lysed and total RNA was isolated by centrifugation through spin columns. For cells collected by LCM, total RNA was isolated using the PicoPure RNA Isolation Kit (Arcturus Biosciences, Mt. View, Calif.) following the manufacturer's protocol. Total RNA (0.5 μg per reaction) from both sources was reverse transcribed into cDNA utilizing random primers (Promega). AMV Reverse Transcriptase II enzyme (500 units per reaction; Promega) was used for first strand synthesis and Tfl DNA Polymerase for second strand synthesis (500 units per reaction; Promega) as per the manufacturer's protocol. In each case, 50 pg of cDNA was used per ensuing PCR reaction. Two-step QRT-PCR was performed on cDNA generated using the MultiScribe Reverse Transcripatase from the TaqMan Reverse Transcription System and the SYBR Green PCR Master Mix (Applied Biosystems).

The primer pair for DEFB1 (Table 3) was generated from the published DEFB1 sequence (GenBank Accession No. U50930)[10]. Forty cycles of PCR were performed under standard conditions using an annealing temperature of 56° C. In addition, β-actin (Table 3) was amplified as a housekeeping gene to normalize the initial content of total cDNA. DEFB1 expression was calculated as the relative expression ratio between DEFB1 and β-actin and was compared in cells lines induced and uninduced for DEFB1 expression, as well as LCM benign prostatic tissue. As a negative control, QRT-PCR reactions without cDNA template were also performed. All reactions were run three times in triplicate.

MTT Cell Viability Assay

To examine the effects of DEFB1 on cell growth, metabolic 3-[4,5-dimethylthiazol-2yl]-2,5 diphenyl tetrazolium bromide (MTT) assays were performed. PC3, DU145 and LNCaP cells co-transfected with pVgRXR plasmid and pIND/DEFB1 construct or empty pIND vector were seeded onto a 96-well plate at $1-5 \times 10^3$ cells per well. Twenty-four hours after seeding, fresh growth medium was added containing 10 μM Ponasterone A daily to induce DEFB1 expression for 24-, 48- and 72 hours after which the MTT assay was performed according to the manufacturer's instructions (Promega). Reactions were performed three times in triplicate.

Flow Cytometry

PC3 and DU145 cells co-transfected with the DEFB1 expression system were grown in 60-mm dishes and induced for 12, 24, and 48 hours with 10 μM Ponasterone A. Following each incubation period, the medium was collected from the plates (to retain any detached cells) and combined with PBS used to wash the plates. The remaining attached cells were harvested by trypsinization and combined with the detached cells and PBS. The cells were then pelleted at 4° C. (500×g) for 5 min, washed twice in PBS, and resuspended in 100 ul of 1× Annexin binding buffer (0.1 M Hepes/NaOH at pH 7.4, 1.4 M NaCl, 25 mM $CaCl_2$) containing 5 μl of Annexin V-FITC and 5 μl of PI. The cells were incubated at RT for 15 min in the dark, then diluted with 400 μl of 1× Annexin binding buffer and analyzed by FACscan (Becton Dickinson, San Jose, Calif.). All reactions were performed three times.

Microscopic Analysis

Cell morphology was analyzed by phase contrast microscopy. DU145, PC3 and LNCaP cells containing no vector, empty plasmid or DEFB1 plasmid were seeded onto 6 well culture plates (BD Falcon, USA). The following day plasmid-containing cells were induced for a period of 48 h with media containing 10 μM Ponasterone A, while control cells received fresh media. The cells were then viewed under an inverted Zeiss IM 35 microscope (Carl Zeiss, Germany). Phase contrast pictures of a field of cells were obtained using the SPOT Insight Mosaic 4.2 camera (Diagnostic Instruments, USA). Cells were examined by phase contrast microscopy under 32× magnification and digital images were stored as uncompressed TIFF files and exported into Photoshop CS software (Adobe Systems, San Jose, Calif.) for image processing and hard copy presentation.

Caspase Detection

Detection of caspase activity in the prostate cancer cell lines was performed using APO LOGIX™ Carboxyfluorescin Caspase detection kit (Cell Technology, Mountain View, Calif.). Active caspases were detected through the use of a FAM-VAD-FMK inhibitor that irreversibly binds to active caspases. Briefly, DU145 and PC3 cells ($1.5-3 \times 10^5$) containing the DEFB1 expression system were plated in 35 mm glass bottom microwell dishes (Matek, Ashland, Mass.) and treated for 24 hours with media only or with media containing PonA as previously described. Next, 10 μl of a 30× working dilution of carboxyfluorescein labeled peptide fluoromethyl ketone (FAM-VAD-FMK) was added to 300 μl of media and added to each 35 mm dish. Cells were then incubated for 1 hour at 37° C. under 5% $CO_2$. Then, the medium was aspirated and the cells were washed twice with 2 ml of a 1× Working dilution Wash Buffer. Cells were viewed under differential interference contrast (DIC) or under laser excitation at 488 nm. The fluorescent signal was analyzed using a confocal microscope (Zeiss LSM 5 Pascal) and a 63×DIC oil lens with a Vario 2 RGB Laser Scanning Module.

Statistical Analysis

Statistical differences were evaluated using the Student's t-test for unpaired values. P values were determined by a two-sided calculation, and a P value of less than 0.05 was considered statistically significant.

Results

DEFB1 Expression in Prostate Tissue and Cell Lines

Figure 1A:
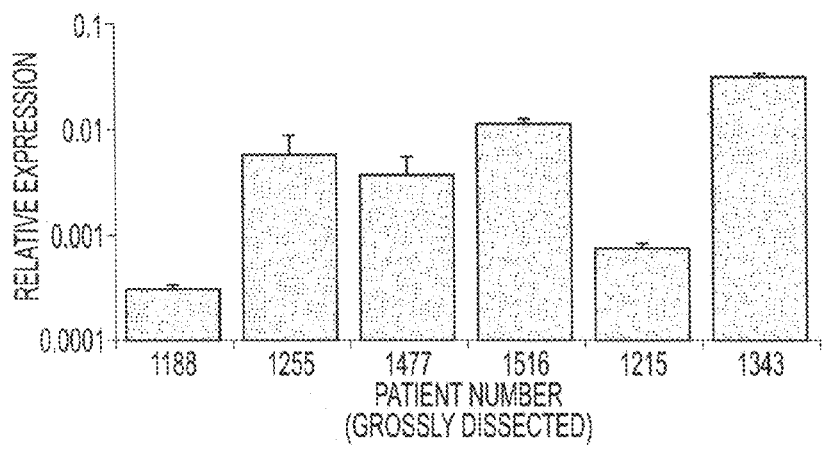
FIG. 1. QRT-PCR analysis of DEFB1 Expression. In order to verify induction of DEFB1 expression, QRT-PCR was performed. A, DEFB1 relative expression levels were compared in clinical samples from 6 patients that underwent radical prostatectomies. B, DEFB1 relative expression levels were compared in benign and malignant prostatic clinical samples, hPrEC cells and in prostate cancer cell lines before and after DEFB1 induction. C, DEFB1 relative expression levels were analyzed in benign tissue, malignant tissue and PIN in a single tissue section. D, DEFB1 expression in benign tissue, malignant tissue and PIN in one patient was compared to the average DEFB1 expression level found in benign tissue.
Figure 1B:
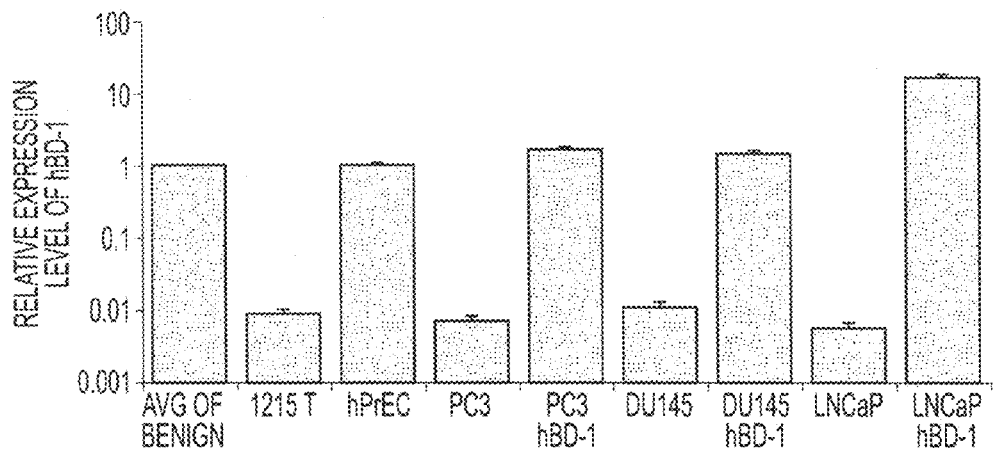

DEFB1 expression levels were measured by QRT-PCR in benign and malignant prostatic tissue, hPrEC prostate epithelial cells and DU145, PC3 and LNCaP prostate cancer cells. DEFB1 expression was detected in all of the benign clinical samples. The average amount of DEFB1 relative expression was 0.0073. In addition, DEFB1 relative expression in hPrEC cells was 0.0089. There was no statistical difference in DEFB1 expression detected in the benign prostatic tissue samples and hPrEC (FIG. 1A). Analysis of the relative DEFB1 expression levels in the prostate cancer cell lines revealed significantly lower levels in DU145, PC3 and LNCaP. As a further point of reference, relative DEFB1 expression was measured in the adjacent malignant section of prostatic tissue from patient #1215. There were no significant differences in the level of DEFB1 expression observed in the three prostate cancer lines compared to malignant prostatic tissue from patient #1215 (FIG. 1B). In addition, expression levels in all four samples were close to the no template negative controls which confirmed little to no endogenous DEFB1 expression (data not shown). QRT-PCR was also performed on the prostate cancer cell lines transfected with the DEFB1 expression system. Following a 24 hour induction period, relative expression levels were 0.01360 in DU145, 0.01503 in PC3 and 0.138 in LNCaP. Amplification products were verified by gel electrophoresis.

Figure 1C:
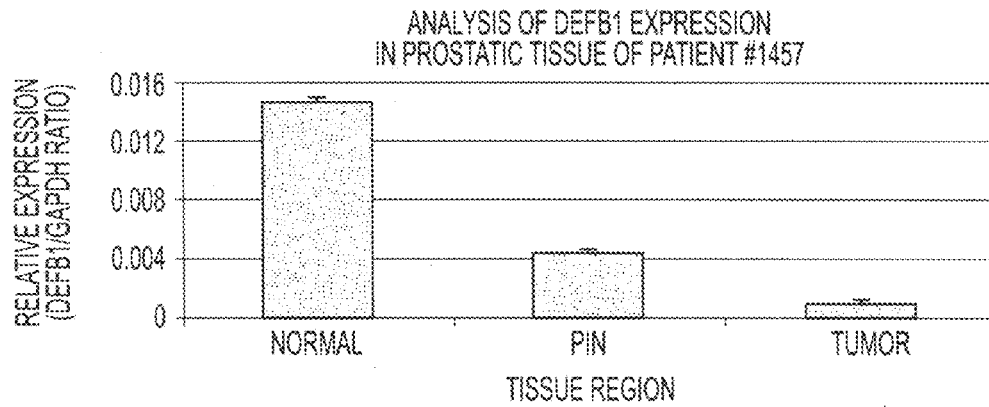
Figure 1D:
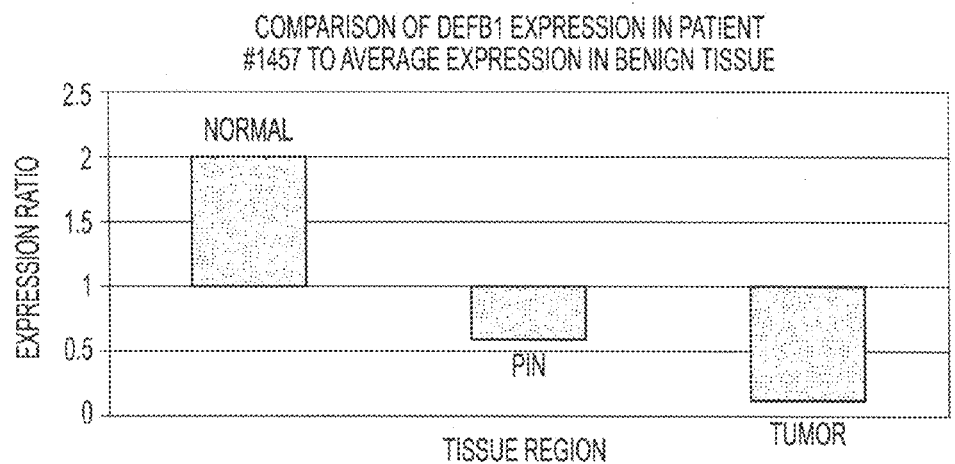

QRT-PCR was performed on LCM tissues regions containing benign, PIN and cancer. DEFB1 relative expression was 0.0146 in the benign region compared to 0.0009 in the malignant region (FIG. 1C.). This represents a 94% decrease which again demonstrates a significant down-regulation of expression. Furthermore, analysis of PIN revealed that DEFB1 expression level was 0.044 which was a 70% decrease. Comparing expression in patient #1457 to the average expression level found in benign regions of six other patients (FIG. 1A.) revealed a ratio of 1.997 representing almost twice as much expression (FIG. 1D.). However, the expression ratio was 0.0595 in PIN and was 0.125 in malignant tissue compared to average expression levels in benign tissue.

DEFB1 Causes Cell Membrane Permeability and Ruffling

Figure 2:
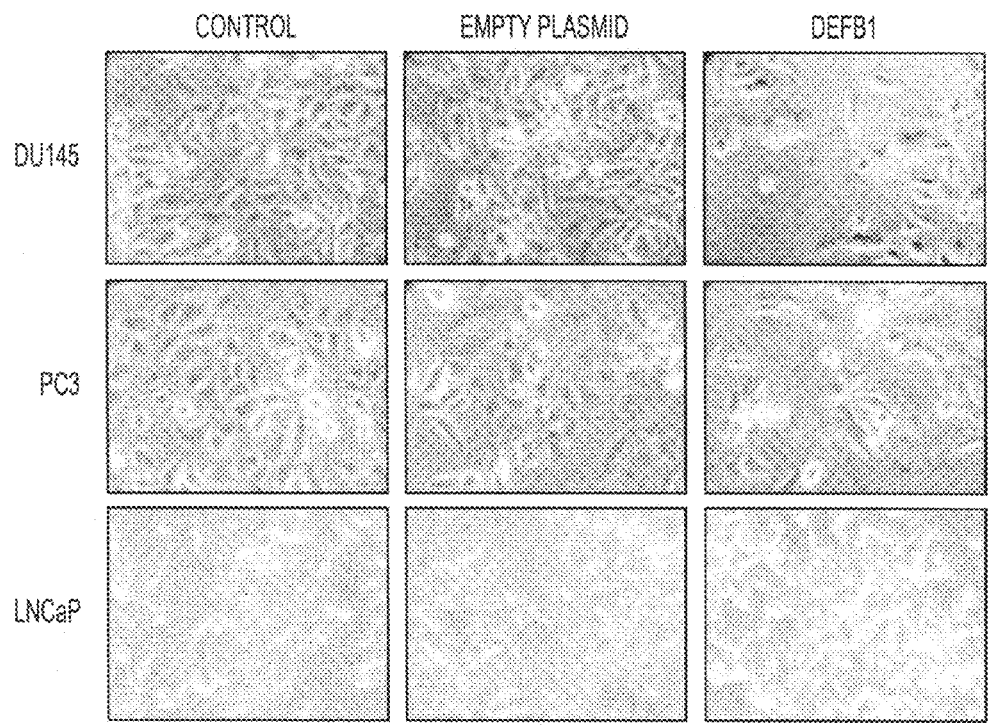
FIG. 2. Microscopic analysis of DEFB1 induced changes in membrane integrity and cell morphology. Cell morphology of DU145, PC3 and LNCaP was analyzed by phase contrast microscopy after 48 hours of DEFB1 induction. Membrane ruffling is indicated by black arrows and apoptotic bodies are indicated white arrows.

Induction of DEFB1 in the prostate cancer cell lines resulted in a significant reduction in cell number in DU145 and PC3, but had no effect on cell proliferation in LNCaP (FIG. 2). As a negative control, cell proliferation was monitored in all three lines containing empty plasmid. There were no observable changes in cell morphology in DU145, PC3 or LNCaP cells following the addition of PonA. In addition, DEFB1 induction resulted in morphological changes in both DU145 and PC3. Here cells appeared more rounded and exhibited membrane ruffling indicative of cell death. Apoptotic bodies were also present in both lines.

Expression of DEFB1 Results in Decreased Cell Viability

Figure 3:
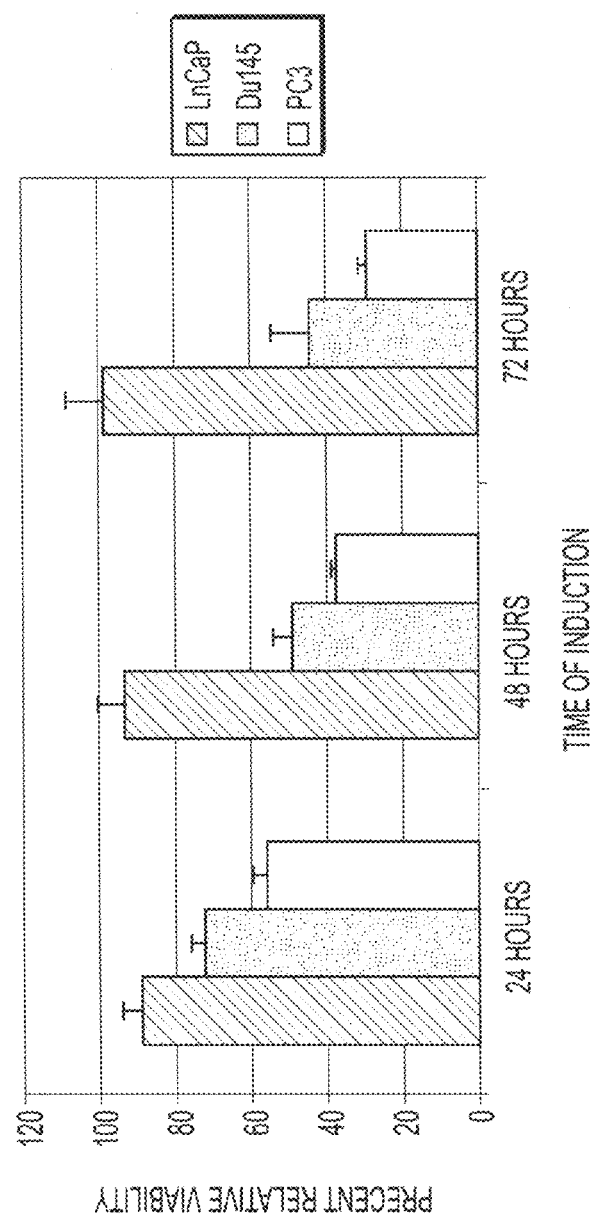
FIG. 3. Analysis of DEFB1 Cytotoxicity in Prostate Cancer Cells. The prostate cell lines DU145, PC3 and LNCaP were treated with PonA to induce DEFB1 expression for 1-3 days after which MTT assay was performed to determine cell viability. Results represent mean±s.d., n=9.

The MTT assay showed a reduction in cell viability by DEFB1 in PC3 and DU145 cells, but no significant effect on LNCaP cells (FIG. 3). After 24 hours, relative cell viability was 72% in DU145 and 56% in PC3. Analysis 48 hours after induction revealed 49% cell viability in DU145 and 37% cell viability in PC3. After 72 hours of DEFB1 expression resulted in 44% and 29% relative cell viability in DU145 and PC3 cells, respectively.

Figure 4A:
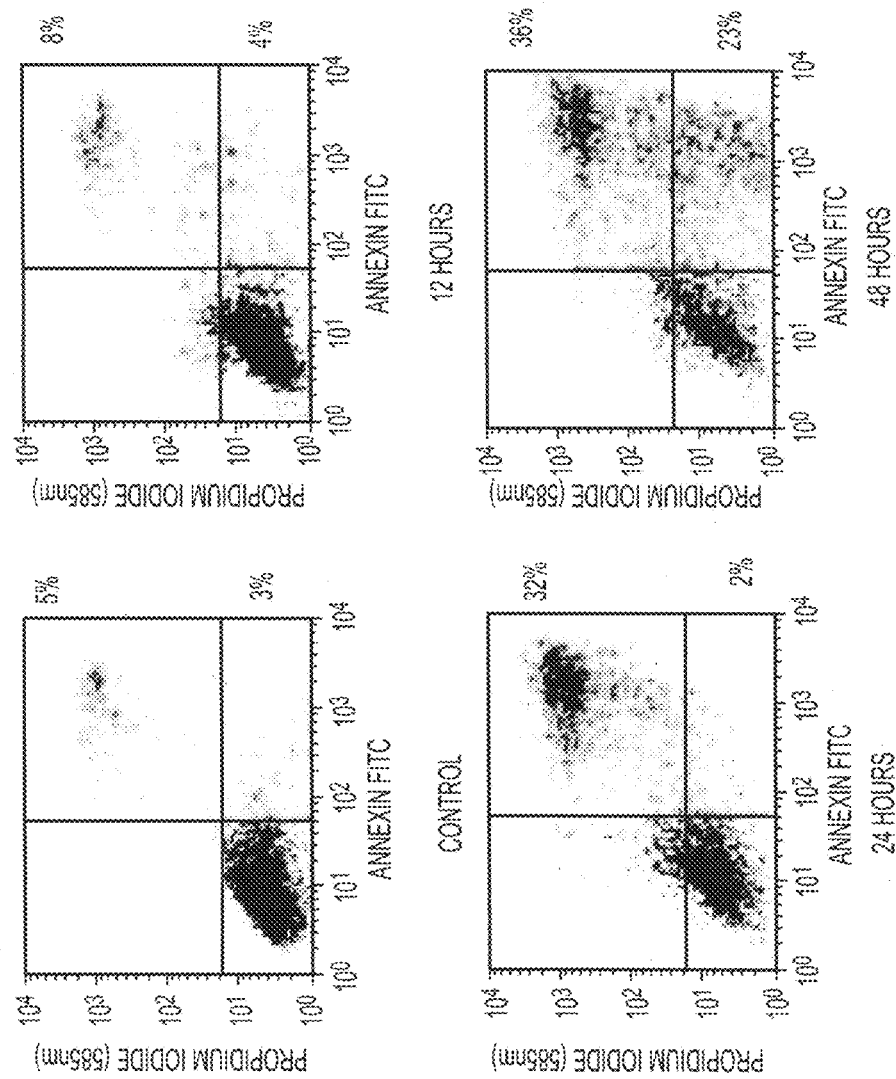
FIG. 4. Induction of cell death in DU145 and PC3 cells by DEFB1. DEFB1 expression was induced in prostate cancer cell lines DU145 (A) and PC3 (B) and then subjected to annexin V/FITC/propidium iodide staining and flow cytometric analysis. Cells positive for propidium iodide and annexin V were considered apoptotic. Times of induction are shown under each panel. Numbers next to the boxes for each time point represent the percentages of propidium iodide (PI)⁻ annexin V⁺ cells (lower right quadrant), and PI⁺ annexin V⁺ cells (upper right quadrant). The data are from a single experiment that is representative of three separate experiments.
Figure 4B:
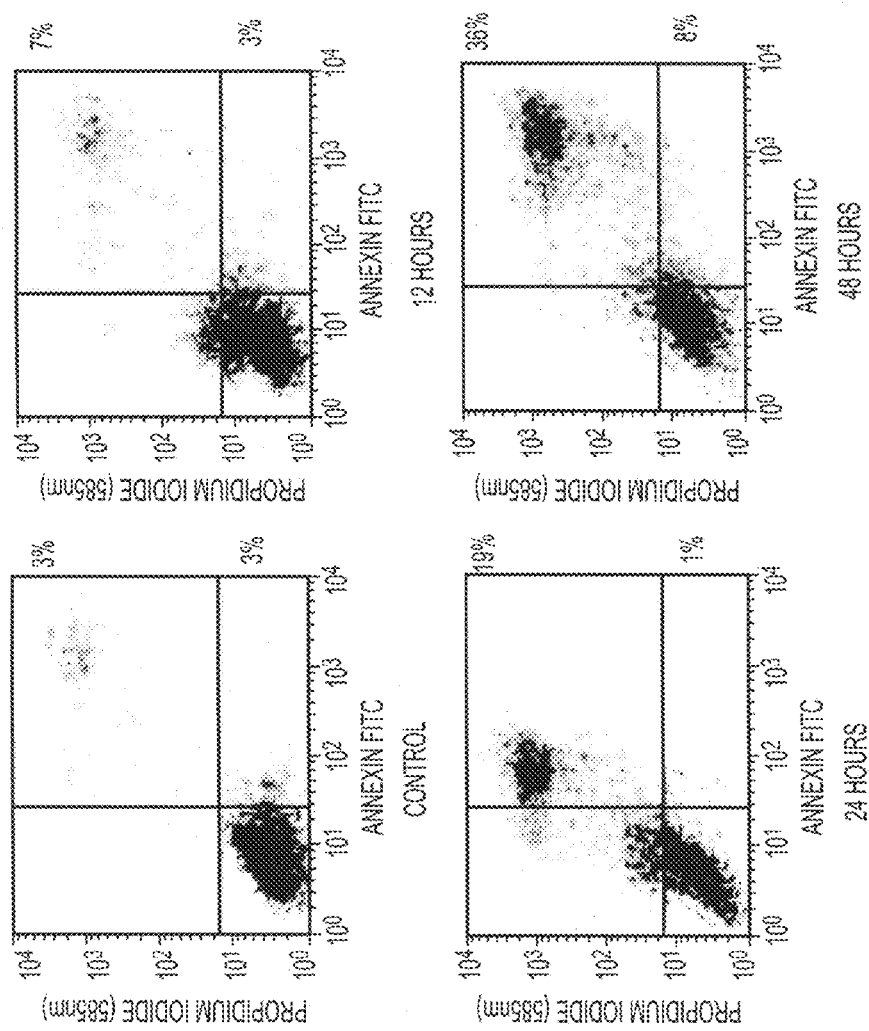

DEFB1 Causes Rapid Caspase-Mediated Apoptosis in Late-Stage Prostate Cancer Cells In order to determine whether the effects of DEFB1 on PC3 and DU145 were cytostatic or cytotoxic, FACS analysis was performed. Under normal growth conditions, more than 90% of PC3 and DU145 cultures were viable and non-apoptotic (lower left quadrant) and did not stain with annexin V or PI (FIG. 4). After inducing DEFB1 expression in PC3 cells, the number of apoptotic cells (lower and upper right quadrants) totaled 10% at 12 hours, 20% at 24 hours, and 44% at 48 hours. For DU145 cells, the number of apoptotic cells totaled 12% after 12 hours, 34% at 24 hours, and 59% after 48 hours of induction. There was no increase in apoptosis observed in cells containing empty plasmid following induction with PonA (data not shown).

Caspase activity was determined by confocal laser microscopic analysis (FIG. 5). DU145 and PC3 cell were induced for DEFB1 expression and activity was monitored based on the binding of green fluorescing FAM-VAD-FMK to caspases in cells actively undergoing apoptosis. Analysis of cells under DIC showed the presence of viable control DU145 (A), PC3 (E) and LNCaP (I) cells at 0 hours. Excitation by the confocal laser at 488 nm produced no detectable green staining which indicates no caspase activity in DU145 (B), PC3 (F) or LNCaP (J). Following induction for 24 hours, DU145 (C), PC3 (G) and LNCaP (K) cells were again visible under DIC. Confocal analysis under fluorescence revealed green staining in DU145 (D) and PC3 (H) cell indicating caspase activity. However, there was no green staining in LNCaP (L), indicating no induction of apoptosis by DEFB1.

Conclusion

To assess its functional role, the DEFB1 gene was cloned into the ecdysone inducible expression system and examined its effect on prostate cancer cells. The present data demonstrate DEFB1 cytotoxic activity against late-stage androgen receptor negative hormone refractory prostate cancer cells. In conclusion, this study provides the functional role of DEFB1 in prostate cancer. Furthermore, these findings show that DEFB1 is part of an innate immune system involved in tumor immunity. Data presented here demonstrate that DEFB1 expressed at physiological levels is cytotoxic to AR⁻ hormone refractory prostate cancer cells, but not to AR+ hormone sensitive prostate cancer cell nor to normal prostate epithelial cells. Given that DEFB1 is constitutively expressed in normal prostate cells without cytotoxicity, it may be that late-stage AR⁻ prostate cancer cells possess distinct phenotypic characteristics that render them sensitive to DEFB1 cytotoxicity. Thus, DEFB1 is a viable therapeutic agent for the treatment of late-stage prostate cancer.

Example II siRNA Mediated Knockdown of PAX2 Expression Results in Prostate Cancer Cell Death Independent of p53 Status Abstract This example examines the effects of inhibiting PAX2 expression by RNA interference in prostate cancer cells which differ in p53 gene status. These results demonstrate that the inhibition of PAX2 results in cell death irrespective of p53 status, indicating that there are additional tumor suppressor genes or cell death pathways inhibited by PAX2 in prostate cancer.

Materials and Methods

Cell Lines

The cell lines PC3, DU145 and LNCaP were obtained from the American Type Culture Collection (Rockville, Md., USA). PC3 cell were grown in F-12 media, DU145 in DMEM, and LNCaP in RPMI all supplemented with 10% (v/v) fetal bovine serum. Cell were maintained at 37° C. in 5% $CO_2$.

siRNA Silencing of PAX2

In order to achieve efficient gene silencing, a pool of four complementary short interfering ribonucleotides (siRNAs) targeting human PAX2 mRNA (Accession No. NM_003989.1), were synthesized (Dharmacon Research, Lafayette, Colo., USA). A second pool of four siRNAs were used as an internal control to test for the specificity of PAX2 siRNAs. Two of the sequences synthesized target the GL2 luciferase mRNA (Accession No. X65324), and two were non-sequence-specific (Table 4). For annealing of siRNAs, 35 M of single strands were incubated in annealing buffer (100 mM potassium acetate, 30 mM HEPES-KOH at pH 7.4, 2 mM magnesium acetate) for 1 min at 90° C. followed by 1 h incubation at 37° C.

Western Analysis

Briefly, cells were harvested by trypsinization and washed twice with PBS. Lysis buffer was prepared according to the manufacturer's instructions (Sigma), and was then added to the cells. Following a 15 minute incubation period at 4° C. on an orbital shaker, cell lysate were then collected and centrifuged for 10 minutes at 12000×g to pellet cellular debris. The protein-containing supernatant were then collected and quantitated. Next, 25 μg protein extract was loaded onto an 8-16% gradient SDS-PAGE (Novex). Following electrophoresis, proteins were transferred to PVDF membranes, and then blocked with 5% nonfat dry milk in TTBS (0.05% Tween 20 and 100 mM Tris-Cl) for 1 hour. Blots were then probed with rabbit anti-Pax2 primary antibody (Zymed, San Francisco, Calif.) at a 1:2000 dilution. After washing, the membranes were incubated with anti-rabbit antibody conjugated to horseradish peroxidase (HRP) (dilution 1:5000; Sigma), and signal detection was visualized using chemiluminescence reagents (Pierce) on an Alpha Innotech Fluorchem 8900. As a control, blots were stripped and reprobed with mouse anti-β-actin primary antibody (1:5000; Sigma-Aldrich) and HRP-conjugated anti-mouse secondary antibody (1:5000; Sigma-Aldrich) and signal detection was again visualized.

Phase Contrast Microscopy

The effect of PAX2 knock-down on cell growth was analyzed by phase contrast microscopy. Here, $1-2 \times 10^4$ cells were seeded onto 6 well culture plates (BD Falcon, USA).

The following day cells were treated with media only, negative control non-specific siRNA or PAX2 siRNA and allowed to incubate for six days. The cells were then viewed under an inverted Zeiss IM 35 microscope (Carl Zeiss, Germany) at 32× magnification. Phase contrast pictures of a field of cells were obtained using the SPOT Insight Mosaic 4.2 camera (Diagnostic Instruments, USA).

MTT Cytotoxicity Assay

DU145, PC3 and LNCaP cells ($1 \times 10^5$) were transfected with 0.5 μg of the PAX2 siRNA pool or control siRNA pool using Codebreaker transfection reagent according to the manufacturer's protocol (Promega). Next, cell suspensions were diluted and seeded onto a 96-well plate at $1-5 \times 10^3$ cells per well and allowed to grow for 2-, 4- or 6 days. After culture, cell viability was determined by measuring the conversion of 3-[4,5-dimethylthiazol-2yl]-2,5 diphenyl tetrazolium bromide, MTT (Promega), to a colored formazan product. Absorbance was read at 540 nm on a scanning multiwell spectrophotometer.

Pan-Caspase Detection

Detection of caspase activity in the prostate cancer cell lines was performed using APO LOGIX™ Carboxyfluorescin Caspase detection kit (Cell Technology, Mountain View, Calif.). Active caspases were detected through the use of a FAM-VAD-FMK inhibitor that irreversibly binds to active caspases. Briefly, cells ($1-2 \times 10^4$) onto 35 mm glass bottom microwell dishes (Matek, Ashland, Mass.) and treated with media only or PAX2 siRNA as previously described. Next, 10 μl of a 30× working dilution of carboxyfluorescein labeled peptide fluoromethyl ketone (FAM-VAD-FMK) was added to 300 μl of media and added to each 35 mm dish. Cells were then incubated for 1 hour at 37° C. under 5% $CO_2$. Then, the medium was aspirated and the cells were washed twice with 2 ml of a 1× Working dilution Wash Buffer. Cells were viewed under differential interference contrast (DIC) or under laser excitation at 488 nm. The fluorescent signal was analyzed using a confocal microscope (Zeiss LSM 5 Pascal) and a 63×DIC oil lens with a Vario 2 RGB Laser Scanning Module.

Quantitative Real-Time RT-PCR

Quantitative real-time RT-PCR was performed in order to verify gene expression after PAX2 siRNA treatment in PC3, DU145 and LNCaP cell lines. Total RNA was isolated using the SV Total RNA Isolation System (Promega). Briefly, approximately $1 \times 10^6$ cells were harvested by trypsinizing, and rinsed in PBS. Cells were then lysed and total RNA was isolated by centrifugation through spin columns. Total RNA (0.5 μg per reaction) was reverse transcribed into cDNA utilizing Oligo (dT) 15 primer (Promega) and AMV Reverse Transcriptase II enzyme (500 units per reaction; Promega) for first strand synthesis and Tfl DNA Polymerase for second strand synthesis (500 units per reaction; Promega) as per the manufacturers' protocol, with identical control samples treated without RT enzyme. Typically, 50 pg of each cDNA was used per ensuing PCR reaction Two-step QRT-PCR was performed on cDNA generated using the MultiScribe Reverse Transcripatase from the TaqMan Reverse Transcription System and the SYBR Green PCR Master Mix (PE Biosystems). The primer pairs for BAX, BID and BAD were generated from the published sequences (Table 3). Reactions were performed in MicroAmp Optical 96-well Reaction Plate (PE Biosystems). Forty cycles of PCR were performed under standard conditions using an annealing temperature of 60° C. Quantification was determined by the cycle number where exponential amplification began (threshold value) and averaged from the values obtained from the triplicate repeats. There was an inverse relationship between message level and threshold value. In addition, GAPDH was used as a housekeeping gene to normalize the initial content of total cDNA. Gene expression was calculated as the relative expression ratio between the pro-apoptotic genes and GAPDH. All reactions were carried out in triplicate.

Results siRNA Inhibition of PAX2 Protein

Figure 6:
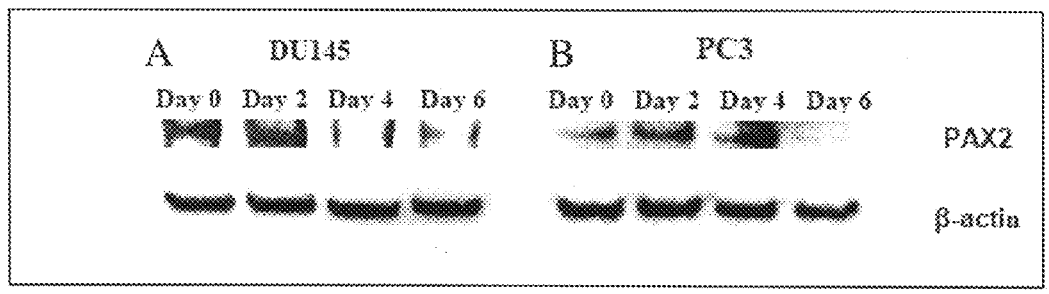
FIG. 6. Silencing of PAX2 Protein Expression Following PAX2 siRNA Treatment. (a) Western blot analysis of PC3 and DU145 cells transfected with PAX2 siRNA duplex at day zero (lane 1), day two (lane 2), and day four (lane 3). (b) Western blot analysis of PC3 and DU145 cells transfected with PAX2 siRNA duplex at day zero (lane 1), day two (lane 2), day four (lane 3) and day 6 (lane 4). PAX2 protein was undetectable as early as after four days of treatment (lane 3) in DU145 cells and after six days of treatment in PC3. Blots were stripped and re-probed for β-actin as an internal control.

In order to confirm that the siRNA effective targeted the PAX2 mRNA, Western Analysis was performed to monitor PAX2 protein expression levels over a six day treatment period. Cells were given a single round of transfection with the pool of PAX2 siRNA. The results confirmed specific targeting of PAX2 mRNA by showing knock-down of PAX2 protein by day four in DU145 (FIG. 6a) and by day six in PC3 (FIG. 6b).

Knock-Down of PAX2 Inhibit Prostate Cancer Cell Growth

Figure 7:
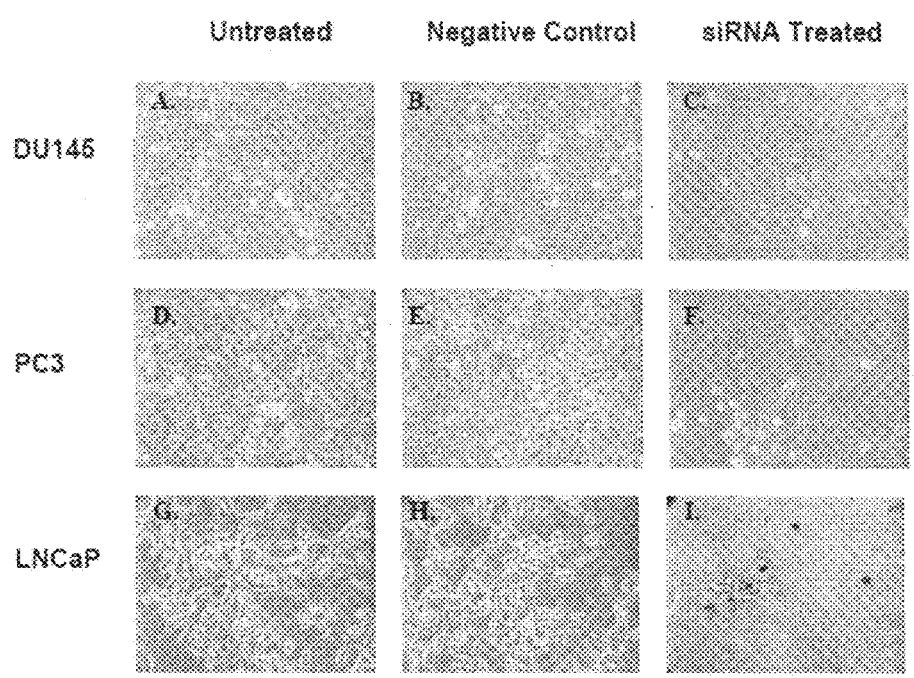
FIG. 7. Analysis of Prostate Cancer Cells Growth after Treatment with Pax 2 siRNA. Phase contrast microscopic analysis of DU145, PC3 and LNCaP at 6 days in the presence of normal growth media. Treatment with negative control siRNA had no effect on the cells. However, there was a significant reduction in cell number in all three lines following treatment with PAX2 siRNA.

Cells were analyzed following a six day treatment period with media only, negative control non-specific siRNA or PAX2 siRNA (FIG. 7). DU145 (a), PC3 (d) and LNCaP (g) cells all reached at least 90% confluency in the culture dishes containing media only. Treatment of DU145 (b), PC3 (e) and LNCaP (h) with negative control non-specific siRNA had no effect on cell growth, and cells again reached confluency after six days. However, treatment with PAX2 siRNA resulted in a significant decrease in cell number. DU145 cells were approximately 15% confluent (c) and PC3 cells were only 10% confluent (f). LNCaP cell were 5% confluent following siRNA treatment.

Cytotoxicity Assays

Figure 8:
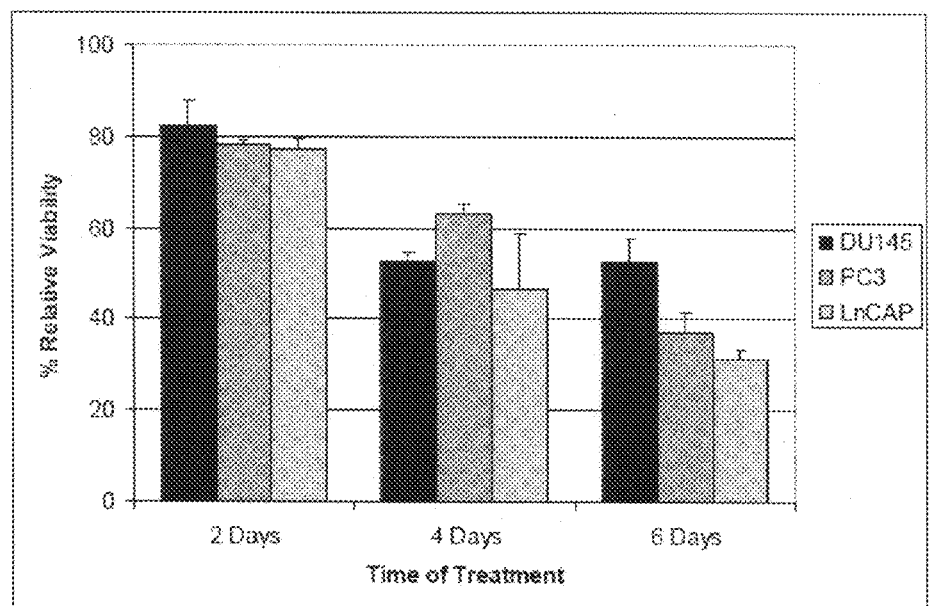
FIG. 8. Analysis of Cell Death Following siRNA Silencing of PAX2. Prostate cancer cell lines PC3, DU145, and LNCaP were treated with 0.5 μg of a pool of four PAX2 siRNA's or four non-specific control siRNA's for 2, 4 or 6 days after which MTT assay was done to determine cell viability. Results represent mean±s.d., n=9.

Cell viability was measured after two-, four-, and six-day exposure times, and is expressed as a ratio of the 570-630 nm absorbance of treated cells divided by that of the untreated control cells (FIG. 8). Relative cell viability following 2 days of treatment was 77% in LNCaP, 82% in DU145 and 78% in PC3. After four days, relative cell viability was 46% in LNCaP, 53% in DU145 and 63% in PC3. After six days of treatment, relative cell viability decreased to 31% in LNCaP, 37% in PC3, and was 53% in DU145. As negative controls, cell viability was measured in after a six day treatment period with negative control non-specific siRNA or transfection reagent alone. For both conditions, there was no statistically significant change in cell viability compared to normal growth media (data not shown).

Pan-Caspase Detection

Figure 9:
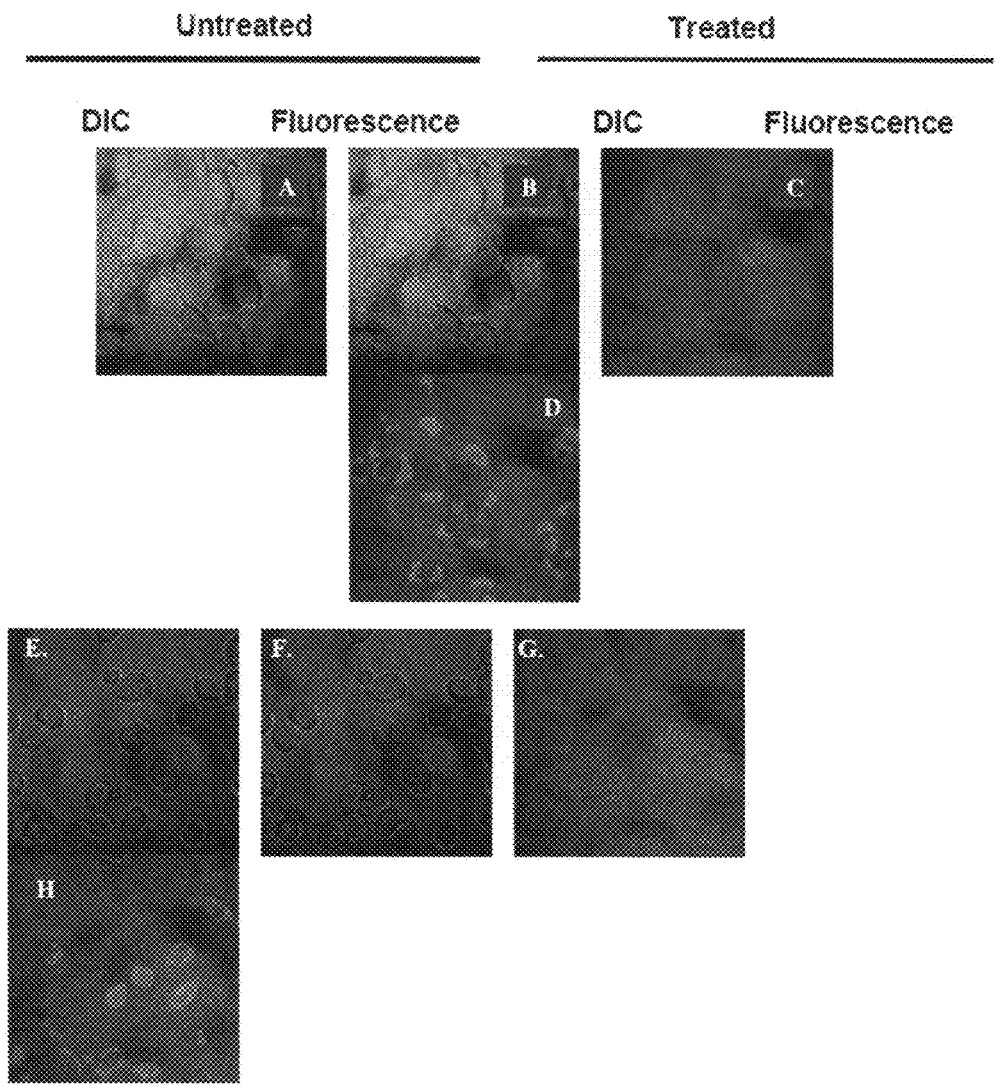
FIG. 9. Analysis of Caspase Activity. DU145, PC3 and LNCaP cells were stained with carboxyfluorescein-labeled fluoromethyl ketone to detected caspase activity following treatment with PAX2 siRNA. Confocal microscopic analysis of untreated and treated cells show cells were visible with DIC. Analysis under fluorescence revealed no caspase staining in control DU145 (B), PC3 cells (F) and LNCaP cells (J).
Figure 9:
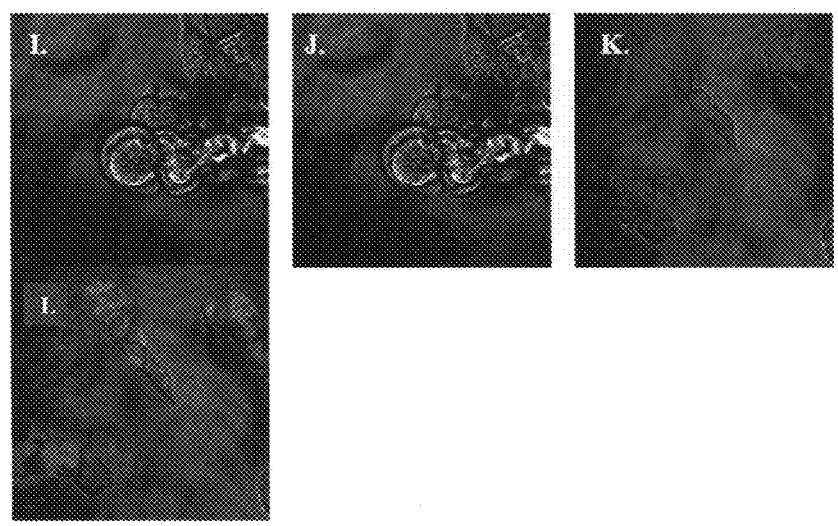

Caspase activity was detected by confocal laser microscopic analysis. DU145, PC3 and LNCaP cells were treated with PAX2 siRNA and activity was monitored based on the binding of FAM-labeled peptide to caspases in cells actively undergoing apoptosis which will fluoresce green. Analysis of cells with media only under DIC shows the presence of viable DU145 (A), PC3 (E) and LNCaP (I) cells at 0 hours (FIG. 9). Excitation by the confocal laser at 488 nm produced no detectable green staining which indicates no caspase activity in untreated DU145 (B), PC3 (F) or LNCaP (J). Following four days of treatment with PAX2 siRNA, DU145 (C), PC3 (G) and LNCaP (K) cells were again visible under DIC. Under fluorescence, the treated DU145 (D), PC3 (H) and LNCaP (L) cells presented green staining indicating caspase activity.

Effect of Pax2 Inhibition on Pro-Apoptotic Factors

Figure 10A:
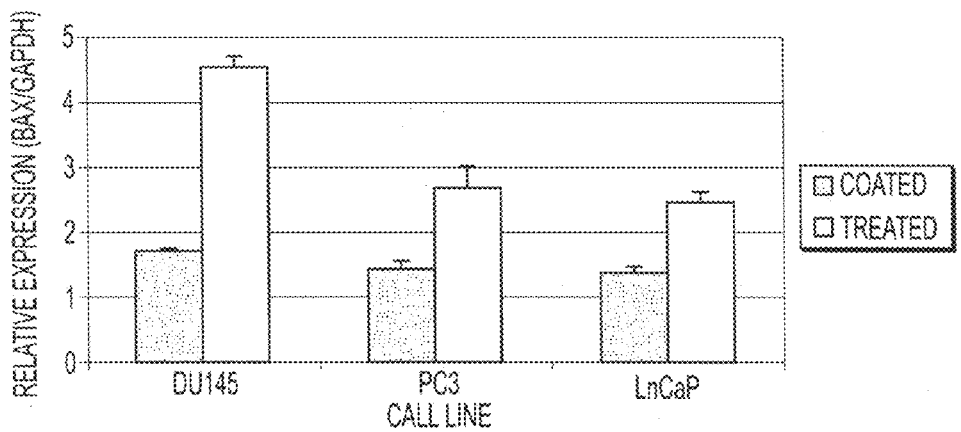
Figure 10B:
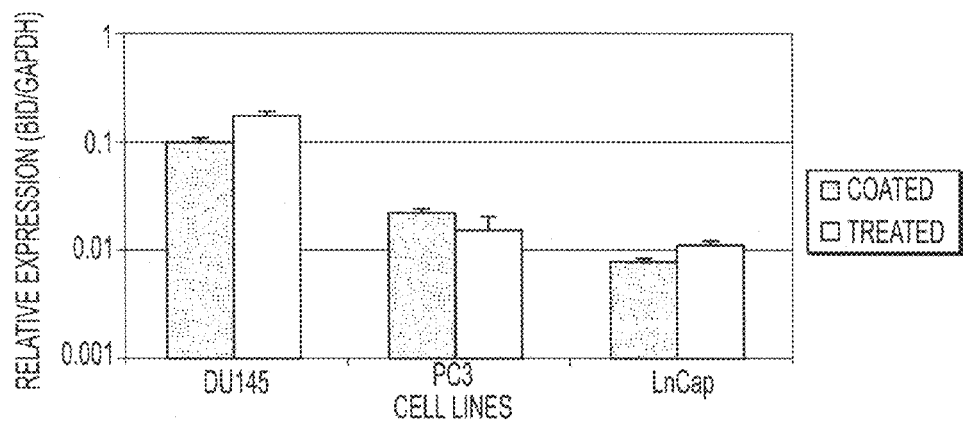
Figure 10C:
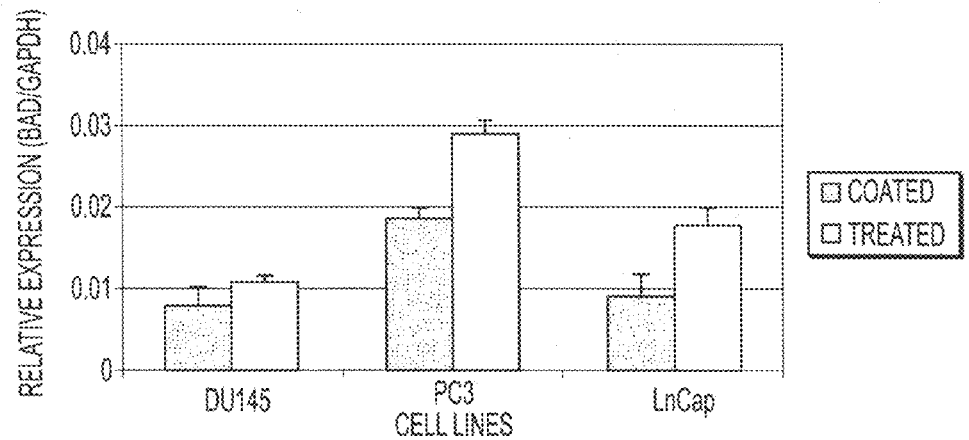

DU145, PC3 and LNCaP cells were treated with siRNA against PAX2 for six days and expression of pro-apoptotic genes dependent and independent of p53 transcription regulation were measured to monitor cell death pathways. For BAX, there was a 1.81-fold increase in LNCaP, a 2.73-fold increase in DU145, and a 1.87-fold increase in PC3 (FIG. 10a). Expression levels of BID increased by 1.38-fold in LNCaP and 1.77-fold in DU145 (FIG. 10b). However, BID expression levels decreased by 1.44-fold in PC3 following treatment (FIG. 10c). Analysis of BAD revealed a 2.0-fold increase in expression in LNCaP, a 1.38-fold increase in DU145, and a 1.58-fold increase in PC3.

Conclusion

Despite significant advances in cancer therapy there is still little progress in the treatment of advanced disease. Successful drug treatment of prostate cancer requires the use of therapeutics with specific effects on target cells while maintaining minimal clinical effects on the host. The goal of cancer therapy is to trigger tumor-selective cell death. Therefore, understanding the mechanisms in such death is critical in determining the efficacy of a specific treatment.

The dependency of prostate cancer cell survival on PAX2 expression is shown here. In order to distinguish between death observed in the p53-expressing cell line LNCaP, the p53-mutated line DU145, and the p53-null line PC3 downstream events that follow p53 activation as a result of PAX2 knock-down were examined. Caspase activity was detected in all three lines indicative of the initiation of programmed cell death. With this, changes in the expression of pro-apoptotic genes were examined. Here, BAX expression was upregulated in all three cell lines independent of p53 status. The expression of pro-apoptotic factor BAD was increased in all three lines following PAX2 inhibition. Following treatment with PAX2 siRNA, BID expression was increased in LNCaP and DU145, but actually decreased in PC3. This indicates that cell death observed in prostate cancer is influenced by but is not dependent on p53 expression. The initiation of apoptosis in prostate cancer cells through different cell death pathways irrespective of p53 status indicates that PAX2 inhibits other tumor suppressors Example III Inhibition of PAX2 Oncogene Results in DEFB1-Mediated Death of Prostate Cancer Cells Abstract The identification of tumor-specific molecules that serve as targets for the development of new cancer drugs is considered to be a major goal in cancer research. Example I demonstrated that there is a high frequency of DEFB1 expression loss in prostate cancer, and that induction of DEFB1 expression results in rapid apoptosis in androgen receptor negative-stage prostate cancer. These data show that DEFB1 plays a role in prostate tumor suppression. In addition, given that it is a naturally occurring component of the immune system of normal prostate epithelium, DEFB1 is expected to be a viable therapeutic agent with little to no side effects. Example II demonstrated that inhibition of PAX2 expression results in prostate cancer cell death independent of p53. These data indicate that there is an addition pro-apoptotic factor or tumor suppressor that is inhibited by PAX2. In addition, the data show that the oncogenic factor PAX2, which is over-expressed in prostate cancer, is a transcriptional repressor of DEFB1. The purpose of this study is to determine if DEFB1 loss of expression is due to aberrant expression of the PAX2 oncogene, and whether inhibiting PAX2 results in DEFB1-mediated cell death.

The data show that loss of DEFB1 expression occurs at the transcriptional level. Furthermore, computational analysis of the DEFB1 promoter revealed the presence of a GTTCC (SEQ ID NO: 2) DNA binding site for the PAX2 transcriptional repressor next to the DEFB1 TATA box (FIG. 1). The results presented here show that PAX2 and DEFB1 exhibit several attributes of suitable cancer targets, including a role in the suppression of cell death. Therefore, DEFB1 plays a role in tumor immunity and its expression is modulated through therapeutic down-regulation of the PAX2 oncogene.

Materials and Methods

RNA Isolation and Quantitative RT-PCR

In order to verify changes in DEFB1 expression levels RNA was collected after 4 days of PAX2 siRNA treatment. Briefly, total RNA was isolated using the SV Total RNA Isolation System (Promega, Madison, Wis.) from approximately $1 \times 10^6$ cells harvested by trypsinizing. Here, cells were lysed and total RNA was isolated by centrifugation through spin columns. Total RNA (0.5 μg per reaction) from both sources was reverse transcribed into cDNA utilizing random primers (Promega). AMV Reverse Transcriptase II enzyme (500 units per reaction; Promega) was used for first strand synthesis and Tfl DNA Polymerase for second strand synthesis (500 units per reaction; Promega) as per the manufacturer's protocol. In each case, 50 pg of cDNA was used per ensuing PCR reaction. Two-step QRT-PCR was performed on cDNA generated using the MultiScribe Reverse Transcripatase from the TaqMan Reverse Transcription System and the SYBR Green PCR Master Mix (Applied Biosystems).

The primer pair for DEFB1 was generated from the published DEFB1 sequence (Accession No. U50930). Forty cycles of PCR were performed under standard conditions using an annealing temperature of 56° C. In addition, GAPDH was amplified as a housekeeping gene to normalize the initial content of total cDNA. DEFB1 expression was calculated as the relative expression ratio between DEFB1 and GAPDH and was compared in cells lines before and after siRNA knock-down of PAX2 expression. All reactions were run three times in triplicate.

Generation of the DEFB1 Reporter Construct

The pGL3 luciferase reporter plasmid was used to monitor DEFB1 reporter activity. Here, a region 160 bases upstream of the DEFB1 transcription initiation site and included the DEFB1 TATA box. The region also included the GTTCC (SEQ ID NO: 2) sequence which is necessary for PAX2 binding. The PCR primers were designed to contain KpnI and NheI restriction sites. The DEFB1 promoter PCR products were restriction digested Kpn I and NheI and ligated into a similarly restriction digested pGL3 plasmid (FIG. 2). The constructs were transfected into E. coli and individual clones were selected and expanded. Plasmids were isolated and sequence integrity of the DEFB1/pGL3 construct was verified by automated sequencing.

Luciferase Reporter Assay

Here, 1 µg of the DEFB1 reporter construct or the control pGL3 plasmid was transfected into $1 \times 10^6$ DU145 cells. Next, $0.5 \times 10^3$ cells were seeded onto each well of a 96-well plate and allowed to grow overnight. Then fresh medium was added containing PAX2 siRNA or media only and the cells were incubated for 48 hours. Luciferase was detected by the BrightGlo kit according to the manufacturer's protocol (Promega) and the plates were read on a Veritas automated 96-well luminometer. Promoter activity was expressed as relative luminescence.

Analysis of Membrane Permeability

Acridine orange (AO)/ethidium bromide (EtBr) dual staining was performed to identify changes in cell membrane integrity, as well as apoptotic cells by staining the condensed chromatin. AO stains viable cells as well as early apoptotic cells, whereas EtBr stains late stage apoptotic cells that have lost membrane permeability. Briefly, cells were seeded into 2 chamber culture slides (BD Falcon, USA). Cells transfected with empty pIND plasmid/pvgRXR or pIND DEFB1/pvgRXR were induced for 24 or 48 h with media containing 10 µM Ponasterone A. Control cells were provided fresh media at 24 and 48 h. In order to determine the effect of PAX2 inhibition on membrane integrity, separate culture slides containing DU145, PC3 and LNCaP were treated with PAX2 siRNA and incubated for 4 days. Following this, cells were washed once with PBS and stained with 2 ml of a mixture (1:1) of AO (Sigma, USA) and EtBr (Promega, USA) (5 ug/ml) solution for 5 min. Following staining, the cells were again washed with PBS. Fluorescence was viewed by a Zeiss LSM 5 Pascal Vario 2 Laser Scanning Confocal Microscope (Carl Zeiss Jena, Germany). The excitation color wheel contain BS505-530 (green) and LP560 (red) filter blocks which allowed for the separation of emitted green light from AO into the green channel and red light from EtBr into the red channel. The laser power output and gain control settings within each individual experiment were identical between control and DEFB1 induced cells. The excitation was provided by a Kr/Ar mixed gas laser at wavelengths of 543 nm for AO and 488 nm for EtBr. Slides were analyzed under 40× magnification and digital images were stored as uncompressed TIFF files and exported into Photoshop CS software (Adobe Systems, San Jose, Calif.) for image processing and hard copy presentation.

ChIP Analysis of PAX2

Chromatin immunoprecipitation (ChIP) allows the identification of binding sites for DNA-binding proteins based upon in vivo occupancy of a promoter by a transcription factor and enrichment of transcription factor bound chromatin by immunoprecipitation (66). A modification of the protocol described by the Farnham laboratory ((67, 68) was used; also on line at http://mcardle.oncology.wisc.edu/farnham/). The DU145 and PC3 cell lines over-expresses the PAX2 protein, but does not express DEFB1. Cells were incubated with PBS containing 1.0% formaldehyde for 10 minutes to crosslink proteins to DNA. Samples were then sonicated to yield DNA with an average length of 600 bp. Sonicated chromatin precleared with Protein A Dynabeads was incubated with PAX2-specific antibody or "no antibody" control [isotype-matched control antibodies]. Washed immunoprecipitates were then collected. After reversal of the crosslinks, DNA was analyzed by PCR using promoter-specific primers to determine whether DEFB1 is represented in the PAX2-immunoprecipitated samples. Primers were designed to amplify the 160 bp region immediately upstream of the DEFB1 mRNA start site which contained the DEFB1 TATA box and the functional GTTCC (SEQ ID NO: 2) PAX2 recognition site. For these studies, positive controls included PCR of an aliquot of the input chromatin (prior to immunoprecipitation, but crosslinks reversed). All steps were performed in the presence of protease inhibitors.

Results siRNA Inhibition of PAX2 Increases DEFB1 Expression

QRT-PCR analysis of DEFB1 expression before siRNA treatment revealed relative expression levels of 0.00097 in DU145, 0.00001 in PC3, and 0.00004 LNCaP (FIG. 13). Following siRNA knock-down of PAX2, relative expression was 0.03294 (338-fold increase) in DU145, 0.00020 (22.2-fold increase) in PC3 and 0.00019 (4.92-fold increase) in LNCaP. As a negative control, the human prostate epithelial cell line (hPrEC) which is PAX2 null, revealed expression levels at 0.00687 before treatment and 0.00661 following siRNA treatment confirming no statistical change in DEFB1 expression.

DEFB1 Causes Cell Membrane Permeability

Membrane integrity was monitored by confocal analysis (FIG. 14). Here, intact cells stain green due to AO which is membrane permeable. In addition, cells with compromised plasma membranes would stain red by EtBr which is membrane impermeable. Here, uninduced DU145 (A) and PC3 (D) cells stained positively with AO and emitted green color, but did not stain with EtBr. However, DEFB1 induction in both DU145 (B) and PC3 (E) resulted in the accumulation of EtBr in the cytoplasm at 24 hours indicated by the red staining. By 48 hours, DU145 (C) and PC3 (F) possessed condensed nuclei and appeared yellow, which was due to the presence of both green and red staining resulting from the accumulation of AO and EtBr, respectively.

Inhibition of PAX2 Results in Membrane Permeability

Cells were treated with PAX2 siRNA for 4 days and membrane integrity was monitored again by confocal analysis (FIG. 15). Here, both DU145 (B) and PC3 (E) possessed condensed nuclei and appeared yellow. However, LNCaP cells' cytoplasm and nuclei remained green following siRNA treatment. Also red staining at the cell periphery indicates the maintenance of cell membrane integrity. These findings indicate that the inhibition of PAX2 results in specifically DEFB1-mediated cell death in DU1145 and PC3, but not LNCaP cells. Death observed in LNCaP (refer to Chapter II) is due to the transactivation of the existing wild-type p53 in LNCap following PAX2 inhibition.

siRNA Inhibition of PAX2 Increases DEFB1 Promoter Activity

Analysis of DEFB1 promoter activity in DU145 cells containing the DEFB1/pGL3 construct revealed a 2.65 fold increase in relative light units following 48 hours of treatment compared to untreated cells (FIG. 16). In PC3 cells, there was a 3.78-fold increase in relative light units compared to untreated cells.

PAX2 Binds to the DEFB1 Promoter

ChIP analysis was performed on DU145 and PC3 cells to determine if the PAX2 transcriptional repressor is bound to the DEFB1 promoter (FIG. 17). Lane 1 contains a 100 bp molecular weight marker. Lane 2 is a positive control representing 160 bp region of the DEFB1 promoter amplified from DU145 before cross-linking and immunoprecipitation. Lane 3 is a negative control representing PCR performed without DNA. Lane 4 and 5 are negative controls representing PCR from immunoprecipitations performed with IgG from cross-linked DU145 and PC3, respectively. PCR amplification of 25 pg of DNA (lane 6 and 8) and 50 pg of DNA (lane 7 and 9) immunoprecititated with anti-PAX2 antibody after crosslinking show 160 bp promoter fragment in DU145 and PC3, respectively.

Conclusion

The present novel data are the first to disclose the role of DEFB1 in prostate cancer tumor immunity. The data also show that the oncogenic factor PAX2 suppresses DEFB1 expression. One of the hallmarks of defensin cytotoxicity is the disruption of membrane integrity. The present results show that ectopic expression of DEFB1 in prostate cancer cells results in a loss of membrane potential due to compromised cell membranes. The same phenomenon is observed after inhibiting PAX2 protein expression. ChIP analysis was also performed and confirmed that PAX2 is bound to the DEFB1 promoter resulting in the repression of DEFB1 expression. Therefore, suppression of PAX2 expression or function, results in the re-establishment of DEFB1 expression and subsequently DEFB1-mediated cell death. Also, the present data establish the utility of DEFB1 as a directed therapy for prostate cancer treatment through innate immunity.

Example IV

Expression of DEFB1 Results in Tumor Shrinkage

The anti-tumoral ability of DEFB1 is evaluated by injecting tumor cells that overexpress DEFB1 into nude mice. DEFB1 is cloned into pBI-EGFP vector, which has a bidirectional tetracycline responsible promoter. Tet-Off Cell lines are generated by transfecting pTet-Off into DU145, PC3 and LNCaP cells and selecting with G418. The pBI-EGFP-DEFB1 plasmid is co-transfected with pTK-Hyg into the Tet-off cell lines and selected with hygromycin. Only single-cell suspensions with a viability of >90% are used. Each animal receives approximately 500,000 cells administered subcutaneously into the right flank of female nude mice. There are two groups, a control group injected with vector only clones and a group injected with the DEFB1 over-expressing clones. 35 mice are in each group as determined by a statistician. Animals are weighed twice weekly, tumor growth monitored by calipers and tumor volumes determined using the following formula: volume=0.5×(width)2×length. All animals are sacrificed by $CO_2$ overdose when tumor size reaches 2 mm³ or 6 months following implantation; tumors are excised, weighed and stored in neutral buffered formalin for pathological examination. Differences in tumor growth between the groups are descriptively characterized through summary statistics and graphical displays. Statistical significance is evaluated with either the t-test or non-parametric equivalent.

Example V

Expression of PAX2 siRNA Results in Up-Regulation of DEFB1 Expression and Tumor Shrinkage In Vivo Hairpin PAX2 siRNA template oligonucleotides utilized in the in vitro studies are utilized to examine the effect of the up-regulation of DEFB1 expression in vivo. The sense and antisense strand (see Table 4) are annealed and cloned into pSilencer 2.1 U6 hygro siRNA expression vector (Ambion) under the control of the human U6 RNA pol III promoter. The cloned plasmid is sequenced, verified and transfected into PC3, Du145, and LNCap cell lines. Scrambled shRNA is cloned and used as a negative control in this study. Hygromycin resistant colonies are selected, cells are introduced into the mice subcutaneously and tumor growth is monitored as described above.

Example VI

Small Molecule Inhibitors of PAX2 Binding Results in Up-Regulation of DEFB1 Expression and Tumor Shrinkage In Vivo The DNA recognition sequence for PAX2 binding resides in the DEFB1 promoter between nucleotides −75 and −71 [+1 refers to the transcriptional start site]. Short oligonucleotides complementary to the PAX2 DNA-binding domain are provided. Examples of such oligonucleotides include the 20-mer and 40-mer oligonucleotides containing the GTTCC (SEQ ID NO: 2) recognition sequence provided below. These lengths were randomly selected, and other lengths are expected to be effective as blockers of binding. As a negative control, oligonucleotides with a scrambled sequence (CTCTG) (SEQ ID NO: 22) were designed to verify specificity. The oligonucleotides are transfected into the prostate cancer cells and the HPrEC cells with lipofectamine reagent or Codebreaker transfection reagent (Promega, Inc). In order to confirm DNA-protein interactions, double stranded oligonucleotides will be labeled with [32P] dCTP and electrophoretic mobility shift assays are performed. In addition, DEFB1 expression is monitored by QRT-PCR and Western analysis following treatment with oligonucleotides. Finally, cell death is detected by MTT assay and flow cytometry as previously described.

```
Recognition Sequence #1:
                                   (SEQ ID NO: 18)
CTCCCTTCAGTTCCGTCGAC Recognition Sequence #2:
                                   (SEQ ID NO: 19)
CTCCCTTCACCTTGGTCGAC Scramble Sequence #1:
                                   (SEQ ID NO: 23)
CTCCCTTCACTCTGGTCGAC Recognition Sequence #3:
                                   (SEQ ID NO: 20)
ACTGTGGCACCTCCCTTCAGTTCCGTCGACGAGGTTGTGC Recognition Sequence #4:
                                   (SEQ ID NO: 21)
ACTGTGGCACCTCCCTTCACCTTGGTCGACGAGGTTGTGC Scramble Sequence #2:
                                   (SEQ ID NO: 24)
ACTGTGGCACCTCCCTTCACTCTGGTCGACGAGGTTGTGC
```

Further examples of oligonucleotides of the invention include:

```
Recognition Sequence #1:
                                        (SEQ ID No: 25)
5'-AGAAGTTCACCCTTGACTGT-3'

Recognition Sequence #2:
                                        (SEQ ID No: 26)
5'-AGAAGTTCACGTTCCACTGT-3'

Scramble Sequence #1:
                                        (SEQ ID No: 27)
5'-AGAAGTTCACGCTCTACTGT-3'

Recognition Sequence #3:
                                        (SEQ ID No: 28)
5'-TTAGCGATTAGAAGTTCACCCTTGACTGTGGCACCTCCC-3'

Recognition Sequence #4:
                                        (SEQ ID No: 29)
5'-GTTAGCGATTAGAAGTTCACGTTCCACTGTGGCACCTCCC-3'

Scramble Sequence #2:
                                        (SEQ ID No: 30)
5'-GTTAGCGATTAGAAGTTCACGCTCTACTGTGGCACCTCCC-3'
```

This set of alternative inhibitory oligonucleotides represents the recognition sequence (along with the CCTTG (SEQ ID NO: 1) core sequence) for the PAX2 binding domain and homeobox. These include actual sequences from the DEFB1 promoter.

The PAX2 gene is required for the growth and survival of various cancer cells including prostate. In addition, the inhibition of PAX2 expression results in cell death mediated by the innate immunity component DEFB1. Suppression of DEFB1 expression and activity is accomplished by binding of the PAX2 protein to a GTTCC (SEQ ID NO: 2) recognition site in the DEFB1 promoter. Therefore, this pathway provides a viable therapeutic target for the treatment of prostate cancer. In this method, the sequences bind to the PAX2 DNA binding site and block PAX2 binding to the DEFB1 promoter thus allowing DEFB1 expression and activity. The oligonucleotide sequences and experiment described above are examples of and demonstrate a model for the design of additional PAX2 inhibitor drugs.

Given that the GTTCC (SEQ ID NO: 2) sequence exists in interleukin-3, interleukin-4, the insulin receptor and others, PAX2 regulates their expression and activity as well. Therefore the PAX2 inhibitors disclosed herein have utility in a number of other diseases including those directed related to inflammation including prostatitis and benign prostatic hypertrophy (BPH).

Example VII

Loss of DEFB1 Expression Results in Increased Tumorigenesis

Generation of Loss of Function Mice

The Cre/loxP system has been useful in elucidating the molecular mechanisms underlying prostate carcinogenesis. Here a DEFB1 Cre conditional KO is used for inducible disruption within the prostate. The DEFB1 Cre conditional KO involves the generation of a targeting vector containing loxP sites flanking DEFB1 coding exons, targeted ES cells with this vector and the generation of germline chimeric mice from these targeted ES cells. Heterozygotes are mated to prostate-specific Cre transgenics and heterozygous intercross is used to generate prostate-specific DEFB1 KO mice. Four genotoxic chemical compounds have been found to induce prostate carcinomas in rodents: N-methyl-N-nitrosourea (MNU), N-nitrosobis 2-oxopropyl. amine (BOP), 3,2X-dimethyl-4-amino-biphenyl (MAB) and 2-amino-1-methyl-6-phenylimidazow 4,5-bxpyridine (PhIP). DEFB1-transgenic mice are treated with these carcinogenic compounds via intra-gastric administration or i.v. injection for prostate adenoma and adenocarcinoma induction studies. Prostate samples are studied for differences in tumor growth and changes gene expression though histological, immunohistological, mRNA and protein analyses.

Generation of GOF Mice

For PAX2 inducible GOF mice, PAX2 GOF (bi-transgenic) and wild-type (mono-transgenic) littermates are administered doxycycline (Dox) from 5 weeks of age to induce prostate-specific PAX2 expression. Briefly, PROBASIN-rtTA mono-transgenic mice (prostate cell-specific expression of tet-dependent rtTA inducer) are crossed to our PAX2 transgenic responder lines. For induction, bi-transgenic mice are fed Dox via the drinking water (500 mg/L freshly prepared twice a week). Initial experiments verify low background levels, good inducibility and cell-type specific expression of PAX2 and the EGFP reporter using transgenic founder line in bi-transgenic mice. Regarding experimental group sizes, 5-7 age- and sex-matched individuals in each group (wild-type and GOF) allow for statistical significance. For all animals in this study, prostate tissues are collected initially at weekly intervals for analysis and comparison, to determine carcinogenic time parameters.

PCR Genotyping, RT-PCR and qPCR

PROBASIN-rtTA transgenic mice are genotyped using the following PCR primers and conditions: PROBASIN5 (forward) 5'-ACTGCCCATTGCCCAAACAC-3' (SEQ ID NO: 31); RTTA3 (reverse) 5'-AAAATCTTGCCAGCTTTCCCC-3' (SEQ ID NO: 32); 95° C. denaturation for 5 min, followed by 30 cycles of 95° C. for 30 sec, 57° C. for 30 sec, 72° C. for 30 sec, followed by a 5 min extension at 72° C., yielding a 600 bp product. PAX2 inducible transgenic mice are genotyped using the following PCR primers and conditions: PAX2 For 5'-GTCGGTTACGGAGCGGACCGGAG-3'(SEQ ID NO: 33); Rev5'IRES 5'-TAACATATAGACAAACGCACACCG-3' (SEQ ID NO: 34); 95° C. denaturation for 5 min, followed by 34 cycles of 95° C. for 30 sec, 63° C. for 30 sec, 72° C. for 30 sec, followed by a 5 min extension at 72° C., yielding a 460 bp product. Immortomouse hemizygotes are be genotyped using the following PCR primers and conditions: Immol1, 5'-GCGCTTGTGTC GCCATTGTATTC-3' (SEQ ID NO: 35); Immol2, 5'-GTCACACCACAGAAGTAAGGTTCC-3' (SEQ ID NO: 36); 94° C. 30 sec, 58° C. 1 min, 72° C. 1 min 30 sec, 30 cycles to yield a 1 kb transgene band. For genotyping PAX2 knockout mice, the following PCR primers and conditions are used: PAX2 For 5'-GTCGGTTACGGAGCG-GACCGGAG-3' (SEQ ID NO: 37); PAX2Rev 5'-CACA-GAGCATTGGCGATCTCGATGC-3' (SEQ ID NO: 38); 94° C. 1 min, 65° C. 1 min, 72° C. 30 sec, 36 cycles to yield a 280 bp band.

DEFB1 Peptide Animal Studies

Six-week-old male athymic (nude) mice purchased from Charles River Laboratories are injected sub-cutaneously over the scapula with $10^6$ viable PC3 cells. One week after injection, the animals are randomly allocated to one of three groups—group I: control; group II: intraperitoneal injections of DEFB1, 100 µg/day, 5 days a week, for weeks 2-14; group III: intraperitoneal injections of DEFB1, 100 mg/day, 5 days a week, for weeks 8-14. Animals are maintained in sterile housing, four animals to a cage, and observed on a daily basis. At 10-day intervals, the tumors are measured by using calipers, and the volumes of the tumors are calculated by using $V=(L \times W2)/2$.

APPENDIX A

```
LOCUS       HUMPAX201               7331 bp    DNA     linear   PRI 28-JAN-2002
DEFINITION  Homo sapiens paired-box protein (PAX2) gene, promoter and exon 1.
ACCESSION   L09748 AF433639
VERSION     L09748.2  GI:18141563
KEYWORDS    .
SEGMENT     1 of 3
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Catarrhini;
            Hominidae; Homo.
REFERENCE   1  (bases 7096 to 7291)
  AUTHORS   Stapleton, P., Weith, A., Urbanek, P., Kozmik, Z. and Busslinger, M.
  TITLE     Chromosomal localization of seven PAX genes and cloning of a novel
            family member, PAX-9
  JOURNAL   Nat. Genet. 3 (4), 292-298 (1993)
  PUBMED    7981748
REFERENCE   2  (bases 1 to 7331)
  AUTHORS   Pfeffer, P. L., Payer, B., Reim, G., di Magliano, M. P. and Busslinger, M.
  TITLE     The activation and maintenance of Pax2 expression at the
            mid-hindbrain boundary is controlled by separate enhancers
  JOURNAL   Development 129 (2), 307-318 (2002)
  PUBMED    11807024
REFERENCE   3  (bases 7096 to 7291)
  AUTHORS   Stapleton, P., Weith, A., Urbanek, P., Kozmik, Z. and Busslinger, M.
  TITLE     Direct Submission
  JOURNAL   Submitted (12-JUN-1993) Research Institute of Molecular Pathology,
            Dr. Bohr-Gasse 7, Vienna, Austria
REFERENCE   4  (bases 1 to 7331)
  AUTHORS   Pfeffer, P. L. and Busslinger, M.
  TITLE     Direct Submission
  JOURNAL   Submitted (14-JAN-2002) Research Institute of Molecular Pathology,
            Dr. Bohr-Gasse 7, Vienna, Austria
  REMARK    Sequence update by submitter
COMMENT     On Jan. 14, 2002 this sequence version replaced gi:292378.
FEATURES             Location/Qualifiers
     source          1..7331
                     /organism="Homo sapiens"
                     /mol_type="genomic DNA"
                     /db_xref="taxon:9606"
                     /chromosome="10"
                     /map="10q22.1-q24.3"
     gene            order(2034..7331,L09746.1:1..206,L09747.1:1..>238)
                     /gene="PAX2"
     enhancer        2034..2518
                     /gene="PAX2"
                     /note="distal (late) enhancer"
     enhancer        2850..2974
                     /gene="PAX2"
                     /note="intermediate (early) enhancer"
     enhancer        3516..3898
                     /gene="PAX2"
                     /note="proximal (late) enhancer"
     mRNA            join(6532..7271,L09746.1:21..186,L09747.1:21..>218)
                     /gene="PAX2"
                     /product="paired-box protein"
     exon            6532..7271
                     /gene="PAX2"
                     /number=1
     CDS             join(7229..7271,L09746.1:21..186,L09747.1:21..>218)
                     /gene="PAX2"
                     /codon_start=1
                     /product="paired-box protein"
                     /protein_id="AAC41711.1"
                     /db_xref="GI:553607"
```

/translation="MDMHCKADPFSAMHRHGGVNQLGGVFVNGRPLPDVVRQRIVELA

HQGVRPCDISRQLRVSHGCVSKILGRYYETGSIKPGVIGGSKPKVATPKVVDKIAEYKR

QNPTMFAWEIRDRLLAEGICDNDTVPSVSSIN" (SEQ ID NO: 39)

```
ORIGIN
        1 ttcccccttt ccangagggc ctaatccgtt gcgcgcgcgc acgcggacac acacacacac
       61 acacacacac acacacacac acacacggcc cccatagcca ccgcaactct cagcagcagn
      121 ncctagctcc tctgacccga ggcccaaga cggcgggcac aggaacccct gggacgtcct
      181 ggctccaggc tggacgtagg cggaggtggc aggagtggac aaacccaggc gggtcccacg
```

APPENDIX A-continued

```
 241 acgccccttt cctcgggtct ctccttgttt cagccagccg ctctcgcccc tggtcccctc
 301 ttccctgcgt tagggtcctt tgtctccagc cacctcgcag cctgtccccg cctcggcggc
 361 cctgcccttt gggcctccca gatctctctg gcgggtcccc ctgccttacc agctcccggc
 421 tgtggcgcgc tcttcgcctg ctcctcacat ncacacagct gctgggagag gaggaaggaa
 481 aggcggncgc gccgcggatg gatccgagac ggtagatttg gtgccggctc gcaaactctg
 541 ggaaacttaa ngccggttct tccgcccctc tncaactatg nccagcgcgg cccggtcgcg
 601 cgcgctcacc ccgcggggac cctttccttt tcctgtattt cggctcgcgc tgtttcgctt
 661 cctctggtct cccagccttt ggagtggctt ccctggccct gcactccgtt cccttcggc
 721 cgcccccggc tgtcgcctgc ccccaccctc cgcaggtccc acggtcgcgg cggcgatgac
 781 tgtggaggta acgccgggga cgtcctgggt cagcctgcac cgtctccctc gaccacagcc
 841 cgatgaggcc gcgggctccg ggccggctgc taagagagtt aatcattact tcgccagcga
 901 cactcagcct ccccttccga ctctctcgcc cggcctaggg aggaggggga ggggacagct
 961 ggccaggtgg ggacttcggc ttcgcacaaa ccagcctctt caggcctccc agagacaggt
1021 ggtggcttct cagttccctc ggcaactctc taaggtcctc tttcttcccc tcctgtctct
1081 ccctccttcg agcctcctcc cagccaggcc tctccccacc gtctcctgtc cgctctggct
1141 ttgactgatt aactgcaggt cctgggagaa ccaactttct ttgtttggaa ccggaccgga
1201 cgggatttcc ttccctaggt ctccgccaat gggccagctc ctcccgacgg ttttggcgga
1261 ctggctgaag aggaccgcgc ctgaggccac aattaacccg gctgttggtg gtggtggttg
1321 gggggtgggc agtgaggaat ttaaccgatc ctctagcagc tgcgctggtg cagttgggag
1381 gggggtgcag gaagtgggaa tggaggagtg gcaggaggta tagacagagg gaagaacgat
1441 aaacctggac aggtgtggca tagccaatag aaggggaaac aaaataaaac aggaaggcgg
1501 cgcggggagg aatccccagt aacctttata ggattgaagt tgggtggaaa acgccacctc
1561 ctgccctacc ttagcactca gatccctcct ttacctcttt gtgaaagggt aagagttcag
1621 aaagctggcc atttactcca taatctacta gagaaatgtc tgggtttgca aaatgcctat
1681 tgattagctc catggagtag acaagacagg cgtaattatc cccattttac aggtgagaaa
1741 actgagtctc aaagaagcaa agggactgtg tatgtagtgg ctgtcacttt ttcctgtagg
1801 ctgtggggtg agtggcccct ttagctgtgc agaggtccat gggtatctag ggaggcggta
1861 caggctgtgt ccaggtctga gccagaagta ccagggcctc acggggctcc tagccctttt
1921 agcttgttct ctgttggaca ggaccttcac tcttactctc tagacctgct ggctgggttt
1981 ctcccagctt cgctattttt tcagttccct agtagagtgg cccatgggcg gtagccacct
2041 ggctggcccg tgccactaag aggcagcttt ggtggccaag tggcttgcat tgttgttgct
2101 cctcaaaggg cctgtgaagg gctgggcagg tcgcaaagac ctcttgtgag gggaaagcta
2161 gattaaaggg ggtaaggatc ctggaggata aaggccaagc acgtgcgcct ggactccaca
2221 ggaccaacag accgagcggg cggggccngc tgggagtcag gccccccggg cttcacgcag
2281 ggagcccaaa tattgggaac aaaagcagga aaagaagagt gagagcagga gggagggagg
2341 gagcgaggaa gcagaaatta gggggtctta gatgaaaaaa aaaagaaagt agctttaggg
2401 ggaatgtgct gtggagtgtg aaattgcagc ccatggtgct ccatattgta ccagaagctc
2461 ttccaaaaaa aaaaaaaaaa accatcctcc aacgtgacca gagggccagg caggggggaag
2521 ggcgggggaga gaatgggggag gaggagggggg aaaggccggg caggagccgg tcaggccttt
2581 ctgcggaagg ggctgggggtg taagtttcgg ctccctggga tctgacagcc gagggtatgc
```

APPENDIX A-continued

```
2641 gccctggggt gcgccgggac ccagagggcg agtgagcctc ggttggtcgg ctctggagtt
2701 cggttgtcag aagaactttt atttttcttt ttggtggtga cttctaaaag tgggaataat
2761 ccagaaatga agctcagctg cggagctgca gctctgttct ccctctctcc cctgcctttc
2821 tgcttctctt cccttcggac tacttttctc cccttggttc taaatagctt tttcccctct
2881 gaactttaat gcatttaatt tggtccgcgc tgtggggagc atttcctggg gagatgcatt
2941 taatttcgga atttctaatc ccctccctca gaccccggtc ctagctcccc tagccgctcc
3001 ccgggaagtg aaggaggaa ggcaggtccc ggccacgggg gaggggcgcg gctgggatgc
3061 tcccgcggcc ccctccgtct caccaaggct cagccgcctt cccaagctac tggaggccgg
3121 gcgcctgggc cccgggtcag ggccctgcan gaagaagaga ggcaacccc gctttctgcc
3181 ttttcttcgc ctgggcaaga aaacgctggg ccaggaact ggaaaccgga aaacaggaga
3241 aagggttttnt ggaaggcanc gggagcgggt ggcagncggg gcancgggca ntggactagg
3301 tctacaccgg cacttcactt ttgcacaaca tgcccagaaa cgcatttgag agccctggag
3361 tcgcgcttgg cttggcttgg ggcgccggtg cgtgggtaca ctcgaggtcg gggtgcctat
3421 ccgccacccc gacacctaca cccagtgcag agcaggcgcg gcccagccag acaaccaggc
3481 cggcagtagc tcggcctgga gggcggaggc aaggttgggg gccgccaggc gcctgggcaa
3541 gcctggcagg aagggagcc gagaaggcaa aggagccgag atccacaagg aagattnntt
3601 gggcagatca gatgcacaga ggcggctaat gaagcaaatc ccgagatggg tttcagagca
3661 actccccaaa agtttatttt gcctttaaat ttccgcaggg aggcgggctc cttgtttgaa
3721 gtgtaaatgc ccctaggttg gggggtggaa gggccgcttt gaaaacacca gagagaaaag
3781 gttcatttag aggcggacgg gaaaagcaac caaccctgac aggtcggagc ccgggtagtg
3841 tttggggttg ggtngttttc tttctttctc tttcttttcc cctttcctct tctttcttcc
3901 cttttgtgnn ttttnnttgt ttttttttntn ttnttttttnt ttaantggct ttcttgcttc
3961 cccccacccc tctactagac tctatagaag aaagagaaca gaaaaggggg agtcagagga
4021 gcggccagtg actggatgaa ggccagccct tcatcctgga gccccaggag aaggcagagc
4081 tttggagaaa aggggttcct aatctccagg gagcattact ctttgactct ctagacccag
4141 gaatgggctg gacgctaatg gggaagcggc caggaacccg gcctggcgga agagtgagtg
4201 tccagctagt gcagtgctgg gaagacgatc ccaggagcag gggggactct caggggctac
4261 ctgggaatgg gactatcaga agggtcttta ctcctcanaa ggtgcatgtg aaggacaggt
4321 gtgtgaggac aacttccagc acacttggcg cattaagtcc ccttctctac aaaatggaaa
4381 atccttctcg cccaacatgt gaaaatgctt gttgtgggca cccacatttc atggtacttg
4441 taacatagga catgtctagc tggttctaga aaatctgtg tctgtgtgga aggggggggg
4501 tttactcaca gctttcttcc ttcaatagtt cacacacccc gagacaaatt cctggatgac
4561 caacttggag agacctgggg caaaggttac tttagttctg agctcctcta aataaggacc
4621 ctttctcaac gttcctttca ccccagttct gggttaatta cttccagtta gtgcgtgttc
4681 gtgggttgt gaggccaaag caaacccggg agcgccatct gcaggcctca agaggaagag
4741 actgaccttta gaggctaggc cctgcgtctt caacctctag cccaagggaa ccaacctgcc
4801 tagccaccca agggaagtgg gataggggct gggaggggca ggcggtgagg agtgttttcc
4861 tcccagactt taccccgcag gtggattaag cttattgggc tctggaggat acaggaggga
4921 gggcaaatgc caggatccca gcggacccag gccccacagg agtgagaggc tcagaacctc
4981 gtcccgctga gcctggcctg agctcctcct gaggaataag ggcatcccaa aaacccgggt
```

APPENDIX A-continued

```
5041 acaagacgcc cagtagtagt agttaggctg agtcaggcag gtgcatctct ccccatggta 5101 tctgccgccc aggctccggc cagagggagg ggagcgcgag tccgcggcgc ttccgcgggg 5161 cgcccggaac tgcagacggg ggctggagga atctcggatt cgggctgcaa gagcgctgcg 5221 caagcttcgc cgagccgccc tttcgcagac ccagggaagc gggggaggg agcgaaggag 5281 ggagagagag ttaaaacatc agcttgaaag tgcccaagat gattttatta agaccgaggg 5341 gaaaattatt ttcatgaaag attctccccg gaatatttct tgtacttaac ccagttagga 5401 agacaaaggg cttctttctg cctggtgcgg tgcgagcgga ccccagcgag caaggagct 5461 agtgccaaag agaactgcgg aggctccggc aggagtgggg acgtccccgt ggttgcgcct 5521 cctgcgctcg ccccggatcc accgagctag cagcgggcgg cgctcagccg cgtccgcagc 5581 ctcctcttct ccccagccgg ggagagccag cctcgtctcc cacatcctct gccgccagcg 5641 acctgcagct ccgcactgtt tccctcccct gtaccccctt cccagtcacc cgagggttca 5701 gaaaccaagt cccccggctc tcccgccatc cgctgggtcc caccgaggca ggtgggtact 5761 cgccggaggt cttcagctcg attctgaacc aagcgttctg gactgcccag acccggtggg 5821 caaggggact ggggaggccc tgcgcacagt cgcgtggaac gggaggggac aagacaaact 5881 gctggacact tttccgtgga atgagaagtg gggggtgcgt gggtgggaag gtacctccgg 5941 agggaaaggc caaagggaag gaccagaaag agaggaagga agagccggga aggaacggaa 6001 gggaactcag agccgagggt ggtgggggttg gggctaggga tgcgcactgg gcccggggcc 6061 gcgcggccca ggcgggcact ggccagtgga tggcagggct gggcgagtta gaactgagag 6121 cccggcttca cagcgcagcg cgctccgagg ccctctgtcg ttacctgaat attcattaga 6181 ctgaccgctc tttatcctta tctaacgttt atcttatcgg cgagtttcgt ttctcagtgt 6241 agttttaatc ccgggctccc attccccctc ccccggtccg ctcccctccc tccctcttcc 6301 ttcgccggct gctccctccc tccctccctc ccatttctcc ctcccctgcc ctccccttgc 6361 cggcaccgga gtgacaggct cggggccctc ctcgccgaag ctcggggctc cagcgctggc 6421 gaatcacaga gtggtggaat ctattgcctt tgtctgacaa gtcatccatc tcccggcgcg 6481 gggaggggga ggaggtctgg aggggggcttt gcagctttta gagagacaca caccgggagc 6541 cgaggctcca gtctccggcc gagtcttcta gcagccgcaa cccacctggg gccagcccag 6601 agctgccagc gccgctcggc tccctccctc cctcccggcc cttcggccgc ggcggcgtgc 6661 gcctgccttt tccgggggcg ggggcctggc ccgcgcgctc cctcccgca ggcgccacct 6721 cggacatccc cgggattgct acttctctgc caacttcgcc aactcgccag cacttggaga 6781 ggcccggctc ccctcccggc gccctctgac cgcccccgcc ccgcgcgctc tccgaccacc 6841 gcctctcgga tgaacaggtt ccaggggagc tgagcgagtc gcctcccccg cccagcttca 6901 gccctggctg cagctgcagc gcgagccatg cgcccccagt gcaccccggc ccggcccacc 6961 gccccggggc cattctgctg accgcccagc cccgagcccc gacagtggca agttgcggct 7021 actgcggttg caagctccgg ccaacccgga ggagcccag cggggagcgc agtgttgcgc 7081 ccccgcccc cgcgcgcgcc gcagcagccg ggcgttcact catcctccct cccccaccgt 7141 ccctcccttt tctcctcaag tcctgaagtt gagtttgaga ggcgacacgg cggcggcggc 7201 cgcgctgctc ccgctcctct gcctcccat ggatatgcac tgcaaagcag accccttctc 7261 cgcgatgcac cgtgagtacc cgcgcccggc tcctgtcccg gctcgggctc tccgtcccaa 7321 ccctgtccag t (SEQ ID NO: 40)
```

APPENDIX B

```
LOCUS       NM_003987   4276 bp    mRNA    linear   PRI 24-SEP-2005
DEFINITION  Homo sapiens paired box gene 2 (PAX2), transcript variant a, mRNA.
ACCESSION   NM_003987
VERSION     NM_003987.2  GI:34878698
KEYWORDS    .
SOURCE      Homo sapiens (human)
ORGANISM    Homo sapiens
            Eukaryota; Metazoa; Chordata; Craniata; Vertebrata; Euteleostomi;
            Mammalia; Eutheria; Euarchontoglires; Primates; Catarrhini;
            Hominidae; Homo.
REFERENCE   1 (bases 1 to 4276)
AUTHORS     Yoshimura, K., Yoshida, S., Yamaji, Y., Komori, A., Yoshida, A.,
            Hatae, K., Kubota, T. and Ishibashi, T.
TITLE       De novo insG619 mutation in PAX2 gene in a Japanese patient with
            papillorenal syndrome
JOURNAL     Am. J. Ophthalmol. 139 (4), 733-735 (2005)
PUBMED      15808183
REMARK      GeneRIF: Molecular genetic analysis of the PAX2 gene in combination
            with renal ultrasonography can help in making an earlier diagnosis
            of the disease.
REFERENCE   2 (bases 1 to 4276)
AUTHORS     Mazal, P. R., Stichenwirth, M., Koller, A., Blach, S., Haitel, A. and
            Susani, M.
TITLE       Expression of aquaporins and PAX-2 compared to CD10 and cytokeratin
            7 in renal neoplasms: a tissue microarray study
JOURNAL     Mod. Pathol. 18 (4), 535-540 (2005)
PUBMED      15502805
REMARK      GeneRIF: PAX-2 is a reliable marker for clear cell renal cell
            carcinomas of lower grades but not for higher grades.
REFERENCE   3 (bases 1 to 4276)
AUTHORS     Higashide, T., Wada, T., Sakurai, M., Yokoyama, H. and Sugiyama, K.
TITLE       Macular abnormalities and optic disk anomaly associated with a new
            PAX2 missense mutation
JOURNAL     Am. J. Ophthalmol. 139 (1), 203-205 (2005)
PUBMED      15652857
REMARK      GeneRIF: A new PAX2 missense mutation, R71T, may cause macular
            abnormalities in addition to anomalies of the optic disk and the
            kidney.
REFERENCE   4 (bases 1 to 4276)
AUTHORS     Buttiglieri, S., Deregibus, M. C., Bravo, S., Cassoni, P., Chiarle, R.,
            Bussolati, B. and Camussi, G.
TITLE       Role of Pax2 in apoptosis resistance and proinvasive phenotype of
            Kaposi's sarcoma cells
JOURNAL     J. Biol. Chem. 279 (6), 4136-4143 (2004)
PUBMED      14627715
REMARK      GeneRIF: expression of Pax2 by Kaposi's sarcoma cells correlated
            with an enhanced resistance against apoptotic signals and with the
            proinvasive phenotype
REFERENCE   5 (bases 1 to 4276)
AUTHORS     Brophy, P. D., Lang, K. M. and Dressler, G. R.
TITLE       The secreted frizzled related protein 2 (SFRP2) gene is a target of
            the Pax2 transcription factor
JOURNAL     J. Biol. Chem. 278 (52), 52401-52405 (2003)
PUBMED      14561758
REMARK      GeneRIF: Pax2 protein regulates expression of secreted frizzled
            related protein 2
REFERENCE   6 (bases 1 to 4276)
AUTHORS     Schimmenti, L. A., Manligas, G. S. and Sieving, P. A.
TITLE       Optic nerve dysplasia and renal insufficiency in a family with a
            novel PAX2 mutation, Arg115X: further ophthalmologic delineation of
            the renal-coloboma syndrome
JOURNAL     Ophthalmic Genet. 24 (4), 191-202 (2003)
PUBMED      14566649
REMARK      GeneRIF: PAX2 mutation is associated with Optic nerve dysplasia and
            renal insufficiency of the renal-coloboma syndrome
REFERENCE   7 (bases 1 to 4276)
AUTHORS     Muratovska, A., Zhou, C., He, S., Goodyer, P. and Eccles, M. R.
TITLE       Paired-Box genes are frequently expressed in cancer and often
            required for cancer cell survival
JOURNAL     Oncogene 22 (39), 7989-7997 (2003)
PUBMED      12970747
REMARK      GeneRIF: The PAX2 gene was frequently expressed in a panel of 406
            common primary tumor tissues and endogenous PAX gene expression is
            often required for the growth and survival of cancer cells
REFERENCE   8 (bases 1 to 4276)
AUTHORS     Gough, S. M., McDonald, M., Chen, X. N., Korenberg, J. R., Neri, A.,
            Kahn, T., Eccles, M. R. and Morris, C. M.
TITLE       Refined physical map of the human PAX2/HOX11/NFKB2 cancer gene
            region at 10q24 and relocalization of the HPV6AI1 viral integration
            site to 14q13.3-q21.1
```

APPENDIX B-continued

```
JOURNAL     BMC Genomics 4 (1), 9 (2003)
PUBMED      12697057
REFERENCE   9 (bases 1 to 4276)
AUTHORS     Hoffmeister, A., Ropolo, A., Vasseur, S., Mallo, G. V., Bodeker, H.,
            Ritz-Laser, B., Dressler, G. R., Vaccaro, M. I., Dagorn, J. C., Moreno, S.
            and Iovanna, J. L.
TITLE       The HMG-I/Y-related protein p8 binds to p300 and Pax2
            trans-activation domain-interacting protein to regulate the
            trans-activation activity of the Pax2A and Pax2B transcription
            factors on the glucagon gene promoter
JOURNAL     J. Biol. Chem. 277 (25), 22314-22319 (2002)
PUBMED      11940591
REMARK      GeneRIF: The HMG-I/Y-related protein p8 binds to p300 and Pax2
            trans-activation domain-interacting protein to regulate the
            trans-activation activity of the Pax2A and Pax2B transcription
            factors on the glucagon gene promoter.
REFERENCE   10 (bases 1 to 4276)
AUTHORS     Cai, Y., Lechner, M. S., Nihalani, D., Prindle, M. J., Holzman, L. B. and
            Dressler, G. R.
TITLE       Phosphorylation of Pax2 by the c-Jun N-terminal kinase and enhanced
            Pax2-dependent transcription activation
JOURNAL     J. Biol. Chem. 277 (2), 1217-1222 (2002)
PUBMED      11700324
REFERENCE   11 (bases 1 to 4276)
AUTHORS     Becker, K., Beales, P. L., Calver, D. M., Matthijs, G. and Mohammed, S. N.
TITLE       Okihiro syndrome and acro-renal-ocular syndrome: clinical overlap,
            expansion of the phenotype, and absence of PAX2 mutations in two
            new families
JOURNAL     J. Med. Genet. 39 (1), 68-71 (2002)
PUBMED      11826030
REMARK      GeneRIF: The absence of PAX2 mutations has been identified in two
            families with histories of clinical overlap of Okihiro and
            acro-renal-ocular syndromes.
REFERENCE   12 (bases 1 to 4276)
AUTHORS     Eccles, M. R., He, S., Legge, M., Kumar, R., Fox, J., Zhou, C., French, M.
            and Tsai, R. W.
TITLE       PAX genes in development and disease: the role of PAX2 in
            urogenital tract development
JOURNAL     Int. J. Dev. Biol. 46 (4), 535-544 (2002)
PUBMED      12141441
REMARK      Review article
            GeneRIF: PAX2 has a role in urogenital tract development and
            disease [review]
REFERENCE   13 (bases 1 to 4276)
AUTHORS     Chung, G. W., Edwards, A. O., Schimmenti, L. A., Manligas, G. S.,
            Zhang, Y. H. and Ritter, R. III.
TITLE       Renal-coloboma syndrome: report of a novel PAX2 gene mutation
JOURNAL     Am. J. Ophthalmol. 132 (6), 910-914 (2001)
PUBMED      11730657
REMARK      GeneRIF: The causal relationship between PAX2 gene mutations and
            renal-coloboma syndrome is further supported
REFERENCE   14 (bases 1 to 4276)
AUTHORS     Nishimoto, K., Iijima, K., Shirakawa, T., Kitagawa, K., Satomura, K.,
            Nakamura, H. and Yoshikawa, N.
TITLE       PAX2 gene mutation in a family with isolated renal hypoplasia
JOURNAL     J. Am. Soc. Nephrol. 12 (8), 1769-1772 (2001)
PUBMED      11461952
REFERENCE   15 (bases 1 to 4276)
AUTHORS     Ritz-Laser, B., Estreicher, A., Gauthier, B. and Philippe, J.
TITLE       The paired homeodomain transcription factor Pax-2 is expressed in
            the endocrine pancreas and transactivates the glucagon gene
            promoter
JOURNAL     J. Biol. Chem. 275 (42), 32708-32715 (2000)
PUBMED      10938089
REFERENCE   16 (bases 1 to 4276)
AUTHORS     Lechner, M. S., Levitan, I. and Dressler, G. R.
TITLE       PTIP, a novel BRCT domain-containing protein interacts with Pax2
            and is associated with active chromatin
JOURNAL     Nucleic Acids Res. 28 (14), 2741-2751 (2000)
PUBMED      10908331
REFERENCE   17 (bases 1 to 4276)
AUTHORS     Tavassoli, K., Ruger, W. and Horst, J.
TITLE       Alternative splicing in PAX2 generates a new reading frame and an
            extended conserved coding region at the carboxy terminus
JOURNAL     Hum. Genet. 101 (3), 371-375 (1997)
PUBMED      9439670
REFERENCE   18 (bases 1 to 4276)
AUTHORS     Dahl, E., Koseki, H. and Balling, R.
TITLE       Pax genes and organogenesis
JOURNAL     Bioessays 19 (9), 755-765 (1997)
```

APPENDIX B-continued

```
PUBMED      9297966
REMARK      Review article
REFERENCE   19 (bases 1 to 4276)
AUTHORS     Schimmenti, L. A., Cunliffe, H. E., McNoe, L. A., Ward, T. A., French, M. C.,
            Shim, H. H., Zhang, Y. H., Proesmans, W., Leys, A., Byerly, K. A.,
            Braddock, S. R., Masuno, M., Imaizumi, K., Devriendt, K. and Eccles, M. R.
TITLE       Further delineation of renal-coloboma syndrome in patients with
            extreme variability of phenotype and identical PAX2 mutations
JOURNAL     Am. J. Hum. Genet. 60 (4), 869-878 (1997)
PUBMED      9106533
REFERENCE   20 (bases 1 to 4276)
AUTHORS     Narahara, K., Baker, E., Ito, S., Yokoyama, Y., Yu, S., Hewitt, D.,
            Sutherland, G. R., Eccles, M. R. and Richards, R. I.
TITLE       Localisation of a 10q breakpoint within the PAX2 gene in a patient
            with a de novo t(10; 13) translocation and optic nerve
            coloboma-renal disease
JOURNAL     J. Med. Genet. 34 (3), 213-216 (1997)
PUBMED      9132492
REFERENCE   21 (bases 1 to 4276)
AUTHORS     Dehbi, M., Ghahremani, M., Lechner, M., Dressler, G. and Pelletier, J.
TITLE       The paired-box transcription factor, PAX2, positively modulates
            expression of the Wilms' tumor suppressor gene (WT1)
JOURNAL     Oncogene 13 (3), 447-453 (1996)
PUBMED      8760285
REFERENCE   22 (bases 1 to 4276)
AUTHORS     Sanyanusin, P., Norrish, J. H., Ward, T. A., Nebel, A., McNoe, L. A. and
            Eccles, M. R.
TITLE       Genomic structure of the human PAX2 gene
JOURNAL     Genomics 35 (1), 258-261 (1996)
PUBMED      8661132
REFERENCE   23 (bases 1 to 4276)
AUTHORS     Sanyanusin, P., Schimmenti, L. A., McNoe, L. A., Ward, T. A.,
            Pierpont, M. E., Sullivan, M. J., Dobyns, W. B. and Eccles, M. R.
TITLE       Mutation of the PAX2 gene in a family with optic nerve colobomas,
            renal anomalies and vesicoureteral reflux
JOURNAL     Nat. Genet. 9 (4), 358-364 (1995)
PUBMED      7795640
REFERENCE   24 (bases 1 to 4276)
AUTHORS     Ward, T. A., Nebel, A., Reeve, A. E. and Eccles, M. R.
TITLE       Alternative messenger RNA forms and open reading frames within an
            additional conserved region of the human PAX-2 gene
JOURNAL     Cell Growth Differ. 5 (9), 1015-1021 (1994)
PUBMED      7819127
REFERENCE   25 (bases 1 to 4276)
AUTHORS     Noll, M.
TITLE       Evolution and role of Pax genes
JOURNAL     Curr. Opin. Genet. Dev. 3 (4), 595-605 (1993)
PUBMED      8241771
REMARK      Review article
REFERENCE   26 (bases 1 to 4276)
AUTHORS     Stapleton, P., Weith, A., Urbanek, P., Kozmik, Z. and Busslinger, M.
TITLE       Chromosomal localization of seven PAX genes and cloning of a novel
            family member, PAX-9
JOURNAL     Nat. Genet. 3 (4), 292-298 (1993)
PUBMED      7981748
REFERENCE   27 (bases 1 to 4276)
AUTHORS     Pilz, A. J., Povey, S., Gruss, P. and Abbott, C. M.
TITLE       Mapping of the human homologs of the murine paired-box-containing
            genes
JOURNAL     Mamm. Genome 4 (2), 78-82 (1993)
PUBMED      8431641
REFERENCE   28 (bases 1 to 4276)
AUTHORS     Eccles, M. R., Wallis, L. J., Fidler, A. E., Spurr, N. K., Goodfellow, P. J.
            and Reeve, A. E.
TITLE       Expression of the PAX2 gene in human fetal kidney and Wilms' tumor
JOURNAL     Cell Growth Differ. 3 (5), 279-289 (1992)
PUBMED      1378753
COMMENT     REVIEWED REFSEQ: This record has been curated by NCBI staff. The
            reference sequence was derived from U45255.1 and BM671839.1.
            On Sep. 22, 2003 this sequence version replaced gi:4557822.
            Summary: PAX2 encodes paired box gene 2, one of many human
            homologues of the Drosophila melanogaster gene prd. The central
            feature of this transcription factor gene family is the conserved
            DNA-binding paired box domain. PAX2 is believed to be a target of
            transcriptional supression by the tumor supressor gene WT1.
            Mutations within PAX2 have been shown to result in optic nerve
            colobomas and renal hypoplasia. Alternative splicing of this gene
            results in multiple transcript variants.
            Transcript Variant: This variant (a) uses an alternate in-frame
            splice site in the 3' coding region, compared to variant e,
```

APPENDIX B-continued

```
                    resulting in a shorter protein (isoform a) that has a shorter,
                    distinct C-terminus compared to isoform e.
                    COMPLETENESS: complete on the 3' end.
FEATURES            Location/Qualifiers
source              1..4276
                    /organism="Homo sapiens"
                    /mol_type="mRNA"
                    /db_xref="taxon:9606"
                    /chromosome="10"
                    /map="10q24"
gene                1..4276
                    /gene="PAX2"
                    /db_xref="GeneID:5076"
                    /db_xref="HGNC:8616"
                    /db_xref="MIM:167409"
CDS                 687..1937
                    /gene="PAX2"
                    /note="PAX2 gene is a member of the paired-box containing
                    genes which encode transcription factors involved in
                    embryonic and fetal development; the gene product is
                    nuclear protein which binds DNA
                    isoform a is encoded by transcript variant a; paired box
                    homeotic gene 2;
                    go_component: nucleus [goid 0005634][evidence IEA];
                    go_function: ATP binding [goid 0005524][evidence IEA];
                    go_function: DNA binding [goid 0003677][evidence IEA];
                    go_function: DNA binding [goid 0003677][evidence TAS]
                    [pmid 9106533];
                    go_function: nucleoside diphosphate kinase activity [goid
                    0004550][evidence IEA];
                    go_process: development [goid 0007275][evidence IEA];
                    go_process: transcription [goid 0006350][evidence IEA];
                    go_process: CTP biosynthesis [goid 0006241][evidence
                    IEA];
                    go_process: GTP biosynthesis [goid 0006183][evidence
                    IEA];
                    go_process: UTP biosynthesis [goid 0006228][evidence
                    IEA];
                    go_process: axonogenesis [goid 0007409][evidence TAS]
                    [pmid 9106533];
                    go_process: cell differentiation [goid 0030154][evidence
                    IEA];
                    go_process: visual perception [goid 0007601][evidence
                    TAS][pmid 9106533];
                    go_process: regulation of transcription, DNA-dependent
                    [goid 0006355][evidence IEA];
                    go_process: transcription from RNA polymerase II promoter
                    [goid 0006366][evidence TAS][pmid 8760285]"
                    /codon_start=1
                    /product="paired box protein 2 isoform a"
                    /protein_id="NP_003978.2"
                    /db_xref="GI:34878699"
                    /db_xref="GeneID:5076"
                    /db_xref="HGNC:8616"
                    /db_xref="MIM:167409"

/translation="MDMHCKADPFSAMHPGHGGVNQLGGVFVNGRPLPDVVRQRIVELAHQ

GVRPCDISRQLRVSHGCVSKILGRYYETGSIKPGVIGGSKPKVATPKVVDKIAEYKRQN

PTMFAWEIRDRLLAEGICDNDTVPSVSSINRIIRTKVQQPFHPTPDGAGTGVTAPGHTIV

PSTASPPVSSASNDPVGSYSINGILGIPRSNGEKRKRDEVEVYTDPAHIRGGGGLHLVW

TLRDVSEGSVPNGDSQSGVDSLRKHLRADTFTQQQLEALDRVFERPSYPDVFQASEHI

KSEQGNEYSLPALTPGLDEVKSSLSASTNPELGSNVSGTQTYPVVTGRDMASTTLPGYP

PHVPPTGQGSYPTSTLAGMVPGSEFSGNPYSHPQYTAYNEAWRFSNPALL

SSPYYYSAAPRSAPAAAAAAYDRH" (SEQ ID NO: 41)

STS                 1926..2132
                    /gene="PAX2"
                    /standard_name="RH80285"
                    /db_xref="UniSTS:88437"
STS                 3124..3276
                    /gene="PAX2"
                    /standard_name="D10S2478"
                    /db_xref="UniSTS:74159"
```

APPENDIX B-continued

```
polyA_signal    4230..4235
                /gene="PAX2"
polyA_signal    4234..4239
                /gene="PAX2"
polyA_signal    4241..4246
                /gene="PAX2"
polyA_site      4259
                /gene="PAX2"

ORIGIN
       1 aggctccagt ctccggccga gtcttctcgc agccgcaacc cacctggggc cagcccagag
      61 ctgccagcgc cgctcggctc cctccctccc tcccggccct tcggccgcgg cggcgtgcgc
     121 ctgccttttc cgggggcggg ggcctggccc gcgcgctccc ctcccgcagg cgccacctcg
     181 gacatccccg ggattgctac ttctctgcca acttcgccaa ctcgccagca cttggagagg
     241 cccggctccc ctccgcgc cctctgaccg ccccgcccc gcgcgctctc cgaccaccgc
     301 ctctcggatg accaggttcc aggggagctg agcgagtcgc ctcccccgcc cagcttcagc
     361 cctggctgca gctgcagcgc gagccatgcg cccccagtgc accccggccc ggccaccgc
     421 cccggggcca ttctgctgac cgcccagccc cgagccccga cagtggcaag ttgcggctac
     481 tgcagttgca agctccggcc aacccggagg agccccagcg gggagcgcag tgttgcgccc
     541 cccgcccccg cgcgcccgc agcagccggg cgttcactca tcctccctcc cccaccgtcc
     601 ctccctttc tcctcaagtc ctgaagttga gttggagagg cgacacggcg gcggcggccg
     661 cgctgctccc gctcctctgc ctcccatgg atatgcactg caaagcagac cccttctccg
     721 cgatgcaccc agggcacggg ggtgtgaacc agctcggggg ggtgtttgtg aacggccggc
     781 ccctacccga cgtggtgagg cagcgcatcg tggagctggc ccaccagggt gtgcggccct
     841 gtgacatctc ccggcagctg cgggtcagcc acggctgtgt cagcaaaatc ctgggcaggt
     901 actacgagac cggcagcatc aagccgggtg tgatcggtgg ctccaagccc aaagtggcga
     961 cgcccaaagt ggtggacaag attgctgaat acaaacgaca gaacccgact atgttcgcct
    1021 gggagattcg agaccggctc ctggccgagg gcatctgtga caatgacaca gtgcccagcg
    1081 tctcttccat caacagaatc atccggacca aagttcagca gcctttccac ccaacgccgg
    1141 atggggctgg acaggagtg accgcccctg ccacaccat tgttcccagc acggcctccc
    1201 ctcctgtttc cagcgcctcc aatgacccag tgggatccta ctccatcaat gggatcctgg
    1261 ggattcctcg ctccaatggt gagaagagga acgtgatga gttgaggta tacactgatc
    1321 ctgcccacat tagaggaggt ggaggtttgc atctggtctg gactttaaga gatgtgtctg
    1381 agggctcagt ccccaatgga gattcccaga gtggtgtgga cagtttgcgg aagcacttgc
    1441 gagctgacac cttcacccag cagcagctgg aagctttgga tcgggtcttt gagcgtcctt
    1501 cctaccctga cgtcttccag gcatcagagc acatcaaatc agaacagggg aacgagtact
    1561 ccctcccagc cctgacccct gggcttgatg aagtcaagtc gagtctatct gcatccacca
    1621 accctgagct gggcagcaac gtgtcaggca cacagacata cccagttgtg actggtcgtg
    1681 acatggcgag caccactctg cctggttacc ccctcacgt gcccccact ggccagggaa
    1741 gctacccca ctccaccctg cggaatggt gcctgggag cgagttctcc ggcaaccgt
    1801 acagccaccc ccagtacacg gcctacaacg aggcttggag attcagcaac cccgccttac
    1861 taagttcccc ttattattat agtgccgccc ccggtccgc cctgccgct gctgccgctg
    1921 cctatgaccg ccactagtta ccgcggggac cacatcaagc ttcaggccga cagcttcggc
    1981 ctccacatcg tccccgtctg accccacccc ggagggaggg aggaccgacg cgacgcgatg
    2041 cctccggcc accgcccag cctcacccca tcccacgacc cccgcaaccc ttcacatcac
```

APPENDIX B-continued

```
2101 cccctcgaa ggtcggacag gacgggtgga gccgtgggcg ggaccctcag gcccgggccc
2161 gccgccccca gccccgcctg ccgcccctcc ccgcctgcct ggactgcgcg gcgccgtgag
2221 ggggattcgg cccagctcgt cccggcctcc accaagccag ccccgaagcc cgccagccac
2281 cctgccggac tcgggcgcga cctgctggcg cgcgccggat gtttctgtga cacacaatca
2341 gcgcggaccg cagcgcggcc cagccccggg caccgcctc ggacgctcgg gcgccaggag
2401 gcttcgctgg aggggctggg ccaaggagat taagaagaaa acgactttct gcaggaggaa
2461 gagcccgctg ccgaatccct gggaaaaatt cttttccccc agtgccagcc ggactgccct
2521 cgccttccgg gtgtgccctg tcccagaaga tggaatgggg gtgtgggggt ccggctctag
2581 gaacgggctt tgggggcgtc aggtctttcc aaggttggga cccaaggatc gggggccca
2641 gcagcccgca ccgatcgagc cggactctcg gctcttcact gctcctcctg gctgcctag
2701 ttccccaggg cccggcacct cctgctgcga gacccggctc tcagccctgc cttgcccta
2761 cctcagcgtc tcttccacct gctggcctcc cagtttcccc tcctgccagt ccttcgcctg
2821 tcccttgacg ccctgcatcc tcctccctga ctcgcagccc catcggacgc tctcccggga
2881 ccgccgcagg accagtttcc atagactgcg gactgggtc ttcctccagc agttacttga
2941 tgcccctcc cccgacacag actctcaatc tgccggtggt aagaaccggt tctgagctgg
3001 cgtctgagct gctgcggggt ggaagtgggg ggctgcccac tccactcctc ccatcccctc
3061 ccagcctcct cctccggcag gaactgaaca gaaccacaaa aagtctacat ttatttaata
3121 tgatggtctt tgcaaaaagg aacaaaacaa cacaaaagcc caccaggctg ctgctttgtg
3181 gaaagacggt gtgtgtcgtg tgaaggcgaa acccggtgta cataacccct cccctccgc
3241 cccgccccgc ccggccccgt agagtccctg tcgcccgccg gccctgcctg tagatacgcc
3301 ccgctgtctg tgctgtgaga gtcgccgctc gctgggggg aagggggga cacagctaca
3361 cgcccattaa agcacagcac gtcctggggg aggggggcat ttttatgtt acaaaaaaaa
3421 attacgaaag aaaagaaatc tctatgcaaa atgacgaaca tggtcctgtg gactcctctg
3481 gcctgttttg ttggctcttt ctctgtaatt ccgtgttttc gctttttcct ccctgcccct
3541 ctctccctct gccctctct cctctccgct tctctccccc tctgtctctg tctctctccg
3601 tctctgtcgc tcttgtctgt ctgtctctgc tctttcctcg gcctctctcc ccagacctgg
3661 cccggccgcc ctgtctccgc aggctagatc cgaggtggca gctccagccc ccgggctcgc
3721 cccctcgcgg gcgtgccccg cgcgcccgg gcggccgaag gccgggccgc cccgtcccgc
3781 cccgtagttg ctctttcggt agtggcgatg cgccctgcat gtctcctcac ccgtggatcg
3841 tgacgactcg aaataacaga aacaaagtca ataaagtgaa aataaataaa aatccttgaa
3901 caaatccgaa aaggcttgga gtcctcgccc agatctctct cccctgcgag cccttttttat
3961 ttgagaagga aaaagagaaa agagaatcgt ttaagggaac ccggcgccca gccaggctcc
4021 agtggcccga acggggcggc gagggcggcg agggcgccga ggtccggccc atcccagtcc
4081 tgtggggctg gccgggcaga gaccccggac ccaggcccag gcctaacctg ctaaatgtcc
4141 ccggacggtt ctggtctcct cggccacttt cagtgcgtcg gttcgttttg attctttttc
4201 ttttgtgcac ataagaaata aataataata ataaataaag aataaaattt tgtatgtcaa
4261 aaaaaaaaaa aaaaaa (SEQ ID NO: 42)
```

APPENDIX C

```
LOCUS       NM_000278   4207 bp   mRNA   linear  PRI  24-SEP-2005
DEFINITION  Homo sapiens paired box gene 2 (PAX2), transcript variant b, mRNA.
ACCESSION   NM_000278
VERSION     NM_000278.2  GI:34878700
KEYWORDS    .
SOURCE      Homo sapiens (human)
ORGANISM    Homo sapiens
            Eukaryota; Metazoa; Chordata; Craniata; Vertebrata; Euteleostomi;
            Mammalia; Eutheria; Euarchontoglires; Primates; Catarrhini;
            Hominidae; Homo.
REFERENCE   1 (bases 1 to 4207)
AUTHORS     Yoshimura, K., Yoshida, S., Yamaji, Y., Komori, A., Yoshida, A.,
            Hatae, K., Kubota, T. and Ishibashi, T.
TITLE       De novo insG619 mutation in PAX2 gene in a Japanese patient with
            papillorenal syndrome
JOURNAL     Am. J. Ophthalmol. 139 (4), 733-735 (2005)
PUBMED      15808183
REMARK      GeneRIF: Molecular genetic analysis of the PAX2 gene in combination
            with renal ultrasonography can help in making an earlier diagnosis
            of the disease.
REFERENCE   2 (bases 1 to 4207)
AUTHORS     Mazal, P. R., Stichenwirth, M., Koller, A., Blach, S., Haitel, A. and
            Susani, M.
TITLE       Expression of aquaporins and PAX-2 compared to CD10 and cytokeratin
            7 in renal neoplasms: a tissue microarray study
JOURNAL     Mod. Pathol. 18 (4), 535-540 (2005)
PUBMED      15502805
REMARK      GeneRIF: PAX-2 is a reliable marker for clear cell renal cell
            carcinomas of lower grades but not for higher grades.
REFERENCE   3 (bases 1 to 4207)
AUTHORS     Higashide, T., Wada, T., Sakurai, M., Yokoyama, H. and Sugiyama, K.
TITLE       Macular abnormalities and optic disk anomaly associated with a new
            PAX2 missense mutation
JOURNAL     Am. J. Ophthalmol. 139 (1), 203-205 (2005)
PUBMED      15652857
REMARK      GeneRIF: A new PAX2 missense mutation, R71T, may cause macular
            abnormalities in addition to anomalies of the optic disk and the
            kidney.
REFERENCE   4 (bases 1 to 4207)
AUTHORS     Buttiglieri, S., Deregibus, M. C., Bravo, S., Cassoni, P., Chiarle, R.,
            Bussolati, B. and Camussi, G.
TITLE       Role of Pax2 in apoptosis resistance and proinvasive phenotype of
            Kaposi's sarcoma cells
JOURNAL     J. Biol. Chem. 279 (6), 4136-4143 (2004)
PUBMED      14627715
REMARK      GeneRIF: expression of Pax2 by Kaposi's sarcoma cells correlated
            with an enhanced resistance against apoptotic signals and with the
            proinvasive phenotype
REFERENCE   5 (bases 1 to 4207)
AUTHORS     Brophy, P. D., Lang, K. M. and Dressler, G. R.
TITLE       The secreted frizzled related protein 2 (SFRP2) gene is a target of
            the Pax2 transcription factor
JOURNAL     J. Biol. Chem. 278 (52), 52401-52405 (2003)
PUBMED      14561758
REMARK      GeneRIF: Pax2 protein regulates expression of secreted frizzled
            related protein 2
REFERENCE   6 (bases 1 to 4207)
AUTHORS     Schimmenti, L. A., Manligas, G. S. and Sieving, P. A.
TITLE       Optic nerve dysplasia and renal insufficiency in a family with a
            novel PAX2 mutation, Arg115X: further ophthalmologic delineation of
            the renal-coloboma syndrome
JOURNAL     Ophthalmic Genet. 24 (4), 191-202 (2003)
PUBMED      14566649
REMARK      GeneRIF: PAX2 mutation is associated with Optic nerve dysplasia and
            renal insufficiency of the renal-coloboma syndrome
REFERENCE   7 (bases 1 to 4207)
AUTHORS     Muratovska, A., Zhou, C., He, S., Goodyer, P. and Eccles, M. R.
TITLE       Paired-Box genes are frequently expressed in cancer and often
            required for cancer cell survival
JOURNAL     Oncogene 22 (39), 7989-7997 (2003)
PUBMED      12970747
REMARK      GeneRIF: The PAX2 gene was frequently expressed in a panel of 406
            common primary tumor tissues and endogenous PAX gene expression is
            often required for the growth and survival of cancer cells
REFERENCE   8 (bases 1 to 4207)
AUTHORS     Gough, S. M., McDonald, M., Chen, X. N., Korenberg, J. R., Neri, A.,
            Kahn, T., Eccles, M. R. and Morris, C. M.
TITLE       Refined physical map of the human PAX2/HOX11/NFKB2 cancer gene
            region at 10q24 and relocalization of the HPV6AI1 viral integration
            site to 14q13.3-q21.1
```

APPENDIX C-continued

```
JOURNAL     BMC Genomics 4 (1), 9 (2003)
PUBMED      12697057
REFERENCE   9 (bases 1 to 4207)
AUTHORS     Hoffmeister, A., Ropolo, A., Vasseur, S., Mallo, G. V., Bodeker, H.,
            Ritz-Laser, B., Dressler, G. R., Vaccaro, M. I., Dagorn, J. C., Moreno, S.
            and Iovanna, J. L.
TITLE       The HMG-I/Y-related protein p8 binds to p300 and Pax2
            trans-activation domain-interacting protein to regulate the
            trans-activation activity of the Pax2A and Pax2B transcription
            factors on the glucagon gene promoter
JOURNAL     J. Biol. Chem. 277 (25), 22314-22319 (2002)
PUBMED      11940591
REMARK      GeneRIF: The HMG-I/Y-related protein p8 binds to p300 and Pax2
            trans-activation domain-interacting protein to regulate the
            trans-activation activity of the Pax2A and Pax2B transcription
            factors on the glucagon gene promoter.
REFERENCE   10 (bases 1 to 4207)
AUTHORS     Cai, Y., Lechner, M. S., Nihalani, D., Prindle, M. J., Holzman, L. B. and
            Dressler, G. R.
TITLE       Phosphorylation of Pax2 by the c-Jun N-terminal kinase and enhanced
            Pax2-dependent transcription activation
JOURNAL     J. Biol. Chem. 277 (2), 1217-1222 (2002)
PUBMED      11700324
REFERENCE   11 (bases 1 to 4207)
AUTHORS     Becker, K., Beales, P. L., Calver, D. M., Matthijs, G. and Mohammed, S. N.
TITLE       Okihiro syndrome and acro-renal-ocular syndrome: clinical overlap,
            expansion of the phenotype, and absence of PAX2 mutations in two
            new families
JOURNAL     J. Med. Genet. 39 (1), 68-71 (2002)
PUBMED      11826030
REMARK      GeneRIF: The absence of PAX2 mutations has been identified in two
            families with histories of clinical overlap of Okihiro and
            acro-renal-ocular syndromes.
REFERENCE   12 (bases 1 to 4207)
AUTHORS     Eccles, M. R., He, S., Legge, M., Kumar, R., Fox, J., Zhou, C., French, M.
            and Tsai, R. W.
TITLE       PAX genes in development and disease: the role of PAX2 in
            urogenital tract development
JOURNAL     Int. J. Dev. Biol. 46 (4), 535-544 (2002)
PUBMED      12141441
REMARK      Review article
            GeneRIF: PAX2 has a role in urogenital tract development and
            disease [review]
REFERENCE   13 (bases 1 to 4207)
AUTHORS     Chung, G. W., Edwards, A. O., Schimmenti, L. A., Manligas, G. S.,
            Zhang, Y. H. and Ritter, R. III.
TITLE       Renal-coloboma syndrome: report of a novel PAX2 gene mutation
JOURNAL     Am. J. Ophthalmol. 132 (6), 910-914 (2001)
PUBMED      11730657
REMARK      GeneRIF: The causal relationship between PAX2 gene mutations and
            renal-coloboma syndrome is further supported
REFERENCE   14 (bases 1 to 4207)
AUTHORS     Nishimoto, K., Iijima, K., Shirakawa, T., Kitagawa, K., Satomura, K.,
            Nakamura, H. and Yoshikawa, N.
TITLE       PAX2 gene mutation in a family with isolated renal hypoplasia
JOURNAL     J. Am. Soc. Nephrol. 12 (8), 1769-1772 (2001)
PUBMED      11461952
REFERENCE   15 (bases 1 to 4207)
AUTHORS     Ritz-Laser, B., Estreicher, A., Gauthier, B. and Philippe, J.
TITLE       The paired homeodomain transcription factor Pax-2 is expressed in
            the endocrine pancreas and transactivates the glucagon gene
            promoter
JOURNAL     J. Biol. Chem. 275 (42), 32708-32715 (2000)
PUBMED      10938089
REFERENCE   16 (bases 1 to 4207)
AUTHORS     Lechner, M. S., Levitan, I. and Dressler, G. R.
TITLE       PTIP, a novel BRCT domain-containing protein interacts with Pax2
            and is associated with active chromatin
JOURNAL     Nucleic Acids Res. 28 (14), 2741-2751 (2000)
PUBMED      10908331
REFERENCE   17 (bases 1 to 4207)
AUTHORS     Tavassoli, K., Ruger, W. and Horst, J.
TITLE       Alternative splicing in PAX2 generates a new reading frame and an
            extended conserved coding region at the carboxy terminus
JOURNAL     Hum. Genet. 101 (3), 371-375 (1997)
PUBMED      9439670
REFERENCE   18 (bases 1 to 4207)
AUTHORS     Dahl, E., Koseki, H. and Balling, R.
TITLE       Pax genes and organogenesis
JOURNAL     Bioessays 19 (9), 755-765 (1997)
```

APPENDIX C-continued

```
PUBMED      9297966
REMARK      Review article
REFERENCE   19 (bases 1 to 4207)
AUTHORS     Schimmenti, L. A., Cunliffe, H. E., McNoe, L. A., Ward, T. A., French, M. C.,
            Shim, H. H., Zhang, Y. H., Proesmans, W., Leys, A., Byerly, K. A.,
            Braddock, S. R., Masuno, M., Imaizumi, K., Devriendt, K. and Eccles, M. R.
TITLE       Further delineation of renal-coloboma syndrome in patients with
            extreme variability of phenotype and identical PAX2 mutations
JOURNAL     Am. J. Hum. Genet. 60 (4), 869-878 (1997)
PUBMED      9106533
REFERENCE   20 (bases 1 to 4207)
AUTHORS     Narahara, K., Baker, E., Ito, S., Yokoyama, Y., Yu, S., Hewitt, D.,
            Sutherland, G. R., Eccles, M. R. and Richards, R. I.
TITLE       Localisation of a 10q breakpoint within the PAX2 gene in a patient
            with a de novo t(10; 13) translocation and optic nerve
            coloboma-renal disease
JOURNAL     J. Med. Genet. 34 (3), 213-216 (1997)
PUBMED      9132492
REFERENCE   21 (bases 1 to 4207)
AUTHORS     Dehbi, M., Ghahremani, M., Lechner, M., Dressler, G. and Pelletier, J.
TITLE       The paired-box transcription factor, PAX2, positively modulates
            expression of the Wilms' tumor suppressor gene (WT1)
JOURNAL     Oncogene 13 (3), 447-453 (1996)
PUBMED      8760285
REFERENCE   22 (bases 1 to 4207)
AUTHORS     Sanyanusin, P., Norrish, J. H., Ward, T. A., Nebel, A., McNoe, L. A. and
            Eccles, M. R.
TITLE       Genomic structure of the human PAX2 gene
JOURNAL     Genomics 35 (1), 258-261 (1996)
PUBMED      8661132
REFERENCE   23 (bases 1 to 4207)
AUTHORS     Sanyanusin, P., Schimmenti, L. A., McNoe, L. A., Ward, T. A.,
            Pierpont, M. E., Sullivan, M. J., Dobyns, W. B. and Eccles, M. R.
TITLE       Mutation of the PAX2 gene in a family with optic nerve colobomas,
            renal anomalies and vesicoureteral reflux
JOURNAL     Nat. Genet. 9 (4), 358-364 (1995)
PUBMED      7795640
REFERENCE   24 (bases 1 to 4207)
AUTHORS     Ward, T. A., Nebel, A., Reeve, A. E. and Eccles, M. R.
TITLE       Alternative messenger RNA forms and open reading frames within an
            additional conserved region of the human PAX-2 gene
JOURNAL     Cell Growth Differ. 5 (9), 1015-1021 (1994)
PUBMED      7819127
REFERENCE   25 (bases 1 to 4207)
AUTHORS     Noll, M.
TITLE       Evolution and role of Pax genes
JOURNAL     Curr. Opin. Genet. Dev. 3 (4), 595-605 (1993)
PUBMED      8241771
REMARK      Review article
REFERENCE   26 (bases 1 to 4207)
AUTHORS     Stapleton, P., Weith, A., Urbanek, P., Kozmik, Z. and Busslinger, M.
TITLE       Chromosomal localization of seven PAX genes and cloning of a novel
            family member, PAX-9
JOURNAL     Nat. Genet. 3 (4), 292-298 (1993)
PUBMED      7981748
REFERENCE   27 (bases 1 to 4207)
AUTHORS     Pilz, A. J., Povey, S., Gruss, P. and Abbott, C. M.
TITLE       Mapping of the human homologs of the murine paired-box-containing
            genes
JOURNAL     Mamm. Genome 4 (2), 78-82 (1993)
PUBMED      8431641
REFERENCE   28 (bases 1 to 4207)
AUTHORS     Eccles, M. R., Wallis, L. J., Fidler, A. E., Spurr, N. K., Goodfellow, P. J.
            and Reeve, A. E.
TITLE       Expression of the PAX2 gene in human fetal kidney and Wilms' tumor
JOURNAL     Cell Growth Differ. 3 (5), 279-289 (1992)
PUBMED      1378753
COMMENT     REVIEWED REFSEQ: This record has been curated by NCBI staff. The
            reference sequence was derived from U45255.1 and BM671839.1.
            On Sep. 22, 2003 this sequence version replaced gi:4557820.
            Summary: PAX2 encodes paired box gene 2, one of many human
            homologues of the Drosophila melanogaster gene prd. The central
            feature of this transcription factor gene family is the conserved
            DNA-binding paired box domain. PAX2 is believed to be a target of
            transcriptional supression by the tumor suppressor gene WT1.
            Mutations within PAX2 have been shown to result in optic nerve
            colobomas and renal hypoplasia. Alternative splicing of this gene
            results in multiple transcript variants.
            Transcript Variant: This variant (b) lacks an alternate in-frame
            exon and uses an alternate splice site in the 3' coding region,
```

APPENDIX C-continued

```
                compared to variant e. This results in a protein (isoform b) with a
                shorter, distinct C-terminus compared to isoform e.
                COMPLETENESS: complete on the 3' end.
FEATURES        Location/Qualifiers
source          1..4207
                /organism="Homo sapiens"
                /mol_type="mRNA"
                /db_xref="taxon:9606"
                /chromosome="10"
                /map="10q24"
gene            1..4207
                /gene="PAX2"
                /db_xref="GeneID:5076"
                /db_xref="HGNC:8616"
                /db_xref="MIM:167409"
CDS             687..1868
                /gene="PAX2"
                /note="PAX2 gene is a member of the paired-box containing
                genes which encode transcription factors involved in
                embryonic and fetal development; the gene product is
                nuclear protein which binds DNA
                isoform b is encoded by transcript variant b; paired box
                homeotic gene 2;
                go_component: nucleus [goid 0005634][evidence IEA];
                go_function: ATP binding [goid 0005524][evidence IEA];
                go_function: DNA binding [goid 0003677][evidence IEA];
                go_function: DNA binding [goid 0003677][evidence TAS]
                [pmid 9106533];
                go_function: nucleoside diphosphate kinase activity [goid
                0004550][evidence IEA];
                go_process: development [goid 0007275][evidence IEA];
                go_process: transcription [goid 0006350][evidence IEA];
                go_process: CTP biosynthesis [goid 0006241][evidence
                IEA];
                go_process: GTP biosynthesis [goid 0006183][evidence
                IEA];
                go_process: UTP biosynthesis [goid 0006228][evidence
                IEA];
                go_process: axonogenesis [goid 0007409][evidence TAS]
                [pmid 9106533];
                go_process: cell differentiation [goid 0030154][evidence
                IEA];
                go_process: visual perception [goid 0007601][evidence
                TAS][pmid 9106533];
                go_process: regulation of transcription, DNA-dependent
                [goid 0006355][evidence IEA];
                go_process: transcription from RNA polymerase II promoter
                [goid 0006366][evidence TAS][pmid 8760285]"
                /codon_start=1
                /product="paired box protein 2 isoform b"
                /protein_id="NP_000269.2"
                /db_xref="GI:34878701"
                /db_xref="GeneID:5076"
                /db_xref="HGNC:8616"
                /db_xref="MIM:167409"
```

/translation="MDMHCKADPFSAMHPGHGGVNQLGGVFVNGRPLPDVVRQRIVELAHQ

GVRPCDISRQLRVSHGCVSKILGRYYETGSIKPGVIGGSKPKVATPKVVDKIAEYKRQN

PTMFAWEIRDRLLAEGICDNDTVPSVSSINRIIRTKVQQPFHPTPDGAGTGVTAPGHTIV

PSTASPPVSSASNDPVGSYSINGILGIPRSNGEKRKRDEDVSEGSVPNGDSQSGVDSLRK

HLRADTFTQQQLEALDRVFERPSYPDVFQASEHIKSEQGNEYSLPALTPGLDEVKSSLS

ASTNPELGSNVSGTQTYPVVTGRDMASTTLPGYPPHVPPTGQGSYPTSTLAGMVPGSE

FSGNPYSHPQYTAYNEAWRFSNPALLSSPYYYSAAPRSAPAAAAAAYDRH" (SEQ ID NO: 43)

```
STS             1857..2063
                /gene="PAX2"
                /standard_name="RH80285"
                /db_xref="UniSTS:88437"
STS             3055..3207
                /gene="PAX2"
                /standard_name="D10S2478"
                /db_xref="UniSTS:74159"
polyA_signal    4161..4166
                /gene="PAX2"
```

APPENDIX C-continued

```
polyA_signal    4165..4170
                /gene="PAX2"
polyA_signal    4172..4177
                /gene="PAX2"
polyA_site      4190
                /gene="PAX2"

ORIGIN
       1 aggctccagt ctccggccga gtcttctcgc agccgcaacc cacctggggc cagcccagag
      61 ctgccagcgc cgctcggctc cctccctccc tcccggccct tcggccgcgg cggcgtgcgc
     121 ctgccttttc cggggggcggg ggcctggccc gcgcgctccc ctcccgcagg cgccacctcg
     181 gacatccccg ggattgctac ttctctgcca acttcgccaa ctcgccagca cttggagagg
     241 cccggctccc ctcccggcgc cctctgaccg ccccgcccc gcgcgctctc cgaccaccgc
     301 ctctcggatg accaggttcc aggggagctg agcgagtcgc ctcccccgcc cagcttcagc
     361 cctggctgca gctgcagcgc gagccatgcg cccccagtgc accccggccc ggcccaccgc
     421 cccggggcca ttctgctgac cgcccagccc cgagcccga cagtggcaag ttgcggctac
     481 tgcagttgca agctccggcc aacccggagg agcccagcg gggagcgcag tgttgcgccc
     541 cccgccccg cgcgcccgc agcagccggg cgttcactca tcctccctcc cccaccgtcc
     601 ctccctttc tcctcaagtc ctgaagttga gtttgagagg cgacacggcg gcggcggccg
     661 cgctgctccc gctcctctgc ctccccatgg atatgcactg caaagcagac cccttctccg
     721 cgatgcaccc agggcacggg ggtgtgaacc agctcggggg ggtgtttgtg aacggccggc
     781 ccctacccga cgtggtgagg cagcgcatcg tggagctggc ccaccagggt gtgcggccct
     841 gtgacatctc ccggcagctg cgggtcagcc acggctgtgt cagcaaaatc ctgggcaggt
     901 actacgagac cggcagcatc aagccgggtg tgatcggtgg ctccaagccc aaagtggcga
     961 cgcccaaagt ggtggacaag attgctgaat acaaacgaca gaacccgact atgttcgcct
    1021 gggagattcg agaccggctc ctggccgagg gcatctgtga caatgacaca gtgcccagcg
    1081 tctcttccat caacagaatc atccggacca agttcagca gcctttccac ccaacgccgg
    1141 atggggctgg gacaggagtg accgcccctg gccacaccat tgttcccagc acggcctccc
    1201 ctcctgtttc cagcgcctcc aatgacccag tgggatccta ctccatcaat gggatcctgg
    1261 ggattcctcg ctccaatggt gagaagagga aacgtgatga agatgtgtct gagggctcag
    1321 tccccaatgg agattcccag agtggtgtgg acagtttgcg gaagcacttg cgagctgaca
    1381 ccttcaccca gcagcagctg gaagctttgg atcgggtctt tgagcgtcct tcctaccctg
    1441 acgtcttcca ggcatcagag cacatcaaat cagaacaggg gaacagagtac tccctcccag
    1501 ccctgacccc tgggcttgat gaagtcaagt cgagtctatc tgcatccacc aaccctgagc
    1561 tgggcagcaa cgtgtcaggc acacagacat acccagttgt gactggtcgt gacatggcga
    1621 gcaccactct gcctggttac ccccctcacg tgccccccac tggccaggga agctacccca
    1681 cctccacccct ggcaggaatg gtgcctggga gcgagttctc cggcaacccg tacagccacc
    1741 cccagtacac ggcctacaac gaggcttgga gattcagcaa ccccgcctta ctaagttccc
    1801 cttattatta tagtgccgcc cccggtccg ccctgccgc tgctgccgct gcctatgacc
    1861 gccactagtt accgcgggga ccacatcaag cttcaggccg acagcttcgg cctccacatc
    1921 gtccccgtct gaccccaccc cggagggagg gaggaccgac gcgacgcgat gcctcccggc
    1981 caccgcccca gcctcacccc atcccacgac ccccgcaacc cttcacatca ccccctcga
    2041 aggtcggaca ggacgggtgg agccgtgggc gggaccctca ggcccgggcc cgccgccccc
    2101 agccccgcct gccgccccte cccgcctgcc tggactgcgc ggcgccgtga gggggattcg
```

APPENDIX C-continued

```
2161 gcccagctcg tcccggcctc caccaagcca gccccgaagc ccgccagcca ccctgccgga 2221 ctcgggcgcg acctgctggc gcgcgccgga tgtttctgtg acacacaatc agcgcggacc 2281 gcagcgcggc ccagccccgg gcacccgcct cggacgctcg ggcgccagga ggcttcgctg 2341 gagggggctgg gccaaggaga ttaagaagaa acgactttc tgcaggagga agagcccgct 2401 gccgaatccc tgggaaaaat tcttttcccc cagtgccagc cggactgccc tcgccttccg 2461 ggtgtgccct gtcccagaag atggaatggg ggtgtggggg tccggctcta ggaacgggct 2521 ttgggggcgt caggtctttc caaggttggg acccaaggat cggggggccc agcagcccgc 2581 accgatcgag ccggactctc ggctcttcac tgctcctcct ggcctgccta gttccccagg 2641 gcccggcacc tcctgctgcg agacccggct tcagccctg ccttgcccct acctcagcgt 2701 ctcttccacc tgctggcctc ccagtttccc ctcctgccag tccttcgcct gtcccttgac 2761 gccctgcatc ctcctccctg actcgcagcc ccatcggacg ctctcccggg accgccgcag 2821 gaccagtttc catagactgc ggactggggt cttcctccag cagttacttg atgccccctc 2881 ccccgacaca gactctcaat ctgccggtgg taagaaccgg ttctgagctg cgtctgagc 2941 tgctgcgggg tggaagtggg gggctgccca ctccactcct cccatccct cccagcctcc 3001 tcctccggca ggaactgaac agaaccacaa aaagtctaca tttatttaat atgatggtct 3061 ttgcaaaaag gaacaaaaca acacaaaagc ccaccaggct gctgctttgt ggaaagacgg 3121 tgtgtgtcgt gtgaaggcga aacccggtgt acataacccc tcccctccg ccccgccccg 3181 cccggccccg tagagtccct gtcgcccgcc ggccctgcct gtagatacgc cccgctgtct 3241 gtgctgtgag agtcgccgct cgctgggggg gaagggggg acacagctac acgcccatta 3301 aagcacagca cgtcctgggg gaggggggca ttttttatgt tacaaaaaaa aattacgaaa 3361 gaaaagaaat ctctatgcaa aatgacgaac atggtcctgt ggactcctct ggcctgtttt 3421 gttggctctt tctctgtaat tccgtgtttt cgcttttttcc tccctgcccc tctctccctc 3481 tgcccctctc tcctctccgc ttctctcccc ctctgtctct gtctctctcc gtctctgtcg 3541 ctcttgtctg tctgtctctg ctctttcctc ggcctctctc cccagacctg gcccggccgc 3601 cctgtctccg caggctagat ccgaggtggc agctccagcc cccgggctcg cccctcgcg 3661 ggcgtgcccc gcgcgccccg ggcggccgaa ggccgggccg cccgtcccg ccccgtagtt 3721 gctctttcgg tagtggcgat gcgccctgca tgtctcctca cccgtggatc gtgacgactc 3781 gaaataacag aaacaaagtc aataaagtga aaataaataa aaatccttga acaaatccga 3841 aaaggcttgg agtcctcgcc cagatctctc tcccctgcga gccctttta tttgagaagg 3901 aaaaagagaa aagagaatcg tttaagggaa cccggcgccc agccaggctc cagtggcccg 3961 aacggggcgg cgagggcggc gagggcgccg aggtccggcc catcccagtc ctgtggggct 4021 ggccgggcag agaccccgga cccaggccca ggcctaacct gctaaatgtc cccggacggt 4081 tctggtctcc tcggccactt tcagtgcgtc ggttcgtttt gattcttttt cttttgtgca 4141 cataagaaat aaataataat aataaataaa gaataaaatt ttgtatgtca aaaaaaaaa 4201 aaaaaaa (SEQ ID NO: 44)
```

APPENDIX D

```
LOCUS       NM_003988   4290 bp  mRNA   linear  PRI  24-SEP-2005
DEFINITION  Homo sapiens paired box gene 2 (PAX2), transcript variant c, mRNA.
ACCESSION   NM_003988
VERSION     NM_003988.2  GI:34878708
KEYWORDS    .
SOURCE      Homo sapiens (human)
ORGANISM    Homo sapiens
            Eukaryota; Metazoa; Chordata; Craniata; Vertebrata; Euteleostomi;
            Mammalia; Eutheria; Euarchontoglires; Primates; Catarrhini;
            Hominidae; Homo.
REFERENCE   1 (bases 1 to 4290)
AUTHORS     Yoshimura, K., Yoshida, S., Yamaji, Y., Komori, A., Yoshida, A.,
            Hatae, K., Kubota, T. and Ishibashi, T.
TITLE       De novo insG619 mutation in PAX2 gene in a Japanese patient with
            papillorenal syndrome
JOURNAL     Am. J. Ophthalmol. 139 (4), 733-735 (2005)
PUBMED      15808183
REMARK      GeneRIF: Molecular genetic analysis of the PAX2 gene in combination
            with renal ultrasonography can help in making an earlier diagnosis
            of the disease.
REFERENCE   2 (bases 1 to 4290)
AUTHORS     Mazal, P. R., Stichenwirth, M., Koller, A., Blach, S., Haitel, A. and
            Susani, M.
TITLE       Expression of aquaporins and PAX-2 compared to CD10 and cytokeratin
            7 in renal neoplasms: a tissue microarray study
JOURNAL     Mod. Pathol. 18 (4), 535-540 (2005)
PUBMED      15502805
REMARK      GeneRIF: PAX-2 is a reliable marker for clear cell renal cell
            carcinomas of lower grades but not for higher grades.
REFERENCE   3 (bases 1 to 4290)
AUTHORS     Higashide, T., Wada, T., Sakurai, M., Yokoyama, H. and Sugiyama, K.
TITLE       Macular abnormalities and optic disk anomaly associated with a new
            PAX2 missense mutation
JOURNAL     Am. J. Ophthalmol. 139 (1), 203-205 (2005)
PUBMED      15652857
REMARK      GeneRIF: A new PAX2 missense mutation, R71T, may cause macular
            abnormalities in addition to anomalies of the optic disk and the
            kidney.
REFERENCE   4 (bases 1 to 4290)
AUTHORS     Buttiglieri, S., Deregibus, M. C., Bravo, S., Cassoni, P., Chiarle, R.,
            Bussolati, B. and Camussi, G.
TITLE       Role of Pax2 in apoptosis resistance and proinvasive phenotype of
            Kaposi's sarcoma cells
JOURNAL     J. Biol. Chem. 279 (6), 4136-4143 (2004)
PUBMED      14627715
REMARK      GeneRIF: expression of Pax2 by Kaposi's sarcoma cells correlated
            with an enhanced resistance against apoptotic signals and with the
            proinvasive phenotype
REFERENCE   5 (bases 1 to 4290)
AUTHORS     Brophy, P. D., Lang, K. M. and Dressler, G. R.
TITLE       The secreted frizzled related protein 2 (SFRP2) gene is a target of
            the Pax2 transcription factor
JOURNAL     J. Biol. Chem. 278 (52), 52401-52405 (2003)
PUBMED      14561758
REMARK      GeneRIF: Pax2 protein regulates expression of secreted frizzled
            related protein 2
REFERENCE   6 (bases 1 to 4290)
AUTHORS     Schimmenti, L. A., Manligas, G. S. and Sieving, P. A.
TITLE       Optic nerve dysplasia and renal insufficiency in a family with a
            novel PAX2 mutation, Arg115X: further ophthalmologic delineation of
            the renal-coloboma syndrome
JOURNAL     Ophthalmic Genet. 24 (4), 191-202 (2003)
PUBMED      14566649
REMARK      GeneRIF: PAX2 mutation is associated with Optic nerve dysplasia and
            renal insufficiency of the renal-coloboma syndrome
REFERENCE   7 (bases 1 to 4290)
AUTHORS     Muratovska, A., Zhou, C., He, S., Goodyer, P. and Eccles, M. R.
TITLE       Paired-Box genes are frequently expressed in cancer and often
            required for cancer cell survival
JOURNAL     Oncogene 22 (39), 7989-7997 (2003)
PUBMED      12970747
REMARK      GeneRIF: The PAX2 gene was frequently expressed in a panel of 406
            common primary tumor tissues and endogenous PAX gene expression is
            often required for the growth and survival of cancer cells
REFERENCE   8 (bases 1 to 4290)
AUTHORS     Gough, S. M., McDonald, M., Chen, X. N., Korenberg, J. R., Neri, A.,
            Kahn, T., Eccles, M. R. and Morris, C. M.
TITLE       Refined physical map of the human PAX2/HOX11/NFKB2 cancer gene
            region at 10q24 and relocalization of the HPV6AI1 viral integration
            site to 14q13.3-q21.1
```

APPENDIX D-continued

```
JOURNAL     BMC Genomics 4 (1), 9 (2003)
PUBMED      12697057
REFERENCE   9 (bases 1 to 4290)
AUTHORS     Hoffmeister, A., Ropolo, A., Vasseur, S., Mallo, G. V., Bodeker, H.,
            Ritz-Laser, B., Dressler, G. R., Vaccaro, M. I., Dagorn, J. C., Moreno, S.
            and Iovanna, J. L.
TITLE       The HMG-I/Y-related protein p8 binds to p300 and Pax2
            trans-activation domain-interacting protein to regulate the
            trans-activation activity of the Pax2A and Pax2B transcription
            factors on the glucagon gene promoter
JOURNAL     J. Biol. Chem. 277 (25), 22314-22319 (2002)
PUBMED      11940591
REMARK      GeneRIF: The HMG-I/Y-related protein p8 binds to p300 and Pax2
            trans-activation domain-interacting protein to regulate the
            trans-activation activity of the Pax2A and Pax2B transcription
            factors on the glucagon gene promoter.
REFERENCE   10 (bases 1 to 4290)
AUTHORS     Cai, Y., Lechner, M. S., Nihalani, D., Prindle, M. J., Holzman, L. B. and
            Dressler, G. R.
TITLE       Phosphorylation of Pax2 by the c-Jun N-terminal kinase and enhanced
            Pax2-dependent transcription activation
JOURNAL     J. Biol. Chem. 277 (2), 1217-1222 (2002)
PUBMED      11700324
REFERENCE   11 (bases 1 to 4290)
AUTHORS     Becker, K., Beales, P. L., Calver, D. M., Matthijs, G. and Mohammed, S. N.
TITLE       Okihiro syndrome and acro-renal-ocular syndrome: clinical overlap,
            expansion of the phenotype, and absence of PAX2 mutations in two
            new families
JOURNAL     J. Med. Genet. 39 (1), 68-71 (2002)
PUBMED      11826030
REMARK      GeneRIF: The absence of PAX2 mutations has been identified in two
            families with histories of clinical overlap of Okihiro and
            acro-renal-ocular syndromes.
REFERENCE   12 (bases 1 to 4290)
AUTHORS     Eccles, M. R., He, S., Legge, M., Kumar, R., Fox, J., Zhou, C., French, M.
            and Tsai, R. W.
TITLE       PAX genes in development and disease: the role of PAX2 in
            urogenital tract development
JOURNAL     Int. J. Dev. Biol. 46 (4), 535-544 (2002)
PUBMED      12141441
REMARK      Review article
            GeneRIF: PAX2 has a role in urogenital tract development and
            disease [review]
REFERENCE   13 (bases 1 to 4290)
AUTHORS     Chung, G. W., Edwards, A. O., Schimmenti, L. A., Manligas, G. S.,
            Zhang, Y. H. and Ritter, R. III.
TITLE       Renal-coloboma syndrome: report of a novel PAX2 gene mutation
JOURNAL     Am. J. Ophthalmol. 132 (6), 910-914 (2001)
PUBMED      11730657
REMARK      GeneRIF: The causal relationship between PAX2 gene mutations and
            renal-coloboma syndrome is further supported
REFERENCE   14 (bases 1 to 4290)
AUTHORS     Nishimoto, K., Iijima, K., Shirakawa, T., Kitagawa, K., Satomura, K.,
            Nakamura, H. and Yoshikawa, N.
TITLE       PAX2 gene mutation in a family with isolated renal hypoplasia
JOURNAL     J. Am. Soc. Nephrol. 12 (8), 1769-1772 (2001)
PUBMED      11461952
REFERENCE   15 (bases 1 to 4290)
AUTHORS     Ritz-Laser, B., Estreicher, A., Gauthier, B. and Philippe, J.
TITLE       The paired homeodomain transcription factor Pax-2 is expressed in
            the endocrine pancreas and transactivates the glucagon gene
            promoter
JOURNAL     J. Biol. Chem. 275 (42), 32708-32715 (2000)
PUBMED      10938089
REFERENCE   16 (bases 1 to 4290)
AUTHORS     Lechner, M. S., Levitan, I. and Dressler, G. R.
TITLE       PTIP, a novel BRCT domain-containing protein interacts with Pax2
            and is associated with active chromatin
JOURNAL     Nucleic Acids Res. 28 (14), 2741-2751 (2000)
PUBMED      10908331
REFERENCE   17 (bases 1 to 4290)
AUTHORS     Tavassoli, K., Ruger, W. and Horst, J.
TITLE       Alternative splicing in PAX2 generates a new reading frame and an
            extended conserved coding region at the carboxy terminus
JOURNAL     Hum. Genet. 101 (3), 371-375 (1997)
PUBMED      9439670
REFERENCE   18 (bases 1 to 4290)
AUTHORS     Dahl, E., Koseki, H. and Balling, R.
TITLE       Pax genes and organogenesis
JOURNAL     Bioessays 19 (9), 755-765 (1997)
```

APPENDIX D-continued

```
PUBMED      9297966
REMARK      Review article
REFERENCE   19 (bases 1 to 4290)
AUTHORS     Schimmenti, L. A., Cunliffe, H. E., McNoe, L. A., Ward, T. A., French, M. C.,
            Shim, H. H., Zhang, Y. H., Proesmans, W., Leys, A., Byerly, K. A.,
            Braddock, S. R., Masuno, M., Imaizumi, K., Devriendt, K. and Eccles, M. R.
TITLE       Further delineation of renal-coloboma syndrome in patients with
            extreme variability of phenotype and identical PAX2 mutations
JOURNAL     Am. J. Hum. Genet. 60 (4), 869-878 (1997)
PUBMED      9106533
REFERENCE   20 (bases 1 to 4290)
AUTHORS     Narahara, K., Baker, E., Ito, S., Yokoyama, Y., Yu, S., Hewitt, D.,
            Sutherland, G. R., Eccles, M. R. and Richards, R. I.
TITLE       Localisation of a 10q breakpoint within the PAX2 gene in a patient
            with a de novo t(10; 13) translocation and optic nerve
            coloboma-renal disease
JOURNAL     J. Med. Genet. 34 (3), 213-216 (1997)
PUBMED      9132492
REFERENCE   21 (bases 1 to 4290)
AUTHORS     Dehbi, M., Ghahremani, M., Lechner, M., Dressler, G. and Pelletier, J.
TITLE       The paired-box transcription factor, PAX2, positively modulates
            expression of the Wilms' tumor suppressor gene (WT1)
JOURNAL     Oncogene 13 (3), 447-453 (1996)
PUBMED      8760285
REFERENCE   22 (bases 1 to 4290)
AUTHORS     Sanyanusin, P., Norrish, J. H., Ward, T. A., Nebel, A., McNoe, L. A. and
            Eccles, M. R.
TITLE       Genomic structure of the human PAX2 gene
JOURNAL     Genomics 35 (1), 258-261 (1996)
PUBMED      8661132
REFERENCE   23 (bases 1 to 4290)
AUTHORS     Sanyanusin, P., Schimmenti, L. A., McNoe, L. A., Ward, T. A.,
            Pierpont, M. E., Sullivan, M. J., Dobyns, W. B. and Eccles, M. R.
TITLE       Mutation of the PAX2 gene in a family with optic nerve colobomas,
            renal anomalies and vesicoureteral reflux
JOURNAL     Nat. Genet. 9 (4), 358-364 (1995)
PUBMED      7795640
REFERENCE   24 (bases 1 to 4290)
AUTHORS     Ward, T. A., Nebel, A., Reeve, A. E. and Eccles, M. R.
TITLE       Alternative messenger RNA forms and open reading frames within an
            additional conserved region of the human PAX-2 gene
JOURNAL     Cell Growth Differ. 5 (9), 1015-1021 (1994)
PUBMED      7819127
REFERENCE   25 (bases 1 to 4290)
AUTHORS     Noll, M.
TITLE       Evolution and role of Pax genes
JOURNAL     Curr. Opin. Genet. Dev. 3 (4), 595-605 (1993)
PUBMED      8241771
REMARK      Review article
REFERENCE   26 (bases 1 to 4290)
AUTHORS     Stapleton, P., Weith, A., Urbanek, P., Kozmik, Z. and Busslinger, M.
TITLE       Chromosomal localization of seven PAX genes and cloning of a novel
            family member, PAX-9
JOURNAL     Nat. Genet. 3 (4), 292-298 (1993)
PUBMED      7981748
REFERENCE   27 (bases 1 to 4290)
AUTHORS     Pilz, A. J., Povey, S., Gruss, P. and Abbott, C. M.
TITLE       Mapping of the human homologs of the murine paired-box-containing
            genes
JOURNAL     Mamm. Genome 4 (2), 78-82 (1993)
PUBMED      8431641
REFERENCE   28 (bases 1 to 4290)
AUTHORS     Eccles, M. R., Wallis, L. J., Fidler, A. E., Spurr, N. K., Goodfellow, P. J.
            and Reeve, A. E.
TITLE       Expression of the PAX2 gene in human fetal kidney and Wilms' tumor
JOURNAL     Cell Growth Differ. 3 (5), 279-289 (1992)
PUBMED      1378753
COMMENT     REVIEWED REFSEQ: This record has been curated by NCBI staff. The
            reference sequence was derived from U45255.1 and BM671839.1.
            On Sep. 22, 2003 this sequence version replaced gi:4557824.
            Summary: PAX2 encodes paired box gene 2, one of many human
            homologues of the Drosophila melanogaster gene prd. The central
            feature of this transcription factor gene family is the conserved
            DNA-binding paired box domain. PAX2 is believed to be a target of
            transcriptional supression by the tumor supressor gene WT1.
            Mutations within PAX2 have been shown to result in optic nerve
            colobomas and renal hypoplasia. Alternative splicing of this gene
            results in multiple transcript variants.
```

APPENDIX D-continued

```
                Transcript Variant: This variant (c) has multiple differences in
                the coding region, compared to variant e, one of which results in a
                translational frameshift. The resulting protein (isoform c) has a
                distinct C-terminus and is shorter than isoform e.
                COMPLETENESS: complete on the 3' end.
FEATURES        Location/Qualifiers
source          1..4290
                /organism="Homo sapiens"
                /mol_type="mRNA"
                /db_xref="taxon:9606"
                /chromosome="10"
                /map="10q24"
gene            1..4290
                /gene="PAX2"
                /db_xref="GeneID:5076"
                /db_xref="HGNC:8616"
                /db_xref="MIM:167409"
CDS             687..1877
                /gene="PAX2"
                /note="PAX2 gene is a member of the paired-box containing
                genes which encode transcription factors involved in
                embryonic and fetal development; the gene product is
                nuclear protein which binds DNA
                isoform c is encoded by transcript variant c; paired box
                homeotic gene 2;
                go_component: nucleus [goid 0005634][evidence IEA];
                go_function: ATP binding [goid 0005524][evidence IEA];
                go_function: DNA binding [goid 0003677][evidence IEA];
                go_function: DNA binding [goid 0003677][evidence TAS]
                [pmid 9106533];
                go_function: nucleoside diphosphate kinase activity [goid
                0004550][evidence IEA];
                go_process: development [goid 0007275][evidence IEA];
                go_process: transcription [goid 0006350][evidence IEA];
                go_process: CTP biosynthesis [goid 0006241][evidence
                IEA];
                go_process: GTP biosynthesis [goid 0006183][evidence
                IEA];
                go_process: UTP biosynthesis [goid 0006228][evidence
                IEA];
                go_process: axonogenesis [goid 0007409][evidence TAS]
                [pmid 9106533];
                go_process: cell differentiation [goid 0030154][evidence
                IEA];
                go_process: visual perception [goid 0007601][evidence
                TAS][pmid 9106533];
                go_process: regulation of transcription, DNA-dependent
                [goid 0006355][evidence IEA];
                go_process: transcription from RNA polymerase II promoter
                [goid 0006366][evidence TAS][pmid 8760285]"
                /codon_start=1
                /product="paired box protein 2 isoform c"
                /protein_id="NP_003979.2"
                /db_xref="GI:34878709"
                /db_xref="CCDS:CCDS7499.1"
                /db_xref="GeneID:5076"
                /db_xref="HGNC:8616"
                /db_xref="MIM:167409"
```

/translation="MDMHCKADPFSAMHPGHGGVNQLGGVFVNGRPLPDVVRQRIVELAHQ

GVRPCDISRQLRVSHGCVSKILGRYYETGSIKPGVIGGSKPKVATPKVVDKIAEYKRQN

PTMFAWEIRDRLLAEGICDNDTVPSVSSINRIIRTKVQQPFHPTPDGAGTGVTAPGHTIV

PSTASPPVSSASNDPVGSYSINGILGIPRSNGEKRKRDEDVSEGSVPNGDSQSGVDSLRK

HLRADTFTQQQLEALDRVFERPSYPDVFQASEHIKSEQGNEYSLPALTPGLDEVKSSLS

ASTNPELGSNVSGTQTYPVVTGRDMASTTLPGYPPHVPPTGQGSYPTSTLAGMVPEAA

VGPSSSLMSKPGRKLAEVPPCVQPTGASSPATRTATPSTRPTTRLGDSATPPY" (SEQ ID NO: 45)

```
STS             1940..2146
                /gene="PAX2"
                /standard_name="RH80285"
                /db_xref="UniSTS:88437"
```

APPENDIX D-continued

```
STS             3138..3290
                /gene="PAX2"
                /standard_name="D10S2478"
                /db_xref="UniSTS:74159"
polyA_signal    4244..4249
                /gene="PAX2"
polyA_signal    4248..4253
                /gene="PAX2"
polyA_signal    4255..4260
                /gene="PAX2"
polyA_site      4273
                /gene="PAX2"

ORIGIN
    1 aggctccagt ctccggccga gtcttctcgc agccgcaacc cacctggggc cagcccagag
   61 ctgccagcgc cgctcggctc cctccctccc tcccggccct tcggccgcgg cggcgtgcgc
  121 ctgccttttc cgggggcggg ggcctggccc gcgcgctccc ctcccgcagg cgccacctcg
  181 gacatccccg ggattgctac ttctctgcca acttcgccaa ctcgccagca cttggagagg
  241 cccggctccc ctccgcgcgc cctctgaccg cccccgcccc gcgcgctctc cgaccaccgc
  301 ctctcggatg accaggttcc aggggagctg agcgagtcgc ctccccccgcc cagcttcagc
  361 cctggctgca gctgcagcgc gagccatgcg cccccagtgc accccggccc ggcccaccgc
  421 cccggggcca ttctgctgac cgcccagccc cgagccccga cagtggcaag ttgcggctac
  481 tgcagttgca agctccggcc aacccggagg agccccagcg gggagcgcag tgttgcgccc
  541 cccgcccccg cgcgcccgc agcagccggg cgttcactca tcctcccctcc cccaccgtcc
  601 ctcccttttc tcctcaagtc ctgaagttga gtttgagagg cgacacggcg gcggcggccg
  661 cgctgctccc gctcctctgc ctccccatgg atatgcactg caaagcagac cccttctccg
  721 cgatgcaccc agggcacggg ggtgtgaacc agctcggggg ggtgtttgtg aacggccggc
  781 ccctacccga cgtggtgagg cagcgcatcg tggagctggc ccaccagggt gtgcggccct
  841 gtgacatctc ccggcagctg cgggtcagcc acggctgtgt cagcaaaatc ctgggcaggt
  901 actacgagac cggcagcatc aagccgggtg tgatcggtgg ctccaagccc aaagtggcga
  961 cgcccaaagt ggtggacaag attgctgaat acaaacgaca gaacccgact atgttcgcct
 1021 gggagattcg agaccggctc ctggccgagg gcatctgtga caatgacaca gtgcccagcg
 1081 tctcttccat caacagaatc atccggacca aagttcagca gcctttccac ccaacgccgg
 1141 atggggctgg acaggagtg accgccctg ccacaccat tgttcccagc acggcctccc
 1201 ctcctgtttc cagcgcctcc aatgacccag tgggatccta ctccatcaat gggatcctgg
 1261 ggattcctcg ctccaatggt gagaagagga aacgtgatga agatgtgtct gagggctcag
 1321 tccccaatgg agattcccag agtggtgtgg acagtttgcg gaagcacttg cgagctgaca
 1381 ccttcaccca gcagcagctg gaagctttgg atcgggtctt tgagcgtcct tcctaccctg
 1441 acgtcttcca ggcatcagag cacatcaaat cagaacaggg gaacgagtac tccctcccag
 1501 ccctgacccc tgggcttgat gaagtcaagt cgagtctatc tgcatccacc aaccctgagc
 1561 tgggcagcaa cgtgtcaggc acacagacat acccagttgt gactggtcgt gacatggcga
 1621 gcaccactct gcctggttac ccccctcacg tgcccccac tggccaggga agctacccca
 1681 cctccaccct ggcaggaatg gtgcctgagg ctgcagttgg tccctcatcc tccctcatga
 1741 gcaagccggg gaggaagctt gcagaagtgc ccccttgtgt gcaacccact ggagcgagtt
 1801 ctccggcaac ccgtacagcc accccagta cacggcctac aacgaggctt ggagattcag
 1861 caaccccgcc ttactaagtt cccttatta ttatagtgcc gccccggt ccgcccctgc
 1921 cgctgctgcc gctgcctatg accgccacta gttaccgcgg ggaccacatc aagcttcagg
```

APPENDIX D-continued

```
1981 ccgacagctt cggcctccac atcgtccccg tctgacccca ccccggaggg agggaggacc
2041 gacgcgacgc gatgcctccc ggccaccgcc ccagcctcac cccatcccac gaccccgca
2101 acccttcaca tccccccct cgaaggtcgg acaggacggg tggagccgtg ggcgggaccc
2161 tcaggcccgg gcccgccgcc cccagccccg cctgccgccc ctccccgcct gcctggactg
2221 cgcggcgccg tgagggggat tcggcccagc tcgtcccggc ctccaccaag ccagccccga
2281 agcccgccag ccaccctgcc ggactcgggc gcgacctgct ggcgcgcgcc ggatgtttct
2341 gtgacacaca atcagcgcgg accgcagcgc ggcccagccc cgggcacccg cctcggacgc
2401 tcgggcgcca ggaggcttcg ctggaggggc tgggccaagg agattaagaa gaaaacgact
2461 ttctgcagga ggaagagccc gctgccgaat ccctgggaaa aattcttttc ccccagtgcc
2521 agccggactg ccctcgcctt ccgggtgtgc cctgtcccag aagatggaat gggggtgtgg
2581 gggtccggct ctaggaacgg gctttggggg cgtcaggtct ttccaaggtt gggacccaag
2641 gatcggggg cccagcagcc cgcaccgatc gagccggact ctcggctctt cactgctcct
2701 cctggcctgc ctagttcccc agggcccggc acctcctgct gcgagacccg gctctcagcc
2761 ctgccttgcc cctacctcag cgtctcttcc acctgctggc ctcccagttt cccctcctgc
2821 cagtccttcg cctgtccctt gacgccctgc atcctcctcc ctgactcgca gccccatcgg
2881 acgctctccc gggaccgccg caggaccagt ttccatagac tgcggactgg ggtcttcctc
2941 cagcagttac ttgatgcccc ctcccccgac acagactctc aatctgccgg tggtaagaac
3001 cggttctgag ctggcgtctg agctgctgcg gggtggaagt gggggggctgc ccactccact
3061 cctcccatcc cctcccagcc tcctcctccg gcaggaactg aacagaacca caaaaagtct
3121 acatttattt aatatgatgg tctttgcaaa aaggaacaaa acaacacaaa agcccaccag
3181 gctgctgctt tgtggaaaga cggtgtgtgt cgtgtgaagg cgaaacccgg tgtacataac
3241 ccctcccct ccgcccgcc ccgcccggcc ccgtagagtc cctgtcgccc gccggccctg
3301 cctgtagata cgccccgctg tctgtgctgt gagagtcgcc gctcgctggg ggggaagggg
3361 gggacacagc tacacgccca ttaaagcaca gcacgtcctg ggggaggggg gcattttta
3421 tgttacaaaa aaaaattacg aaagaaaaga aatctctatg caaaatgacg aacatggtcc
3481 tgtggactcc tctggcctgt tttgttggct ctttctctgt aattccgtgt tttcgctttt
3541 tcctccctgc ccctctctcc ctctgcccct ctctcctctc cgcttctctc cccctctgtc
3601 tctgtctctc tccgtctctg tcgctcttgt ctgtctgtct ctgctctttc ctcggcctct
3661 ctccccagac ctggcccggc cgccctgtct ccgcaggcta gatccgaggt ggcagctcca
3721 gccccgggc tcgcccctc gcgggcgtgc cccgcgcgcc ccggcggcc gaaggccggg
3781 ccgccccgtc ccgccccgta gttgctcttt cggtagtggc gatgcgccct gcatgtctcc
3841 tcacccgtgg atcgtgacga ctcgaaataa cagaaacaaa gtcaataaag tgaaaataaa
3901 taaaaatcct tgaacaaatc cgaaaggct tggagtcctc gcccagatct ctctcccctg
3961 cgagcccttt ttatttgaga aggaaaaaga gaaagagaa tcgtttaagg gaacccggcg
4021 cccagccagg ctccagtggc ccgaacgggg cggcgagggc ggcgagggcg ccgaggtccg
4081 gcccatccca gtcctgtggg gctggccggg cagagacccc ggacccaggc ccaggcctaa
4141 cctgctaaat gtccccggac ggttctggtc tcctcggcca ctttcagtgc gtcggttcgt
4201 tttgattctt tttcttttgt gcacataaga aataaataat aataataaat aaagaataaa
4261 attttgtatg tcaaaaaaaa aaaaaaaaaa (SEQ ID NO: 46)
```

APPENDIX E

```
LOCUS       NM_003989 4188 bp mRNA linear PRI 24-SEP-2005
DEFINITION  Homo sapiens paired box gene 2 (PAX2), transcript variant d, mRNA.
ACCESSION   NM_003989
VERSION     NM_003989.2  GI:34878715
KEYWORDS    .
SOURCE      Homo sapiens (human)
ORGANISM    Homo sapiens
            Eukaryota; Metazoa; Chordata; Craniata; Vertebrata; Euteleostomi;
            Mammalia; Eutheria; Euarchontoglires; Primates; Catarrhini;
            Hominidae; Homo.
REFERENCE   1 (bases 1 to 4188)
AUTHORS     Yoshimura, K., Yoshida, S., Yamaji, Y., Komori, A., Yoshida, A.,
            Hatae, K., Kubota, T. and Ishibashi, T.
TITLE       De novo insG619 mutation in PAX2 gene in a Japanese patient with
            papillorenal syndrome
JOURNAL     Am. J. Ophthalmol. 139 (4), 733-735 (2005)
PUBMED      15808183
REMARK      GeneRIF: Molecular genetic analysis of the PAX2 gene in combination
            with renal ultrasonography can help in making an earlier diagnosis
            of the disease.
REFERENCE   2 (bases 1 to 4188)
AUTHORS     Mazal, P. R., Stichenwirth, M., Koller, A., Blach, S., Haitel, A. and
            Susani, M.
TITLE       Expression of aquaporins and PAX-2 compared to CD10 and cytokeratin
            7 in renal neoplasms: a tissue microarray study
JOURNAL     Mod. Pathol. 18 (4), 535-540 (2005)
PUBMED      15502805
REMARK      GeneRIF: PAX-2 is a reliable marker for clear cell renal cell
            carcinomas of lower grades but not for higher grades.
REFERENCE   3 (bases 1 to 4188)
AUTHORS     Higashide, T., Wada, T., Sakurai, M., Yokoyama, H. and Sugiyama, K.
TITLE       Macular abnormalities and optic disk anomaly associated with a new
            PAX2 missense mutation
JOURNAL     Am. J. Ophthalmol. 139 (1), 203-205 (2005)
PUBMED      15652857
REMARK      GeneRIF: A new PAX2 missense mutation, R71T, may cause macular
            abnormalities in addition to anomalies of the optic disk and the
            kidney.
REFERENCE   4 (bases 1 to 4188)
AUTHORS     Buttiglieri, S., Deregibus, M. C., Bravo, S., Cassoni, P., Chiarle, R.,
            Bussolati, B. and Camussi, G.
TITLE       Role of Pax2 in apoptosis resistance and proinvasive phenotype of
            Kaposi's sarcoma cells
JOURNAL     J. Biol. Chem. 279 (6), 4136-4143 (2004)
PUBMED      14627715
REMARK      GeneRIF: expression of Pax2 by Kaposi's sarcoma cells correlated
            with an enhanced resistance against apoptotic signals and with the
            proinvasive phenotype
REFERENCE   5 (bases 1 to 4188)
AUTHORS     Brophy, P. D., Lang, K. M. and Dressler, G. R.
TITLE       The secreted frizzled related protein 2 (SFRP2) gene is a target of
            the Pax2 transcription factor
JOURNAL     J. Biol. Chem. 278 (52), 52401-52405 (2003)
PUBMED      14561758
REMARK      GeneRIF: Pax2 protein regulates expression of secreted frizzled
            related protein 2
REFERENCE   6 (bases 1 to 4188)
AUTHORS     Schimmenti, L. A., Manligas, G. S. and Sieving, P. A.
TITLE       Optic nerve dysplasia and renal insufficiency in a family with a
            novel PAX2 mutation, Arg115X: further ophthalmologic delineation of
            the renal-coloboma syndrome
JOURNAL     Ophthalmic Genet. 24 (4), 191-202 (2003)
PUBMED      14566649
REMARK      GeneRIF: PAX2 mutation is associated with Optic nerve dysplasia and
            renal insufficiency of the renal-coloboma syndrome
REFERENCE   7 (bases 1 to 4188)
AUTHORS     Muratovska, A., Zhou, C., He, S., Goodyer, P. and Eccles, M. R.
TITLE       Paired-Box genes are frequently expressed in cancer and often
            required for cancer cell survival
JOURNAL     Oncogene 22 (39), 7989-7997 (2003)
PUBMED      12970747
REMARK      GeneRIF: The PAX2 gene was frequently expressed in a panel of 406
            common primary tumor tissues and endogenous PAX gene expression is
            often required for the growth and survival of cancer cells
REFERENCE   8 (bases 1 to 4188)
AUTHORS     Gough, S. M., McDonald, M., Chen, X. N., Korenberg, J. R., Neri, A.,
            Kahn, T., Eccles, M. R. and Morris, C. M.
```

APPENDIX E-continued

| | |
|---|---|
| TITLE | Refined physical map of the human PAX2/HOX11/NFKB2 cancer gene region at 10q24 and relocalization of the HPV6AI1 viral integration site to 14q13.3-q21.1 |
| JOURNAL | BMC Genomics 4 (1), 9 (2003) |
| PUBMED | 12697057 |
| REFERENCE | 9 (bases 1 to 4188) |
| AUTHORS | Hoffmeister, A., Ropolo, A., Vasseur, S., Mallo, G. V., Bodeker, H., Ritz-Laser, B., Dressler, G. R., Vaccaro, M. I., Dagorn, J. C., Moreno, S. and Iovanna, J. L. |
| TITLE | The HMG-I/Y-related protein p8 binds to p300 and Pax2 trans-activation domain-interacting protein to regulate the trans-activation activity of the Pax2A and Pax2B transcription factors on the glucagon gene promoter |
| JOURNAL | J. Biol. Chem. 277 (25), 22314-22319 (2002) |
| PUBMED | 11940591 |
| REMARK | GeneRIF: The HMG-I/Y-related protein p8 binds to p300 and Pax2 trans-activation domain-interacting protein to regulate the trans-activation activity of the Pax2A and Pax2B transcription factors on the glucagon gene promoter. |
| REFERENCE | 10 (bases 1 to 4188) |
| AUTHORS | Cai, Y., Lechner, M. S., Nihalani, D., Prindle, M. J., Holzman, L. B. and Dressler, G. R. |
| TITLE | Phosphorylation of Pax2 by the c-Jun N-terminal kinase and enhanced Pax2-dependent transcription activation |
| JOURNAL | J. Biol. Chem. 277 (2), 1217-1222 (2002) |
| PUBMED | 11700324 |
| REFERENCE | 11 (bases 1 to 4188) |
| AUTHORS | Becker, K., Beales, P. L., Calver, D. M., Matthijs, G. and Mohammed, S. N. |
| TITLE | Okihiro syndrome and acro-renal-ocular syndrome: clinical overlap, expansion of the phenotype, and absence of PAX2 mutations in two new families |
| JOURNAL | J. Med. Genet. 39 (1), 68-71 (2002) |
| PUBMED | 11826030 |
| REMARK | GeneRIF: The absence of PAX2 mutations has been identified in two families with histories of clinical overlap of Okihiro and acro-renal-ocular syndromes. |
| REFERENCE | 12 (bases 1 to 4188) |
| AUTHORS | Eccles, M. R., He, S., Legge, M., Kumar, R., Fox, J., Zhou, C., French, M. and Tsai, R. W. |
| TITLE | PAX genes in development and disease: the role of PAX2 in urogenital tract development |
| JOURNAL | Int. J. Dev. Biol. 46 (4), 535-544 (2002) |
| PUBMED | 12141441 |
| REMARK | Review article<br>GeneRIF: PAX2 has a role in urogenital tract development and disease [review] |
| REFERENCE | 13 (bases 1 to 4188) |
| AUTHORS | Chung, G. W., Edwards, A. O., Schimmenti, L. A., Manligas, G. S., Zhang, Y. H. and Ritter, R. III. |
| TITLE | Renal-coloboma syndrome: report of a novel PAX2 gene mutation |
| JOURNAL | Am. J. Ophthalmol. 132 (6), 910-914 (2001) |
| PUBMED | 11730657 |
| REMARK | GeneRIF: The causal relationship between PAX2 gene mutations and renal-coloboma syndrome is further supported |
| REFERENCE | 14 (bases 1 to 4188) |
| AUTHORS | Nishimoto, K., Iijima, K., Shirakawa, T., Kitagawa, K., Satomura, K., Nakamura, H. and Yoshikawa, N. |
| TITLE | PAX2 gene mutation in a family with isolated renal hypoplasia |
| JOURNAL | J. Am. Soc. Nephrol. 12 (8), 1769-1772 (2001) |
| PUBMED | 11461952 |
| REFERENCE | 15 (bases 1 to 4188) |
| AUTHORS | Ritz-Laser, B., Estreicher, A., Gauthier, B. and Philippe, J. |
| TITLE | The paired homeodomain transcription factor Pax-2 is expressed in the endocrine pancreas and transactivates the glucagon gene promoter |
| JOURNAL | J. Biol. Chem. 275 (42), 32708-32715 (2000) |
| PUBMED | 10938089 |
| REFERENCE | 16 (bases 1 to 4188) |
| AUTHORS | Lechner, M. S., Levitan, I. and Dressler, G. R. |
| TITLE | PTIP, a novel BRCT domain-containing protein interacts with Pax2 and is associated with active chromatin |
| JOURNAL | Nucleic Acids Res. 28 (14), 2741-2751 (2000) |
| PUBMED | 10908331 |
| REFERENCE | 17 (bases 1 to 4188) |
| AUTHORS | Tavassoli, K., Ruger, W. and Horst, J. |
| TITLE | Alternative splicing in PAX2 generates a new reading frame and an extended conserved coding region at the carboxy terminus |
| JOURNAL | Hum. Genet. 101 (3), 371-375 (1997) |
| PUBMED | 9439670 |
| REFERENCE | 18 (bases 1 to 4188) |

APPENDIX E-continued

| | |
|---|---|
| AUTHORS | Dahl, E., Koseki, H. and Balling, R. |
| TITLE | Pax genes and organogenesis |
| JOURNAL | Bioessays 19 (9), 755-765 (1997) |
| PUBMED | 9297966 |
| REMARK | Review article |
| REFERENCE | 19 (bases 1 to 4188) |
| AUTHORS | Schimmenti, L. A., Cunliffe, H. E., McNoe, L. A., Ward, T. A., French, M. C., Shim, H. H., Zhang, Y. H., Proesmans, W., Leys, A., Byerly, K. A., Braddock, S. R., Masuno, M., Imaizumi, K., Devriendt, K. and Eccles, M. R. |
| TITLE | Further delineation of renal-coloboma syndrome in patients with extreme variability of phenotype and identical PAX2 mutations |
| JOURNAL | Am. J. Hum. Genet. 60 (4), 869-878 (1997) |
| PUBMED | 9106533 |
| REFERENCE | 20 (bases 1 to 4188) |
| AUTHORS | Narahara, K., Baker, E., Ito, S., Yokoyama, Y., Yu, S., Hewitt, D., Sutherland, G. R., Eccles, M. R. and Richards, R. I. |
| TITLE | Localisation of a 10q breakpoint within the PAX2 gene in a patient with a de novo t(10; 13) translocation and optic nerve coloboma-renal disease |
| JOURNAL | J. Med. Genet. 34 (3), 213-216 (1997) |
| PUBMED | 9132492 |
| REFERENCE | 21 (bases 1 to 4188) |
| AUTHORS | Dehbi, M., Ghahremani, M., Lechner, M., Dressler, G. and Pelletier, J. |
| TITLE | The paired-box transcription factor, PAX2, positively modulates expression of the Wilms' tumor suppressor gene (WT1) |
| JOURNAL | Oncogene 13 (3), 447-453 (1996) |
| PUBMED | 8760285 |
| REFERENCE | 22 (bases 1 to 4188) |
| AUTHORS | Sanyanusin, P., Norrish, J. H., Ward, T. A., Nebel, A., McNoe, L. A. and Eccles, M. R. |
| TITLE | Genomic structure of the human PAX2 gene |
| JOURNAL | Genomics 35 (1), 258-261 (1996) |
| PUBMED | 8661132 |
| REFERENCE | 23 (bases 1 to 4188) |
| AUTHORS | Sanyanusin, P., Schimmenti, L. A., McNoe, L. A., Ward, T. A., Pierpont, M. E., Sullivan, M. J., Dobyns, W. B. and Eccles, M. R. |
| TITLE | Mutation of the PAX2 gene in a family with optic nerve colobomas, renal anomalies and vesicoureteral reflux |
| JOURNAL | Nat. Genet. 9 (4), 358-364 (1995) |
| PUBMED | 7795640 |
| REFERENCE | 24 (bases 1 to 4188) |
| AUTHORS | Ward, T. A., Nebel, A., Reeve, A. E. and Eccles, M. R. |
| TITLE | Alternative messenger RNA forms and open reading frames within an additional conserved region of the human PAX-2 gene |
| JOURNAL | Cell Growth Differ. 5 (9), 1015-1021 (1994) |
| PUBMED | 7819127 |
| REFERENCE | 25 (bases 1 to 4188) |
| AUTHORS | Noll, M. |
| TITLE | Evolution and role of Pax genes |
| JOURNAL | Curr. Opin. Genet. Dev. 3 (4), 595-605 (1993) |
| PUBMED | 8241771 |
| REMARK | Review article |
| REFERENCE | 26 (bases 1 to 4188) |
| AUTHORS | Stapleton, P., Weith, A., Urbanek, P., Kozmik, Z. and Busslinger, M. |
| TITLE | Chromosomal localization of seven PAX genes and cloning of a novel family member, PAX-9 |
| JOURNAL | Nat. Genet. 3 (4), 292-298 (1993) |
| PUBMED | 7981748 |
| REFERENCE | 27 (bases 1 to 4188) |
| AUTHORS | Pilz, A. J., Povey, S., Gruss, P. and Abbott, C. M. |
| TITLE | Mapping of the human homologs of the murine paired-box-containing genes |
| JOURNAL | Mamm. Genome 4 (2), 78-82 (1993) |
| PUBMED | 8431641 |
| REFERENCE | 28 (bases 1 to 4188) |
| AUTHORS | Eccles, M. R., Wallis, L. J., Fidler, A. E., Spurr, N. K., Goodfellow, P. J. and Reeve, A. E. |
| TITLE | Expression of the PAX2 gene in human fetal kidney and Wilms' tumor |
| JOURNAL | Cell Growth Differ. 3 (5), 279-289 (1992) |
| PUBMED | 1378753 |
| COMMENT | REVIEWED REFSEQ: This record has been curated by NCBI staff. The reference sequence was derived from U45255.1 and BM671839.1. On Sep. 22, 2003 this sequence version replaced gi:4557826. Summary: PAX2 encodes paired box gene 2, one of many human homologues of the Drosophila melanogaster gene prd. The central feature of this transcription factor gene family is the conserved DNA-binding paired box domain. PAX2 is believed to be a target of transcriptional supression by the tumor supressor gene WT1. Mutations within PAX2 have been shown to result in optic nerve colobomas and renal hypoplasia. Alternative splicing of this gene |

APPENDIX E-continued

```
                    results in multiple transcript variants.
                    Transcript Variant: This variant (d) lacks an alternate in-frame
                    exon compared to variant e. This results in an isoform (isoform d)
                    that is shorter than isoform e.
                    COMPLETENESS: complete on the 3' end.
FEATURES            Location/Qualifiers
source              1..4188
                    /organism="Homo sapiens"
                    /mol_type="mRNA"
                    /db_xref="taxon:9606"
                    /chromosome="10"
                    /map="10q24"
gene                1..4188
                    /gene="PAX2"
                    /db_xref="GeneID:5076"
                    /db_xref="HGNC:8616"
                    /db_xref="HPRD:HPRD_01330"
                    /db_xref="MIM:167409"
CDS                 687..1913
                    /gene="PAX2"
                    /note="PAX2 gene is a member of the paired-box containing
                    genes which encode transcription factors involved in
                    embryonic and fetal development; the gene product is
                    nuclear protein which binds DNA
                    isoform d is encoded by transcript variant d; paired box
                    homeotic gene 2;
                    go_component: nucleus [goid 0005634][evidence IEA];
                    go_function: ATP binding [goid 0005524][evidence IEA];
                    go_function: DNA binding [goid 0003677][evidence IEA];
                    go_function: DNA binding [goid 0003677][evidence TAS]
                    [pmid 9106533];
                    go_function: nucleoside diphosphate kinase activity [goid
                    0004550][evidence IEA];
                    go_process: development [goid 0007275][evidence IEA];
                    go_process: transcription [goid 0006350][evidence IEA];
                    go_process: CTP biosynthesis [goid 0006241][evidence
                    IEA];
                    go_process: GTP biosynthesis [goid 0006183][evidence
                    IEA];
                    go_process: UTP biosynthesis [goid 0006228][evidence
                    IEA];
                    go_process: axonogenesis [goid 0007409][evidence TAS]
                    [pmid 9106533];
                    go_process: cell differentiation [goid 0030154][evidence
                    IEA];
                    go_process: visual perception [goid 0007601][evidence
                    TAS][pmid 9106533];
                    go_process: regulation of transcription, DNA-dependent
                    [goid 0006355][evidence IEA];
                    go_process: transcription from RNA polymerase II promoter
                    [goid 0006366][evidence TAS][pmid 8760285]"
                    /codon_start=1
                    /product="paired box protein 2 isoform d"
                    /protein_id="NP_003980.2"
                    /db_xref="GI:34878716"
                    /db_xref="GeneID:5076"
                    /db_xref="HGNC:8616"
                    /db_xref="HPRD:HPRD_01330"
                    /db_xref="MIM:167409"
```

/translation="MDMHCKADPFSAMHPGHGGVNQLGGVFVNGRPLPDVVRQRIVELAHQ

GVRPCDISRQLRVSHGCVSKILGRYYETGSIKPGVIGGSKPKVATPKVVDKIAEYKRQN

PTMFAWEIRDRLLAEGICDNDTVPSVSSINRIIRTKVQQPFHPTPDGAGTGVTAPGHTIV

PSTASPPVSSASNDPVGSYSINGILGIPRSNGEKRKRDEDVSEGSVPNGDSQSGVDSLRK

HLRADTFTQQQLEALDRVFERPSYPDVFQASEHIKSEQGNEYSLPALTPGLDEVKSSLS

ASTNPELGSNVSGTQTYPVVTGRDMASTTLPGYPPHVPPTGQGSYPTSTLAGMVPGSE

FSGNPYSHPQYTAYNEAWRFSNPALLMPPPGPPLPLLPLPMTATSYRGDHIKLQADSFG

LHIVPV" (SEQ ID NO: 47)

```
STS                 1838..2044
                    /gene="PAX2"
                    /standard_name="RH80285"
                    /db_xref="UniSTS:88437"
```

APPENDIX E-continued

```
STS             3036..3188
                /gene="PAX2"
                /standard_name="D10S2478"
                /db_xref="UniSTS:74159"
polyA_signal    4142..4147
                /gene="PAX2"
polyA_signal    4146..4151
                /gene="PAX2"
polyA_signal    4153..4158
                /gene="PAX2"
polyA_site      4171
                /gene="PAX2"

ORIGIN
    1 aggctccagt ctccggccga gtcttctcgc agccgcaacc cacctggggc cagcccagag
   61 ctgccagcgc cgctcggctc cctccctccc tcccggccct tcggccgcgg cggcgtgcgc
  121 ctgccttttc cggggccggg ggcctggccc gcgcgctccc ctcccgcagg cgccacctcg
  181 gacatccccg ggattgctac ttctctgcca acttcgccaa ctcgccagca cttggagagg
  241 cccggctccc ctcccggcgc cctctgaccg ccccgccccc gcgcgctctc cgaccaccgc
  301 ctctcggatg accaggttcc aggggagctg agcgagtcgc ctcccccgcc cagcttcagc
  361 cctggctgca gctgcagcgc gagccatgcg cccccagtgc accccggccc ggcccaccgc
  421 cccggggcca ttctgctgac cgcccagccc cgagccccga cagtggcaag ttgcggctac
  481 tgcagttgca agctccggcc aacccggagg agcccagcg gggagcgcag tgttgcgccc
  541 cccgcccccg cgcgcccgc agcagccggg cgttcactca tcctccctcc cccaccgtcc
  601 ctccctttc tcctcaagtc ctgaagttga gtttgagagg cgacacggcg gcggcggccg
  661 cgctgctccc gctcctctgc ctccccatgg atatgcactg caaagcagac cccttctccg
  721 cgatgcaccc agggcacggg ggtgtgaacc agctcggggg ggtgtttgtg aacggccggc
  781 ccctacccga cgtggtgagg cagcgcatcg tggagctggc ccaccagggt gtgcggccct
  841 gtgacatctc ccggcagctg cgggtcagcc acggctgtgt cagcaaaatc ctgggcaggt
  901 actacgagac cggcagcatc aagccgggtg tgatcggtgg ctccaagccc aaagtggcga
  961 cgcccaaagt ggtggacaag attgctgaat acaaacgaca gaacccgact atgttcgcct
 1021 gggagattcg agaccggctc ctggccgagg gcatctgtga caatgacaca gtgcccagcg
 1081 tctcttccat caacagaatc atccggacca agttcagca gcctttccac ccaacgccgg
 1141 atgggctgg acaggagtg accgcccctg ccacaccat gttcccagc acggcctccc
 1201 ctcctgtttc cagcgcctcc aatgacccag tgggatccta ctccatcaat gggatcctgg
 1261 ggattcctcg ctccaatggt gagaagagga acgtgatga agatgtgtct gagggctcag
 1321 tccccaatgg agattcccag agtggtgtgg acagtttgcg gaagcacttg cgagctgaca
 1381 ccttcaccca gcagcagctg gaagctttgg atcgggtctt tgagcgtcct tcctaccctg
 1441 acgtcttcca ggcatcagag cacatcaaat cagaacaggg gaacgagtac tccctcccag
 1501 ccctgacccc tgggcttgat gaagtcaagt cgagtctatc tgcatccacc aaccctgagc
 1561 tgggcagcaa cgtgtcaggc acacagacat acccagttgt gactggtcgt gacatggcga
 1621 gcaccactct gcctggttac ccccctcacg tgccccccac tggccaggga agctaccccca
 1681 cctccaccct ggcaggaatg gtgcctggga gcgagttctc cggcaacccg tacagccacc
 1741 cccagtacac ggcctacaac gaggcttgga gattcagcaa cccgccctta ctaatgccgc
 1801 cccccggtcc gcccctgccg ctgctgccgc tgcctatgac cgccactagt taccgcgggg
 1861 accacatcaa gcttcaggcc gacagcttcg gcctcacat cgtcccgtc tgaccccacc
 1921 ccggagggag ggaggaccga cgcgacgcga tgcctcccgg ccaccgcccc agcctcaccc
```

APPENDIX E-continued

```
1981  catcccacga ccccccgcaac ccttcacatc acccccctcg aaggtcggac aggacgggtg
2041  gagccgtggg cgggaccctc aggcccgggc ccgccgcccc cagccccgcc tgccgcccct
2101  ccccgcctgc ctggactgcg cggcgccgtg aggggggattc ggcccagctc gtcccggcct
2161  ccaccaagcc agccccgaag cccgccagcc accctgccgg actcgggcgc gacctgctgg
2221  cgcgcgccgg atgtttctgt gacacacaat cagcgcggac cgcagcgcgg cccagccccg
2281  ggcacccgcc tcggacgctc gggcgccagg aggcttcgct ggaggggctg ggccaaggag
2341  attaagaaga aaacgacttt ctgcaggagg aagagcccgc tgccgaatcc ctgggaaaaa
2401  ttcttttccc ccagtgccag ccggactgcc ctcgccttcc gggtgtgccc tgtcccagaa
2461  gatggaatgg gggtgtgggg gtccggctct aggaacgggc tttgggggcg tcaggtcttt
2521  ccaaggttgg gacccaagga tcggggggcc cagcagcccg caccgatcga gccggactct
2581  cggctcttca ctgctcctcc tggcctgcct agttccccag ggcccggcac ctcctgctgc
2641  gagacccggc tctcagccct gccttgcccc tacctcagcg tctcttccac ctgctggcct
2701  cccagtttcc cctcctgcca gtccttcgcc tgtcccttga cgccctgcat cctcctccct
2761  gactcgcagc cccatcggac gctctcccgg gaccgccgca ggaccagttt ccatagactg
2821  cggactgggg tcttcctcca gcagttactt gatgcccccct cccccgcacac agactctcaa
2881  tctgccggtg gtaagaaccg gttctgagct ggcgtctgag ctgctgcggg gtggaagtgg
2941  ggggctgccc actccactcc tcccatcccc tcccagcctc ctcctccggc aggaactgaa
3001  cagaaccaca aaaagtctac atttatttaa tatgatggtc tttgcaaaaa ggaacaaaac
3061  aacacaaaag cccaccaggc tgctgctttg tggaaagacg gtgtgtgtcg tgtgaaggcg
3121  aaacccggtg tacataaccc ctcccccctcc gccccgcccc gccggcccc gtagagtccc
3181  tgtcgcccgc cggccctgcc tgtagatacg ccccgctgtc tgtgctgtga gagtcgccgc
3241  tcgctggggg ggaaggggggg gacacagcta cacgcccatt aaagcacagc acgtcctggg
3301  ggaggggggc atttttttatg ttacaaaaaa aaattacgaa agaaaagaaa tctctatgca
3361  aaatgacgaa catggtcctg tggactcctc tggcctgttt tgttggctct ttctctgtaa
3421  ttccgtgttt tcgctttttc ctccctgccc ctctctccct ctgcccctct ctcctctccg
3481  cttctctccc cctctgtctc tgtctctctc cgtctctgtc gctcttgtct gtctgtctct
3541  gctctttcct cggcctctct ccccagacct ggcccggccg ccctgtctcc gcaggctaga
3601  tccgaggtgg cagctccagc ccccgggctc gcccctcgc gggcgtgccc cgcgcgcccc
3661  gggcggccga aggccgggcc gccccgtccc gccccgtagt tgctctttcg gtagtggcga
3721  tgcgccctgc atgtctcctc acccgtggat cgtgacgact cgaaataaca gaaacaaagt
3781  caataaagtg aaaataaata aaaatccttg aacaaatccg aaaaggcttg gagtcctcgc
3841  ccagatctct ctcccctgcg agcccttttt atttgagaag gaaaagagaa aagagaatc
3901  gtttaaggga acccggcgcc cagccaggct ccagtggccc gaacggggcg gcgagggcgg
3961  cgagggcgcc gaggtccggc ccatcccagt cctgtggggc tggccgggca gagaccccgg
4021  acccaggccc aggcctaacc tgctaaatgt ccccggacgg ttctggtctc ctcggccact
4081  ttcagtgcgt cggttcgttt tgattctttt tcttttgtgc acataagaaa taaataataa
4141  taataaataa agaataaaat tttgtatgtc aaaaaaaaaa aaaaaaaa (SEQ ID NO: 48)
```

APPENDIX F

```
LOCUS       NM_003990 4257 bp mRNA linear PRI 24-SEP-2005
DEFINITION  Homo sapiens paired box gene 2 (PAX2), transcript variant e, mRNA.
ACCESSION   NM_003990
VERSION     NM_003990.2 GI:34878702
KEYWORDS    .
SOURCE      Homo sapiens (human)
ORGANISM    Homo sapiens
            Eukaryota; Metazoa; Chordata; Craniata; Vertebrata; Euteleostomi;
            Mammalia; Eutheria; Euarchontoglires; Primates; Catarrhini;
            Hominidae; Homo.
REFERENCE   1 (bases 1 to 4257)
AUTHORS     Yoshimura, K., Yoshida, S., Yamaji, Y., Komori, A., Yoshida, A.,
            Hatae, K., Kubota, T. and Ishibashi, T.
TITLE       De novo insG619 mutation in PAX2 gene in a Japanese patient with
            papillorenal syndrome
JOURNAL     Am. J. Ophthalmol. 139 (4), 733-735 (2005)
PUBMED      15808183
REMARK      GeneRIF: Molecular genetic analysis of the PAX2 gene in combination
            with renal ultrasonography can help in making an earlier diagnosis
            of the disease.
REFERENCE   2 (bases 1 to 4257)
AUTHORS     Mazal, P. R., Stichenwirth, M., Koller, A., Blach, S., Haitel, A. and
            Susani, M.
TITLE       Expression of aquaporins and PAX-2 compared to CD10 and cytokeratin
            7 in renal neoplasms: a tissue microarray study
JOURNAL     Mod. Pathol. 18 (4), 535-540 (2005)
PUBMED      15502805
REMARK      GeneRIF: PAX-2 is a reliable marker for clear cell renal cell
            carcinomas of lower grades but not for higher grades.
REFERENCE   3 (bases 1 to 4257)
AUTHORS     Higashide, T., Wada, T., Sakurai, M., Yokoyama, H. and Sugiyama, K.
TITLE       Macular abnormalities and optic disk anomaly associated with a new
            PAX2 missense mutation
JOURNAL     Am. J. Ophthalmol. 139 (1), 203-205 (2005)
PUBMED      15652857
REMARK      GeneRIF: A new PAX2 missense mutation, R71T, may cause macular
            abnormalities in addition to anomalies of the optic disk and the
            kidney.
REFERENCE   4 (bases 1 to 4257)
AUTHORS     Buttiglieri, S., Deregibus, M. C., Bravo, S., Cassoni, P., Chiarle, R.,
            Bussolati, B. and Camussi, G.
TITLE       Role of Pax2 in apoptosis resistance and proinvasive phenotype of
            Kaposi's sarcoma cells
JOURNAL     J. Biol. Chem. 279 (6), 4136-4143 (2004)
PUBMED      14627715
REMARK      GeneRIF: expression of Pax2 by Kaposi's sarcoma cells correlated
            with an enhanced resistance against apoptotic signals and with the
            proinvasive phenotype
REFERENCE   5 (bases 1 to 4257)
AUTHORS     Brophy, P. D., Lang, K. M. and Dressler, G. R.
TITLE       The secreted frizzled related protein 2 (SFRP2) gene is a target of
            the Pax2 transcription factor
JOURNAL     J. Biol. Chem. 278 (52), 52401-52405 (2003)
PUBMED      14561758
REMARK      GeneRIF: Pax2 protein regulates expression of secreted frizzled
            related protein 2
REFERENCE   6 (bases 1 to 4257)
AUTHORS     Schimmenti, L. A., Manligas, G. S. and Sieving, P. A.
TITLE       Optic nerve dysplasia and renal insufficiency in a family with a
            novel PAX2 mutation, Arg115X: further ophthalmologic delineation of
            the renal-coloboma syndrome
JOURNAL     Ophthalmic Genet. 24 (4), 191-202 (2003)
PUBMED      14566649
REMARK      GeneRIF: PAX2 mutation is associated with Optic nerve dysplasia and
            renal insufficiency of the renal-coloboma syndrome
REFERENCE   7 (bases 1 to 4257)
AUTHORS     Muratovska, A., Zhou, C., He, S., Goodyer, P. and Eccles, M. R.
TITLE       Paired-Box genes are frequently expressed in cancer and often
            required for cancer cell survival
JOURNAL     Oncogene 22 (39), 7989-7997 (2003)
PUBMED      12970747
REMARK      GeneRIF: The PAX2 gene was frequently expressed in a panel of 406
            common primary tumor tissues and endogenous PAX gene expression is
            often required for the growth and survival of cancer cells
REFERENCE   8 (bases 1 to 4257)
AUTHORS     Gough, S. M., McDonald, M., Chen, X. N., Korenberg, J. R., Neri, A.,
            Kahn, T., Eccles, M. R. and Morris, C. M.
TITLE       Refined physical map of the human PAX2/HOX11/NFKB2 cancer gene
            region at 10q24 and relocalization of the HPV6AI1 viral integration
            site to 14q13.3-q21.1
```

APPENDIX F-continued

```
JOURNAL      BMC Genomics 4 (1), 9 (2003)
PUBMED       12697057
REFERENCE    9 (bases 1 to 4257)
AUTHORS      Hoffmeister, A., Ropolo, A., Vasseur, S., Mallo, G. V., Bodeker, H.,
             Ritz-Laser, B., Dressler, G. R., Vaccaro, M. I., Dagorn, J. C., Moreno, S.
             and Iovanna, J. L.
TITLE        The HMG-I/Y-related protein p8 binds to p300 and Pax2
             trans-activation domain-interacting protein to regulate the
             trans-activation activity of the Pax2A and Pax2B transcription
             factors on the glucagon gene promoter
JOURNAL      J. Biol. Chem. 277 (25), 22314-22319 (2002)
PUBMED       11940591
REMARK       GeneRIF: The HMG-I/Y-related protein p8 binds to p300 and Pax2
             trans-activation domain-interacting protein to regulate the
             trans-activation activity of the Pax2A and Pax2B transcription
             factors on the glucagon gene promoter.
REFERENCE    10 (bases 1 to 4257)
AUTHORS      Cai, Y., Lechner, M. S., Nihalani, D., Prindle, M. J., Holzman, L. B. and
             Dressler, G. R.
TITLE        Phosphorylation of Pax2 by the c-Jun N-terminal kinase and enhanced
             Pax2-dependent transcription activation
JOURNAL      J. Biol. Chem. 277 (2), 1217-1222 (2002)
PUBMED       11700324
REFERENCE    11 (bases 1 to 4257)
AUTHORS      Becker, K., Beales, P. L., Calver, D. M., Matthijs, G. and Mohammed, S. N.
TITLE        Okihiro syndrome and acro-renal-ocular syndrome: clinical overlap,
             expansion of the phenotype, and absence of PAX2 mutations in two
             new families
JOURNAL      J. Med. Genet. 39 (1), 68-71 (2002)
PUBMED       11826030
REMARK       GeneRIF: The absence of PAX2 mutations has been identified in two
             families with histories of clinical overlap of Okihiro and
             acro-renal-ocular syndromes.
REFERENCE    12 (bases 1 to 4257)
AUTHORS      Eccles, M. R., He, S., Legge, M., Kumar, R., Fox, J., Zhou, C., French, M.
             and Tsai, R. W.
TITLE        PAX genes in development and disease: the role of PAX2 in
             urogenital tract development
JOURNAL      Int. J. Dev. Biol. 46 (4), 535-544 (2002)
PUBMED       12141441
REMARK       Review article
             GeneRIF: PAX2 has a role in urogenital tract development and
             disease [review]
REFERENCE    13 (bases 1 to 4257)
AUTHORS      Chung, G. W., Edwards, A. O., Schimmenti, L. A., Manligas, G. S.,
             Zhang, Y. H. and Ritter, R. III.
TITLE        Renal-coloboma syndrome: report of a novel PAX2 gene mutation
JOURNAL      Am. J. Ophthalmol. 132 (6), 910-914 (2001)
PUBMED       11730657
REMARK       GeneRIF: The causal relationship between PAX2 gene mutations and
             renal-coloboma syndrome is further supported
REFERENCE    14 (bases 1 to 4257)
AUTHORS      Nishimoto, K., Iijima, K., Shirakawa, T., Kitagawa, K., Satomura, K.,
             Nakamura, H. and Yoshikawa, N.
TITLE        PAX2 gene mutation in a family with isolated renal hypoplasia
JOURNAL      J. Am. Soc. Nephrol. 12 (8), 1769-1772 (2001)
PUBMED       11461952
REFERENCE    15 (bases 1 to 4257)
AUTHORS      Ritz-Laser, B., Estreicher, A., Gauthier, B. and Philippe, J.
TITLE        The paired homeodomain transcription factor Pax-2 is expressed in
             the endocrine pancreas and transactivates the glucagon gene
             promoter
JOURNAL      J. Biol. Chem. 275 (42), 32708-32715 (2000)
PUBMED       10938089
REFERENCE    16 (bases 1 to 4257)
AUTHORS      Lechner, M. S., Levitan, I. and Dressler, G. R.
TITLE        PTIP, a novel BRCT domain-containing protein interacts with Pax2
             and is associated with active chromatin
JOURNAL      Nucleic Acids Res. 28 (14), 2741-2751 (2000)
PUBMED       10908331
REFERENCE    17 (bases 1 to 4257)
AUTHORS      Tavassoli, K., Ruger, W. and Horst, J.
TITLE        Alternative splicing in PAX2 generates a new reading frame and an
             extended conserved coding region at the carboxy terminus
JOURNAL      Hum. Genet. 101 (3), 371-375 (1997)
PUBMED       9439670
REFERENCE    18 (bases 1 to 4257)
AUTHORS      Dahl, E., Koseki, H. and Balling, R.
TITLE        Pax genes and organogenesis
JOURNAL      Bioessays 19 (9), 755-765 (1997)
```

APPENDIX F-continued

```
PUBMED      9297966
REMARK      Review article
REFERENCE   19 (bases 1 to 4257)
AUTHORS     Schimmenti, L. A., Cunliffe, H. E., McNoe, L. A., Ward, T. A., French, M. C.,
            Shim, H. H., Zhang, Y. H., Proesmans, W., Leys, A., Byerly, K. A.,
            Braddock, S. R., Masuno, M., Imaizumi, K., Devriendt, K. and Eccles, M. R.
TITLE       Further delineation of renal-coloboma syndrome in patients with
            extreme variability of phenotype and identical PAX2 mutations
JOURNAL     Am. J. Hum. Genet. 60 (4), 869-878 (1997)
PUBMED      9106533
REFERENCE   20 (bases 1 to 4257)
AUTHORS     Narahara, K., Baker, E., Ito, S., Yokoyama, Y., Yu, S., Hewitt, D.,
            Sutherland, G. R., Eccles, M. R. and Richards, R. I.
TITLE       Localisation of a 10q breakpoint within the PAX2 gene in a patient
            with a de novo t(10; 13) translocation and optic nerve
            coloboma-renal disease
JOURNAL     J. Med. Genet. 34 (3), 213-216 (1997)
PUBMED      9132492
REFERENCE   21 (bases 1 to 4257)
AUTHORS     Dehbi, M., Ghahremani, M., Lechner, M., Dressler, G. and Pelletier, J.
TITLE       The paired-box transcription factor, PAX2, positively modulates
            expression of the Wilms' tumor suppressor gene (WT1)
JOURNAL     Oncogene 13 (3), 447-453 (1996)
PUBMED      8760285
REFERENCE   22 (bases 1 to 4257)
AUTHORS     Sanyanusin, P., Norrish, J. H., Ward, T. A., Nebel, A., McNoe, L. A. and
            Eccles, M. R.
TITLE       Genomic structure of the human PAX2 gene
JOURNAL     Genomics 35 (1), 258-261 (1996)
PUBMED      8661132
REFERENCE   23 (bases 1 to 4257)
AUTHORS     Sanyanusin, P., Schimmenti, L. A., McNoe, L. A., Ward, T. A.,
            Pierpont, M. E., Sullivan, M. J., Dobyns, W. B. and Eccles, M. R.
TITLE       Mutation of the PAX2 gene in a family with optic nerve colobomas,
            renal anomalies and vesicoureteral reflux
JOURNAL     Nat. Genet. 9 (4), 358-364 (1995)
PUBMED      7795640
REFERENCE   24 (bases 1 to 4257)
AUTHORS     Ward, T. A., Nebel, A., Reeve, A. E. and Eccles, M. R.
TITLE       Alternative messenger RNA forms and open reading frames within an
            additional conserved region of the human PAX-2 gene
JOURNAL     Cell Growth Differ. 5 (9), 1015-1021 (1994)
PUBMED      7819127
REFERENCE   25 (bases 1 to 4257)
AUTHORS     Noll, M.
TITLE       Evolution and role of Pax genes
JOURNAL     Curr. Opin. Genet. Dev. 3 (4), 595-605 (1993)
PUBMED      8241771
REMARK      Review article
REFERENCE   26 (bases 1 to 4257)
AUTHORS     Stapleton, P., Weith, A., Urbanek, P., Kozmik, Z. and Busslinger, M.
TITLE       Chromosomal localization of seven PAX genes and cloning of a novel
            family member, PAX-9
JOURNAL     Nat. Genet. 3 (4), 292-298 (1993)
PUBMED      7981748
REFERENCE   27 (bases 1 to 4257)
AUTHORS     Pilz, A. J., Povey, S., Gruss, P. and Abbott, C. M.
TITLE       Mapping of the human homologs of the murine paired-box-containing
            genes
JOURNAL     Mamm. Genome 4 (2), 78-82 (1993)
PUBMED      8431641
REFERENCE   28 (bases 1 to 4257)
AUTHORS     Eccles, M. R., Wallis, L. J., Fidler, A. E., Spurr, N. K., Goodfellow, P. J.
            and Reeve, A. E.
TITLE       Expression of the PAX2 gene in human fetal kidney and Wilms' tumor
JOURNAL     Cell Growth Differ. 3 (5), 279-289 (1992)
PUBMED      1378753
COMMENT     REVIEWED REFSEQ: This record has been curated by NCBI staff.
            The
            reference sequence was derived from U45255.1 and BM671839.1.
            On Sep. 22, 2003 this sequence version replaced gi:4557828.
            Summary: PAX2 encodes paired box gene 2, one of many human
            homologues of the Drosophila melanogaster gene prd. The central
            feature of this transcription factor gene family is the conserved
            DNA-binding paired box domain. PAX2 is believed to be a target of
            transcriptional supression by the tumor supressor gene WT1.
```

APPENDIX F-continued

```
                Mutations within PAX2 have been shown to result in optic nerve
                colobomas and renal hypoplasia. Alternative splicing of this gene
                results in multiple transcript variants.
                Transcript Variant: This variant (e) encodes the longest isoform
                (e).
                COMPLETENESS: complete on the 3' end.
FEATURES        Location/Qualifiers
source          1..4257
                /organism="Homo sapiens"
                /mol_type="mRNA"
                /db_xref="taxon:9606"
                /chromosome="10"
                /map="10q24"
gene            1..4257
                /gene="PAX2"
                /db_xref="GeneID:5076"
                /db_xref="HGNC:8616"
                /db_xref="MIM:167409"
CDS             687..1982
                /gene="PAX2"
                /note="PAX2 gene is a member of the paired-box containing
                genes which encode transcription factors involved in
                embryonic and fetal development; the gene product is
                nuclear protein which binds DNA
                isoform e is encoded by transcript variant e; paired box
                homeotic gene 2;
                go_component: nucleus [goid 0005634][evidence IEA];
                go_function: ATP binding [goid 0005524][evidence IEA];
                go_function: DNA binding [goid 0003677][evidence IEA];
                go_function: DNA binding [goid 0003677][evidence TAS]
                [pmid 9106533];
                go_function: nucleoside diphosphate kinase activity [goid
                0004550][evidence IEA];
                go_process: development [goid 0007275][evidence IEA];
                go_process: transcription [goid 0006350][evidence IEA];
                go_process: CTP biosynthesis [goid 0006241][evidence
                IEA];
                go_process: GTP biosynthesis [goid 0006183][evidence
                IEA];
                go_process: UTP biosynthesis [goid 0006228][evidence
                IEA];
                go_process: axonogenesis [goid 0007409][evidence TAS]
                [pmid 9106533];
                go_process: cell differentiation [goid 0030154][evidence
                IEA];
                go_process: visual perception [goid 0007601][evidence
                TAS][pmid 9106533];
                go_process: regulation of transcription, DNA-dependent
                [goid 0006355][evidence IEA];
                go_process: transcription from RNA polymerase II promoter
                [goid 0006366][evidence TAS][pmid 8760285]"
                /codon_start=1
                /product="paired box protein 2 isoform e"
                /protein_id="NP_003981.2"
                /db_xref="GI:34878703"
                /db_xref="GeneID:5076"
                /db_xref="HGNC:8616"
                /db_xref="MIM:167409"
```

/translation="MDMHCKADPFSAMHPGHGGVNQLGGVFVNGRPLPDVVRQRIVELAHQ

GVRPCDISRQLRVSHGCVSKILGRYYETGSIKPGVIGGSKPKVATPKVVDKIAEYKRQN

PTMFAWEIRDRLLAEGICDNDTVPSVSSINRIIRTKVQQPFHPTPDGAGTGVTAPGHTIV

PSTASPPVSSASNDPVGSYSINGILGIPRSNGEKRKRDEVEVYTDPAHIRGGGGLHLVW

TLRDVSEGSVPNGDSQSGVDSLRKHLRADTFTQQQLEALDRVFERPSYPDVFQASEHI

KSEQGNEYSLPALTPGLDEVKSSLSASTNPELGSNVSGTQTYPVVTGRDMASTTLPGYP

PHVPPTGQGSYPTSTLAGMVPGSEFSGNPYSHPQYTAYNEAWRFSNPALLMPPPGPPLP

LLPLPMTATSYRGDHIKLQADSFGLHIVPV" (SEQ ID NO: 49)

```
STS             1907..2113
                /gene="PAX2"
                /standard_name="RH80285"
                /db_xref="UniSTS:88437"
```

APPENDIX F-continued

```
STS             3105..3257
                /gene="PAX2"
                /standard_name="D10S2478"
                /db_xref="UniSTS:74159"
polyA_signal    4211..4216
                /gene="PAX2"
polyA_signal    4215..4220
                /gene="PAX2"
polyA_signal    4222..4227
                /gene="PAX2"
polyA_site      4240
                /gene="PAX2"

ORIGIN
     1  aggctccagt ctccggccga gtcttctcgc agccgcaacc cacctggggc cagcccagag
    61  ctgccagcgc cgctcggctc cctccctccc tcccggccct tcggccgcgg cggcgtgcgc
   121  ctgcctttc cggggcggg ggcctggccc gcgcgctccc ctcccgcagg cgccacctcg
   181  gacatccccg ggattgctac ttctctgcca acttcgccaa ctcgccagca cttggagagg
   241  cccggctccc ctcccggcgc cctctgaccg cccccgcccc gcgcgctctc cgaccaccgc
   301  ctctcggatg accaggttcc aggggagctg agcgagtcgc ctcccccgcc cagcttcagc
   361  cctggctgca gctgcagcgc gagccatgcg cccccagtgc accccggccc ggcccaccgc
   421  cccggggcca ttctgctgac cgcccagccc cgagccccga cagtggcaag ttgcggctac
   481  tgcagttgca agctccggcc aacccggagg agcccagcg gggagcgcag tgttgcgccc
   541  cccgcccccg cgcgccccgc agcagccggg cgttcactca tcctccctcc cccaccgtcc
   601  ctcccttttc tcctcaagtc ctgaagttga gtttgagagg cgacacggcg gcggcggccg
   661  cgctgctccc gctcctctgc ctccccatgg atatgcactg caaagcagac cccttctccg
   721  cgatgcaccc agggcacggg ggtgtgaacc agctcggggg ggtgtttgtg aacggccggc
   781  ccctacccga cgtggtgagg cagcgcatcg tggagctggc ccaccagggt gtgcggccct
   841  gtgacatctc ccggcagctg cgggtcagcc acggctgtgt cagcaaaatc ctgggcaggt
   901  actacgagac cggcagcatc aagccgggtg tgatcggtgg ctccaagccc aaagtggcga
   961  cgcccaaagt ggtggacaag attgctgaat acaaacgaca gaacccgact atgttcgcct
  1021  gggagattcg agaccggctc ctggccgagg gcatctgtga caatgacaca gtgcccagcg
  1081  tctcttccat caacagaatc atccggacca agttcagca gcctttccac ccaacgccgg
  1141  atgggctgg acaggagtg accgcccctg ccacaccat tgttcccagc acggcctccc
  1201  ctcctgtttc cagcgcctcc aatgacccag tgggatccta ctccatcaat gggatcctgg
  1261  ggattcctcg ctccaatggt gagaagagga acgtgatga agttgaggta tacactgatc
  1321  ctgcccacat tagaggaggt ggaggtttgc atctggtctg gctttaaga gatgtgtctg
  1381  agggctcagt ccccaatgga gattcccaga gtggtgtgga cagtttgcgg aagcacttgc
  1441  gagctgacac cttcacccag cagcagctgg aagctttgga tcgggtcttt gagcgtcctt
  1501  cctaccctga cgtcttccag gcatcagagc acatcaaatc agaacagggg aacgagtact
  1561  ccctcccagc cctgacccct gggcttgatg aagtcaagtc gagtctatct gcatccacca
  1621  accctgagct gggcagcaac gtgtcaggca cacagacata cccagttgtg actggtcgtg
  1681  acatggcgag caccactctg cctggttacc cccctcacgt gccccccact ggccagggaa
  1741  gctaccccac ctccaccctg gcaggaatgg tgcctgggag cgagttctcc ggcaacccgt
  1801  acagccaccc ccagtacacg gcctacaacg aggcttggag attcagcaac cccgccttac
  1861  taatgccgcc cccggtccg ccctgccgc tgctgccgct gcctatgacc gccactagtt
  1921  accgcgggga ccacatcaag cttcaggccg acagcttcgg cctccacatc gtccccgtct
```

APPENDIX F-continued

```
1981  gaccccaccc cggagggagg gaggaccgac gcgacgcgat gcctcccggc caccgcccca
2041  gcctcacccc atcccacgac ccccgcaacc cttcacatca ccccctcga aggtcggaca
2101  ggacgggtgg agccgtgggc gggaccctca ggcccgggcc cgccgccccc agccccgcct
2161  gccgccctc cccgcctgcc tggactgcgc ggcgccgtga gggggattcg gcccagctcg
2221  tcccggcctc caccaagcca gccccgaagc ccgccagcca ccctgccgga ctcgggcgcg
2281  acctgctggc gcgcgccgga tgtttctgtg acacacaatc agcgcggacc gcagcgcggc
2341  ccagccccgg gcaccgcct cggacgctcg ggcgccagga ggcttcgctg gaggggctgg
2401  gccaaggaga ttaagaagaa aacgactttc tgcaggagga agagcccgct gccgaatccc
2461  tgggaaaaat tcttttcccc cagtgccagc cggactgccc tcgccttccg ggtgtgccct
2521  gtcccagaag atggaatggg ggtgtggggg tccggctcta ggaacgggct ttgggggcgt
2581  caggtctttc caaggttggg acccaaggat cgggggggccc agcagccgc accgatcgag
2641  ccggactctc ggctcttcac tgctcctcct ggcctgccta gttccccagg gcccggcacc
2701  tcctgctgcg agacccggct ctcagccctg ccttgcccct acctcagcgt ctcttccacc
2761  tgctggcctc ccagtttccc ctcctgccag tccttcgcct gtcccttgac gccctgcatc
2821  ctcctccctg actcgcagcc ccatcggacg ctctcccggg accgccgcag gaccagtttc
2881  catagactgc ggactggggt cttcctccag cagttacttg atgcccctc ccccgacaca
2941  gactctcaat ctgccggtgg taagaaccgg ttctgagctg gcgtctgagc tgctgcgggg
3001  tggaagtggg gggctgccca ctccactcct cccatcccct cccagcctcc tcctccggca
3061  ggaactgaac agaaccacaa aaagtctaca tttatttaat atgatggtct ttgcaaaaag
3121  gaacaaaaca acacaaaagc ccaccaggct gctgctttgt ggaaagacgg tgtgtgtcgt
3181  gtgaaggcga aacccggtgt acataacccc tcccctccg ccccgccccg cccggccccg
3241  tagagtccct gtcgcccgcc ggccctgcct gtagatacgc cccgctgtct gtgctgtgag
3301  agtcgccgct cgctggggggg aagggggggg acacagctac acgcccatta agcacagca
3361  cgtcctgggg gagggggggca ttttttatgt tacaaaaaaa aattacgaaa gaaagaaat
3421  ctctatgcaa aatgacgaac atggtcctgt ggactcctct ggcctgtttt gttggctctt
3481  tctctgtaat tccgtgtttt cgcttttcc tccctgcccc tctctccctc tgcccctctc
3541  tcctctccgc ttctctcccc ctctgtctct gtctctctcc gtctctgtcg ctcttgtctg
3601  tctgtctctg ctctttcctc ggcctctctc cccagacctg gcccggccgc cctgtctccg
3661  caggctagat ccgaggtggc agctccagcc cccgggctcg cccctcgcg ggcgtgcccc
3721  gcgcgccccg ggcggccgaa ggccgggccg ccccgtcccg ccccgtagtt gctctttcgg
3781  tagtggcgat gcgccctgca tgtctcctca cccgtggatc gtgacgactc gaaataacag
3841  aaacaaagtc aataaagtga aaataaataa aaatccttga acaaatccga aaaggcttgg
3901  agtcctcgcc cagatctctc tcccctgcga gcccttttta tttgagaagg aaaaagagaa
3961  aagagaatcg tttaagggaa cccggcgccc agccaggctc cagtggcccg aacggggcgg
4021  cgagggcggc gagggcgccg aggtccggcc catcccagtc ctgtggggct ggccgggcag
4081  agaccccgga cccaggccca ggcctaacct gctaaatgtc cccggacggt tctggtctcc
4141  tcggccactt tcagtgcgtc ggttcgtttt gattcttttt cttttgtgca cataagaaat
4201  aaataataat aataaataaa gaataaaatt ttgtatgtca aaaaaaaaaa aaaaaaa (SEQ ID NO: 50)
```

TABLE 3

Sequences of QRT-PCR Primers.

| | Sense (5'-3') | Antisense (5'-3') |
|---|---|---|
| β-actin | 5'-CCTGGCACCCAGCACAAT-3' (SEQ ID NO: 51) | 5'-GCC GATCCACACGGAGTACT-3' (SEQ ID NO: 52) |
| DEFB1 | 5'-GTTGCCTGCCAGTC GCCAT GAGAACTTCCTAC-3' (SEQ ID NO: 53) | 5'-TGGCCTTCCCTCTGTA ACAGGTGCCTTGAATT-3' (SEQ ID NO: 54) |

TABLE 4

PAX2 siRNA Sequences: a pool of four siRNA was utilized to inhibit PAX2 protein expression.

| | Sense (5'-3') | Antisense (5'-3') |
|---|---|---|
| Sequence A | 5'-GAAGUCAAGUCGAGUCUAUUU-3' (SEQ ID NO: 7) | 5'-AUAGACUCGACUUGACUUCUU-3' (SEQ ID NO: 3) |
| Sequence B | 5'-GAGGAAACGUGAUGAAGAUUU-3' (SEQ ID NO: 8) | 5'-AUCUUCAUCACGUUUCCUCUU-3' (SEQ ID NO: 4) |
| Sequence C | 5'-GGACAAGAUUGCUGAAUACUU-3' (SEQ ID NO: 9) | 5'-GUAUUCAGCAAUCUUGUCCUU-3' (SEQ ID NO: 5) |
| Sequence D | 5'-CAUCAGAGCACAUCAAAUCUU-3' (SEQ ID NO: 10) | 5'-GAUUUGAUGUGCUCUGAUGUU-3' (SEQ ID NO: 6) |

TABLE 5

Quantitative RT-PCR Primers: nucleotide sequences of primers used to amplify PAX2 and GAPDH.

| | Sense (5'-3') | Antisense (5'-3') |
|---|---|---|
| GAPDH | 5'-CCACCCATGGCAAATTCCATGGCA-3' (SEQ ID NO: 55) | 5'-TCTAGACGGCAGGTCAGGTCAACC-3' (SEQ ID NO: 56) |
| BAD | 5'-CTCAGGCCTATGCAAAAAGAGGA-3' (SEQ ID NO: 57) | 5'-GCCCTCCCTCCAAAGGAGAC-3' (SEQ ID NO: 58) |
| BID | 5'-AACCTACGCACCTACGTGAGGAG-3' (SEQ ID NO: 59) | 5'-CGTTCAGTCCATCCCATTTCTG-3' (SEQ ID NO: 60) |
| BAX | 5'-GACACCTGAGCTGACCTTGG-3' (SEQ ID NO: 61) | 5'-GAGGAAGTCCAGTGTCCAGC-3' (SEQ ID NO: 62) |

Throughout this application, various publications are referenced. The disclosures of these publications in their entireties are hereby incorporated by reference into this application in order to more fully describe the state of the art to which this invention pertains.

REFERENCES

1. Jemal, A.; Tiwari, R. C.; Murray, T.; Ghafoor, A.; Samuels, A.; Ward, E.; Feuer, E. J.; Thun, M. J., Cancer statistics, 2004. *CA Cancer J Clin* 2004, 54, (1), 8-29.
2. Prasad, M. A.; Trybus, T. M.; Wojno, K. J.; Macoska, J. A., Homozygous and frequent deletion of proximal 8p sequences in human prostate cancers: identification of a potential tumor suppressor gene site. *Genes Chromosomes Cancer* 1998, 23, (3), 255-62.
3. McNeel, D. G.; Malkovsky, M., Immune-based therapies for prostate cancer. *Immunology Letters* 2005, 96, (1), 3.
4. Tien, A. H.; Xu, L.; Helgason, C. D., Altered Immunity Accompanies Disease Progression in a Mouse Model of Prostate Dysplasia. *Cancer Res* 2005, 65, (7), 2947-2955.
5. Banchereau, J.; Palucka, A. K.; Dhodapkar, M.; Burkeholder, S.; Taquet, N.; Rolland, A.; Taquet, S.; Coquery, S.; Wittkowski, K. M.; Bhardwaj, N.; Pineiro, L.; Steinman, R.; Fay, J., Immune and Clinical Responses in Patients with Metastatic Melanoma to CD34+ Progenitor-derived Dendritic Cell Vaccine. *Cancer Res* 2001, 61, (17), 6451-6458.
6. Fong, L.; Brockstedt, D.; Benike, C.; Breen, J. K.; Strang, G.; Ruegg, C. L.; Engleman, E. G., Dendritic Cell-Based Xenoantigen Vaccination for Prostate Cancer Immunotherapy. *J Immunol* 2001, 167, (12), 7150-7156.
7. Linzmeier, R.; Ho, C. H.; Hoang, B. V.; Ganz, T., A 450-kb contig of defensin genes on human chromosome 8p23. *Gene* 1999, 233, (1-2), 205-11.
8. Yang, D.; Biragyn, A.; Hoover, D. M.; Lubkowski, J.; Oppenheim, J. J., Multiple Roles of Antimicrobial Defensins, Cathelicidins, and Eosinophil-Derived Neurotoxin in Host Defense. *Annual Review of Immunology* 2004, 22, (1), 181-215.
9. Donald, C. D.; Sun, C. Q.; Lim, S. D.; Macoska, J.; Cohen, C.; Amin, M. B.; Young, A. N.; Ganz, T. A.; Marshall, F. F.; Petros, J. A., Cancer-specific loss of beta-defensin 1 in renal and prostatic carcinomas. *Lab Invest* 2003, 83, (4), 501-5.
10. Ganz, T., Defensins: antimicrobial peptides of vertebrates. *C R Biol* 2004, 327, (6), 539-49.

11. Mazzucchelli, R.; Barbisan, F.; Tarquini, L. M.; Galosi, A. B.; Stramazzotti, D., Molecular mechanisms in prostate cancer. A review. *Anal Quant Cytol Histol* 2004, 26, (3), 127-33.

12. Ganz, T., Defensins and host defense. *Science* 1999, 286, (5439), 420-1.

13. Ganz, T., Immunology. Versatile defensins. *Science* 2002, 298, (5595), 977-9.

14. Braida, L.; Boniotto, M.; Pontillo, A.; Tovo, P. A.; Amoroso, A.; Crovella, S., A single-nucleotide polymorphism in the human beta-defensin 1 gene is associated with HIV-1 infection in Italian children. *Aids* 2004, 18, (11), 1598-600.

15. Gropp, R.; Frye, M.; Wagner, T. O.; Bargon, J., Epithelial defensins impair adenoviral infection: implication for adenovirus-mediated gene therapy. *Hum Gene Ther* 1999, 10, (6), 957-64.

16. Catalano, M. G.; Pfeffer, U.; Raineri, M.; Ferro, P.; Curto, A.; Capuzzi, P.; Como, F.; Berta, L.; Fortunati, N., Altered expression of androgen-receptor isoforms in human colon-cancer tissues. *Int J Cancer* 2000, 86, (3), 325-30.

17. Takeuchi, S.; Iida, M.; Kobayashi, S.; Jin, K.; Matsuda, T.; Kojima, H., Differential effects of phthalate esters on transcriptional activities via human estrogen receptors alpha and beta, and androgen receptor. *Toxicology* 2005, 210, (2-3), 223-33.

18. Zucht, H. D.; Grabowsky, J.; Schrader, M.; Liepke, C.; Jurgens, M.; Schulz-Knappe, P.; Forssmann, W. G., Human beta-defensin-1: A urinary peptide present in variant molecular forms and its putative functional implication. *Eur J Med Res* 1998, 3, (7), 315-23.

19. Nishimura, M.; Abiko, Y.; Kurashige, Y.; Takeshima, M.; Yamazaki, M.; Kusano, K.; Saitoh, M.; Nakashima, K.; Inoue, T.; Kaku, T., Effect of defensin peptides on eukaryotic cells: primary epithelial cells, fibroblasts and squamous cell carcinoma cell lines. *Journal of Dermatological Science* 2004, 36, (2), 87.

20. Fromont, G.; Joulin, V.; Chantrel-Groussard, K.; Vallancien, G.; Guillonneau, B.; Validire, P.; Latil, A.; Cussenot, O., Allelic losses in localized prostate cancer: association with prognostic factors. *J Urol* 2003, 170, (4 Pt 1), 1394-7.

21. Wang, Z.; Lai, F. M., [Analysis of loss of heterozygosity on chromosome 8 in human prostate carcinoma and high grade prostatic intraepithelial neoplasia]. *Zhonghua Nan Ke Xue* 2004, 10, (1), 26-8, 31.

22. Hugel, A.; Wernert, N., Loss of heterozygosity (LOH), malignancy grade and clonality in microdissected prostate cancer. *Br J Cancer* 1999, 79, (3-4), 551-7.

23. Bockmuhl, U.; Ishwad, C. S.; Ferrell, R. E.; Gollin, S. M., Association of 8p23 deletions with poor survival in head and neck cancer. *Otolaryngol Head Neck Surg* 2001, 124, (4), 451-5.

24. Macoska, J. A.; Paris, P.; Collins, C.; Andaya, A.; Beheshti, B.; Chaib, H.; Kant, R.; Begley, L.; MacDonald, J. W.; Squire, J. A., Evolution of 8p loss in transformed human prostate epithelial cells. *Cancer Genet Cytogenet* 2004, 154, (1), 36-43.

25. Chaib, H.; MacDonald, J. W.; Vessella, R. L.; Washburn, J. G.; Quinn, J. E.; Odman, A.; Rubin, M. A.; Macoska, J. A., Haploinsufficiency and reduced expression of genes localized to the 8p chromosomal region in human prostate tumors. *Genes Chromosomes Cancer* 2003, 37, (3), 306-13.

26. Teixeira, M. R.; Ribeiro, F. R.; Eknaes, M.; Waehre, H.; Stenwig, A. E.; Giercksky, K. E.; Heim, S.; Lothe, R. A., Genomic analysis of prostate carcinoma specimens obtained via ultrasound-guided needle biopsy may be of use in preoperative decision-making. *Cancer* 2004, 101, (8), 1786-93.

27. Vecchione, A.; Ishii, H.; Baldassarre, G.; Bassi, P.; Trapasso, F.; Alder, H.; Pagano, F.; Gomella, L. G.; Croce, C. M.; Baffa, R., FEZ1/LZTS1 is down-regulated in high-grade bladder cancer, and its restoration suppresses tumorigenicity in transitional cell carcinoma cells. *Am J Pathol* 2002, 160, (4), 1345-52.

28. Valore, E. V.; Park, C. H.; Quayle, A. J.; Wiles, K. R.; McCray, P. B., Jr.; Ganz, T., Human beta-defensin-1: an antimicrobial peptide of urogenital tissues. *J Clin Invest* 1998, 101, (8), 1633-42.

29. Gunther, M.; Wagner, E.; Ogris, M., Specific targets in tumor tissue for the delivery of therapeutic genes. *Curr Med Chem Anti-Canc Agents* 2005, 5, (2), 157-71.

30. Dressler, G. R., Pax-2, kidney development, and oncogenesis. *Med Pediatr Oncol* 1996, 27, (5), 440-4.

31. Eccles, M. R.; He, S.; Legge, M.; Kumar, R.; Fox, J.; Zhou, C.; French, M.; Tsai, R. W., PAX genes in development and disease: the role of PAX2 in urogenital tract development. *Int J Dev Biol* 2002, 46, (4), 535-44.

32. Dressler, G. R.; Woolf, A. S., Pax2 in development and renal disease. *Int J Dev Biol* 1999, 43, (5), 463-8.

33. Khoubehi, B.; Kessling, A. M.; Adshead, J. M.; Smith, G. L.; Smith, R. D.; Ogden, C. W., Expression of the developmental and oncogenic PAX2 gene in human prostate cancer. *J Urol* 2001, 165, (6 Pt 1), 2115-20.

34. Havik, B.; Ragnhildstveit, E.; Lorens, J. B.; Saelemyr, K.; Fauske, O.; Knudsen, L. K.; Fjose, A., A novel paired domain DNA recognition motif can mediate Pax2 repression of gene transcription. *Biochem Biophys Res Commun* 1999, 266, (2), 532-41.

35. Discenza, M. T.; He, S.; Lee, T. H.; Chu, L. L.; Bolon, B.; Goodyer, P.; Eccles, M.; Pelletier, J., WT1 is a modifier of the Pax2 mutant phenotype: cooperation and interaction between WT1 and Pax2. *Oncogene* 2003, 22, (50), 8145-55.

36. McConnell, M. J.; Cunliffe, H. E.; Chua, L. J.; Ward, T. A.; Eccles, M. R., Differential regulation of the human Wilms tumour suppressor gene (WT1) promoter by two isoforms of PAX2. *Oncogene* 1997, 14, (22), 2689-700.

37. Yuan, S. S.; Yeh, Y. T.; Lee, E. Y., Pax-2 interacts with RB and reverses its repression on the promoter of Rig-1, a Robo member. *Biochem Biophys Res Commun* 2002, 296, (4), 1019-25.

38. Stuart, E. T.; Haffner, R.; Oren, M.; Gruss, P., Loss of p53 function through PAX-mediated transcriptional repression. *Embo J* 1995, 14, (22), 5638-45.

39. Michalak, E.; Villunger, A.; Erlacher, M.; Strasser, A., Death squads enlisted by the tumour suppressor p53. *Biochem Biophys Res Commun* 2005, 331, (3), 786-98.

40. Tokino, T.; Nakamura, Y., The role of p53-target genes in human cancer. *Crit Rev Oncol Hematol* 2000, 33, (1), 1-6.

41. Muratovska, A.; Zhou, C.; He, S.; Goodyer, P.; Eccles, M. R., Paired-Box genes are frequently expressed in cancer and often required for cancer cell survival. *Oncogene* 2003, 22, (39), 7989-97.

42. Tagge, E. P.; Hanson, P.; Re, G. G.; Othersen, H. B., Jr.; Smith, C. D.; Garvin, A. J., Paired box gene expression in Wilms' tumor. *J Pediatr Surg* 1994, 29, (2), 134-41.

43. Murer, L.; Caridi, G.; Della Vella, M.; Montini, G.; Carasi, C.; Ghiggeri, G.; Zacchello, G., Expression of nuclear transcription factor PAX2 in renal biopsies of juvenile nephronophthisis. *Nephron* 2002, 91, (4), 588-93.

44. Eccles, M. R.; Wallis, L. J.; Fidler, A. E.; Spurr, N. K.; Goodfellow, P. J.; Reeve, A. E., Expression of the PAX2 gene in human fetal kidney and Wilms' tumor. *Cell Growth Differ* 1992, 3, (5), 279-89.
45. Ogata, T.; Muroya, K.; Sasagawa, I.; Kosho, T.; Wakui, K.; Sakazume, S.; Ito, K.; Matsuo, N.; Ohashi, H.; Nagai, T., Genetic evidence for a novel gene(s) involved in urogenital development on 10q26. *Kidney Int* 2000, 58, (6), 2281-90.
46. Ostrom, L.; Tang, M. J.; Gruss, P.; Dressler, G. R., Reduced Pax2 gene dosage increases apoptosis and slows the progression of renal cystic disease. *Dev Biol* 2000, 219, (2), 250-8.
47. Mazal, P. R.; Stichenwirth, M.; Koller, A.; Blach, S.; Haitel, A.; Susani, M., Expression of aquaporins and PAX-2 compared to CD10 and cytokeratin 7 in renal neoplasms: a tissue microarray study. *Mod Pathol* 2005, 18, (4), 535-40.
48. Buttiglieri, S.; Deregibus, M. C.; Bravo, S.; Cassoni, P.; Chiarle, R.; Bussolati, B.; Camussi, G., Role of Pax2 in apoptosis resistance and proinvasive phenotype of Kaposi's sarcoma cells. *J Biol Chem* 2004, 279, (6), 4136-43.
49. Gnarra, J. R.; Dressler, G. R., Expression of Pax-2 in human renal cell carcinoma and growth inhibition by antisense oligonucleotides. *Cancer Res* 1995, 55, (18), 4092-8.
50. Strasser, A., The role of BH3-only proteins in the immune system. *Nat Rev Immunol* 2005, 5, (3), 189-200.
51. Lin, S.; Ying, S. Y., Differentially expressed genes in activin-induced apoptotic LNCaP cells. *Biochem Biophys Res Commun* 1999, 257, (1), 187-92.
52. Perfettini, J. L.; Kroemer, R. T.; Kroemer, G., Fatal liaisons of p53 with Bax and Bak. *Nat Cell Biol* 2004, 6, (5), 386-8.
53. Coultas, L.; Strasser, A., The role of the Bcl-2 protein family in cancer. *Semin Cancer Biol* 2003, 13, (2), 115-23.
54. Margue, C. M.; Bernasconi, M.; Barr, F. G.; Schafer, B. W., Transcriptional modulation of the anti-apoptotic protein BCL-XL by the paired box transcription factors PAX3 and PAX3/FKHR. *Oncogene* 2000, 19, (25), 2921-9.
55. Nakamura, Y., Isolation of p53-target genes and their functional analysis. *Cancer Sci* 2004, 95, (1), 7-11.
56. Perfettini, J. L.; Roumier, T.; Kroemer, G., Mitochondrial fusion and fission in the control of apoptosis. *Trends Cell Biol* 2005, 15, (4), 179-83.
57. Orlando, V. Mapping chromosomal proteins in vivo by formaldehyde-crosslinked-chromatin immunoprecipitation. Trends Biochem Sci, 25: 99-104, 2000.
58. Boyd, K. E. and Farnham, P. J. Coexamination of site-specific transcription factor binding and promoter activity in living cells. Mol Cell Biol, 19: 8393-8399, 1999.
59. Wells, J. and Farnham, P. J. Characterizing transcription factor binding sites using formaldehyde crosslinking and immunoprecipitation. Methods, 26: 48-56, 2002.
60. Sikorski, R. S. and Hieter, P. A system of shuttle vectors and yeast host strains designed for efficient manipulation of DNA in *Saccharomyces cerevisiae*. Genetics, 122: 19-27, 1989.
61. Nigro, J. M., Sikorski, R., Reed, S. I., and Vogelstein, B. Human p53 and CDC2Hs genes combine to inhibit the proliferation of *Saccharomyces cerevisiae*. Mol Cell Biol, 12: 1357-1365, 1992.
62. Wilson, T. E., Fahrner, T. J., Johnston, M., and Milbrandt, J. Identification of the DNA binding site for NGFI-B by genetic selection in yeast. Science, 252: 1296-1300, 1991.
63. Liu, J., Wilson, T. E., Milbrandt, J., and Johnsen, M. Identifying DNA-binding sites and analyzing DNA-binding domains using a yeast selection system. METHODS: A companion to Methods in Enzymology, 5: 125-137, 1993.
64. Jackers, P., Szalai, G., and Watson, D. K. Ets-dependent regulation of target gene expression during megakaryopoiesis. in preparation, 2003.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating breast cancer in a subject, comprising:
   administering to a breast tissue of said subject an effective amount of an anti-PAX2 agent,
   wherein said anti-PAX2 agent is a functional nucleic acid that inhibits PAX2 expression or an expression vector that is capable of expression of a functional nucleic acid that inhibits PAX2 expression,
   wherein said functional nucleic acid is selected from the group consisting of aptamers, ribozymes and external guide sequences.

2. The method of claim 1, wherein said functional nucleic acid is administered with a pharmaceutically acceptable carrier.

3. The method of claim 1, wherein said functional nucleic acid is conjugated to an antibody, a receptor or a receptor ligand to target a tumor tissue in said subject.

4. The method of claim 1, wherein said functional nucleic acid is formulated for sustained release.

5. The method of claim 1, wherein said expression vector is a viral vector that is capable of expression of said functional nucleic acid in vivo.

6. The method of claim 1, wherein said anti-PAX2 agent comprises a plasmid vector that is capable of expression of said functional nucleic acid in vivo.

* * * * *

SEQUENCE LISTING

```
<160> NUMBER OF SEQ ID NOS: 74

<210> SEQ ID NO 1
<211> LENGTH: 5
<212> TYPE: DNA
<213> ORGANISM: Homo sapiens

<400> SEQUENCE: 1 ccttg                                                                    5

<210> SEQ ID NO 2
<211> LENGTH: 5
<212> TYPE: DNA
<213> ORGANISM: Homo sapiens

<400> SEQUENCE: 2 gttcc                                                                    5

<210> SEQ ID NO 3
<211> LENGTH: 21
<212> TYPE: RNA
<213> ORGANISM: Homo sapiens
```

-continued

```
<400> SEQUENCE: 3
auagacucga cuugacuucu u                                              21

<210> SEQ ID NO 4
<211> LENGTH: 21
<212> TYPE: RNA
<213> ORGANISM: Homo sapiens

<400> SEQUENCE: 4
aucuucauca cguuccucu u                                               21

<210> SEQ ID NO 5
<211> LENGTH: 21
<212> TYPE: RNA
<213> ORGANISM: Homo sapiens

<400> SEQUENCE: 5
guauucagca aucuuguccu u                                              21

<210> SEQ ID NO 6
<211> LENGTH: 21
<212> TYPE: RNA
<213> ORGANISM: Homo sapiens

<400> SEQUENCE: 6
gauuugaugu gcucugaugu u                                              21

<210> SEQ ID NO 7
<211> LENGTH: 21
<212> TYPE: RNA
<213> ORGANISM: Homo sapiens

<400> SEQUENCE: 7
gaagucaagu cgagucuauu u                                              21

<210> SEQ ID NO 8
<211> LENGTH: 21
<212> TYPE: RNA
<213> ORGANISM: Homo sapiens

<400> SEQUENCE: 8
gaggaaacgu gaugaagauu u                                              21

<210> SEQ ID NO 9
<211> LENGTH: 21
<212> TYPE: RNA
<213> ORGANISM: Homo sapiens

<400> SEQUENCE: 9
ggacaagauu gcugaauacu u                                              21

<210> SEQ ID NO 10
<211> LENGTH: 21
<212> TYPE: RNA
<213> ORGANISM: Homo sapiens

<400> SEQUENCE: 10
caucagagca caucaaaucu u                                              21

<210> SEQ ID NO 11
<211> LENGTH: 20
<212> TYPE: DNA
<213> ORGANISM: Homo sapiens
```

-continued

```
<400> SEQUENCE: 11
acccgactat gttcgcctgg                                              20

<210> SEQ ID NO 12
<211> LENGTH: 21
<212> TYPE: DNA
<213> ORGANISM: Homo sapiens

<400> SEQUENCE: 12
aagctctgga tcgagtcttt g                                            21

<210> SEQ ID NO 13
<211> LENGTH: 20
<212> TYPE: DNA
<213> ORGANISM: Homo sapiens

<400> SEQUENCE: 13
atgtgtcagg cacacagacg                                              20

<210> SEQ ID NO 14
<211> LENGTH: 21
<212> TYPE: RNA
<213> ORGANISM: Homo sapiens

<400> SEQUENCE: 14
gucgagucua ucugcauccu u                                            21

<210> SEQ ID NO 15
<211> LENGTH: 21
<212> TYPE: RNA
<213> ORGANISM: Homo sapiens

<400> SEQUENCE: 15
ggaugcagau agacucgacu u                                            21

<210> SEQ ID NO 16
<211> LENGTH: 19
<212> TYPE: DNA
<213> ORGANISM: Homo sapiens

<400> SEQUENCE: 16
aagttcaccc ttgactgtg                                               19

<210> SEQ ID NO 17
<211> LENGTH: 7
<212> TYPE: DNA
<213> ORGANISM: Homo sapiens
<220> FEATURE:
<221> NAME/KEY: misc_structure
<222> LOCATION: (1)..(1)
<223> OTHER INFORMATION: each n independently represents 1 to 35
      continuous flanking nucleotides of DEFB1 DNA core sequence of PAX2
      protein binding site
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_structure
<222> LOCATION: (7)..(7)
<223> OTHER INFORMATION: each n independently represents 1 to 35
      continuous flanking nucleotides of DEFB1 DNA core sequence of PAX2
      protein binding site
<220> FEATURE:
<221> NAME/KEY: misc_feature
<222> LOCATION: (7)..(7)
<223> OTHER INFORMATION: n is a, c, g, or t
```

```
<400> SEQUENCE: 17 nccttgn                                                              7

<210> SEQ ID NO 18
<211> LENGTH: 20
<212> TYPE: DNA
<213> ORGANISM: Homo sapiens

<400> SEQUENCE: 18
ctcccttcag ttccgtcgac                                               20

<210> SEQ ID NO 19
<211> LENGTH: 20
<212> TYPE: DNA
<213> ORGANISM: Homo sapiens

<400> SEQUENCE: 19
ctcccttcac cttggtcgac                                               20

<210> SEQ ID NO 20
<211> LENGTH: 40
<212> TYPE: DNA
<213> ORGANISM: Homo sapiens

<400> SEQUENCE: 20
actgtggcac ctcccttcag ttccgtcgac gaggttgtgc                         40

<210> SEQ ID NO 21
<211> LENGTH: 40
<212> TYPE: DNA
<213> ORGANISM: Homo sapiens

<400> SEQUENCE: 21
actgtggcac ctcccttcac cttggtcgac gaggttgtgc                         40

<210> SEQ ID NO 22
<211> LENGTH: 5
<212> TYPE: DNA
<213> ORGANISM: Homo sapiens

<400> SEQUENCE: 22 ctctg                                                                5

<210> SEQ ID NO 23
<211> LENGTH: 20
<212> TYPE: DNA
<213> ORGANISM: Homo sapiens

<400> SEQUENCE: 23
ctcccttcac tctggtcgac                                               20

<210> SEQ ID NO 24
<211> LENGTH: 40
<212> TYPE: DNA
<213> ORGANISM: Homo sapiens

<400> SEQUENCE: 24
actgtggcac ctcccttcac tctggtcgac gaggttgtgc                         40

<210> SEQ ID NO 25
<211> LENGTH: 20
<212> TYPE: DNA
<213> ORGANISM: Homo sapiens
```

```
<400> SEQUENCE: 25
agaagttcac ccttgactgt                                            20

<210> SEQ ID NO 26
<211> LENGTH: 20
<212> TYPE: DNA
<213> ORGANISM: Homo sapiens

<400> SEQUENCE: 26
agaagttcac gttccactgt                                            20

<210> SEQ ID NO 27
<211> LENGTH: 20
<212> TYPE: DNA
<213> ORGANISM: Homo sapiens

<400> SEQUENCE: 27
agaagttcac gctctactgt                                            20

<210> SEQ ID NO 28
<211> LENGTH: 39
<212> TYPE: DNA
<213> ORGANISM: Homo sapiens

<400> SEQUENCE: 28
ttagcgatta gaagttcacc cttgactgtg gcacctccc                       39

<210> SEQ ID NO 29
<211> LENGTH: 40
<212> TYPE: DNA
<213> ORGANISM: Homo sapiens

<400> SEQUENCE: 29
gttagcgatt agaagttcac gttccactgt ggcacctccc                      40

<210> SEQ ID NO 30
<211> LENGTH: 40
<212> TYPE: DNA
<213> ORGANISM: Homo sapiens

<400> SEQUENCE: 30
gttagcgatt agaagttcac gctctactgt ggcacctccc                      40

<210> SEQ ID NO 31
<211> LENGTH: 20
<212> TYPE: DNA
<213> ORGANISM: Homo sapiens

<400> SEQUENCE: 31
actgcccatt gcccaaacac                                            20

<210> SEQ ID NO 32
<211> LENGTH: 21
<212> TYPE: DNA
<213> ORGANISM: Homo sapiens

<400> SEQUENCE: 32
aaaatcttgc cagctttccc c                                          21

<210> SEQ ID NO 33
<211> LENGTH: 23
<212> TYPE: DNA
<213> ORGANISM: Homo sapiens
```

```
<400> SEQUENCE: 33
gtcggttacg gagcggaccg gag                                           23

<210> SEQ ID NO 34
<211> LENGTH: 24
<212> TYPE: DNA
<213> ORGANISM: Homo sapiens

<400> SEQUENCE: 34
taacatatag acaaacgcac accg                                          24

<210> SEQ ID NO 35
<211> LENGTH: 23
<212> TYPE: DNA
<213> ORGANISM: Homo sapiens

<400> SEQUENCE: 35
gcgcttgtgt cgccattgta ttc                                           23

<210> SEQ ID NO 36
<211> LENGTH: 24
<212> TYPE: DNA
<213> ORGANISM: Homo sapiens

<400> SEQUENCE: 36
gtcacaccac agaagtaagg ttcc                                          24

<210> SEQ ID NO 37
<211> LENGTH: 23
<212> TYPE: DNA
<213> ORGANISM: Homo sapiens

<400> SEQUENCE: 37
gtcggttacg gagcggaccg gag                                           23

<210> SEQ ID NO 38
<211> LENGTH: 25
<212> TYPE: DNA
<213> ORGANISM: Homo sapiens

<400> SEQUENCE: 38
cacagagcat tggcgatctc gatgc                                         25

<210> SEQ ID NO 39
<211> LENGTH: 135
<212> TYPE: PRT
<213> ORGANISM: Homo sapiens

<400> SEQUENCE: 39
```

Met Asp Met His Cys Lys Ala Asp Pro Phe Ser Ala Met His Arg His
1               5                   10                  15

Gly Gly Val Asn Gln Leu Gly Gly Val Phe Val Asn Gly Arg Pro Leu
            20                  25                  30

Pro Asp Val Val Arg Gln Arg Ile Val Glu Leu Ala His Gln Gly Val
        35                  40                  45

Arg Pro Cys Asp Ile Ser Arg Gln Leu Arg Val Ser His Gly Cys Val
    50                  55                  60

Ser Lys Ile Leu Gly Arg Tyr Tyr Glu Thr Gly Ser Ile Lys Pro Gly
65                  70                  75                  80

Val Ile Gly Gly Ser Lys Pro Lys Val Ala Thr Pro Lys Val Val Asp
                85                  90                  95

```
Lys Ile Ala Glu Tyr Lys Arg Gln Asn Pro Thr Met Phe Ala Trp Glu
        100                 105                 110

Ile Arg Asp Arg Leu Leu Ala Glu Gly Ile Cys Asp Asn Asp Thr Val
        115                 120                 125

Pro Ser Val Ser Ser Ile Asn
        130                 135

<210> SEQ ID NO 40
<211> LENGTH: 7331
<212> TYPE: DNA
<213> ORGANISM: Homo sapiens
<220> FEATURE:
<221> NAME/KEY: misc_feature
<222> LOCATION: (1)..(7331)
<223> OTHER INFORMATION: n= a, c, g, or t

<400> SEQUENCE: 40
ttcccccttt ccangagggc ctaatccgtt gcgcgcgcgc acgcggacac acacacacac        60
acacacacac acacacggcc cccatagcca ccgcaactct cagcagcagn               120
ncctagctcc tctgacccga ggccccaaga cggcgggcac aggaacccct gggacgtcct       180
ggctccaggc tggacgtagg cggaggtggc aggagtggac aaacccaggc gggtcccacg       240
acgccccttt cctcgggtct ctccttgttt cagccagccg ctctcgcccc tggtcccctc       300
ttccctgcgt tagggtcctt tgtctccagc cacctcgcag cctgtccccg cctcggcggc       360
cctgcccttt gggcctccca gatctctctg gcgggtcccc ctgccttacc agctcccggc       420
tgtggcgcgc tcttcgcctg ctcctcacat ncacacagct gctgggagag gaggaaggaa       480
aggcggncgc gccgcggatg gatccgagac ggtagatttg gtgccggctc gcaaactctg       540
ggaaacttaa ngccggttct ccgcccctc tncaactatg nccagcgcgg cccggtcgcg        600
cgcgctcacc ccgcggggac cctttccttt tcctgtattt cggctgcggc tgtttcgctt       660
cctctggtct cccagccttt ggagtggctt ccctggccct gcactccgtt cccttcggc       720 cgccccggc tgtcgcctgc cccaccctc cgcaggtccc acggtcgcgg cggcgatgac         780
tgtggaggta acgccgggga cgtcctgggt cagcctgcac cgtctccctc gaccacagcc       840
cgatgaggcc gcgggctccg ggccggctgc taagagagtt aatcattact tcgccagcga       900
cactcagcct cccctttccga ctctctcgcc cggcctaggg gaggagggga ggggacagct      960
ggccaggtgg ggacttcggc ttcgcacaaa ccagcctctt caggcctccc agagacaggt      1020
ggtggcttct cagttccctc ggcaactctc taaggtcctc tttcttcccc tcctgtctct      1080
ccctccttcg agcctcctcc cagccaggcc tctccccacc gtctcctgtc cgctctggct      1140
ttgactgatt aactgcaggt cctgggagaa ccaactttct ttgtttggaa ccggaccgga      1200
cgggatttcc ttccctaggt ctccgccaat gggccagctc ctcccgacgg ttttggcgga      1260
ctggctgaag aggaccgcgc ctgaggccac aattaacccg gctgttggtg gtggtggttg      1320
gggggtgggc agtgaggaat ttaaccgatc ctctagcagc tgcgctggtg cagttgggag      1380
gggggtgcag gaagtgggaa tggaggagtg gcaggaggta tagacagagg gaagaacgat      1440
aaacctggac aggtgtggca tagccaatag aaggggaaac aaaataaaac aggaaggcgg      1500
cgcggggagg aatccccagt aacctttata ggattgaagt tgggtggaaa acgccacctc      1560
ctgccctacc ttagcactca gatccctcct ttacctcttt gtgaaagggt aagagttcag      1620
aaagctggcc atttactcca taatctacta gagaaatgtc tgggtttgca aaatgcctat      1680
tgattagctc catggagtag acaagacagg cgtaattatc cccattttac aggtgagaaa      1740
```

```
actgagtctc aaagaagcaa agggactgtg tatgtagtgg ctgtcacttt ttcctgtagg    1800
ctgtggggtg agtggcccct ttagctgtgc agaggtccat gggtatctag ggaggcggta    1860
caggctgtgt ccaggtctga gccagaagta ccagggcctc acgggctcc tagccctttt    1920
agcttgttct ctgttggaca ggaccttcac tcttactctc tagacctgct ggctgggttt    1980
ctcccagctt cgctattttt tcagttccct agtagagtgg cccatgggcg gtagccacct    2040
ggctggcccg tgccactaag aggcagcttt ggtggccaag tggcttgcat tgttgttgct    2100
cctcaaaggg cctgtgaagg gctgggcagg tcgcaaagac ctcttgtgag gggaaagcta    2160
gattaaaggg ggtaaggatc ctggaggata aaggccaagc acgtgcgcct ggactccaca    2220
ggaccaacag accgagcggg cggggccngc tgggagtcag gccccccggg cttcacgcag    2280
ggagcccaaa tattgggaac aaaagcagga aagaagagt gagagcagga gggagggagg    2340
gagcgaggaa gcagaaatta gggggtctta gatgaaaaaa aaagaaagt agctttaggg    2400
ggaatgtgct gtgagtgtg aaattgcagc ccatggtgct ccatattgta ccagaagctc    2460
ttccaaaaaa aaaaaaaaaa accatcctcc aacgtgacca gagggccagg caggggaag    2520
ggcggggaga gaatgggag gaggaggggg aaaggccggg caggagccgg tcaggccttt    2580
ctgcggaagg ggctggggtg taagtttcgg ctccctggga tctgacagcc gagggtatgc    2640
gccctggggt gcgccgggac ccagagggcg agtgagcctc ggttggtcgg ctctggagtt    2700
cggttgtcag aagaactttt atttttcttt ttggtggtga cttctaaaag tgggaataat    2760
ccagaaatga agctcagctg cggagctgca gtctctgttct ccctctctcc cctgcctttc    2820
tgcttctctt cccttcggac tacttttctc cccttggttc taaatagctt tttcccctct    2880
gaactttaat gcatttaatt tggtccgcgc tgtggggagc atttcctggg gagatgcatt    2940
taatttcgga atttctaatc ccctccctca gaccccggtc ctagctcccc tagccgctcc    3000
ccggaaagtg gaaggaggaa ggcaggtccc ggccacgggg gaggggcgcg gctgggatgc    3060
tcccgcggcc ccctccgtct caccaaggct cagccgcctt cccaagctac tggaggccgg    3120
gcgcctgggc cccgggtcag ggccctgcan gaagaagaga ggcaaccccc gctttctgcc    3180
ttttcttcgc ctgggcaaga aaacgctggg ccagggaact ggaaaccgga aaacaggaga    3240
aagggtttnt ggaaggcanc gggagcgggt ggcagncggg gcancgggca ntggactagg    3300
tctacaccgg cacttcactt ttgcacaaca tgcccagaaa cgcatttgag agccctggag    3360
tcgcgcttgg cttggcttgg ggcgccggtg cgtgggtaca ctcgaggtcg gggtgcctat    3420
ccgccacccc gacacctaca cccagtgcag agcaggcgcg gccagccag acaaccaggc    3480
cggcagtagc tcggcctgga gggcggaggc aaggttgggg gccgccaggc gcctgggcaa    3540
gcctggcagg gaagggagcc gagaaggcaa aggagccgag atccacaagg aagattnntt    3600
gggcagatca gatgcacaga ggcggctaat gaagcaaatc ccgagatggg tttcagagca    3660
actcccaaa agtttatttt gcctttaaat ttccgcaggg aggcgggctc cttgtttgaa    3720
gtgtaaatgc ccctaggttg gggggtggaa gggccgcttt gaaaacacca gagagaaaag    3780
gttcatttag aggcggacgg gaaagcaac caacccctgac aggtcggagc ccgggtagtg    3840
tttggggttg ggtngttttc tttctttctc tttcttttcc cctttcctct tctttcttcc    3900
cttttgtgnn ttttnnttgt ttttttttntn ttntttttnt ttaantggct ttcttgcttc    3960
ccccacccc tctactagac tctatagaag aaagagaaca gaaaggggg agtcaggaga    4020
gcggccagtg actggatgaa ggccagccct tcatcctgga gccccaggag aaggcagagc    4080
tttggagaaa aggggttcct aatctccagg gagcattact ctttgactct ctagacccag    4140
```

```
gaatgggctg gacgctaatg gggaagcggc caggaacccg gcctggcgga agagtgagtg   4200
tccagctagt gcagtgctgg gaagacgatc ccaggagcag gggggactct caggggctac   4260
ctgggaatgg gactatcaga agggtcttta ctcctcanaa ggtgcatgtg aaggacaggt   4320
gtgtgaggac aacttccagc acacttggcg cattaagtcc ccttctctac aaaatggaaa   4380
atccttctcg cccaacatgt gaaaatgctt gttgtgggca cccacatttc atggtacttg   4440
taacatagga catgtctagc tggttctaga aaaatctgtg tctgtgtgga agggggggg    4500 tttactcaca gctttcttcc ttcaatagtt cacacacccc gagacaaatt cctggatgac   4560
caacttggag agacctgggg caaaggttac tttagttctg agctcctcta aataaggacc   4620
ctttctcaac gttcctttca ccccagttct gggttaatta cttccagtta gtgcgtgttc   4680
gtggggttgt gaggccaaag caaacccggg agcgccatct gcaggcctca agaggaagag   4740
actgacctta gaggctaggc cctgcgtctt caacctctag cccaagggaa ccaacctgcc   4800
tagccaccca agggaagtgg gataggggct gggaggggca ggcggtgagg agtgttttcc   4860
tcccagactt taccccgcag gtggattaag cttattgggc tctggaggat acaggaggga   4920
gggcaaatgc caggatccca gcggaccag gccccacagg agtgagaggc tcagaacctc    4980
gtcccgctga gcctggcctg agctcctcct gaggaataag ggcatcccaa aaacccgggt   5040
acaagacgcc cagtagtagt agttaggctg agtcaggcag gtgcatctct ccccatggta   5100
tctgccgccc aggctccggc cagagggagg ggagcgcgag tccgcggcgc ttccgcgggg   5160
cgcccggaac tgcagacggg ggctggagga atctcggatt cgggctgcaa gagcgctgcg   5220
caagcttcgc cgagccgccc tttcgcagac ccagggaagc gggggagg agcgaaggag      5280 ggagagagag ttaaaacatc agcttgaaag tgcccaagat gattttatta agaccgaggg   5340
gaaaattatt ttcatgaaag attctccccg gaatatttct tgtacttaac ccagttagga   5400
agacaaaggg cttcttttctg cctggtgcgg tgcgagcgga ccccagcgag caagggagct   5460
agtgccaaag agaactgcgg aggctccggc aggagtgggg acgtccccgt ggttgcgcct   5520
cctgcgctcg ccccggatcc accgagctag cagcggcgg cgctcagccg cgtccgcagc    5580
ctcctcttct ccccagccgg ggagagccag cctcgtctcc cacatcctct gccgccagcg   5640
acctgcagct ccgcactgtt tccctccccct gtaccccctt cccagtcacc cgagggttca   5700
gaaaccaagt ccccggctc tcccgccatc cgctgggtcc caccgaggca ggtgggtact    5760
cgccggaggt cttcagctcg attctgaacc aagcgttctg gactgcccag acccggtggg   5820
caaggggact ggggaggccc tgcgcacagt cgcgtggaac gggaggggac aagacaaact   5880
gctggacact tttccgtgga atgagaagtg gggggtgcgt gggtgggaag gtacctccgg   5940
agggaaaggc caaagggaag gaccagaaag agaggaagga agagccggga aggaacggaa   6000
gggaactcag agccgagggt ggtgggggttg gggctaggga tgcgcactgg gcccggggcc   6060
gcgcggccca ggcgggcact ggccagtgga tggcagggct gggcgagtta gaactgagag   6120
cccggcttca cagcgcagcg cgctccgagg ccctctgtcg ttacctgaat attcattaga   6180
ctgaccgctc tttatcctta tctaacgttt atcttatcgg cgagtttcgt ttctcagtgt   6240
agttttaatc ccgggctccc attccccctc ccccggtccg ctcccctccc tcctcttcc    6300 ttcgccggct gctccctccc tccctccctc ccatttctcc ctcccctgcc ctcccttgc    6360 cggcaccgga gtgacaggct cggggccctc ctcgccgaag ctcgggctc cagcgctggc    6420 gaatcacaga gtggtggaat ctattgcctt tgtctgacaa gtcatccatc tcccggcgcg   6480 gggagggggga ggaggtctgg aggggcttt gcagctttta gagagacaca caccgggagc    6540
```

-continued

```
cgaggctcca gtctccggcc gagtcttcta gcagccgcaa cccacctggg gccagcccag    6600
agctgccagc gccgctcggc tccctccctc cctcccggcc cttcggccgc ggcggcgtgc    6660
gcctgccttt tccggggggcg ggggcctggc ccgcgcgctc ccctcccgca ggcgccacct    6720
cggacatccc cggattgct acttctctgc caacttcgcc aactcgccag cacttggaga    6780
ggcccggctc ccctcccggc gccctctgac cgccccgcc ccgcgcgctc tccgaccacc    6840
gcctctcgga tgaacaggtt ccaggggagc tgagcgagtc gcctccccg cccagcttca    6900 gccctggctg cagctgcagc gcgagccatg cgccccagt gcaccccggc ccggcccacc    6960
gccccggggc cattctgctg accgccagc cccgagcccc gacagtggca agttgcggct    7020
actgcggttg caagctccgg ccaacccgga ggagcccag cggggagcgc agtgttgcgc    7080 ccccgcccc cgcgcgcgcc gcagcagccg ggcgttcact catcctccct cccccaccgt    7140
ccctcccttt tctcctcaag tcctgaagtt gagtttgaga ggcgacacgg cggcggcggc    7200
cgcgctgctc ccgctcctct gcctccccat ggatatgcac tgcaaagcag accccttctc    7260
cgcgatgcac cgtgagtacc cgcgcccggc tcctgtcccg gctcgggctc tccgtcccaa    7320
ccctgtccag t                                                         7331
```

<210> SEQ ID NO 41
<211> LENGTH: 416
<212> TYPE: PRT
<213> ORGANISM: Homo sapiens

<400> SEQUENCE: 41

```
Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
                20                  25                  30

Leu Pro Asp Val Val Arg Gln Arg Ile Val Glu Leu Ala His Gln Gly
            35                  40                  45

Val Arg Pro Cys Asp Ile Ser Arg Gln Leu Arg Val Ser His Gly Cys
        50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
    130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Val Glu Val
        195                 200                 205

Tyr Thr Asp Pro Ala His Ile Arg Gly Gly Gly Leu His Leu Val
    210                 215                 220

Trp Thr Leu Arg Asp Val Ser Glu Gly Ser Val Pro Asn Gly Asp Ser
225                 230                 235                 240
```

Gln Ser Gly Val Asp Ser Leu Arg Lys His Leu Arg Ala Asp Thr Phe
              245                 250                 255

Thr Gln Gln Gln Leu Glu Ala Leu Asp Arg Val Phe Glu Arg Pro Ser
          260                 265                 270

Tyr Pro Asp Val Phe Gln Ala Ser Glu His Ile Lys Ser Glu Gln Gly
              275                 280                 285

Asn Glu Tyr Ser Leu Pro Ala Leu Thr Pro Gly Leu Asp Glu Val Lys
          290                 295                 300

Ser Ser Leu Ser Ala Ser Thr Asn Pro Glu Leu Gly Ser Asn Val Ser
305                 310                 315                 320

Gly Thr Gln Thr Tyr Pro Val Val Thr Gly Arg Asp Met Ala Ser Thr
                  325                 330                 335

Thr Leu Pro Gly Tyr Pro Pro His Val Pro Pro Thr Gly Gln Gly Ser
              340                 345                 350

Tyr Pro Thr Ser Thr Leu Ala Gly Met Val Pro Gly Ser Glu Phe Ser
          355                 360                 365

Gly Asn Pro Tyr Ser His Pro Gln Tyr Thr Ala Tyr Asn Glu Ala Trp
      370                 375                 380

Arg Phe Ser Asn Pro Ala Leu Leu Ser Ser Pro Tyr Tyr Tyr Ser Ala
385                 390                 395                 400

Ala Pro Arg Ser Ala Pro Ala Ala Ala Ala Ala Tyr Asp Arg His
              405                 410                 415

<210> SEQ ID NO 42
<211> LENGTH: 4276
<212> TYPE: DNA
<213> ORGANISM: Homo sapiens

<400> SEQUENCE: 42

```
aggctccagt ctccggccga gtcttctcgc agccgcaacc cacctggggc cagcccagag      60
ctgccagcgc cgctcggctc cctccctccc tccggccct tcggccgcgg cggcgtgcgc      120
ctgccttttc cggggcggg ggcctggccc gcgcgctccc ctcccgcagg cgccacctcg      180
gacatccccg ggattgctac ttctctgcca acttcgccaa ctcgccagca cttggagagg      240
cccggctccc ctcccggcgc cctctgaccg ccccgccc gcgcgctctc cgaccaccgc      300
ctctcggatg accaggttcc aggggagctg agcgagtcgc ctccccgcc cagcttcagc      360
cctggctgca gctgcagcgc gagccatgcg ccccccagtgc accccggccc ggcccaccgc      420
cccggggcca ttctgctgac cgcccagccc cgagccccga cagtggcaag ttgcggctac      480
tgcagttgca agctccggcc aacccggagg agcccagcg gggagcgcag tgttgcgccc      540
cccgcccccg cgcgcccgc agcagccggg cgttcactca tcctccctcc cccaccgtcc      600
ctccctttc tcctcaagtc ctgaagttga gtttgagagg cgacacggcg gcggcggccg      660
cgctgctccc gctcctctgc ctccccatgg atatgcactg caaagcagac ccttctcccg      720
cgatgcaccc agggcacggg ggtgtgaacc agctcggggg ggtgtttgtg aacggccggc      780
ccctaccga cgtggtgagg cagcgcatcg tggagctggc ccaccagggt gtgcggccct      840
gtgacatctc ccggcagctg cgggtcagcc acggctgtgt cagcaaaatc ctgggcaggt      900
actacgagac cggcagcatc aagcgggtg tgatcggtgg ctccaagccc aaagtggcga      960
cgcccaaagt ggtggacaag attgctgaat acaaacgaca gaacccgact atgttcgcct      1020
gggagattcg agaccggctc ctggccgagg gcatctgtga caatgacaca gtgcccagcg      1080
tctcttccat caacagaatc atccggacca agttcagca gcctttccac ccaacgccgg      1140
```

```
atggggctgg  gacaggagtg  accgcccctg  gccacaccat  tgttcccagc  acggcctccc  1200
ctcctgtttc  cagcgcctcc  aatgaccccag tgggatccta  ctccatcaat  gggatcctgg  1260
ggattcctcg  ctccaatggt  gagaagagga  aacgtgatga  agttgaggta  tacactgatc  1320
ctgcccacat  tagaggaggt  ggaggtttgc  atctggtctg  gactttaaga  gatgtgtctg  1380
agggctcagt  ccccaatgga  gattcccaga  gtggtgtgga  cagtttgcgg  aagcacttgc  1440
gagctgacac  cttcacccag  cagcagctgg  aagctttgga  tcgggtcttt  gagcgtcctt  1500
cctaccctga  cgtcttccag  gcatcagagc  acatcaaatc  agaacagggg  aacgagtact  1560
ccctcccagc  cctgaccccct gggcttgatg  aagtcaagtc  gagtctatct  gcatccacca  1620
accctgagct  gggcagcaac  gtgtcaggca  cacagacata  cccagttgtg  actggtcgtg  1680
acatggcgag  caccactctg  cctggttacc  cccctcacgt  gccccccact  ggccagggaa  1740
gctaccccac  ctccaccctg  gcaggaatgg  tgcctgggag  cgagttctcc  ggcaacccgt  1800
acagccaccc  ccagtacacg  gcctacaacg  aggcttggag  attcagcaac  cccgccttac  1860
taagttcccc  ttattattat  agtgccgccc  cccggtccgc  ccctgccgct  gctgccgctg  1920
cctatgaccg  ccactagtta  ccgcggggac  cacatcaagc  ttcaggccga  cagcttcggc  1980
ctccacatcg  tccccgtctg  accccacccc  ggagggaggg  aggaccgacg  cgacgcgatg  2040
cctcccggcc  accgcccccag cctcacccca  tcccacgacc  cccgcaaccc  ttcacatcac  2100
cccctcgaa   ggtcggacag  gacgggtgga  gccgtgggcg  ggaccctcag  gcccgggccc  2160
gccgccccca  gccccgcctg  ccgccctcc   ccgcctgcct  ggactgcgcg  gcgccgtgag  2220
ggggattcgg  cccagctcgt  cccggcctcc  accaagccag  cccccgaagcc  cgccagccac  2280
cctgccggac  tcgggcgcga  cctgctggcg  cgcgccggat  gtttctgtga  cacacaatca  2340
gcgcggaccg  cagcgcggcc  cagccccggg  cacccgcctc  ggacgctcgg  gcgccaggag  2400
gcttcgctgg  aggggctggg  ccaaggagat  taagaagaaa  acgactttct  gcaggaggaa  2460
gagcccgctg  ccgaatccct  gggaaaaatt  cttttccccc  agtgccagcc  ggactgccct  2520
cgccttccgg  gtgtgccctg  tcccagaaga  tggaatgggg  gtgtgggggt  ccggctctag  2580
gaacgggctt  tgggggcgtc  aggtctttcc  aaggttggga  cccaaggatc  ggggggccca  2640
gcagcccgca  ccgatcgagc  cggactctcg  gctcttcact  gctcctcctg  gcctgcctag  2700
ttccccaggg  cccggcacct  cctgctgcga  gacccggctc  tcagccctgc  cttgccccta  2760
cctcagcgtc  tcttccacct  gctggcctcc  cagtttcccc  tcctgccagt  ccttcgcctg  2820
tcccttgacg  ccctgcatcc  tcctccctga  ctcgcagccc  catcggacgc  tctcccggga  2880
ccgccgcagg  accagtttcc  atagactgcg  gactggggtc  ttcctccagc  agttacttga  2940
tgccccctcc  cccgacacag  actctcaatc  tgccggtggt  aagaaccggt  tctgagctgg  3000
cgtctgagct  gctgcggggt  ggaagtgggg  ggctgcccac  tccactcctc  ccatcccctc  3060
ccagcctcct  cctccggcag  gaactgaaca  gaaccacaaa  aagtctacat  ttatttaata  3120
tgatggtctt  tgcaaaaagg  aacaaaacaa  cacaaaagcc  caccaggctg  ctgctttgtg  3180
gaaagacggt  gtgtgtcgtg  tgaaggcgaa  acccggtgta  cataacccct  ccccctccgc  3240
cccgccccgc  ccggccccgt  agagtccctg  tcgcccgccg  gccctgcctg  tagatacgcc  3300
ccgctgtctg  tgctgtgaga  gtcgccgctc  gctgggggg   aagggggga   cacagctaca  3360
cgcccattaa  agcacagcac  gtcctggggg  agggggcat   ttttatgtt   acaaaaaaaa  3420
attacgaaag  aaaagaaatc  tctatgcaaa  atgacgaaca  tggtcctgtg  gactcctctg  3480
gcctgttttg  ttggctcttt  ctctgtaatt  ccgtgttttc  gcttttttcct  ccctgccccct 3540
```

```
ctctccctct gcccctctct cctctccgct tctctccccc tctgtctctg tctctctccg    3600
tctctgtcgc tcttgtctgt ctgtctctgc tctttcctcg gcctctctcc ccagacctgg    3660
cccggccgcc ctgtctccgc aggctagatc cgaggtggca gctccagccc ccgggctcgc    3720
cccctcgcgg gcgtgccccg cgcgcccccgg gcggccgaag gccgggccgc ccgtcccgc    3780
cccgtagttg ctctttcggt agtggcgatg cgccctgcat gtctcctcac ccgtggatcg    3840
tgacgactcg aaataacaga aacaaagtca ataaagtgaa aataaataaa aatccttgaa    3900
caaatccgaa aaggcttgga gtcctcgccc agatctctct cccctgcgag ccctttttat    3960
ttgagaagga aaaagagaaa agagaatcgt ttaagggaac ccggcgccca gccaggctcc    4020
agtggcccga acggggcggc gagggcggcg agggcgccga ggtccggccc atcccagtcc    4080
tgtgggctg gccgggcaga gaccccggac ccaggcccag gcctaacctg ctaaatgtcc    4140
ccggacggtt ctggtctcct cggccacttt cagtgcgtcg gttcgttttg attctttttc    4200
ttttgtgcac ataagaaata aataataata ataaataaag aataaaattt tgtatgtcaa    4260
aaaaaaaaaa aaaaaa                                                    4276
```

<210> SEQ ID NO 43
<211> LENGTH: 393
<212> TYPE: PRT
<213> ORGANISM: Homo sapiens

<400> SEQUENCE: 43

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
    130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
        195                 200                 205

Glu Gly Ser Val Pro Asn Gly Asp Ser Gln Ser Gly Val Asp Ser Leu
    210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala

```
                        245                 250                 255
Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
            275                 280                 285

Asn Pro Glu Leu Gly Ser Asn Val Ser Gly Thr Gln Thr Tyr Pro Val
            290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Gly Ser Glu Phe Ser Gly Asn Pro Tyr Ser His Pro
            340                 345                 350

Gln Tyr Thr Ala Tyr Asn Glu Ala Trp Arg Phe Ser Asn Pro Ala Leu
            355                 360                 365

Leu Ser Ser Pro Tyr Tyr Tyr Ser Ala Ala Pro Arg Ser Ala Pro Ala
            370                 375                 380

Ala Ala Ala Ala Ala Tyr Asp Arg His
385                 390

<210> SEQ ID NO 44
<211> LENGTH: 4207
<212> TYPE: DNA
<213> ORGANISM: Homo sapiens

<400> SEQUENCE: 44
aggctccagt ctccggccga gtcttctcgc agccgcaacc cacctggggc cagcccagag      60
ctgccagcgc cgctcggctc cctccctccc tcccggccct tcggccgcgg cggcgtgcgc     120
ctgccttttc cggggggcggg ggcctggccc gcgcgctccc ctcccgcagg cgccacctcg    180
gacatccccg ggattgctac ttctctgcca acttcgccaa ctcgccagca cttggagagg     240
cccggctccc ctcccggcgc cctctgaccg ccccgcccc gcgcgctctc cgaccaccgc      300
ctctcggatg accaggttcc aggggagctg agcgagtcgc ctcccccgcc cagcttcagc     360
cctggctgca gctgcagcgc gagccatgcg ccccagtgc accccggccc ggcccaccgc     420
cccggggcca ttctgctgac cgcccagccc cgagccccga cagtggcaag ttgcggctac     480
tgcagttgca agctccggcc aacccggagg agccccagcg gggagcgcag tgttgcgccc     540 cccgccccg cgcgcccgc agcagccggg cgttcactca tcctccctcc cccaccgtcc      600
ctcccttttc tcctcaagtc ctgaagttga gtttgagagg cgacacggcg gcggcggccg     660
cgctgctccc gctcctctgc ctccccatgg atatgcactg caaagcagac cccttctccg     720
cgatgcaccc agggcacggg ggtgtgaacc agctcggggg ggtgtttgtg aacggccggc     780
ccctacccga cgtggtgagg cagcgcatcg tggagctggc ccaccagggt gtgcggccct     840
gtgacatctc ccggcagctg cgggtcagcc acggctgtgt cagcaaaatc ctgggcaggt     900
actacgagac cggcagcatc aagcgggtg tgatcggtgg ctccaagccc aaagtggcga     960
cgcccaaagt ggtggacaag attgctgaat acaaacgaca gaacccgact atgttcgcct    1020
gggagattcg agaccggctc ctggccgagg gcatctgtga caatgacaca gtgcccagcg    1080
tctcttccat caacagaatc atccggacca agttcagca gcctttccac ccaacgccgg    1140
atggggctgg acaggagtg accgcccctg ccacaccat tgttcccagc acggcctccc    1200
ctcctgtttc cagcgcctcc aatgaccag tgggatccta ctccatcaat gggatcctgg    1260
ggattcctcg ctccaatggt gagaagagga acgtgatga agatgtgtct gagggctcag    1320
```

```
tccccaatgg agattcccag agtggtgtgg acagtttgcg aagcacttg cgagctgaca    1380
ccttcaccca gcagcagctg gaagctttgg atcgggtctt tgagcgtcct tcctaccctg    1440
acgtcttcca ggcatcagag cacatcaaat cagaacaggg gaacgagtac tccctcccag    1500
ccctgacccc tgggcttgat gaagtcaagt cgagtctatc tgcatccacc aaccctgagc    1560
tgggcagcaa cgtgtcaggc acacagacat acccagttgt gactggtcgt gacatggcga    1620
gcaccactct gcctggttac cccctcacg tgcccccac tggccaggga agctacccca    1680
cctccaccct ggcaggaatg gtgcctggga gcgagttctc cggcaacccg tacagccacc    1740
cccagtacac ggcctacaac gaggcttgga gattcagcaa ccccgcctta ctaagttccc    1800
cttattatta tagtgccgcc ccccggtccg ccctgccgc tgctgccgct gcctatgacc    1860
gccactagtt accgcgggga ccacatcaag cttcaggccg acagcttcgg cctccacatc    1920
gtccccgtct gacccaccc cggagggagg gaggaccgac gcgacgcgat gcctcccggc    1980
caccgcccca gcctcacccc atcccacgac ccccgcaacc cttcacatca ccccccctcga    2040
aggtcggaca ggacgggtgg agccgtgggc gggaccctca ggcccgggcc cgccgccccc    2100
agccccgcct gccgcccctc cccgcctgcc tggactgcgc ggcgccgtga gggggattcg    2160
gcccagctcg tcccggcctc caccaagcca gccccgaagc ccgccagcca cctgccgga    2220
ctcgggcgcg acctgctggc gcgcgccgga tgtttctgtg acacacaatc agcgcggacc    2280
gcagcgcggc ccagccccgg gcacccgcct cggacgctcg ggcgccagga ggcttcgctg    2340
gaggggctgg gccaaggaga ttaagaagaa acgactttc tgcaggagga agagcccgct    2400
gccgaatccc tgggaaaaat tcttttcccc cagtgccagc cggactgccc tcgccttccg    2460
ggtgtgccct gtcccagaag atggaatggg ggtgtggggg tccggctcta ggaacgggct    2520
ttgggggcgt caggtctttc caaggttggg acccaaggat cgggggggccc agcagcccgc    2580
accgatcgag ccggactctc ggctcttcac tgctcctcct ggcctgccta gttccccagg    2640
gcccggcacc tcctgctgcg agacccggct ctcagccctg ccttgcccct acctcagcgt    2700
ctcttccacc tgctggcctc ccagtttccc ctcctgccag tccttcgcct gtcccttgac    2760
gccctgcatc ctcctccctg actcgcagcc ccatcggacg ctctcccggg accgccgcag    2820
gaccagtttc catagactgc ggactggggt cttcctccag cagttacttg atgccccctc    2880
ccccgacaca gactctcaat ctgccggtgg taagaaccgg ttctgagctg gcgtctgagc    2940
tgctgcgggg tggaagtggg gggctgccca ctccactcct cccatccct cccagcctcc    3000
tcctccggca ggaactgaac agaaccacaa aaagtctaca tttatttaat atgatggtct    3060
ttgcaaaaag gaacaaaaca acacaaaagc ccaccaggct gctgctttgt ggaaagacgg    3120
tgtgtgtcgt gtgaaggcga aacccggtgt acataacccc tccccctccg ccccgccccg    3180
cccggccccg tagagtccct gtcgcccgcc ggccctgcct gtagatacgc cccgctgtct    3240
gtgctgtgag agtcgccgct cgctgggggg gaagggggg acacagctac acgcccatta    3300
aagcacagca cgtcctgggg gagggggca ttttttatgt tacaaaaaaa aattacgaaa    3360
gaaaagaaat ctctatgcaa aatgacgaac atggtcctgt ggactcctct ggcctgtttt    3420
gttggctctt tctctgtaat tccgtgtttt cgcttttttcc tccctgcccc tctctccctc    3480
tgcccctctc tcctctccgc ttctctcccc ctctgtctct gtctctctcc gtctctgtcg    3540
ctcttgtctg tctgtctctg ctcttttcctc ggcctctctc cccagacctg gccggccgc    3600
cctgtctccg caggctagat ccgaggtggc agctccagcc cccgggctcg cccctcgcg    3660
ggcgtgcccc gcgcgccccg ggcggccgaa ggccgggccg ccccgtcccg ccccgtagtt    3720
```

```
gctctttcgg tagtggcgat gcgccctgca tgtctcctca cccgtggatc gtgacgactc    3780
gaaataacag aaacaaagtc aataaagtga aaataaataa aaatccttga acaaatccga    3840
aaaggcttgg agtcctcgcc cagatctctc tccctgcga gccttttta tttgagaagg      3900 aaaaagagaa aagagaatcg tttaagggaa cccggcgccc agccaggctc cagtggcccg    3960
aacggggcgg cgagggcggc gagggcgccg aggtccggcc catcccagtc ctgtggggct    4020
ggccgggcag agaccccgga cccaggccca ggcctaacct gctaaatgtc cccggacggt    4080
tctggtctcc tcggccactt tcagtgcgtc ggttcgtttt gattcttttt cttttgtgca    4140
cataagaaat aaataataat aataaataaa gaataaaatt ttgtatgtca aaaaaaaaa     4200 aaaaaaa                                                             4207
```

<210> SEQ ID NO 45
<211> LENGTH: 396
<212> TYPE: PRT
<213> ORGANISM: Homo sapiens

<400> SEQUENCE: 45

```
Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
    130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
        195                 200                 205

Glu Gly Ser Val Pro Asn Gly Asp Ser Gln Ser Gly Val Asp Ser Leu
    210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285
```

```
Asn Pro Glu Leu Gly Ser Asn Val Ser Gly Thr Gln Thr Tyr Pro Val
    290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Glu Ala Ala Val Gly Pro Ser Ser Ser Leu Met Ser
            340                 345                 350

Lys Pro Gly Arg Lys Leu Ala Glu Val Pro Pro Cys Val Gln Pro Thr
        355                 360                 365

Gly Ala Ser Ser Pro Ala Thr Arg Thr Ala Thr Pro Ser Thr Arg Pro
    370                 375                 380

Thr Thr Arg Leu Gly Asp Ser Ala Thr Pro Pro Tyr
385                 390                 395

<210> SEQ ID NO 46
<211> LENGTH: 4290
<212> TYPE: DNA
<213> ORGANISM: Homo sapiens

<400> SEQUENCE: 46
aggctccagt ctccggccga gtcttctcgc agccgcaacc cacctggggc cagcccagag     60
ctgccagcgc cgctcggctc cctccctccc tccggccct  tcggccgcgg cggcgtgcgc    120
ctgccttttc cggggcggg  ggcctggccc gcgcgctccc ctcccgcagg cgccacctcg    180
gacatccccg ggattgctac ttctctgcca acttcgccaa ctcgccagca cttggagagg    240
cccggctccc ctccggcgc  cctctgaccg ccccgcccc  gcgcgctctc cgaccaccgc    300
ctctcggatg accaggttcc aggggagctg agcgagtcgc ctccccgcc  cagcttcagc    360
cctggctgca gctgcagcgc gagccatgcg ccccagtgc  accccggccc ggcccaccgc    420
cccgggccca ttctgctgac cgcccagccc cgagccccga cagtggcaag ttgcggctac    480
tgcagttgca agctccggcc aacccggagg agccccagcg gggagcgcag tgttgcgccc    540
cccgccccg  cgcgccccgc agcagccggg cgttcactca tcctccctcc ccaccgtcc    600
ctcccttttc tcctcaagtc ctgaagttga gtttgagagg cgacacggcg gcggcggccg    660
cgctgctccc gctcctctgc ctccccatgg atatgcactg caaagcagac cccttctccg    720
cgatgcaccc agggcacggg ggtgtgaacc agctcggggg ggtgtttgtg aacggccggc    780
ccctacccga cgtggtgagg cagcgcatcg tggagctggc ccaccagggt gtgcggccct    840
gtgacatctc ccggcagctg cgggtcagcc acggctgtgt cagcaaaatc ctgggcaggt    900
actacgagac cggcagcatc aagccgggtg tgatcggtgg ctccaagccc aaagtggcga    960
cgcccaaagt ggtggacaag attgctgaat acaaacgaca gaacccgact atgttcgcct   1020
gggagattcg agaccggctc ctggccgagg catctgtga  caatgacaca gtgcccagcg   1080
tctcttccat caacagaatc atccggacca agttcagca  gcctttccac ccaacgccgg   1140
atggggctgg acaggagtg  accgcccctg gccacaccat tgttcccagc acggcctccc   1200
ctcctgtttc cagcgcctcc aatgacccag tgggatccta ctccatcaat gggatcctgg   1260
ggattcctcg ctccaatggt gagaagagga acgtgatga  agatgtgtct gagggctcag   1320
tccccaatgg agattcccag agtggtgtgg acagtttgcg gaagcacttg cgagctgaca   1380
ccttcacccc agcagcagctg gaagctttgg atcgggtctt tgagcgtcct tcctaccctg   1440
acgtcttcca ggcatcagag cacatcaaat cagaacaggg gaacgagtac tccctcccag   1500
```

```
ccctgacccc tgggcttgat gaagtcaagt cgagtctatc tgcatccacc aaccctgagc   1560
tgggcagcaa cgtgtcaggc acacagacat acccagttgt gactggtcgt gacatggcga   1620
gcaccactct gcctggttac cccctcacg tgcccccac tggccaggga agctacccca    1680
cctccaccct ggcaggaatg gtgcctgagg ctgcagttgg tccctcatcc tccctcatga   1740
gcaagccggg gaggaagctt gcagaagtgc cccttgtgt gcaacccact ggagcgagtt    1800
ctccggcaac ccgtacagcc accccagta cacggcctac aacgaggctt ggagattcag    1860
caaccccgcc ttactaagtt ccccttatta ttatagtgcc gcccccggt ccgcccctgc    1920 cgctgctgcc gctgcctatg accgccacta gttaccgcgg ggaccacatc aagcttcagg   1980
ccgacagctt cggcctccac atcgtcccg tctgacccca ccccggaggg agggaggacc    2040
gacgcgacgc gatgcctccc ggccaccgcc ccagcctcac cccatcccac gaccccgca    2100 acccttcaca tcaccccct cgaaggtcgg acaggacggg tggagccgtg ggcgggaccc    2160 tcaggccccgg gcccgccgcc cccagccccg cctgccgccc ctccccgcct gcctggactg   2220
cgcggcgccg tgagggggat tcggcccagc tcgtcccggc ctccaccaag ccagccccga   2280
agcccgccag ccaccctgcc ggactcgggc gcgacctgct ggcgcgcgcc ggatgtttct    2340
gtgacacaca atcagcgcgg accgcagcgc ggcccagccc cgggcacccg cctcggacgc    2400 tcggggcgcca ggaggcttcg ctggaggggc tgggccaagg agattaagaa gaaaacgact   2460
ttctgcagga ggaagagccc gctgccgaat ccctgggaaa aattcttttc ccccagtgcc   2520
agccggactg ccctcgcctt ccgggtgtgc cctgtcccag aagatggaat ggggggtgtgg  2580 gggtccggct ctaggaacgg gctttggggg cgtcaggtct ttccaaggtt gggacccaag    2640
gatcgggggg cccagcagcc cgcaccgatc gagccggact ctcggctctt cactgctcct    2700
cctggcctgc ctagttcccc agggcccggc acctcctgct gcgagacccg gctctcagcc    2760
ctgccttgcc cctacctcag cgtctcttcc acctgctggc ctcccagttt ccctcctgc    2820 cagtccttcg cctgtcccctt gacgcccctgc atcctcctcc ctgactcgca gccccatcgg   2880
acgctctccc gggaccgccg caggaccagt ttccatagac tgcggactgg ggtcttcctc    2940
cagcagttac ttgatgcccc ctcccccgac acagactctc aatctgccgg tggtaagaac   3000
cggttctgag ctggcgtctg agctgctgcg gggtggaagt gggggggctgc ccactccact   3060 cctcccatcc cctcccagcc tcctcctccg gcaggaactg aacagaacca caaaaagtct    3120
acatttattt aatatgatgg tctttgcaaa aaggaacaaa acaacacaaa gcccaccag    3180 gctgctgctt tgtggaaaga cggtgtgtgt cgtgtgaagg cgaaacccgg tgtacataac    3240 ccctcccct ccgccccgcc ccgcccggcc ccgtagagtc cctgtcgccc gccggccctg    3300
cctgtagata cgccccgctg tctgtgctgt gagagtcgcc gctcgctggg ggggaagggg    3360
gggacacagc tacacgccca ttaaagcaca gcacgtcctg ggggagggg gcatttttta    3420 tgttacaaaa aaaaattacg aaagaaaaga aatctctatg caaaatgacg aacatggtcc    3480
tgtggactcc tctggcctgt tttgttggct cttttctctgt aattccgtgt tttcgctttt    3540 tcctcccctgc ccctctctcc ctctgcccct ctctcctctc cgcttctctc ccctctgtc    3600 tctgtctctc tccgtctctg tcgctcttgt ctgtctgtct ctgctctttc ctcggcctct    3660
ctccccagac ctgccccggc cgccctgtct ccgcaggcta gatccgaggt ggcagctcca   3720 gccccgggc tcgccccctc gcgggcgtgc cccgcgcgcc ccgggcggcc gaaggccggg    3780 ccgcccgtc ccgcccgta gttgctcttt cggtagtggc gatgcgccct gcatgtctcc     3840
tcacccgtgg atcgtgacga ctcgaaataa cagaaacaaa gtcaataaag tgaaaataaa    3900
```

-continued

```
taaaaatcct tgaacaaatc cgaaaaggct tggagtcctc gcccagatct ctctcccctg   3960
cgagcccttt ttatttgaga aggaaaaaga gaaaagagaa tcgtttaagg gaacccggcg   4020
cccagccagg ctccagtggc ccgaacgggg cggcgagggc ggcgagggcg ccgaggtccg   4080
gcccatccca gtcctgtggg gctggccggg cagagacccc ggacccaggc ccaggcctaa   4140
cctgctaaat gtccccggac ggttctggtc tcctcggcca ctttcagtgc gtcggttcgt   4200
tttgattctt tttcttttgt gcacataaga aataataat aataataaat aaagaataaa   4260
attttgtatg tcaaaaaaaa aaaaaaaaa                                     4290
```

<210> SEQ ID NO 47
<211> LENGTH: 408
<212> TYPE: PRT
<213> ORGANISM: Homo sapiens

<400> SEQUENCE: 47

```
Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
    130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
        195                 200                 205

Glu Gly Ser Val Pro Asn Gly Asp Ser Gln Ser Gly Val Asp Ser Leu
    210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285

Asn Pro Glu Leu Gly Ser Asn Val Ser Gly Thr Gln Thr Tyr Pro Val
    290                 295                 300

Val Thr Gly Arg Asp Met Ala Ser Thr Thr Leu Pro Gly Tyr Pro Pro
```

```
                305                 310                 315                 320
His Val Pro Pro Thr Gly Gln Gly Ser Tyr Pro Thr Ser Thr Leu Ala
                325                 330                 335

Gly Met Val Pro Gly Ser Glu Phe Ser Gly Asn Pro Tyr Ser His Pro
                340                 345                 350

Gln Tyr Thr Ala Tyr Asn Glu Ala Trp Arg Phe Ser Asn Pro Ala Leu
                355                 360                 365

Leu Met Pro Pro Gly Pro Pro Leu Pro Leu Leu Pro Leu Pro Met
                370                 375                 380

Thr Ala Thr Ser Tyr Arg Gly Asp His Ile Lys Leu Gln Ala Asp Ser
385                 390                 395                 400

Phe Gly Leu His Ile Val Pro Val
                405

<210> SEQ ID NO 48
<211> LENGTH: 4188
<212> TYPE: DNA
<213> ORGANISM: Homo sapiens

<400> SEQUENCE: 48
aggctccagt ctccggccga gtcttctcgc agccgcaacc cacctggggc cagcccagag     60
ctgccagcgc cgctcggctc cctccctccc tcccggccct tcggccgcgg cggcgtgcgc    120 ctgcctttc  cggggggcggg ggcctggccc gcgcgctccc ctcccgcagg cgccacctcg    180
gacatccccg ggattgctac ttctctgcca acttcgccaa ctcgccagca cttggagagg    240
cccggctccc ctcccggcgc cctctgaccg ccccgcccc gcgcgctctc cgaccaccgc    300
ctctcggatg accaggttcc aggggagctg agcgagtcgc ctcccccgcc cagcttcagc    360
cctggctgca gctgcagcgc gagccatgcg ccccagtgc accccggccc ggcccaccgc    420
cccggggcca ttctgctgac cgcccagccc gagccccga cagtggcaag ttgcggctac    480
tgcagttgca agctccggcc aacccggagg agccccagcg gggagcgcag tgttgcgccc    540
cccgcccccg cgcgcccgc agcagccggg cgttcactca tcctccctcc cccaccgtcc    600 ctccctttc  tcctcaagtc ctgaagttga gtttgagagg cgacacggcg gcggcggccg    660
cgctgctccc gctcctctgc ctccccatgg atatgcactg caaagcagac cccttctccg    720
cgatgcaccc agggcacggg ggtgtgaacc agctcggggg ggtgtttgtg aacgccggc    780 ccctacccga cgtggtgagg cagcgcatcg tggagctggc ccaccagggt gtgcggccct    840
gtgacatctc ccggcagctg cgggtcagcc acggctgtgt cagcaaaatc ctgggcaggt    900
actacgagac cggcagcatc aagccgggtg tgatcggtgg ctccaagccc aaagtggcga    960
cgcccaaagt ggtggacaag attgctgaat acaaacgaca gaacccgact atgttcgcct   1020
gggagattcg agaccggctc ctggccgagg gcatctgtga caatgacaca gtgcccagcg   1080
tctcttccat caacagaatc atccggacca aagttcagca gcctttccac ccaacgccgg   1140
atggggctgg acaggagtg accgcccctg gccacaccat tgttcccagc acggcctccc   1200
ctcctgtttc cagcgcctcc aatgacccag tgggatccta ctccatcaat gggatcctgg   1260
ggattcctcg ctccaatggt gagaagagga aacgtgatga agatgtgtct gagggctcag   1320
tccccaatgg agattcccag agtggtgtgg acagtttgcg gaagcacttg cgagctgaca   1380
ccttcaccca gcagcagctg gaagctttgg atcgggtctt tgagcgtcct cctaccctg    1440 acgtcttcca ggcatcagag cacatcaaat cagaacaggg gaacgagtac tccctcccag   1500
ccctgacccc tgggcttgat gaagtcaagt cgagtctatc tgcatccacc aaccctgagc   1560
```

```
tgggcagcaa cgtgtcaggc acacagacat acccagttgt gactggtcgt gacatggcga   1620
gcaccactct gcctggttac cccctcacg  tgcccccac  tggccaggga agctacccca   1680
cctccaccct ggcaggaatg gtgcctggga gcgagttctc cggcaacccg tacagccacc   1740
cccagtacac ggcctacaac gaggcttgga gattcagcaa ccccgcctta ctaatgccgc   1800
cccccggtcc gccctgccg  ctgctgccgc tgcctatgac cgccactagt taccgcgggg   1860
accacatcaa gcttcaggcc gacagcttcg gcctccacat cgtccccgtc tgaccccacc   1920
ccggagggag ggaggaccga cgcgacgcga tgcctcccgg ccaccgcccc agcctcaccc   1980
catcccacga ccccgcaac  ccttcacatc accccctcg  aaggtcggac aggacgggtg   2040
gagccgtggg cgggaccctc aggcccgggc ccgccgcccc cagccccgcc tgccgcccct   2100
ccccgcctgc ctggactgcg cggcgccgtg aggggattc  ggcccagctc gtcccggcct   2160
ccaccaagcc agcccgaag  cccgccagcc accctgccgg actcgggcgc gacctgctgg   2220
cgcgcgccg  atgtttctgt gacacacaat cagcgcggac cgcagcgcgg cccagccccg   2280
ggcacccgcc tcggacgctc gggcgccagg aggcttcgct ggaggggctg ggccaaggag   2340
attaagaaga aaacgacttt ctgcaggagg aagagcccgc tgccgaatcc ctgggaaaaa   2400
ttctttcccc ccagtgccag ccggactgcc ctcgccttcc gggtgtgccc tgtcccagaa   2460
gatggaatgg gggtgtgggg gtccggctct aggaacgggc tttggggggcg tcaggtcttt   2520
ccaaggttgg gacccaagga tcgggggggcc cagcagcccg caccgatcga gccggactct   2580
cggctcttca ctgctcctcc tggcctgcct agttccccag gcccggcac  ctcctgctgc   2640
gagacccggc tctcagccct gccttgcccc tacctcagcg tctcttccac ctgctggcct   2700
cccagttccc cctcctgcca gtccttcgcc tgtcccttga cgccctgcat cctcctccct   2760
gactcgcagc cccatcggac gctctcccgg gaccgccgca ggaccagttt ccatagactg   2820
cggactgggg tcttcctcca gcagttactt gatgccccct cccccgacac agactctcaa   2880
tctgccggtg gtaagaaccg gttctgagct ggcgtctgag ctgctgcggg gtggaagtgg   2940
ggggctgccc actccactcc tcccatcccc tcccagcctc ctcctccggc aggaactgaa   3000
cagaaccaca aaaagtctac atttatttaa tatgatggtc tttgcaaaaa ggaacaaaac   3060
aacacaaaag cccaccaggc tgctgctttg tggaaagacg gtgtgtgtcg tgtgaaggcg   3120
aaacccggtg tacataaccc ctccccctcc gcccgcccc  gccggcccc  gtagagtccc   3180
tgtcgcccgc cggccctgcc tgtagatacg ccccgctgtc tgtgctgtga gagtcgccgc   3240
tcgctggggg ggaagggggg gacacagcta cacgcccatt aaagcacagc acgtcctggg   3300
ggaggggggc attttttatg ttacaaaaaa aaattacgaa agaaaagaaa tctctatgca   3360
aaatgacgaa catggtcctg tggactcctc tggcctgttt tgttggctct ttctctgtaa   3420
ttccgtgttt tcgcttttc  ctccctgccc ctctctccct ctgcccctct ctcctctccg   3480
cttctctcccc cctctgtctc tgtctctctc cgtctctgtc gctcttgtct gtctgtctct   3540
gctctttcct cggcctctct cccagacct  ggcccggccg ccctgtctcc gcaggctaga   3600
tccgaggtgg cagctccagc cccgggctc  gccctcgc   gggcgtgccc cgcgcgcccc   3660
gggcggccga aggccgggcc gccccgtccc gccccgtagt tgctctttcg gtagtggcga   3720
tgcgccctgc atgtctcctc acccgtggat cgtgacgact cgaaataaca gaaacaaagt   3780
caataaagtg aaaataaata aaaatccttg aacaaatccg aaaaggcttg gagtcctcgc   3840
ccagatctct ctccctgcg  agcccttttt atttgagaag gaaaagagaa aagagaatc   3900
gtttaaggga acccggcgcc cagccaggct ccagtggccc gaacggggcg gcgagggcgg   3960
```

```
cgagggcgcc gaggtccggc ccatcccagt cctgtggggc tggccgggca gagaccccgg   4020
acccaggccc aggcctaacc tgctaaatgt ccccggacgg ttctggtctc ctcggccact   4080
ttcagtgcgt cggttcgttt tgattctttt tcttttgtgc acataagaaa taaataataa   4140
taataaataa agaataaaat tttgtatgtc aaaaaaaaaa aaaaaaaa                4188
```

<210> SEQ ID NO 49
<211> LENGTH: 431
<212> TYPE: PRT
<213> ORGANISM: Homo sapiens

<400> SEQUENCE: 49

```
Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
    130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Val Glu Val
        195                 200                 205

Tyr Thr Asp Pro Ala His Ile Arg Gly Gly Gly Leu His Leu Val
    210                 215                 220

Trp Thr Leu Arg Asp Val Ser Glu Gly Ser Val Pro Asn Gly Asp Ser
225                 230                 235                 240

Gln Ser Gly Val Asp Ser Leu Arg Lys His Leu Arg Ala Asp Thr Phe
                245                 250                 255

Thr Gln Gln Gln Leu Glu Ala Leu Asp Arg Val Phe Glu Arg Pro Ser
            260                 265                 270

Tyr Pro Asp Val Phe Gln Ala Ser Glu His Ile Lys Ser Glu Gln Gly
        275                 280                 285

Asn Glu Tyr Ser Leu Pro Ala Leu Thr Pro Gly Leu Asp Glu Val Lys
    290                 295                 300

Ser Ser Leu Ser Ala Ser Thr Asn Pro Glu Leu Gly Ser Asn Val Ser
305                 310                 315                 320

Gly Thr Gln Thr Tyr Pro Val Val Thr Gly Arg Asp Met Ala Ser Thr
                325                 330                 335

Thr Leu Pro Gly Tyr Pro Pro His Val Pro Pro Thr Gly Gln Gly Ser
```

```
            340             345             350
Tyr Pro Thr Ser Thr Leu Ala Gly Met Val Pro Gly Ser Glu Phe Ser
            355             360             365
Gly Asn Pro Tyr Ser His Pro Gln Tyr Thr Ala Tyr Asn Glu Ala Trp
        370             375             380
Arg Phe Ser Asn Pro Ala Leu Leu Met Pro Pro Gly Pro Pro Leu
385             390             395             400
Pro Leu Leu Pro Leu Pro Met Thr Ala Thr Ser Tyr Arg Gly Asp His
                405             410             415
Ile Lys Leu Gln Ala Asp Ser Phe Gly Leu His Ile Val Pro Val
            420             425             430

<210> SEQ ID NO 50
<211> LENGTH: 4257
<212> TYPE: DNA
<213> ORGANISM: Homo sapiens

<400> SEQUENCE: 50
```

| | | | | | |
|---|---|---|---|---|---|
| aggctccagt | ctccggccga | gtcttctcgc | agccgcaacc | cacctggggc | cagcccagag | 60 |
| ctgccagcgc | cgctcggctc | cctccctccc | tcccggccct | tcggccgcgg | cggcgtgcgc | 120 |
| ctgccttttc | cggggggcggg | ggcctggccc | gcgcgctccc | ctcccgcagg | cgccacctcg | 180 |
| gacatccccg | ggattgctac | ttctctgcca | acttcgccaa | ctcgccagca | cttggagagg | 240 |
| cccggctccc | ctcccggcgc | cctctgaccg | ccccgcccc | gcgcgctctc | cgaccaccgc | 300 |
| ctctcggatg | accaggttcc | aggggagctg | agcgagtcgc | ctcccccgcc | cagcttcagc | 360 |
| cctggctgca | gctgcagcgc | gagccatgcg | ccccccagtgc | accccggccc | ggcccaccgc | 420 |
| cccgggggcca | ttctgctgac | cgcccagccc | cgagccccga | cagtggcaag | ttgcggctac | 480 |
| tgcagttgca | agctccggcc | aacccggagg | agccccagcg | gggagcgcag | tgttgcgccc | 540 |
| cccgccccg | cgcgccccgc | agcagccggg | cgttcactca | tcctccctcc | cccaccgtcc | 600 |
| ctcccttttc | tcctcaagtc | ctgaagttga | gtttgagagg | cgacacggcg | gcggcggccg | 660 |
| cgctgctccc | gctcctctgc | ctcccccatgg | atatgcactg | caaagcagac | cccttctccg | 720 |
| cgatgcaccc | agggcacggg | ggtgtgaacc | agctcggggg | ggtgtttgtg | aacggccggc | 780 |
| ccctacccga | cgtggtgagg | cagcgcatcg | tggagctggc | ccaccagggt | gtgcggccct | 840 |
| gtgacatctc | ccggcagctg | cgggtcagcc | acggctgtgt | cagcaaaatc | ctgggcaggt | 900 |
| actacgagac | cggcagcatc | aagccgggtg | tgatcggtgg | ctccaagccc | aaagtggcga | 960 |
| cgcccaaagt | ggtggacaag | attgctgaat | acaaacgaca | gaacccgact | atgttcgcct | 1020 |
| gggagattcg | agaccggctc | ctggccgagg | gcatctgtga | caatgacaca | gtgcccagcg | 1080 |
| tctcttccat | caacagaatc | atccggacca | agttcagca | gcctttccac | ccaacgccgg | 1140 |
| atggggctgg | gacaggagtg | accgcccctg | gccacaccat | tgttcccagc | acggcctccc | 1200 |
| ctcctgtttc | cagcgcctcc | aatgacccag | tgggatccta | ctccatcaat | gggatcctgg | 1260 |
| ggattcctcg | ctccaatggt | gagaagagga | acgtgatga | agttgaggta | tacactgatc | 1320 |
| ctgcccacat | tagaggaggt | ggaggtttgc | atctggtctg | gactttaaga | gatgtgtctg | 1380 |
| agggctcagt | ccccaatgga | gattcccaga | gtggtgtgga | cagtttgcgg | aagcacttgc | 1440 |
| gagctgacac | cttcacccag | cagcagctgg | aagctttgga | tcgggtcttt | gagcgtcctt | 1500 |
| cctaccctga | cgtcttccag | gcatcagagc | acatcaaatc | agaacagggg | aacgagtact | 1560 |
| ccctcccagc | cctgacccct | gggcttgatg | aagtcaagtc | gagtctatct | gcatccacca | 1620 |
| accctgagct | gggcagcaac | gtgtcaggca | cacagacata | cccagttgtg | actggtcgtg | 1680 |

```
acatggcgag caccactctg cctggttacc cccctcacgt gcccccact ggccagggaa   1740
gctaccccac ctccaccctg gcaggaatgg tgcctgggag cgagttctcc ggcaacccgt   1800
acagccaccc ccagtacacg gcctacaacg aggcttggag attcagcaac cccgccttac   1860
taatgccgcc cccggtccg cccctgccgc tgctgccgct gcctatgacc gccactagtt   1920
accgcgggga ccacatcaag cttcaggccg acagcttcgg cctccacatc gtccccgtct   1980
gaccccaccc cggagggagg gaggaccgac gcgacgcgat gcctcccggc caccgcccca   2040
gcctcacccc atcccacgac ccccgcaacc cttcacatca ccccctcga aggtcggaca   2100
ggacgggtgg agccgtgggc gggaccctca ggcccgggcc cgccgccccc agcccgcct   2160
gccgcccctc cccgcctgcc tggactgcgc ggcgccgtga gggggattcg gcccagctcg   2220
tcccggcctc caccaagcca gccccgaagc ccgccagcca cctgccgga ctcgggcgcg   2280
acctgctggc gcgcgccgga tgtttctgtg acacacaatc agcgcggacc gcagcgcggc   2340
ccagccccgg gcacccgcct cggacgctcg ggcgccagga ggcttcgctg gaggggctgg   2400
gccaaggaga ttaagaagaa aacgactttc tgcaggagga agagcccgct gccgaatccc   2460
tgggaaaaat tctttttcccc cagtgccagc cggactgccc tcgccttccg ggtgtgccct   2520
gtcccagaag atggaatggg ggtgtggggg tccggctcta ggaacgggct ttggggcgt   2580
caggtctttc caaggttggg acccaaggat cggggggccc agcagcccgc accgatcgag   2640
ccggactctc ggctcttcac tgctcctcct ggcctgccta gttccccagg gcccggcacc   2700
tcctgctgcg agaccgggct ctcagccctg ccttgcccct acctcagcgt ctcttccacc   2760
tgctggcctc ccagtttccc ctcctgccag tccttcgcct gtcccttgac gccctgcatc   2820
ctcctccctg actcgcagcc ccatcggacg ctctcccggg accgccgcag gaccagtttc   2880
catagactgc ggactggggt cttcctccag cagttacttg atgccccctc ccccgacaca   2940
gactctcaat ctgccggtgg taagaaccgg ttctgagctg gcgtctgagc tgctgcgggg   3000
tggaagtggg gggctgccca ctccactcct cccatcccct cccagcctcc tcctccggca   3060
ggaactgaac agaaccacaa aaagtctaca tttatttaat atgatggtct ttgcaaaaag   3120
gaacaaaaca acacaaaagc ccaccaggct gctgctttgt ggaaagacgg tgtgtgtcgt   3180
gtgaaggcga aacccggtgt acataacccc tcccccctccg ccccgccccg cccgcccccg   3240
tagagtccct gtcgcccgcc ggccctgcct gtagatacgc cccgctgtct gtgctgtgag   3300
agtcgccgct cgctgggggg gaagggggg acacagctac acgcccatta aagcacagca   3360
cgtcctgggg gagggggca ttttttatgt tacaaaaaaa aattacgaaa gaaaagaaat   3420
ctctatgcaa aatgacgaac atggtcctgt ggactcctct ggcctgtttt gttggctctt   3480
tctctgtaat tccgtgtttt cgcttttcc tccctgcccc tctctccctc tgcccctctc   3540
tcctctccgc ttctctcccc ctctgtctct gtctctctcc gtctctgtcg ctcttgtctg   3600
tctgtctctg ctctttcctc ggcctctctc cccagacctg gccggccgc cctgtctccg   3660
caggctagat ccgaggtggc agctccagcc cccgggctcg cccctcgcg ggcgtgcccc   3720
gcgcgccccg ggcggccgaa ggcgggccg ccccgtcccg ccccgtagtt gctctttcgg   3780
tagtggcgat gcgccctgca tgtctcctca cccgtggatc gtgacgactc gaaataacag   3840
aaacaaagtc aataaagtga aaataaataa aaatccttga acaaatccga aaaggcttgg   3900
agtcctcgcc cagatctctc tcccctgcga gccctttta tttgagaagg aaaaagagaa   3960
aagagaatcg tttaagggaa cccggcgccc agccaggctc cagtggcccg aacggggcgg   4020
cgagggcggc gagggcgccg aggtccggcc catcccagtc ctgtggggct ggccgggcag   4080
```

```
agaccccgga cccaggccca ggcctaacct gctaaatgtc cccggacggt tctggtctcc   4140
tcggccactt tcagtgcgtc ggttcgtttt gattcttttt cttttgtgca cataagaaat   4200
aaataataat aataaataaa gaataaaatt ttgtatgtca aaaaaaaaaa aaaaaaa      4257
```

<210> SEQ ID NO 51
<211> LENGTH: 18
<212> TYPE: DNA
<213> ORGANISM: Homo sapiens

<400> SEQUENCE: 51

```
cctggcaccc agcacaat                                                   18
```

<210> SEQ ID NO 52
<211> LENGTH: 20
<212> TYPE: DNA
<213> ORGANISM: Homo sapiens

<400> SEQUENCE: 52

```
gccgatccac acggagtact                                                 20
```

<210> SEQ ID NO 53
<211> LENGTH: 32
<212> TYPE: DNA
<213> ORGANISM: Homo sapiens

<400> SEQUENCE: 53

```
gttgcctgcc agtcgccatg agaacttcct ac                                   32
```

<210> SEQ ID NO 54
<211> LENGTH: 32
<212> TYPE: DNA
<213> ORGANISM: Homo sapiens

<400> SEQUENCE: 54

```
tggccttccc tctgtaacag gtgccttgaa tt                                   32
```

<210> SEQ ID NO 55
<211> LENGTH: 24
<212> TYPE: DNA
<213> ORGANISM: Homo sapiens

<400> SEQUENCE: 55

```
ccacccatgg caaattccat ggca                                            24
```

<210> SEQ ID NO 56
<211> LENGTH: 24
<212> TYPE: DNA
<213> ORGANISM: Homo sapiens

<400> SEQUENCE: 56

```
tctagacggc aggtcaggtc aacc                                            24
```

<210> SEQ ID NO 57
<211> LENGTH: 23
<212> TYPE: DNA
<213> ORGANISM: Homo sapiens

<400> SEQUENCE: 57

```
ctcaggccta tgcaaaaaga gga                                             23
```

<210> SEQ ID NO 58
<211> LENGTH: 20

```
<212> TYPE: DNA
<213> ORGANISM: Homo sapiens

<400> SEQUENCE: 58
gccctccctc caaaggagac                                              20

<210> SEQ ID NO 59
<211> LENGTH: 23
<212> TYPE: DNA
<213> ORGANISM: Homo sapiens

<400> SEQUENCE: 59
aacctacgca cctacgtgag gag                                          23

<210> SEQ ID NO 60
<211> LENGTH: 22
<212> TYPE: DNA
<213> ORGANISM: Homo sapiens

<400> SEQUENCE: 60
cgttcagtcc atcccatttc tg                                           22

<210> SEQ ID NO 61
<211> LENGTH: 20
<212> TYPE: DNA
<213> ORGANISM: Homo sapiens

<400> SEQUENCE: 61
gacacctgag ctgaccttgg                                              20

<210> SEQ ID NO 62
<211> LENGTH: 20
<212> TYPE: DNA
<213> ORGANISM: Homo sapiens

<400> SEQUENCE: 62
gaggaagtcc agtgtccagc                                              20

<210> SEQ ID NO 63
<211> LENGTH: 68
<212> TYPE: PRT
<213> ORGANISM: Homo sapiens

<400> SEQUENCE: 63

Met Arg Thr Ser Tyr Leu Leu Leu Phe Thr Leu Cys Leu Leu Leu Ser
1               5                   10                  15

Glu Met Ala Ser Gly Gly Asn Phe Leu Thr Gly Leu Gly His Arg Ser
            20                  25                  30

Asp His Tyr Asn Cys Val Ser Ser Gly Gly Gln Cys Leu Tyr Ser Ala
        35                  40                  45

Cys Pro Ile Phe Thr Lys Ile Gln Gly Thr Cys Tyr Arg Gly Lys Ala
    50                  55                  60

Lys Cys Cys Lys
65

<210> SEQ ID NO 64
<211> LENGTH: 914
<212> TYPE: DNA
<213> ORGANISM: Homo sapiens
<220> FEATURE:
<221> NAME/KEY: misc_feature
<222> LOCATION: (1)..(914)
<223> OTHER INFORMATION: n= a, c, g, or t
```

-continued

```
<400> SEQUENCE: 64
ctgcagggtg ggcccaggct gggccnagac cctcaccctc aagggccac actgggggct      60
cactttctga ggagtgccct ttggaaacgt cccaggaaca cgtctagtgg gaaaagagaa     120
aagttggtcc atcgaggaga gtgttctgca taagggaga gatgagaagg tagccttggc     180
cagaggaaga aacttcatta caaccagctc tccttctsca agggaagagg gtgaagtttg    240
agtttgtctt gcaggaagac aatcaaacta aagaggccaa caccagctta gagccgagcg    300
gccccctgct cagagcttcc ctgtggctct cctccatgtg atccagaagg agggactcca    360
gtgtgaactg cctgttccag aaaccccatc agaactgcct aacctagaaa accaaacagg    420
aggagctggc accagggctc caggctgaaa gctaaatcca gcggcagcca gatggagaca    480
atgtgccatg tgactgctga ctgctcaggg caaatgacac caggggttag cgattagaag    540
ttcacccttg actgtggcac ctcccttcag ttccgtcgac gaggttgtgc aatccaccag    600
tcttataaat acagtgacgc tccagcctct ggaagcctct gtcagctcag cctccaaagg    660
agccagcctc tccccagttc ctgaaatcct gagtgttgcc tgccagtcgc catgagaact    720
tcctaccttc tgctgtttac tctctgctta cttttgtctg agatggcctc aggtaagctc    780
tggtacctgc tagagtttcc catccccagg gctggggaca atggggctga tgtgagtctc    840
ggatggctgc ctccgtgtcc caagggacga ggaacaagca gcaggaaagc atcccgtggt    900
tgagtggcct gcag                                                      914

<210> SEQ ID NO 65
<211> LENGTH: 104
<212> TYPE: DNA
<213> ORGANISM: Homo Sapiens

<400> SEQUENCE: 65
ttcacccttg actgtggcac ctcccttcag ttccgtcgac gaggttgtgc aatccaccag     60
tcttataaat acagtgacgc tccagcctct ggaagcctct gtca                     104

<210> SEQ ID NO 66
<211> LENGTH: 17
<212> TYPE: DNA
<213> ORGANISM: Homo Sapiens

<400> SEQUENCE: 66
tcaagcgtga ctaattg                                                    17

<210> SEQ ID NO 67
<211> LENGTH: 12
<212> TYPE: DNA
<213> ORGANISM: Homo Sapiens

<400> SEQUENCE: 67
cggcacggtt ga                                                         12

<210> SEQ ID NO 68
<211> LENGTH: 13
<212> TYPE: DNA
<213> ORGANISM: Homo Sapiens
<220> FEATURE:
<221> NAME/KEY: misc_feature
<222> LOCATION: (1)..(13)
<223> OTHER INFORMATION: n is a, g, c or t

<400> SEQUENCE: 68
nntnnygcgt gar                                                        13
```

```
<210> SEQ ID NO 69
<211> LENGTH: 13
<212> TYPE: DNA
<213> ORGANISM: Homo Sapiens
<220> FEATURE:
<221> NAME/KEY: misc_feature
<222> LOCATION: (1)..(13)
<223> OTHER INFORMATION: n is a, g, c or t

<400> SEQUENCE: 69
tngtcaygcr tga                                                       13

<210> SEQ ID NO 70
<211> LENGTH: 18
<212> TYPE: DNA
<213> ORGANISM: Homo Sapiens
<220> FEATURE:
<221> NAME/KEY: misc_feature
<222> LOCATION: (1)..(18)
<223> OTHER INFORMATION: n is a, g, c or t

<400> SEQUENCE: 70
rncantgnng cgkracsr                                                  18

<210> SEQ ID NO 71
<211> LENGTH: 18
<212> TYPE: DNA
<213> ORGANISM: Homo Sapiens

<400> SEQUENCE: 71
atatctagag cggaacgg                                                  18

<210> SEQ ID NO 72
<211> LENGTH: 11
<212> TYPE: DNA
<213> ORGANISM: Homo Sapiens

<400> SEQUENCE: 72
ttcacgcwts a                                                         11

<210> SEQ ID NO 73
<211> LENGTH: 13
<212> TYPE: DNA
<213> ORGANISM: Homo Sapiens
<220> FEATURE:
<221> NAME/KEY: misc_feature
<222> LOCATION: (1)..(13)
<223> OTHER INFORMATION: n is a, g, c or t

<400> SEQUENCE: 73
tcgtcacrcn yna                                                       13

<210> SEQ ID NO 74
<211> LENGTH: 12
<212> TYPE: DNA
<213> ORGANISM: Homo Sapiens

<400> SEQUENCE: 74
cgtcacgstt sr                                                        12
```